US009593157B2

(12) United States Patent
Steyaert et al.

(10) Patent No.: US 9,593,157 B2
(45) Date of Patent: Mar. 14, 2017

(54) CHIMERIC POLYPEPTIDES COMPRISING G PROTEIN-COUPLED RECEPTORS AND VHH ANTIBODIES

(71) Applicants: VIB VZW, Ghent (BE); Vrije Universiteit Brussel, Brussels (BE)

(72) Inventors: Jan Steyaert, Beersel (BE); Toon Laeremans, Dworp (BE); Els Pardon, Lubbeek (BE)

(73) Assignees: VIB VZW, Ghent (BE); Vrije Universiteit Brussel, Brussels (BE)

( * ) Notice: Subject to any disclaimer, the term of this patent is extended or adjusted under 35 U.S.C. 154(b) by 0 days.

(21) Appl. No.: 14/764,548

(22) PCT Filed: Jan. 30, 2014

(86) PCT No.: PCT/EP2014/051845
§ 371 (c)(1),
(2) Date: Jul. 29, 2015

(87) PCT Pub. No.: WO2014/118297
PCT Pub. Date: Aug. 7, 2014

(65) Prior Publication Data
US 2015/0376261 A1    Dec. 31, 2015

Related U.S. Application Data

(60) Provisional application No. 61/758,518, filed on Jan. 30, 2013.

(30) Foreign Application Priority Data

Feb. 8, 2013  (EP) .................................. 13154552
Oct. 3, 2013  (EP) .................................. 13187265

(51) Int. Cl.
| C07K 14/72 | (2006.01) |
| C07K 14/705 | (2006.01) |
| C07K 16/28 | (2006.01) |
| C12N 15/62 | (2006.01) |
| G01N 33/566 | (2006.01) |
| C07K 16/00 | (2006.01) |
| C07K 16/18 | (2006.01) |
| C07K 16/26 | (2006.01) |

(52) U.S. Cl.
CPC .......... *C07K 14/723* (2013.01); *C07K 14/705* (2013.01); *C07K 16/00* (2013.01); *C07K 16/18* (2013.01); *C07K 16/26* (2013.01); *C07K 16/28* (2013.01); *C07K 16/286* (2013.01); *C07K 16/2869* (2013.01); *C12N 15/62* (2013.01); *G01N 33/566* (2013.01); *C07K 2317/22* (2013.01); *C07K 2317/32* (2013.01); *C07K 2317/569* (2013.01); *C07K 2317/75* (2013.01); *C07K 2319/74* (2013.01); *G01N 2333/726* (2013.01); *G01N 2500/04* (2013.01)

(58) Field of Classification Search
CPC .... C07K 14/705; C07K 14/723; C07K 16/00; C07K 16/18; C07K 16/26; C07K 16/28; C07K 16/286; C07K 16/2869; C07K 2317/22; C07K 2317/32; C07K 2317/569; C07K 2317/75; C07K 2319/74; G01N 33/566; G01N 2500/04; G01N 2333/726; C12N 15/62
See application file for complete search history.

(56) References Cited

U.S. PATENT DOCUMENTS

| 5,721,121 A | 2/1998 | Etcheverry et al. |
| 8,765,414 B2* | 7/2014 | Kobilka ........... C07K 14/70571 435/69.7 |
| 8,835,362 B2* | 9/2014 | Downtown ........ G01N 33/5302 204/451 |
| 2011/0027910 A1 | 2/2011 | Weir et al. |
| 2013/0137856 A1 | 5/2013 | Steyaert et al. |
| 2013/0183287 A1 | 7/2013 | Steyaert et al. |

FOREIGN PATENT DOCUMENTS

| EP | 1134231 A1 | 9/2001 |
| WO | 9404678 A1 | 3/1994 |
| WO | 9425591 A1 | 11/1994 |
| WO | 9504079 A1 | 2/1995 |

(Continued)

OTHER PUBLICATIONS

Chun E, et al. Structure. 20(6):967-976. Jun. 6, 2012. Available online at—doi:10.1016/j.str.2012.04.010.*
Rosenbaum DM, et al. Nature. 469(7329):236-240. Jan. 13, 2011. Available online at—doi:10.1038/nature09665.*
Molinari et al., Promiscous coupling at receptor-Galpha fusion proteins. The receptor of one covalent complex interacts with the alpha-subunit of another, Journal of Biological Chemistry, American Society for Biochemistry and Molecular Biology, US. May 2, 2003, pp. 15778-88, vol. 278, No. 18. 111.
Rasmussen et al., Structure of a nanobody-stabilized active state of the beta2 adrenoceptor, Nature, Jan. 13, 2011, pp. 175-181, Macmillan Publishers Limited.

(Continued)

*Primary Examiner* — Robert Landsman
(74) *Attorney, Agent, or Firm* — TraskBritt, P.C.

(57) ABSTRACT

Described are polypeptides and their use for screening and drug discovery. More specifically, the disclosure provides chimeric polypeptides comprising a membrane protein, in particular a GPCR, fused to a binding domain, wherein the binding domain is directed against and/or specifically binds to the membrane protein. In particular, the chimeric polypeptides are single proteins wherein, in an intramolecular reaction, the binding domain stabilizes the membrane protein in a conformation of interest. Also provided are nucleic acid sequences encoding such chimeric polypeptides, cells capable of expressing such chimeric polypeptides as well as cellular compositions derived thereof. Also screening methods for compounds using the chimeric polypeptides.

22 Claims, 21 Drawing Sheets

(56) References Cited

FOREIGN PATENT DOCUMENTS

| | | |
|---|---|---|
| WO | 9634103 A1 | 10/1996 |
| WO | 9749805 A2 | 12/1997 |
| WO | 9937681 A2 | 7/1999 |
| WO | 0040968 A1 | 7/2000 |
| WO | 0043507 A1 | 7/2000 |
| WO | 0065057 A1 | 11/2000 |
| WO | 0121817 A1 | 3/2001 |
| WO | 0140310 A2 | 6/2001 |
| WO | 0144301 A1 | 6/2001 |
| WO | 02085945 A2 | 10/2002 |
| WO | 03035694 A2 | 5/2003 |
| WO | 03054016 A2 | 7/2003 |
| WO | 03055527 A2 | 7/2003 |
| WO | 2004035614 | 4/2004 |
| WO | 2004041862 A2 | 5/2004 |
| WO | 2004041863 A2 | 5/2004 |
| WO | 2004041865 A2 | 5/2004 |
| WO | 2004041867 A2 | 5/2004 |
| WO | 2004049794 A2 | 6/2004 |
| WO | 2004062551 A2 | 7/2004 |
| WO | 2005044858 A1 | 5/2005 |
| WO | 2006079372 A1 | 8/2006 |
| WO | 2006122786 A2 | 11/2006 |
| WO | 2006122787 A1 | 11/2006 |
| WO | 2006122825 A2 | 11/2006 |
| WO | 2008020079 A1 | 2/2008 |
| WO | 2008101985 A2 | 8/2008 |
| WO | 2008114020 A2 | 9/2008 |
| WO | 2008142164 A2 | 11/2008 |
| WO | 2009051633 | 4/2009 |
| WO | 2009071914 A2 | 6/2009 |
| WO | 2009081136 A2 | 7/2009 |
| WO | 2010066740 A1 | 6/2010 |
| WO | 2010070145 A2 | 6/2010 |
| WO | 2010149964 A2 | 12/2010 |
| WO | 2011083141 A1 | 7/2011 |
| WO | 2012007593 A1 | 1/2012 |
| WO | 2012007594 A1 | 1/2012 |
| WO | 2012030735 A1 | 3/2012 |
| WO | 2012098413 A1 | 7/2012 |
| WO | 2012148586 A1 | 11/2012 |
| WO | 2012158555 A2 | 11/2012 |
| WO | 2014118297 A1 | 8/2014 |

OTHER PUBLICATIONS

Steyaert et al., Nanobody stabilization of G protein-coupled receptor conformational states, Current Opinion in Structural Biology, Jul. 21, 2011, pp. 467-472, vol. 21, No. 4.
PCT International Search Report, PCT/EP2014/051845, dated Mar. 27, 2014.
Japanese Notice of Rejection dated May 17, 2016, Japanese Patent Application No. 2014-516358.
Staus et al., Regulation of beta2-Adrenergic Receptor Function by Conformationally Selective Single-Domain Intrabodies, Molecular Pharmacology, Mar. 2014, pp. 472-481, vol. 85, No. 3.

\* cited by examiner

FIG. 1

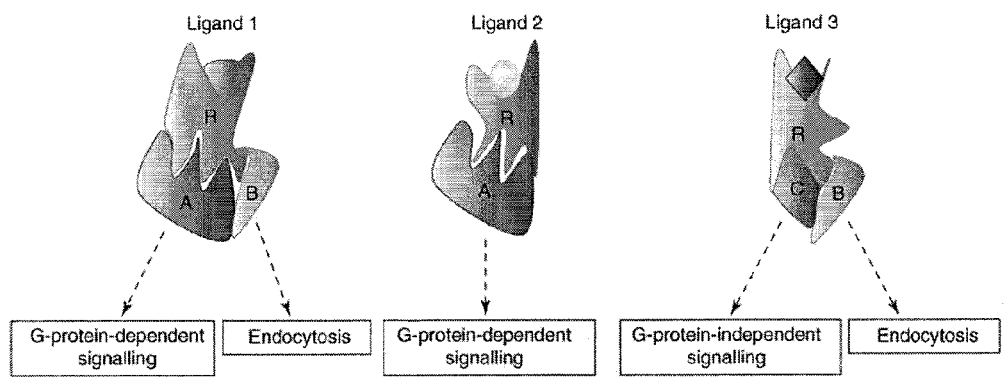

FIG. 2A

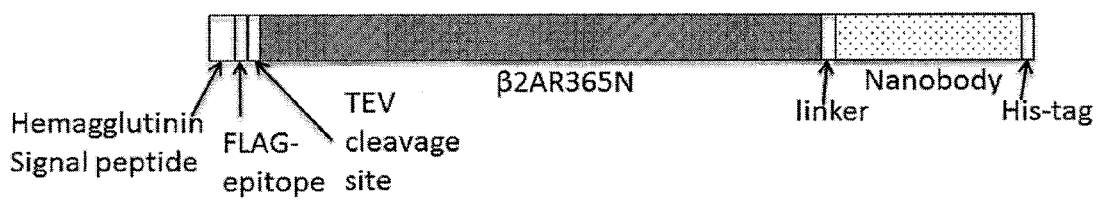

FIG. 2B

β2AR365N-Nb80, SEQ ID NO: 1

MKTIIALSYIFCLVFADYKDDDDAENLYFQGFGQPGNGSAFLLAPNRSHAPDHDVTQQRD
EVWVVGMGIVMSLIVLAIVFGNVLVITAIAKFERLQTVTNYFITSLACADLVMGLAVVPF
GAAHILMKMWTFGNFWCEFWTSIDVLCVTASIETLCVIAVDRYFAITSPFKYQSLLTKNK
ARVIILMVWIVSGLTSFLPIQMHWYRATHQEAINCYAEETCCDFFTNQAYAIASSIVSFY
VPLVIMVFVYSRVFQEAKRQLQKIDKSEGRFHVQNLSQVEQDGRTGHGLRRSSKFCLKEH
KALKTLGIIMGTFTLCWLPFFIVNIVHVIQDNLIREKVYILLNWIGYVNSGFNPLIYCRS
PDFRIAFQELLCLRRSSLKAYGNGYSSNGNTGEQSGGGGGSGGGSQVQLQESGGGLVQAG
GSLRLSCAASGSIFSINTMGWYRQAPGKQRELVAAIHSGGSTNYANSVKGRFTISRDNAA
NTVYLQMNSLKPEDTAVYYCNVKDYGAVLYEYDYWGQGTQVTVSSHHHHHH

FIG. 2C

β2AR365N-Nb71, SEQ ID NO: 2

MKTIIALSYIFCLVFADYKDDDDAENLYFQGFGQPGNGSAFLLAPNRSHAPDHDVTQQRD
EVWVVGMGIVMSLIVLAIVFGNVLVITAIAKFERLQTVTNYFITSLACADLVMGLAVVPF
GAAHILMKMWTFGNFWCEFWTSIDVLCVTASIETLCVIAVDRYFAITSPFKYQSLLTKNK
ARVIILMVWIVSGLTSFLPIQMHWYRATHQEAINCYAEETCCDFFTNQAYAIASSIVSFY
VPLVIMVFVYSRVFQEAKRQLQKIDKSEGRFHVQNLSQVEQDGRTGHGLRRSSKFCLKEH
KALKTLGIIMGTFTLCWLPFFIVNIVHVIQDNLIREKVYILLNWIGYVNSGFNPLIYCRS
PDFRIAFQELLCLRRSSLKAYGNGYSSNGNTGEQSGGGGGSGGGSQVQLQESGGGLVQPG
GSLRLSCAASGFAFSSYELRWYRQAPGKQHELVAGITTGGNTYYADSVKGRFTISRDNAK
NTVYLQMNSLRPEDTAVYACNAKWDLLSDYWGQGTQVTVSSHHHHHH

FIG. 2D

β2AR365N-Nb69, SEQ ID NO: 3

MKTIIALSYIFCLVFADYKDDDDAENLYFQGFGQPGNGSAFLLAPNRSHAPDHDVTQQRD
EVWVVGMGIVMSLIVLAIVFGNVLVITAIAKFERLQTVTNYFITSLACADLVMGLAVVPF
GAAHILMKMWTFGNFWCEFWTSIDVLCVTASIETLCVIAVDRYFAITSPFKYQSLLTKNK
ARVIILMVWIVSGLTSFLPIQMHWYRATHQEAINCYAEETCCDFFTNQAYAIASSIVSFY
VPLVIMVFVYSRVFQEAKRQLQKIDKSEGRFHVQNLSQVEQDGRTGHGLRRSSKFCLKEH
KALKTLGIIMGTFTLCWLPFFIVNIVHVIQDNLIRKEVYILLNWIGYVNSGFNPLIYCRS
PDFRIAFQELLCLRRSSLKAYGNGYSSNGNTGEQSG<u>GGGGSGGGS</u>QVQLQESGGGLVQAG
GSLRLSCTASGLTLSNYAMGWFRQAPGKEREFVAADTWNGNTYHQDSVKGRFTISRDNAK
NTVYLQMNYLKPEDTAVYYCAARGSRRSAYYSSSDYTYRGQGTQVTVSS<u>HHHHHH</u>

FIG. 2E

β2AR365N-Nb60, SEQ ID NO: 4

<u>MKTIIALSYIFCLVFA</u>DYKDDDDAENLYFQGFGQPGNGSAFLLAPNRSHAPDHDVTQQRDEVWVVGMGIVMSLIVLAI
VFGNVLVITAIAKFERLQTVTNYFITSLACADLVMGLAVVPFGAAHILMKMWTFGNFWCEFWTSIDVLCVTASIETLCVI
AVDRYFAITSPFKYQSLLTKNKARVIILMVWIVSGLTSFLPIQMHWYRATHQEAINCYAEETCCDFFTNQAYAIASSIVSFY
VPLVIMVFVYSRVFQEAKRQLQKIDKSEGRFHVQNLSQVEQDGRTGHGLRRSSKFCLKEHKALKTLGIIMGTFTLCWLPF
FIVNIVHVIQDNLIRKEVYILLNWIGYVNSGFNPLIYCRSPDFRIAFQELLCLRRSSLKAYGNGYSSNGNTGEQSG<u>GGGGS
GGGS</u>QVQLQESGGGLVQAGGSLRLSCAASGSIFSLNDMGWYRQAPGKLRELVAAITSGGSTKYADSVKGRFTISRDNA
KNTVYLQMNSLKAEDTAVYYCNAKVAGTFSIYDYWGQGTQVTVSS<u>HHHHHH</u>

FIG. 3

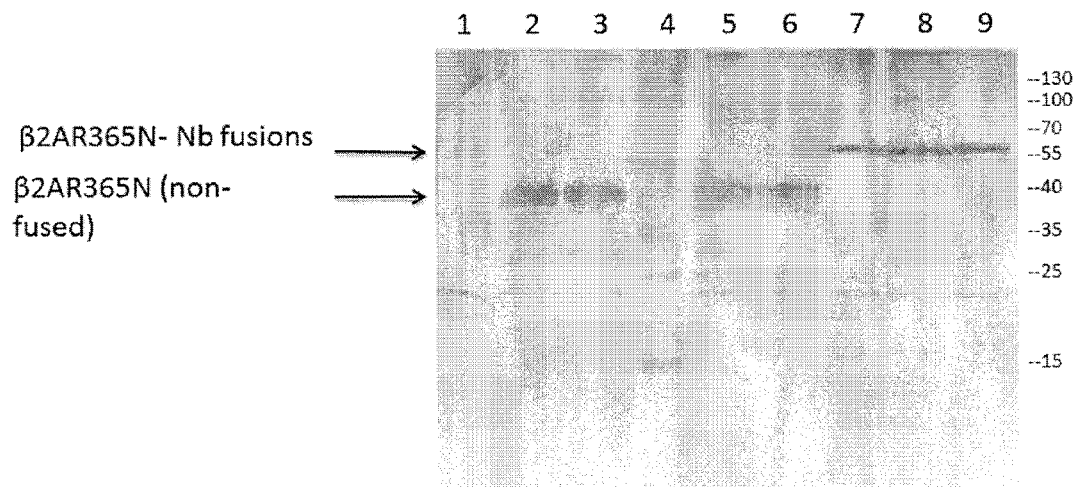

FIG. 9A

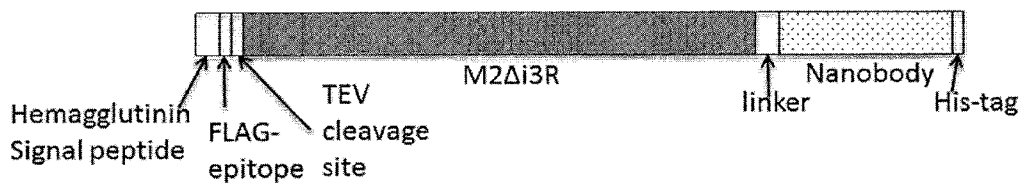

FIG. 9B

M2Δi3R, SEQ ID NO: 5

MKTIIALSYIFCLVFADYKDDDDENLYFQGMDDSTDSSDNSLALTSPYKTFEVVFIVLVAGSLSLVTIIGN
ILVMVSIKVNRHLQTVNNYFLFSLACADLIIGVFSMNLYTLYTVIGYWPLGPVVCDLWLALDYVVSNASVM
NLLIISFDRYFCVTKPLTYPVKRTTKMAGMMIAAAWVLSFILWAPAILFWQFIVGVRTVEDGECYIQFFSN
AAVTFGTAIAAFYLPVIIMTVLYWHISRASKSRIKKDKKEPVANQDPVSTRKKPPPSREKKVTRTILAILL
AFIITWAPYNVMVLINTFCAPCIPNTVWTIGYWLCYINSTINPACYALCNATFKKTFKHLLMCHYKNIGAT
R

FIG. 9C

M2Δi3R-Nb9-1, SEQ ID NO: 6

MKTIIALSYIFCLVFADYKDDDDENLYFQGMDDSTDSSDNSLALTSPYKTFEVVFIVLVAGSLSLVTIIGN
ILVMVSIKVNRHLQTVNNYFLFSLACADLIIGVFSMNLYTLYTVIGYWPLGPVVCDLWLALDYVVSNASVM
NLLIISFDRYFCVTKPLTYPVKRTTKMAGMMIAAAWVLSFILWAPAILFWQFIVGVRTVEDGECYIQFFSN
AAVTFGTAIAAFYLPVIIMTVLYWHISRASKSRIKKDKKEPVANQDPVSTRKKPPPSREKKVTRTILAILL
AFIITWAPYNVMVLINTFCAPCIPNTVWTIGYWLCYINSTINPACYALCNATFKKTFKHLLMCHYKNIGAT
RGGGSGGGGSGGGGSGGGGSGGGSQVQLQESGGGLVQAGGSLRLSCAASGHTFSSARMYWVRQAPGKEREF
VAAISRSGFTYSADSVKGRFTISRDIANNTVYLQMNSLQPEDTAIYTCYAAYLDEFYNDYTHYWGLGTQVT
VSSHHHHHH

FIG. 11A

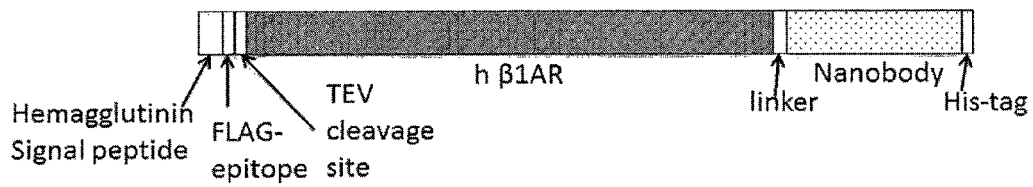

FIG. 11B hβ1AR-Nb80, SEQ ID NO: 7

MKTIIALSYIFCLVFADYKDDDDAENLYFQGPEPLSQQWTAGMGLLMALIVLLIVAGNVLVIVAIAKTPRLQTLTNLFIMS
LASADLVMGLLVVPFGATIVVWGRWEYGSFFCELWTSVDVLCVTASIETLCVIALDRYLAITSPFRYQSLLTRARARGLVC
TVWAISALVSFLPILMHWWRAESDEARRCYNDPKCCDFVTNRAYAIASSVVSFYVPLCIMAFVYLRVFREAQKQVKKID
RAGKRRPSRLVALKEQKALKTLGIIMGVFTLCWLPFFLANVVKAFHRELVPDRLFVFFNWLGYANSAFNPIIYCRSPDFRK
AFQRLLSSARRAARRRGGGGSGGGGSGGGGSGGGGSGGGSQVQLQESGGGLVQAGGSLRLSCAASGSIFSINTMG
WYRQAPGKQRELVAAIHSGGSTNYANSVKGRFTISRDNAANTVYLQMNSLKPEDTAVYYCNVKDYGAVLYEYDYWGQ
GTQVTVSSHHHHHH

FIG. 11C hβ1AR-Nb69, SEQ ID NO: 8

MKTIIALSYIFCLVFADYKDDDDAENLYFQGPEPLSQQWTAGMGLLMALIVLLIVAGNVLVIVAIAKTPRLQTLTNLFIMS
LASADLVMGLLVVPFGATIVVWGRWEYGSFFCELWTSVDVLCVTASIETLCVIALDRYLAITSPFRYQSLLTRARARGLVC
TVWAISALVSFLPILMHWWRAESDEARRCYNDPKCCDFVTNRAYAIASSVVSFYVPLCIMAFVYLRVFREAQKQVKKID
RAGKRRPSRLVALKEQKALKTLGIIMGVFTLCWLPFFLANVVKAFHRELVPDRLFVFFNWLGYANSAFNPIIYCRSPDFRK
AFQRLLSSARRAARRRGGGGSGGGGSGGGGSGGGGSGGGSQVQLQESGGGLVQAGGSLRLSCTASGLTLSNYAMG
WFRQAPGKEREFVAADTWNGNTYHQDSVKGRFTISRDNAKNTVYLQMNYLKPEDTAVYYCAARGSRRSAYYSSSDYT
YRGQGTQVTVSSHHHHHH

FIG. 14

```
P42866|MOUSE  MDSSAGPGNISDCSDPLAPASCSP--APGSWLNLSHVDGNQSDPCGPNRTGLGGSHSLCP  58
P35372|HUMAN  MDSSAAPTNASNCTDALAYSSCSPAPSPGSWVNLSHLDGNLSDPCGPNRTDLGGRDSLCP  60
              ****.*  *  *:*:* **  :****  :****.****:***  ********  ***  .****
                                                                  ICL1
P42866|MOUSE  QTGSPSMVTAITIMALYSIVCVVGLFGNFLVMYVIVRYTKMKTATNIYIFNLALADALAT  118
P35372|HUMAN  PTGSPSMITAITIMALYSIVCVVGLFGNFLVMYVIVRYTKMKTATNIYIFNLALADALAT  120
              ******:************************************************
                                                              ICL2
P42866|MOUSE  STLPFQSVNYLMGTWPFGNILCKIVISIDYYNMFTSIFTLCTMSVDRYIAVCHPVKALDF  178
P35372|HUMAN  STLPFQSVNYLMGTWPFGTILCKIVISIDYYNMFTSIFTLCTMSVDRYIAVCHPVKALDF  180
              ******************.*****************************************

P42866|MOUSE  RTPRNAKIVNVCNWILSSAIGLPVMFMATTKYRQGSIDCTLTFSHPTWYWENLLKICVFI  238
P35372|HUMAN  RTPRNAKIINVCNWILSSAIGLPVMFMATTKYRQGSIDCTLTFSHPTWYWENLLKICVFI  240
              ********:***************************************************
                    ICL3
P42866|MOUSE  FAFTMPVLIITVCYGLMILRLKSVRMLSGSKEKDRNLRRITRMVLVVVAVFIVCWTPIHI  298
P35372|HUMAN  FAFIMPVLIITVCYGLMILRLKSVRMLSGSKEKDRNLRRITRMVLVVVAVFIVCWTPIHI  300
              *** *******************************************************
                                                    C-term
P42866|MOUSE  YVIIKALITIPETTFQTVSWHFCIALGYTNSCLNPVLYAFLDENFKRCFREFCIPTSSTI  358
P35372|HUMAN  YVIIKALVTIPETTFQTVSWHFCIALGYTNSCLNPVLYAFLDENFKRCFREFCIPTSSNI  360
              *******:***************************************************

P42866|MOUSE  EQQNGARIRQNTRBHPSTANTVDRTNHQLENLEAETAPLP  398
P35372|HUMAN  EQQNSTRIRQNTRDHPSTANTVDRTNHQLENLEAETAPLP  400
              ****.:*****:****************************
```

FIG. 15A

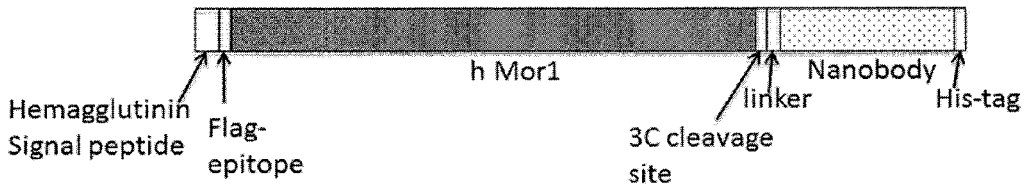

Hemagglutinin Signal peptide  
Flag-epitope  
h Mor1  
3C cleavage site  
linker  
Nanobody  
His-tag

FIG. 15B hMor1-34GS-Nb33, SEQ ID NO: 9

MKTIIALSYIFCLVFADYKDDDDAMAPTNASNCTDALAYSSCSPAPSPGSWVNLSHLDG
NLSDPCGPNRTDLGGRDSLCPPTGSPSMITAITIMALYSIVCVVGLFGNFLVMYVIVRYTK
MKTATNIYIFNLALADALATSTLPFQSVNYLMGTWPFGTILCKIVISIDYYNMFTSIFTLCT
MSVDRYIAVCHPVKALDFRTPRNAKIINVCNWILSSAIGLPVMFMATTKYRQGSIDCTLT
FSHPTWYWENLLKICVFIFAFIMPVLIITVCYGLMILRLKSVRMLSGSKEKDRNLRRITRM
VLVVVAVFIVCWTPIHIYVIIKALVTIPETTFQTVSWHFCIALGYTNSCLNPVLYAFLDENF
KRCFREFCIPTSSNILEVLFQGPGGGGSGGGGSGGGGSGGGGSGGGGSGGGGSGGGS
QVQLQESGGGLVRPGGSRRLSCVDSERTSYPMGWFRRAPGKEREFVASITWSGIDPTYA
DSVADRFTISRDVANNTLYLQMNSLKHEDTAVYYCAARAPVGQSSSPYDYDYWGQGT
QVTVSSHHHHHHHHHH*

FIG. 15C hMor1-34GS-Nb10, SEQ ID NO: 10

<u>MKTIIALSYIFCLVFA</u>DYKDDDDAMAPTNASNCTDALAYSSCSPAPSPGSWVNLSHLDG
NLSDPCGPNRTDLGGRDSLCPPTGSPSMITAITIMALYSIVCVVGLFGNFLVMYVIVRYTK
MKTATNIYIFNLALADALATSTLPFQSVNYLMGTWPFGTILCKIVISIDYYNMFTSIFTLCT
MSVDRYIAVCHPVKALDFRTPRNAKIINVCNWILSSAIGLPVMFMATTKYRQGSIDCTLT
FSHPTWYWENLLKICVFIFAFIMPVLIITVCYGLMILRLKSVRMLSGSKEKDRNLRRITRM
VLVVVAVFIVCWTPIHIYVIIKALVTIPETTFQTVSWHFCIALGYTNSCLNPVLYAFLDENF
KRCFREFCIPTSSNIL<span style="background-color:#ccc">EVLFQGP</span>GGGGSGGGGSGGGGSGGGGSGGGGSGGGGSGGGS
QVQLQESGGGLVQPGGSLRLSCAASGSFRSIVSMAWYRQAPGKQRELVASSNSGGSTN
YADSVKGRFTISRDNAKNTVYLQMNSLKPEDTAVYWCNVQNRLPGFDAFSGRSIAETY
WGQGTQVTVSS<u>HHHHHH</u>*

FIG. 15D mMor1-34GS-Nb33, SEQ ID NO: 11

<u>MKTIIALSYIFCLVFA</u>DYKDDDDAMGPGNISDCSDPLAPASCSPAPGSWLNLSHVDGNQS
DPCGPNRTGLGGSHSLCPQTGSPSMVTAITIMALYSIVCVVGLFGNFLVMYVIVRYTKM
KTATNIYIFNLALADALATSTLPFQSVNYLMGTWPFGNILCKIVISIDYYNMFTSIFTLCT
MSVDRYIAVCHPVKALDFRTPRNAKIVNVCNWILSSAIGLPVMFMATTKYRQGSIDCTL
TFSHPTWYWENLLKICVFIFAFIMPVLIITVCYGLMILRLKSVRMLSGSKEKDRNLRRITR
MVLVVVAVFIVCWTPIHIYVIIKALITIPETTFQTVSWHFCIALGYTNSCLNPVLYAFLDEN
FKRCFREFCIPTSSTIL<span style="background-color:#ccc">EVLFQGP</span>GGGGSGGGGSGGGGSGGGGSGGGGSGGGGSGGG
SQVQLQESGGGLVRPGGSRRLSCVDSERTSYPMGWFRRAPGKEREFVASITWSGIDPTY
ADSVADRFTISRDVANNTLYLQMNSLKHEDTAVYYCAARAPVGQSSSPYDYDYWGQG
TQVTVSS<u>HHHHHH</u>*

FIG. 15E mMor1-34GS-Nb10, SEQ ID NO: 12

<u>MKTIIALSYIFCLVFA</u>DYKDDDDAMGPGNISDCSDPLAPASCSPAPGSWLNLSHVDGNQS
DPCGPNRTGLGGSHSLCPQTGSPSMVTAITIMALYSIVCVVGLFGNFLVMYVIVRYTKM
KTATNIYIFNLALADALATSTLPFQSVNYLMGTWPFGNILCKIVISIDYYNMFTSIFTLCT
MSVDRYIAVCHPVKALDFRTPRNAKIVNVCNWILSSAIGLPVMFMATTKYRQGSIDCTL
TFSHPTWYWENLLKICVFIFAFIMPVLIITVCYGLMILRLKSVRMLSGSKEKDRNLRRITR
MVLVVVAVFIVCWTPIHIYVIIKALITIPETTFQTVSWHFCIALGYTNSCLNPVLYAFLDEN
FKRCFREFCIPTSSTIL<span style="background-color:#ccc">EVLFQGP</span>GGGGSGGGGSGGGGSGGGGSGGGGSGGGGSGGG
SQVQLQESGGGLVQPGGSLRLSCAASGSFRSIVSMAWYRQAPGKQRELVASSNSGGSTN
YADSVKGRFTISRDNAKNTVYLQMNSLKPEDTAVYWCNVQNRLPGFDAFSGRSIAETY
WGQGTQVTVSS<u>HHHHHH</u>*

CHIMERIC POLYPEPTIDES COMPRISING G PROTEIN-COUPLED RECEPTORS AND VHH ANTIBODIES

CROSS-REFERENCE TO RELATED APPLICATIONS

This application is a national phase entry under 35 U.S.C. §371 of International Patent Application PCT/EP2014/051845, filed Jan. 30, 2014, designating the United States of America and published in English as International Patent Publication WO 2014/118297 A1 on Aug. 7, 2014, which claims the benefit under Article 8 of the Patent Cooperation Treaty and under 35 U.S.C. §119(e) to U.S. Provisional Patent Application Ser. No. 61/758,518, filed Jan. 30, 2013, and under Article 8 of the PCT to European Application Serial Nos. 13154552.7, filed Feb. 8, 2013, and 13187265.7, filed Oct. 3, 2013.

STATEMENT ACCORDING TO 37 C.F.R. §1.821(c) or (e) — SEQUENCE LISTING SUBMITTED AS A TXT AND PDF FILES

Pursuant to 37 C.F.R. §1.821(c) or (e), files containing a TXT version and a PDF version of the Sequence Listing have been submitted concomitant with this application, the contents of which are hereby incorporated by reference.

TECHNICAL FIELD

The disclosure relates to novel polypeptides and their use for screening and drug discovery. More specifically, the disclosure provides chimeric polypeptides comprising a membrane protein, in particular a GPCR, fused to a binding domain, wherein the binding domain is directed against and/or specifically binds to the membrane protein. In particular, the chimeric polypeptides of the disclosure are single proteins wherein, in an intramolecular reaction, the binding domain stabilizes the membrane protein in a conformation of interest. Also provided are nucleic acid sequences encoding such chimeric polypeptides, cells capable of expressing such chimeric polypeptides as well as cellular compositions derived thereof. Also envisaged are screening methods for compounds using the chimeric polypeptides of the disclosure.

BACKGROUND

Drug discovery efforts generally focus on the identification of compounds that modulate, inhibit or enhance the activity of the target of interest. Conventional lead identification efforts proceed via biochemical or cell based screening or in silico compound design. These methods have identified and validated a multitude of viable therapeutics in use today. However, as reflected by the high failure rate of new drug compounds (only an estimated 8% of phase I clinical therapeutics eventually gain Food and Drug Administration approval, at a conservative cost of $800 million per drug), many efforts are unsuccessful and often targets are abandoned once they are deemed undruggable (Lee et al., 2009). A considerable part of these failures are due to the fact that most biochemical or cell based assays are performed on targets in their prominent conformation, also referred to as the basal conformation. However, we now know that conformational flexibility is key to the function and the pharmacology of the majority of the current and future drug targets including GPCRs, ion channels, (nuclear) receptors, kinases and phosphatases. And for many of these targets, the most stable conformation, corresponding to the prominent structural species in the absence of ligands or accessory proteins (the basal conformation), does not correspond to the druggable conformation to which a drug must bind to be most effective for the therapeutic indication.

Today, the most commonly targeted protein class for medicinal intervention are G protein-coupled receptors (GPCRs), also called seven-transmembrane receptors (7TMRs). They play essential roles in physiological responses to a diverse set of ligands such as biogenic amines, amino acids, peptides, proteins, prostanoids, phospholipids, fatty acids, nucleosides, nucleotides, $Ca^{2+}$ ions, odorants, bitter and sweet tastants, pheromones and protons (Heilker et al., 2009). Orthosteric ligands that act on a GPCR can induce a spectrum of effects on down-stream signaling pathways. In general, GPCRs require agonist binding for activation. Full agonists maximally activate the receptor. Partial agonists elicit a submaximal stimulation even at saturating concentrations. In some cases, a GPCR may exhibit basal activity towards a specific signaling pathway even in the absence of an agonist (constitutive activity). Inverse agonists can inhibit this basal activity. Notably, whereas neutral antagonists can inhibit binding of agonists, partial agonists, and inverse agonists at the orthosteric binding site of GPCRs, they do not alter the basal receptor activity. In recent years, advances have been made in the discovery of novel ligands for GPCRs that act at allosteric sites to regulate receptor function, including positive and negative allosteric modulators (PAMs and NAMs, respectively) and neutral ligands, which offer novel modes of action over orthosteric ligands (Christopoulos 2002).

It is now well established that GPCRs can signal through several distinct mechanisms including those mediated by G proteins or the multifunctional adaptor proteins β-arrestins (Rajagopal et al., 2010). With the structures of several GPCRs solved in complex with various ligands including inverse agonists, antagonists and agonists (Cherezov et al., 2007, Rasmussen et al., 2011b, Rosenbaum et al., 2011, Shimamura et al., 2011, Xu 2011, Granier et al., 2012, Haga et al., 2012, Hanson et al., 2012, Kruse et al., 2012, Manglik et al., 2012, Wu et al., 2012, Zhang et al., 2012) and the G-protein (Rasmussen et al., 2011a), we now know that GPCRs are conformationally complex molecules with specific conformations causing G protein activation. Of special significance in the context of this disclosure is the observation that in comparison to the basal conformation, only relatively small changes in the structure of the agonist binding pocket led to substantial movement (up to 14Å) and rearrangements in three of the transmembrane segments (Lebon et al., 2012).

Mass-spectrometry-based strategies (Kahsai et al., 2011), biophysical analysis (Yao et al., 2006, Mary et al., 2012) and NMR spectroscopy (Liu et al., 2012; Bokoch et al., 2010) provide direct evidence for the presence of other distinct ligand-specific conformations that lead to arrestin mediated signaling. It follows that different ligands can have differential effects on the conformation and the diverse signaling and regulatory repertoire of a single receptor. The importance of these multiple conformational states is their pharmacological relevance. As illustrated in FIG. 1, each of these receptor conformations can be considered as a separate therapeutic drug target because each of these conformations promotes distinct relative efficacies toward the different effector systems including G proteins and arrestins.

Drug discovery approaches can take considerable advantage from capturing the target in a therapeutically relevant "druggable" conformation. Stabilizing a receptor in a particular functional conformation would inherently freeze the receptor in a single, disease relevant druggable conformation revealing new structural features that are suitable for targeting with small molecules or biologicals and may enable the identification of compounds that are selective for that druggable conformation. The stabilization of a unique druggable conformation, including inactive states corresponding to effector systems below basal activity or particular functional states that activate individual effector systems could not only lead to compounds with better therapeutic efficacies but could also benefit the identification of compounds with less undesirable side effects that result from triggering undesired pathways (Galandrin et al., 2007).

Further to that, conformational flexibility is an issue in high-throughput screening (HTS) and fragment-based drug discovery (FBDD) (Lawson 2012). In HTS, issues of different conformations of a target can in some cases be overcome by using whole-system assays with a functional readout rather than reductionist recombinant systems assays (Kenakin, 2009; Rajagopal et al., 2010). In FBDD, however, whole-system assays cannot be used because of the low efficacy/potency of the initial hits, often requiring mM concentrations of the fragments for biological activity and causing toxicity. It follows that high-throughput primary screens would benefit considerably from target receptors that are stabilized in the desired functional conformation in the absence of ligands or accessory proteins. Access to such conformationally stabilized receptors would allow the identification of the subset of ligands that are specific for that conformation with its particular structural features (FIG. 1). In this way, a first selection of the potentially biologically active compounds can be made using simple assessment of binding before establishing their efficacy profiles in a variety of (whole-system) signaling assays.

Conformational flexibility also obstructs structure based drug discovery starting from fragments. First, many of the potential hits of fragment-based screening (FBS) are not potent enough to quantitatively displace the conformational equilibrium into a single conformation of the protein-ligand complex that can be crystallized in a diffracting crystal. If a complex cannot be crystallized, soaking existing crystals of ligand-free protein with (small) ligands is often the method of choice to obtain crystals of the complex. However, if these ligands displace the conformational equilibrium of a conformationally complex protein, these induced conformational changes will in many cases destroy the crystals (Danley 2006).

With the structures of the first GPCRs solved in 2007 (Rasmussen et al., 2007, Rosenbaum et al., 2007), we entered the new era of GPCR structural biology raising the possibility of applying structure-based approaches to GPCR drug discovery efforts (Shoichet and Kobilka 2012). For a large number of GPCR drug targets relating to several therapeutic indications, the agonist-bound active-state is often the druggable conformation. Resolving the structure at high resolution of a GPCR in this therapeutically relevant "druggable" conformation remains a challenge. Efforts to obtain an agonist-bound active-state GPCR structure have proven difficult due to the inherent instability of this state in the absence of a G protein. Structures of GPCRs in complex with full agonists have been solved but not without difficulties. First, natural agonists generally do not sufficiently stabilize the receptor for the formation of diffraction-quality crystals. In an attempt to solve this problem, agonists have been covalently bound to GPCRs for crystallization purposes. However, for example, the crystal structure of a covalent agonist-bound $\beta_2AR$ reveals a conformation closely resembling an inactive state rather than the active state with only little rearrangements in the transmembrane segments (Rosenbaum et al., 2011) (Lebon et al., 2012).

Another approach towards determining agonist-bound conformations of a GPCR is thermostabilization of the receptor via systematic mutagenesis followed by measuring increased thermostability in the presence of bound agonist (e.g., WO2008114020, WO2009071914, WO2010149964, WO2012098413). For example, thermostabilizing mutations have been discovered for the agonist-bound $A_{2A}AR$ (Lebon et al., 2011), the agonist bound $\beta1$-adrenergic receptor (Warne et al., 2011) and the agonist bound neurotensin receptor (White et al., 2012). However, the structures of these agonist bound stabilized receptors are likely not in the fully active conformation, judged on the small displacement of transmembrane helix 6. More important and in contrast to the active state that is stabilized by a G-protein or a G-protein mimic, these thermostabilized receptors show no significant increase in the affinities for their respective agonists (Serrano-Vega et al., 2008, Shibata et al., 2009, Lebon et al., 2011).

Only recently, it became possible to obtain structures of an agonist-bound active state of a GPCR, making use of conformationally selective Nanobodies (XAPERONE™) that mimic G protein function and increase the affinity for agonists at the orthosteric site (Rasmussen et al., 2011b). XAPERONES™ are useful tools to lock the structure of GPCRs in a therapeutically relevant conformation (Steyaert & Kobilka, 2011) and facilitate the discovery of drug candidates by increasing the sensitivity and selectivity of existing screening methods (WO2012007593). However, this technological approach also has its limitations. Because the binding of the agonist at the orthosteric site increases the affinity for the G-protein mimicking XAPERONE™ at the allosteric intracellular side of the receptor and vice versa (Rasmussen et al., 2011b), the GPCR-XAPERONE™ complex is much more stable in the presence of an agonist. It follows that a GPCR, a stabilizing XAPERONE™ and agonist have to be co-crystallized to obtain crystals of the GPCR in its active conformation and that the disclosure described in WO2012007593 is not very well suited for structure based drug discovery approaches involving, for example, soaking of ligands in existing crystals because the agonist that has been used to grow the crystals will compete with the ligand that is soaked in subsequently.

Thus, the development of new methods that constitutively stabilize GPCRs in a particular druggable conformation, even in the absence of agonists, would be an important asset to improve drug discovery via compound screening and/or structure based drug design.

BRIEF SUMMARY

Provided is a drug target that is stabilized in a therapeutically relevant conformation. This approach captures the target in a conformation of interest to reveal novel structural features suitable for targeting with small molecules or biologicals for therapeutic intervention. The constitutive stabilization of a unique conformation of the drug target is obtained by fusing the drug target of interest with a conformation-selective binding domain, optionally separated by a linker, and is the result of an intramolecular reaction of both moieties within a single protein. The resulting fusion polypeptides, herein also referred to as chimeric polypeptides, are particularly interesting since they may have structural properties that differ significantly from the drug target in the non-chimeric form and as such may serve as novel innovative tools for the development of new, more potent or more selective drugs. It will be appreciated that while the disclosure has been exemplified with GPCRs, it is equally applicable to any membrane protein.

One key advantage of the chimeric polypeptides of the disclosure is that a defined 1:1 stoichiometry of GPCR to binding domain is ensured in a single protein, forcing the physical proximity of the fusion partners, while maintaining the properties of the binding domain to stabilize the receptor in a particular druggable conformation. To illustrate this, and without the purpose of being limitative, several genetic fusions of the gene segments encoding a GPCR and a conformation-selective Single-domain antibody have been constructed (see examples 1, 9, 13, 17, 20) and the pharmacological properties of the expressed GPCR-Single-domain antibody fusion polypeptides have been analyzed (see examples 6, 8, 12, 16, 19, 22, 24-25). We show that the properties of particular panels of Nanobodies, such as those that stabilize active conformations of GPCRs or those that stabilize inactive conformations of GPCRs, are maintained in such 1:1 genetic fusions. For example, the β2 adrenergic receptor (β2AR) fused to Nb80, a Single-domain antibody that mimics G protein function and stabilizes the active conformation coupled to G protein signaling (WO2012007593), shows a 2072 fold increased affinity for the natural agonist epinephrine and exhibits a 43 fold decreased affinity for the inverse agonist ICI118,551, compared to the receptor fused to a mock Single-domain antibody that is not directed against and does not specifically bind to β2AR (see Example 6). The finding that the β2AR-Nb80 fusion binds the natural agonist epinephrine 2000-fold tighter than β2AR fused to a mock Single-domain antibody indicates that these conformationally constrained fusion proteins show increase in ligand affinities relating to a particular effector system like G-protein mediated signaling. The observation that the β2AR-Nb80 fusion also shows an increased affinity for synthetic agonists such as isoproterenol or salbutamol indicates that such conformationally constrained fusion proteins may provide a better starting point to screen for synthetic compounds or biologicals that trigger/inhibit particular signaling pathways. Accordingly, small molecules or fragments that selectively recognize structural features of orthosteric or allosteric sites that are unique to the active conformation of β2AR (leading to G protein coupled signaling) may bind up to 3 orders of magnitude tighter to the β2AR-Nb80 1:1 fusion compared to the receptor not constrained in its active state. For HTS purposes, this means that the sensitivity to pick up test compounds that induce G protein coupled signaling may be increased with 3 orders of magnitude if such screening is performed on a GPCR-Nb fusion such as the β2AR-Nb80 fusion, compared to HTS efforts on β2AR not constrained in its active state.

The well-defined 1:1 stoichiometry of the intramolecular interaction between the GPCR and the binding domain of the chimeric polypeptides of the disclosure cannot be maintained/guaranteed as efficiently in intermolecular interactions, nor with a GPCR that is stabilized in a specific conformation by exogenous addition of a conformation-selective binding domain (WO2012007593), neither in a cellular system whereby a GPCR is co-expressed with a conformation-selective binding domain. A particular advantage related to the defined 1:1 stoichiometry is that the binding domain moiety can constrain a particular receptor conformation at a high, effective intramolecular concentration, even in the absence of any conformation-selective ligand (see Example 8).

HTS based on classical receptor binding techniques such as radioligand competition (inhibition or displacement) assays to selectively screen for a subset of ligands that are specific for a particular druggable conformation of a given GPCR may benefit considerably from the chimeric polypeptides of the disclosure as compared to non-covalent complexes of the GPCR with a Single-domain antibody that stabilizes the druggable conformation (WO2012007593) (Rasmussen et al., 2011b). This is due to the fact that radioligand competition assays (or competition assays of ligands labeled by another means) critically rely on the physical separation of free ligand and receptor-bound ligand. This is commonly done by filtration on a filter, by centrifugation, by size exclusion chromatography or by other biophysical methods. Separating free ligand (labeled by any means) from labeled ligand bound to the GPCR-binding domain fusion can be easily achieved using the same conventional methods because the chimer is covalently linked in a defined 1:1 stoichiometry of GPCR to binding domain. In case the binding domain is not covalently linked to the GPCR (WO2012007593), radioligand competition assays and the subsequent analysis of the data are much more difficult to perform because the 1:1 stoichiometry of GPCR to binding domain does not hold, implying much more molecular species to be separated and analyzed: free ligand, free binding domain, ligand-receptor complex, receptor-binding domain complex, ligand-receptor-binding domain complex versus free ligand, free chimer and ligand-chimer complex in the case of a GPCR-binding domain fusion (see Example 8).

Further, the innovative features of the GPCR-binding domain fusion proteins of the disclosure also allows particular functional conformations of GPCRs to be screened for the binding of lead compounds or fragments using emerging biophysical methods including surface plasmon resonance (Rich et al., 2011) and target immobilized NMR screening (Fruh et al., 2010), because the GPCR can be immobilized as a single protein fusion in the desired functional conformation on the solid phase in a defined 1:1 stoichiometry of GPCR to binding domain.

Furthermore, it is particularly surprising that the GPCR-binding domain fusion proteins of the disclosure allow to screen for and discriminate between agonists, antagonists and inverse agonists in one single comparative radioligand competition assay. The ability to discriminate and predict the mode of action of tested compounds at nM-µM concentrations without the need for a cellular receptor signaling assay is an additional advantage for compound screening (see examples 24-26).

Another advantage of these GPCR-binding domain fusion proteins in a defined 1:1 stoichiometry relates to X-ray crystallography of GPCRs and its applications in structure based drug design. More particularly, one advantage of the GPCR-binding domain fusion is that the fusion protein can be purified and crystallized in a defined 1:1 stoichiometry in the presence or absence of any ligand. Multiple ligand-receptor co-complex structures can thus be determined, just by soaking compounds into the ligand free GPCR-binding domain fusion, with the additional advantage that this crystal system is trapped in a predefined receptor conformation such as, for example, an active conformation leading to G protein and/or β-arrestin coupled signaling, or an inactive conformation unable to promote G protein and/or arrestin-coupled signaling. This possibility to soak/co-crystallize ligand free receptor with (low affinity) lead compounds is a prerequisite for lead generation involving virtual screening and during the lead optimization part of drug discovery, for example, to address selectivity and solubility issues.

Thus, according to a first aspect, the disclosure relates to a chimeric polypeptide comprising a GPCR moiety and a binding domain moiety. More particularly, the chimeric polypeptide of the disclosure comprises a GPCR fused to a binding domain, wherein the binding domain is directed against and/or capable of specifically binding to the GPCR in an intramolecular interaction. According to a particular embodiment, the binding domain is fused to the GPCR either directly or through a linker. In a particular embodiment, the binding domain is not a naturally-occurring binding partner, such as a G protein or an arrestin.

Preferably, the binding domain as comprised in the chimeric polypeptide is a conformation-selective binding domain. According to one particular embodiment, the disclosure relates to a chimeric polypeptide comprising a GPCR fused to a binding domain that is selective for the active conformation, so that the GPCR is stabilized in an active conformation upon binding of the binding domain. According to specific embodiments, the active conformation is an agonist-bound active conformation, such as a full agonist-bound active conformation or a partial agonist-bound active conformation. Alternatively, the disclosure also relates to a chimeric polypeptide comprising a GPCR fused to a binding domain that is selective for an inactive conformation, so that the GPCR is stabilized in an inactive conformation upon binding of the binding domain. According to one embodiment, the inactive conformation is an inverse agonist-bound inactive conformation. Preferably, the chimeric polypeptide of the disclosure comprising a GPCR fused to a conformation-selective binding domain has an increased affinity for a conformation-selective ligand as compared to the corresponding GPCR alone.

According to more specific embodiments, the disclosure provides for chimeric polypeptides, as described above, wherein the binding domain specifically binds to an intracellular conformational epitope of the GPCR, more particularly wherein the intracellular epitope is comprised in a binding site for a downstream signaling protein (e.g., a G protein binding site). Alternatively, the disclosure provides for chimeric polypeptides, as described above, wherein the binding domain binds to an extracellular conformational epitope of the GPCR.

According to other specific embodiments, the binding domain that form part of the chimeric polypeptide, as described above, comprises an amino acid sequence that comprises 4 framework regions (FR1 to FR4) and 3 complementary determining regions (CDR1 to CDR3), or any suitable fragment thereof. More specifically, the binding domain may be an immunoglobulin single variable domain, preferably an immunoglobulin single variable domain that is derived from a heavy chain only antibody. Most preferably, the immunoglobulin single variable domain comprises a VHH sequence or a Single-domain antibody sequence.

In another aspect, the disclosure envisages a complex comprising a chimeric polypeptide, as described above, and a receptor ligand. Such a complex may be in solution or crystalline.

Further, nucleic acid molecules comprising a nucleic acid sequence encoding the chimeric polypeptide, as described above, as well as host cells comprising such nucleic acids are also encompassed. Host cells can be of prokaryotic or eukaryotic origin, such as a bacterial cell, a yeast cell, a mammalian cell, an insect cell. Also envisaged are membrane compositions comprising the chimeric polypeptide or the complex, as described herein.

One other aspect of the disclosure relates to a method to produce a chimeric polypeptide comprising a GPCR fused to a binding domain, the method comprising the steps of culturing a host cell comprising the chimeric polypeptide, as described hereinbefore, under suitable conditions and optionally isolating the chimeric polypeptide.

Further, the disclosure also provides for a method to display a GPCR in an active or inactive conformation at the cellular surface or in a particular cellular membrane fraction of a host cell, the method comprising the steps of providing a host cell comprising a chimeric polypeptide, as described above, and culturing the cell under suitable conditions to express the chimeric polypeptide.

A further aspect of the disclosure is a method of identifying conformation-selective compounds, the method comprising the steps of:

(i) Providing a chimeric polypeptide, as described above, and (ii) Providing a test compound, and (iii) Evaluating the selective binding of the test compound to the GPCR comprised in the chimeric polypeptide.

The conformation-selective compound (a small molecule, an antibody, an antibody derivative, a peptide or any other protein scaffold that may interact with a GPCR) that is identified by the above method may be an unbiased agonist, an unbiased inverse agonist, or biased ligands that trigger or inhibit G-protein coupled or arrestin coupled signaling, respectively. According to a particular embodiment, the method as described above, further comprises the step of classifying the test compounds according to biological activity (agonist activity, inverse agonist activity, antagonist activity). Or in other words, the above-described method allows discriminating between agonists, inverse agonists and antagonist activity.

Also encompassed is the use of a chimeric polypeptide, as described above, or a complex, as described above, to crystallize and/or to solve the structure of the GPCR; to capture a GPCR in a functional conformational state.

Further aspects and preferred embodiments of the disclosure are defined in the description below and in the appended claims.

BRIEF DESCRIPTION OF THE DRAWINGS

FIG. 1: Conformational complexity of GPCR signaling. Schematic representation of ligand-biased efficacy, where three different ligands can induce and/or stabilize different receptor conformations that will each promote distinct relative efficacies toward different effector systems. Abbreviations: R, receptor; A, B and C, proteins or group of proteins implicated in a specific signaling pathway. (Adapted from Galandrin et al., 2007).

FIGS. 2A-2E: The β2AR-Single-domain antibody fusions described in Example 1 contain two different proteins connected with a peptide linker: the GPCR β2AR365N, the linker GGGGSGGGS (underlined and highlighted in bold), a Single-domain antibody. Underlined is the HA signal peptide and the His$_6$ peptide tag. The FLAG-tag is represented in bold, the TEV cleavage site is indicated in grey shade. FIG. 2A. Cartoon representation of the β2AR-Single-domain antibody fusion constructs. FIG. 2B. The amino acid sequence of the open reading frame encoded by pFastBac β2AR365N-Nb80. FIG. 2C. The amino acid sequence of the open reading frame encoded by pFastBac β2AR365N-Nb71. FIG. 2D. The amino acid sequence of the open reading frame encoded by pFastBac β2AR365N-Nb69. FIG. 2E.

Figure 4A:
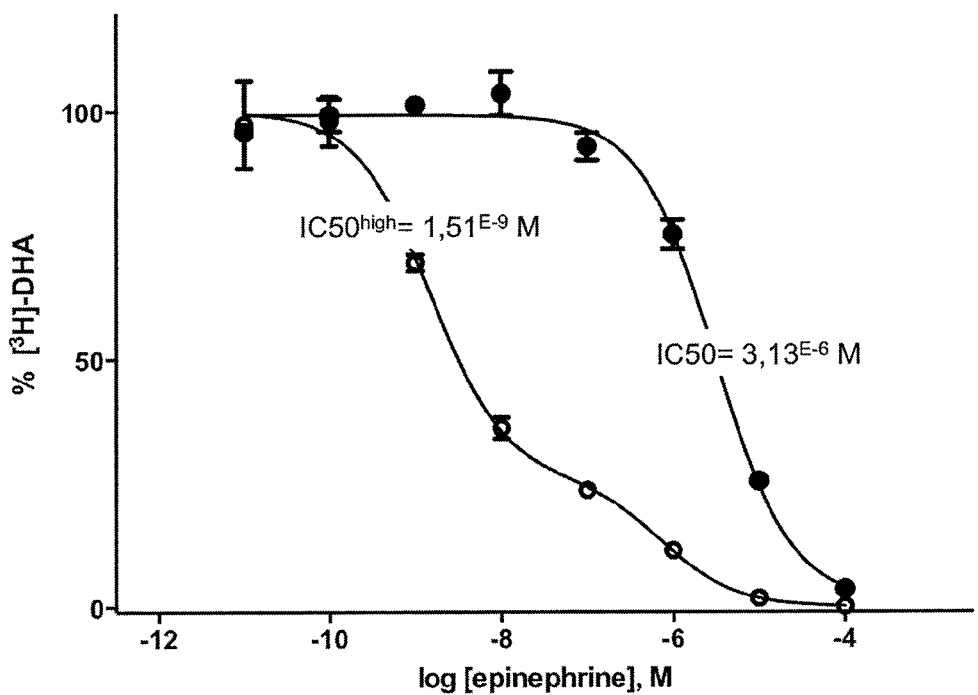
Figure 4B:
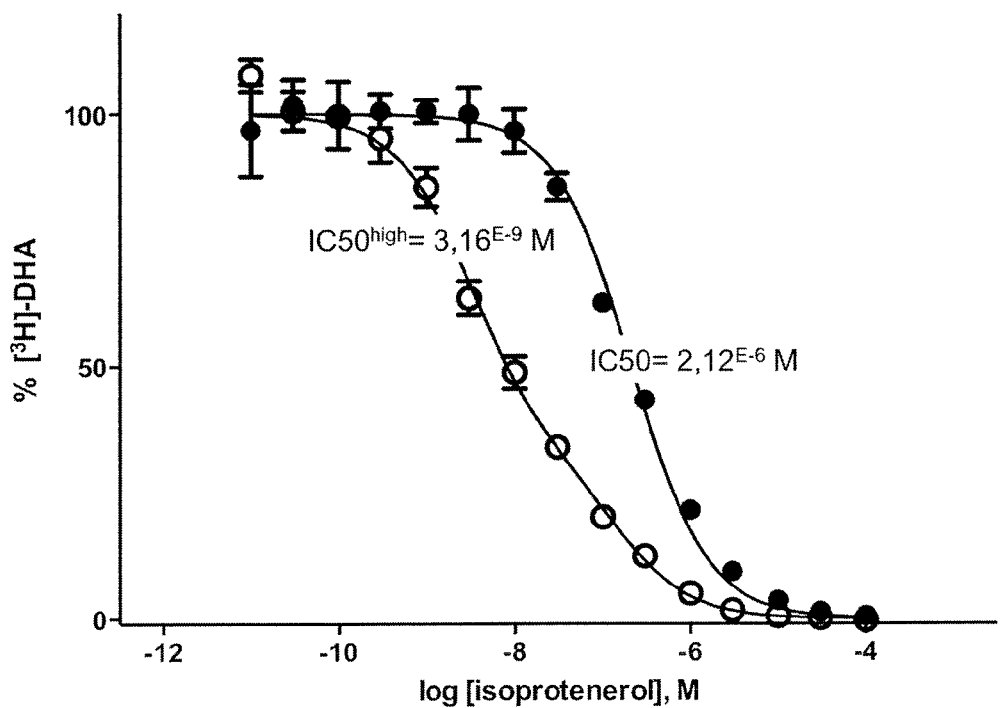
Figure 4C:
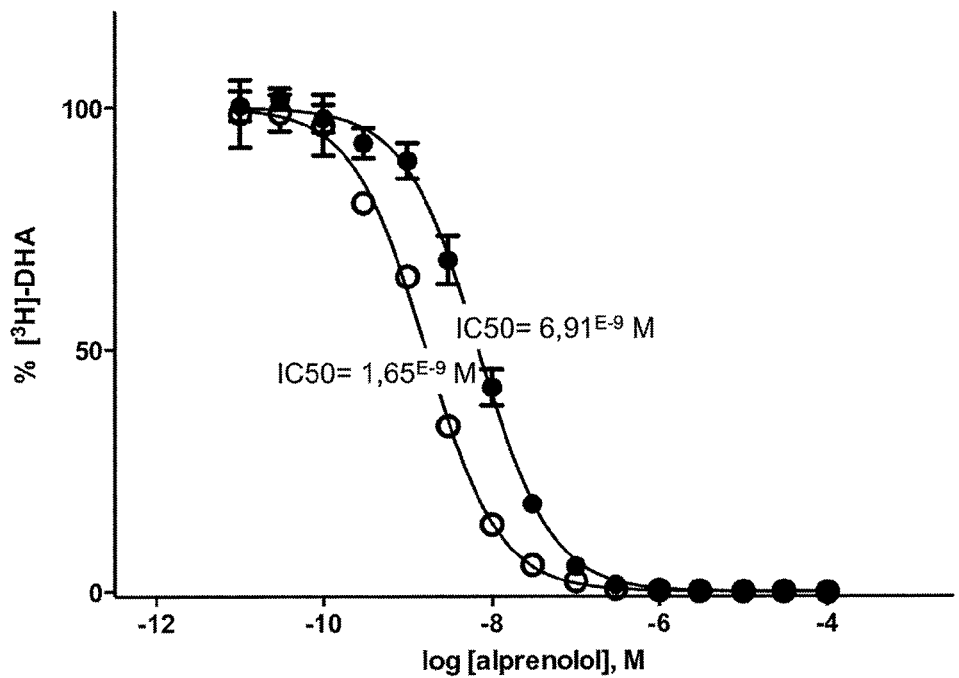
Figure 4D:
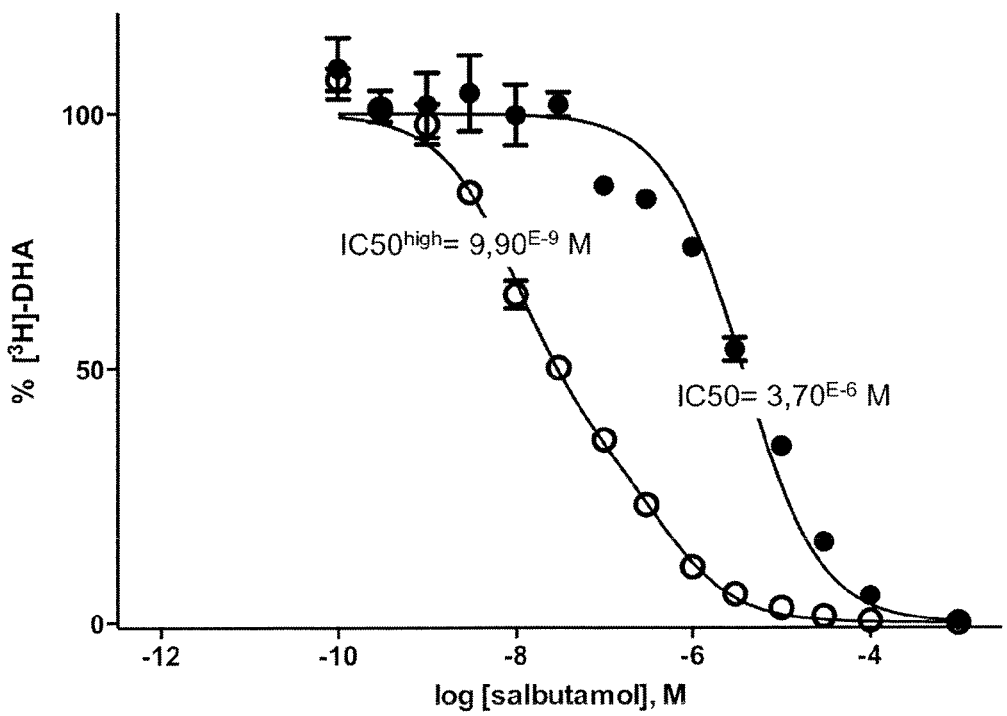

The amino acid sequence of the open reading frame encoded by pFastBac β2AR365N-Nb60.

FIG. 3: Expression of recombinant β2AR-Single-domain antibody fusion proteins in Sf9 cells analyzed by Western Blot. The presence of fusion protein was detected by anti-FLAG detection as explained in Example 4. Membranes of non-infected Sf9 cells (lane 1). Membranes of Sf9 cells expressing recombinant β2AR365N that was not fused to any Nb (lane 2: cells were infected with a 1:250 dilution of P2 and cultured for 48 hours; lane 3: cells were infected with a 1:250 dilution of P2 and cultured for 55 hours; lane 5: cells were infected with a 1:100 dilution of P2 and cultured for 48 hours; lane 6: cells were infected with a 1:100 dilution of P2 and cultured for 55 hours). Protein marker (PAGERULER™ Prestained Protein Ladder, Fermentas cat. Nr SM0671) (lane 4). Membranes of Sf9 cells expressing recombinant β2AR365N-Nb80 (lane 7: cells were infected with a 1:100 dilution of P2 and cultured for 55 hours). Membranes of Sf9 cells expressing recombinant β2AR365N-Nb71 (lane 8: cells were infected with a 1:100 dilution of P2 and cultured for 55 hours). Membranes of Sf9 cells expressing recombinant β2AR365N-Nb69 (lane 9: cells were infected with a 1:100 dilution of P2 and cultured for 55 hours).

FIGS. 4A-4F: Ligand binding properties of β2AR365N-Nb80 fusion compared to β2AR365N-Nb69 mock fusion. Radioligand displacement assays of different ligands competing with [$^3$H]-dihydroalprenolol ([$^3$H]-DHA) for binding to β2AR365N-Nb80 (open circles), and using the β2AR365N-Nb69 chimer (closed circles) as an internal reference for the non-constrained β2 adrenergic receptor as described in Example 6. Competition assays were performed on both receptors using the natural agonist epinephrine (FIG. 4A), the agonist (−)-isoproterenol (FIG. 4B), the neutral antagonist alprenolol (FIG. 4C), the partial agonist salbutamol (FIG. 4D), the inverse agonist ICI-118,551 (FIG. 4E), and the antagonist carvedilol (FIG. 4F) as the competing ligand, respectively. Curves have been fitted by non-linear regression to a model for competitive binding using the standard settings of Graphpad Prism 6.0. IC50 labeled values have been fitted to a one binding site competitive model. IC50$^{high}$ labeled values have been fitted to a two binding site competitive binding model and correspond to the IC50 of the highest affinity site.

Figure 5A:
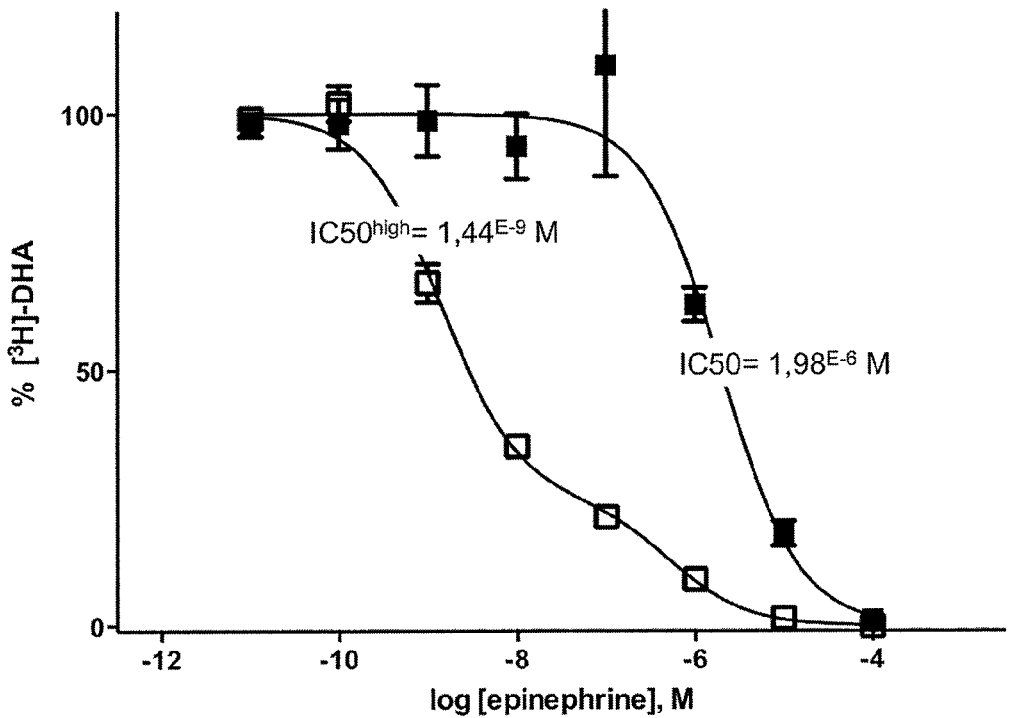
Figure 5B:
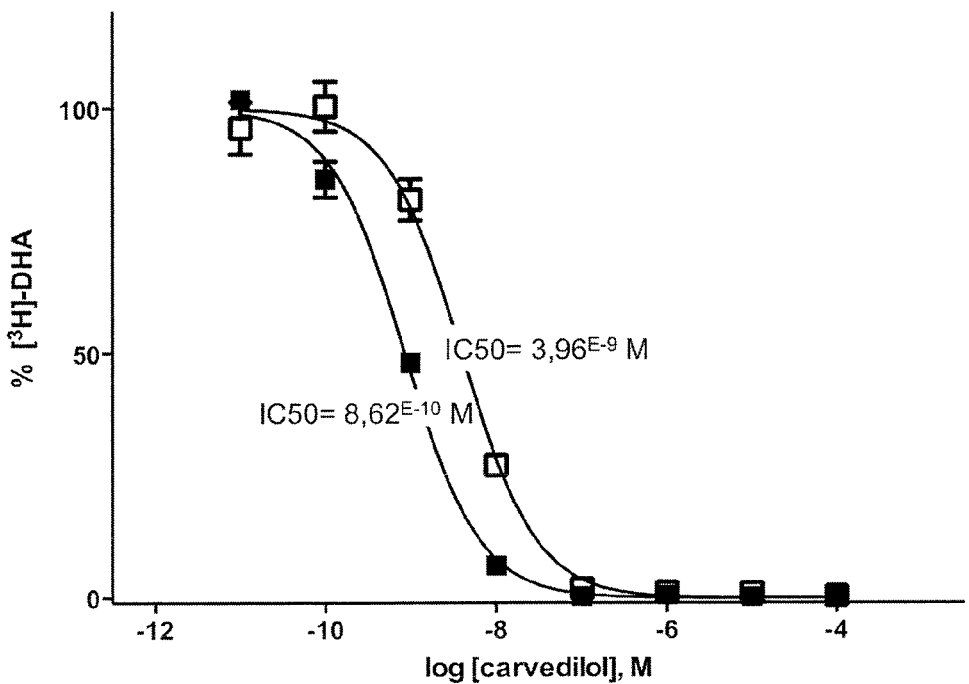

FIGS. 5A & 5B: Ligand binding properties of β2AR365N-Nb80 fusion compared to non-fused β2AR365N. Radioligand displacement assays of different ligands competing with [$^3$H]-dihydroalprenolol ([$^3$H]-DHA) for binding to β2AR365N-Nb80 (open squares), and using the non-fused β2AR365N receptor (closed squares) as an internal reference for the non-constrained β2 adrenergic receptor as described in Example 6. Competition assays were performed on both receptors using the natural agonist epinephrine (FIG. 5A), and the antagonist carvedilol (FIG. 5B) as the competing ligand, respectively. Curves have been fitted by non-linear regression to a model for competitive binding using the standard settings of Graphpad Prism 6.0. IC50 labeled values have been fitted to a one binding site competitive model. IC50$^{high}$ labeled values have been fitted to a two binding site competitive binding model and correspond to the IC50 of the highest affinity site.

FIGS. 6A-6F: Ligand binding properties of β2AR365N-Nb71 fusion compared to β2AR365N-Nb69 fusion. Radioligand displacement assays of different ligands competing with [3H]-dihydroalprenolol ([3H]-DHA) for binding to β2AR365N-Nb71 (open triangles), and using the β2AR365N-Nb69 chimer (closed triangles) as an internal reference for the non-constrained β2 adrenergic receptor as described in Example 6. Competition assays were performed on both receptors using the natural agonist epinephrine (FIG. 6A), the full agonist isoproterenol (FIG. 6B), the neutral antagonist alprenolol (FIG. 6C), the partial agonist salbutamol (FIG. 6D), the inverse agonist ICI-118,551 (FIG. 6E) and the antagonist carvedilol (FIG. 6F) as the competing ligand, respectively. Curves have been fitted by non-linear regression to a model for competitive binding using the standard settings of Graphpad Prism 6.0. IC50 labeled values have been fitted to a one binding site competitive model. IC50$^{high}$ labeled values have been fitted to a two binding site competitive binding model and correspond to the IC50 of the highest affinity site.

Figure 7:
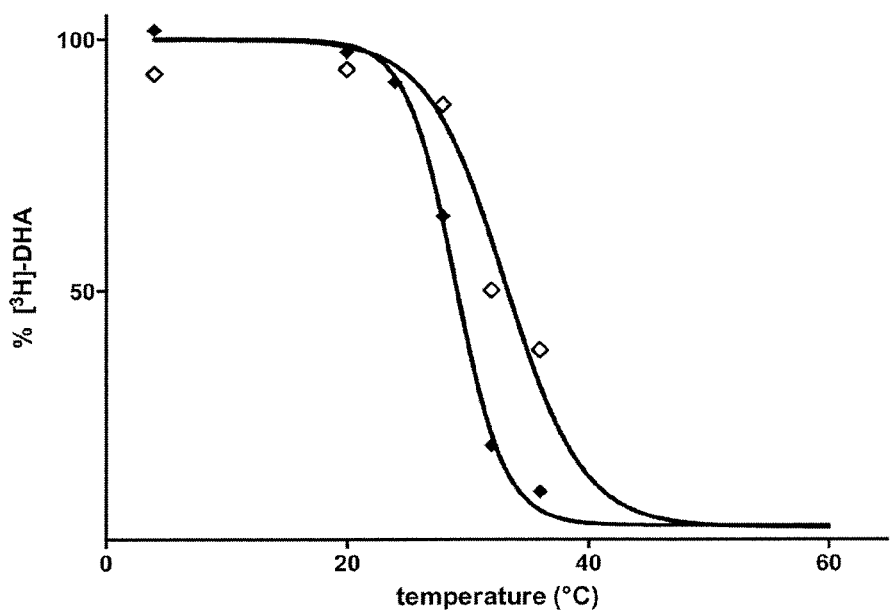

FIG. 7: Thermostability of the β2AR365N-Nb80 fusion compared to β2AR365N-Nb69 fusion. Thermostabilities of the ligand free DDM solubilized fusion proteins β2AR365-Nb80 (open diamonds) and β2AR365N-Nb69 (closed diamonds). Thermostability assays were performed in the absence of any ligand on solubilized receptors in 0.08% DDM, as described in Example 7. Curves have been fitted by non-linear regression with the log(agonist) versus response-variable slope (four parameters) equation using Prism using Graphpad Prism 6.0 (GraphPad Software, San Diego, Calif.).

Figure 8:
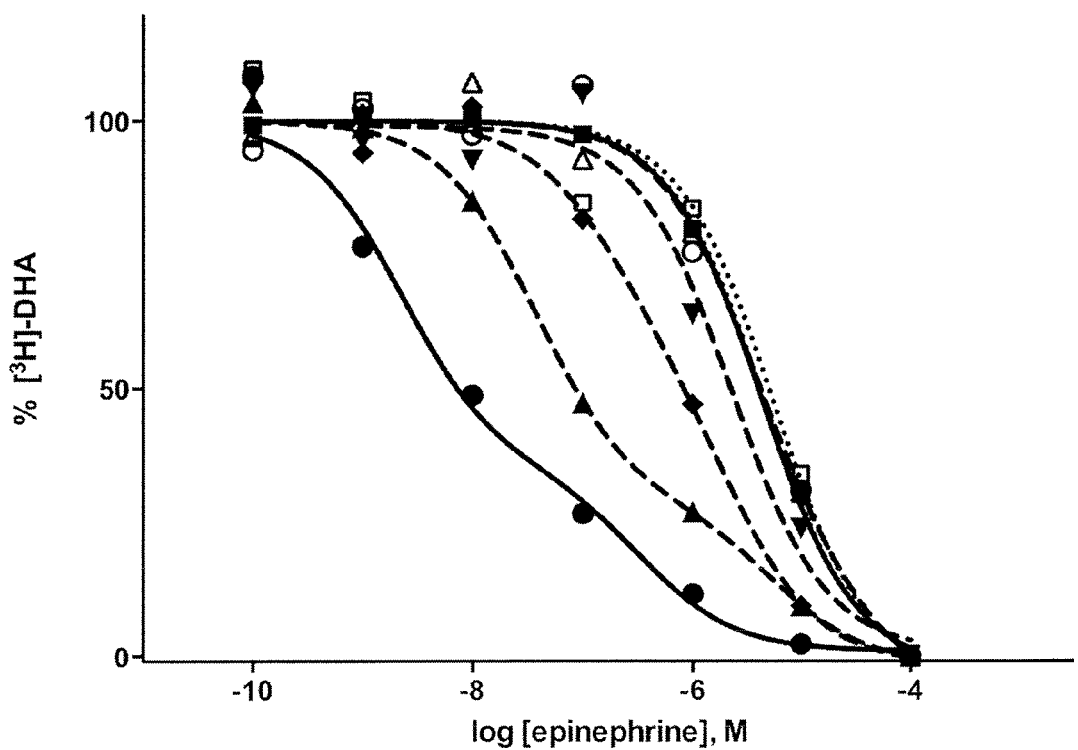

FIG. 8: Ligand binding properties of β2AR365N-Nb80 fusion compared to the non-fused β2AR365N in complex with exogenously added Nb80. Radioligand displacement assays of epinephrine competing with [$^3$H]-dihydroalprenolol ([$^3$H]-DHA) for binding to non-fused β2AR365N receptor in the presence of different concentrations of Nb80 (500 nM Nb80: closed triangles, 50 nM Nb80: closed diamonds, 5 nM Nb80: closed inverted triangles and 50 pM Nb80: closed squares; dashed lines) or in the presence of different concentrations of Nb69 (500 nM Nb69: open triangle, 50 pM Nb69 open squares; dotted lines). The =2AR365N-Nb80 fusion (closed circles, full line) and the β2AR365N-Nb69 fusion (open circles, full line) were used as internal reference in the assay, as described in Example 8. Curves have been fitted by non-linear regression to a model for competitive binding using the standard settings of Graphpad Prism 6.0. IC50 labeled values have been fitted to a one binding site competitive model. IC50$^{high}$ labeled values have been fitted to a two binding site competitive binding model and correspond to the IC50 of the highest affinity site.

FIGS. 9A-9C: The M2R-Single-domain antibody fusion, described in Example 9 contains two different proteins connected with a peptide linker: the GPCR M2Δi3R, the linker GGGSGGGGSGGGGSGGGGSGGGS (underlined and highlighted in bold) (SEQ ID NO:49) and a Single-domain antibody. Underlined is the HA signal peptide and the His$_6$ peptide tag. The FLAG-tag is represented in bold, the TEV cleavage site is indicated in grey shade. FIG. 9A. Cartoon representation of the M2R-Single-domain antibody fusion construct. FIG. 9B. The amino acid sequence of the open reading frame encoded by pFastBac1 M2Δi3R. FIG. 9C. The amino acid sequence of the open reading frame encoded by pFastBac1 M2Δi3R-Nb9-1.

Figure 10A:
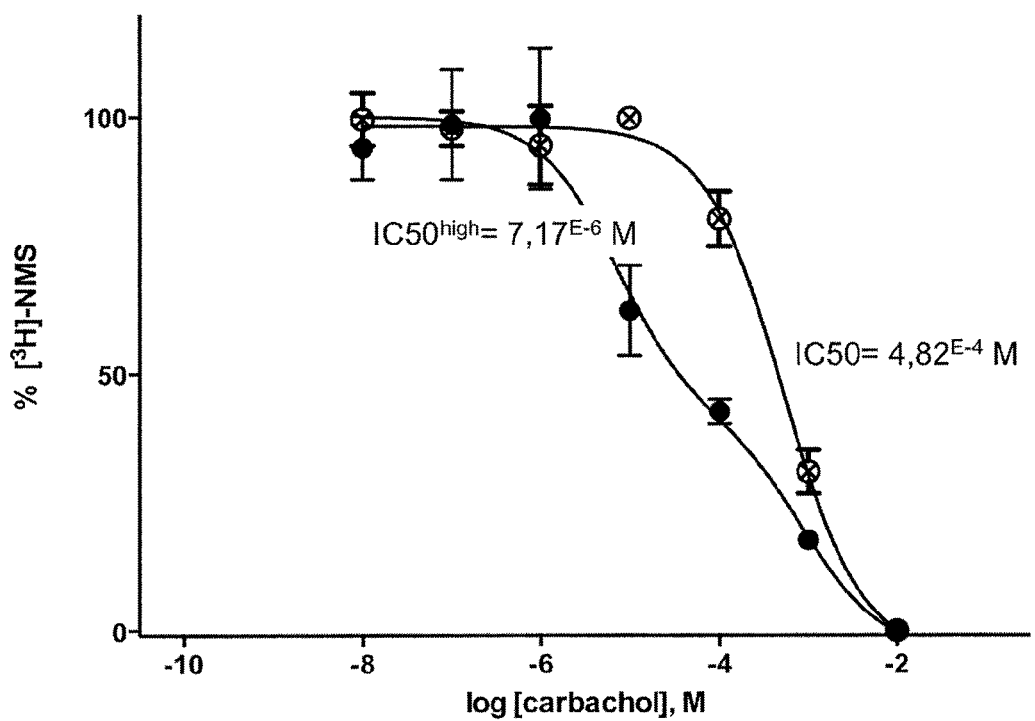
Figure 10B:
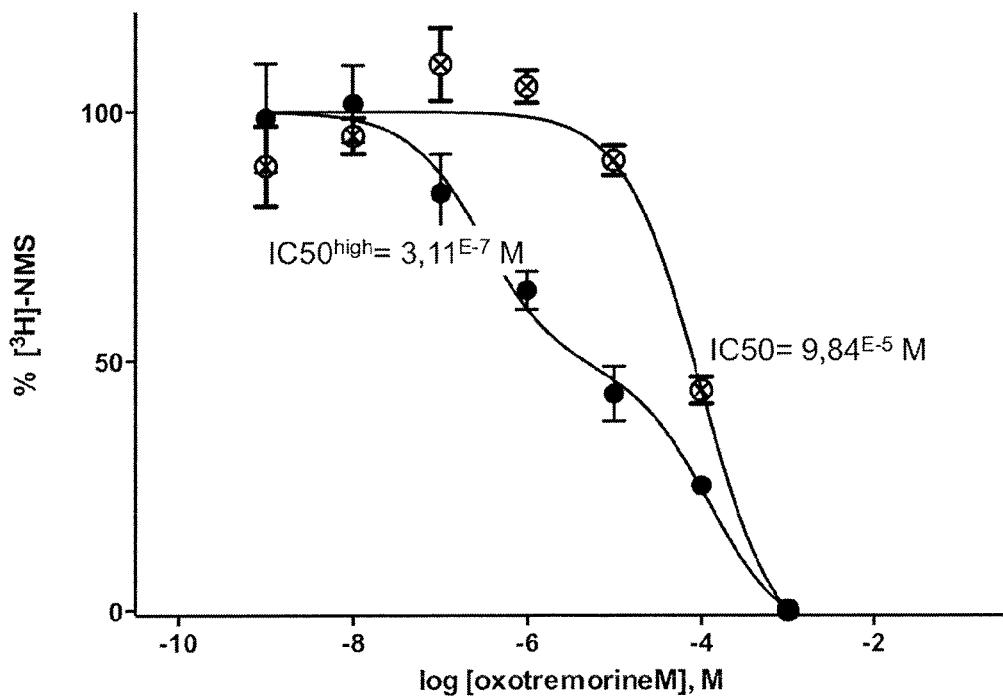

FIGS. 10A & 10B: Ligand binding properties of M2Δi3R-Nb9-1 compared to the free non-fused M2Δi3R. Radioligand displacement assays of different ligands competing with [$^3$H]-N methyl scopolamine ([$^3$H]-NMS) for binding to M2Δi3R-Nb9-1 (closed circles), and using the M2Δi3R (crossed circles) as an internal reference for the non-constrained muscarinic receptor M2, as described in Example 12. Competition assays were performed on both receptors using the agonist carbachol (FIG. 10A) or the agonist oxotremorineM (FIG. 10B) as the competing ligand, respectively. Curves have been fitted by non-linear regression to a model for competitive binding using the standard settings of Graphpad Prism 6.0. IC50 labeled values have been fitted to a one binding site competitive model. IC50$^{high}$ labeled values have been fitted to a two binding site competitive binding model and correspond to the IC50 of the highest affinity site.

FIGS. 11A-11C: The β1AR-Single-domain antibody fusions, described in Example 13 contains two different proteins connected with a peptide linker: the GPCR human β1AR, the linker (SEQ ID NO: 60)
GGGGSGGGGSGGGGSGGGGSGGGS (underlined and highlighted in bold) and a Single-domain antibody. Underlined is the HA signal peptide and the His$_6$ peptide tag. The FLAG-tag is represented in bold, the TEV cleavage site is indicated in grey shade. FIG. 11A. Cartoon representation of the β1AR-Single-domain antibody fusion constructs. FIG. 11B. The amino acid sequence of the open reading frame encoded by pFastBac hβ1AR-Nb80. FIG. 11C. The amino acid sequence of the open reading frame encoded by pFastBac hβ1AR-Nb69.

Figure 12A:
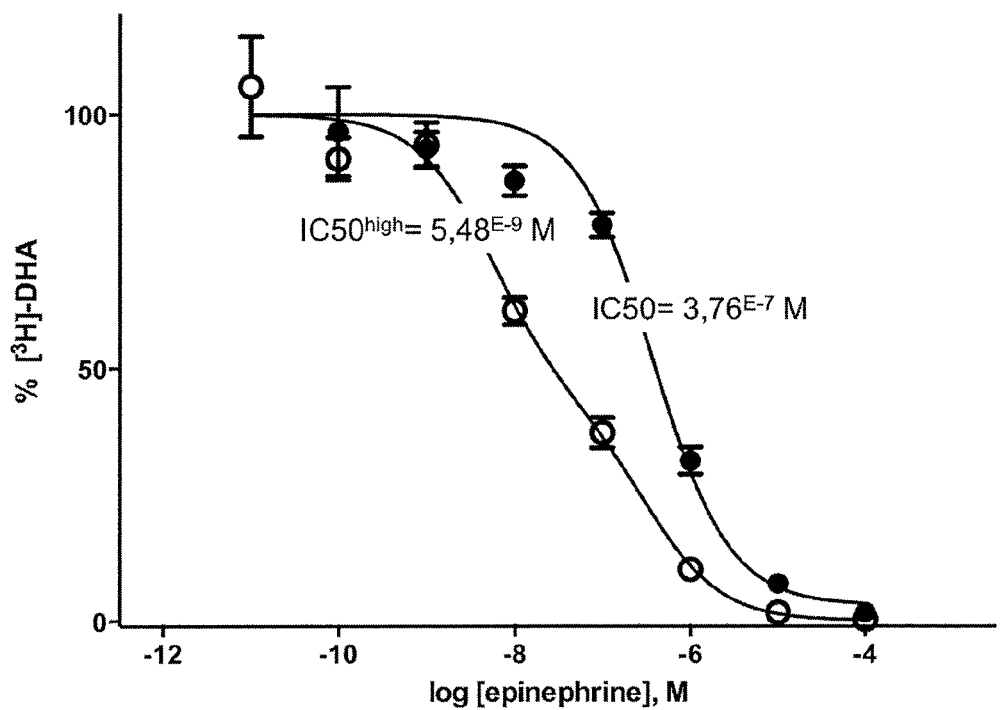
Figure 12B:
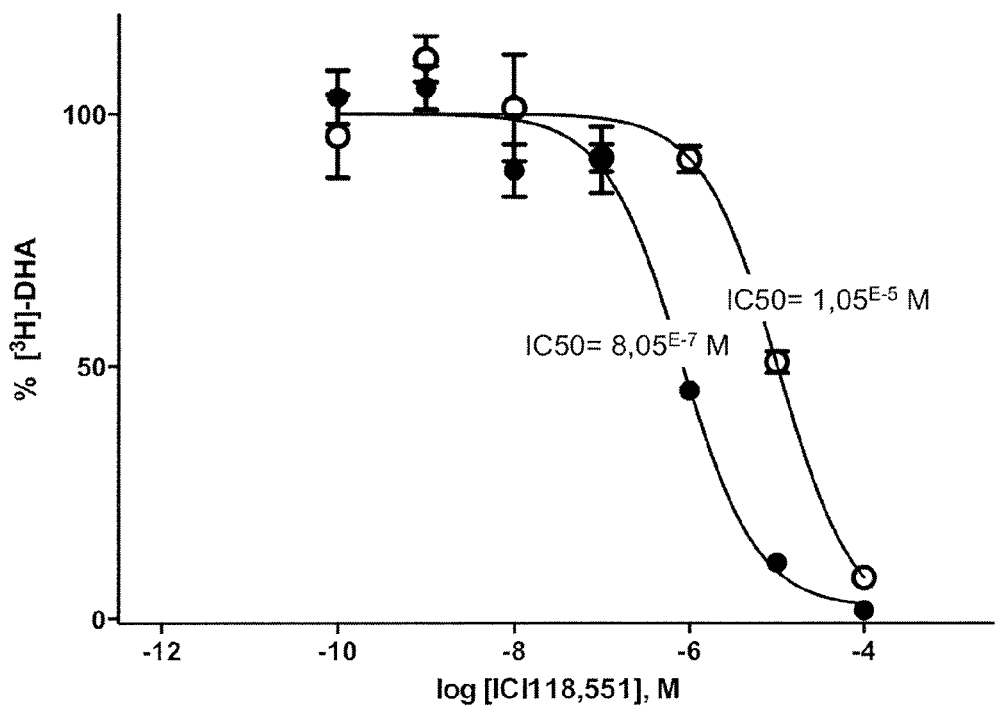
Figure 12C:
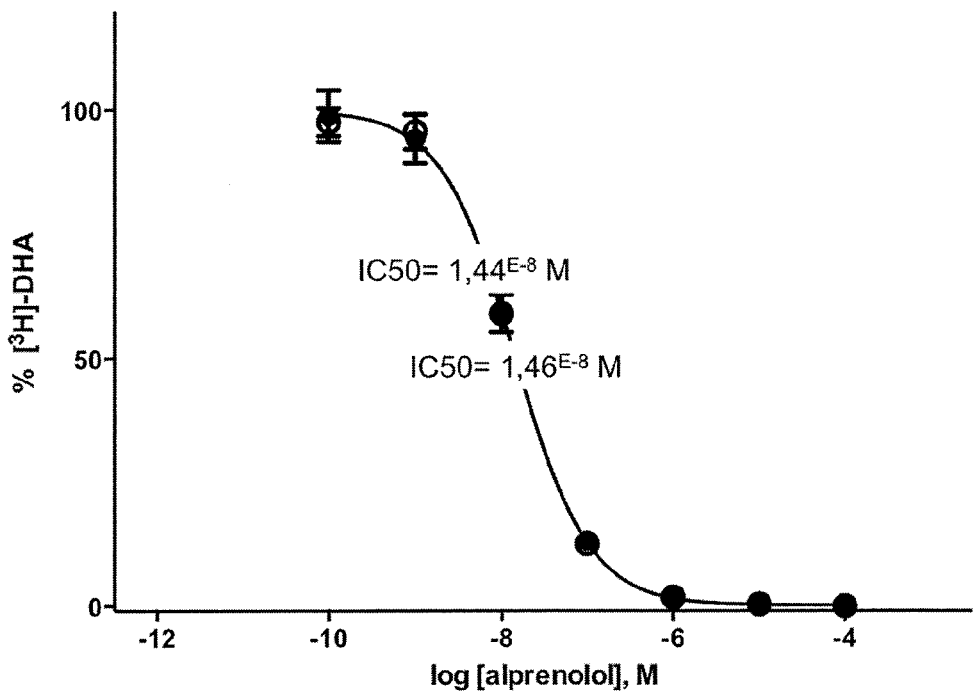

FIGS. 12A-12C: Ligand binding properties of hβ1AR-Nb80 fusion compared to hβ1AR-Nb69 fusion. Radioligand displacement assays of different ligands competing with [$^3$H]-dihydroalprenolol ([$^3$H]-DHA) for binding to hβ1AR-Nb80 (open circles), and using the hβ1AR-Nb69 chimer (closed circles) as an internal reference for the non-constrained β1 adrenergic receptor, as described in Example 16. Competition assays were performed on both β1-receptors fusions using the natural agonist epinephrine (FIG. 12A), the inverse agonist ICI-118,551 (FIG. 12B) and the neutral antagonist alprenolol (FIG. 12C) as the competing ligand, respectively. Curves have been fitted by non-linear regression to a model for competitive binding using the standard settings of Graphpad Prism 6.0. IC50 labeled values have been fitted to a one binding site competitive model. IC50$^{high}$ labeled values have been fitted to a two binding site competitive binding model and correspond to the IC50 of the highest affinity site.

Figure 13A:
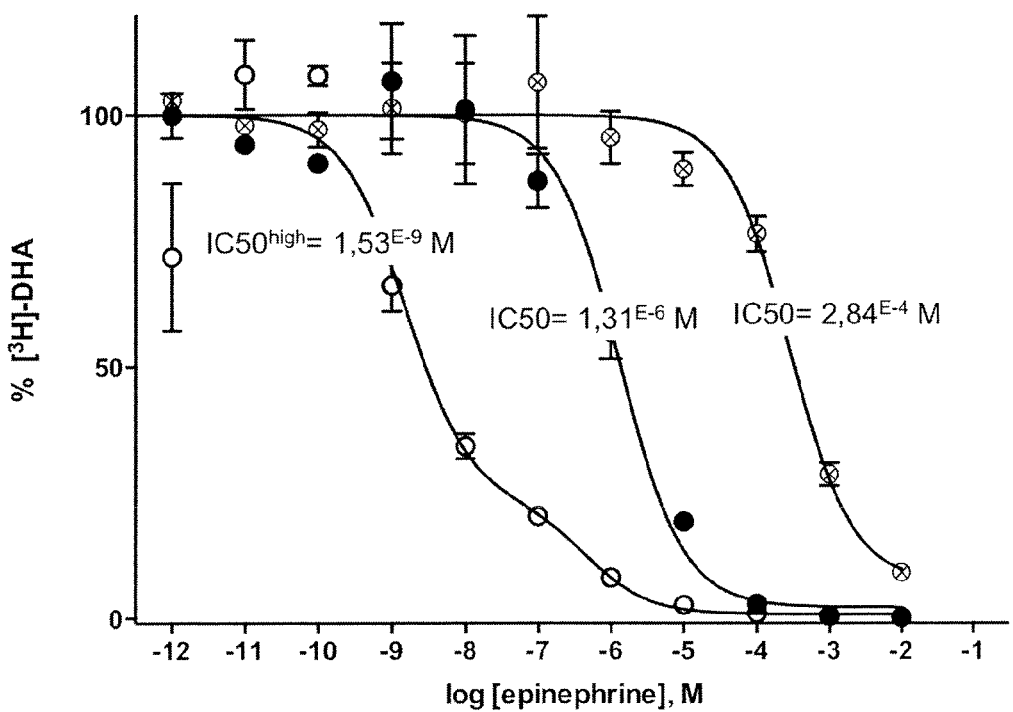
Figure 13B:
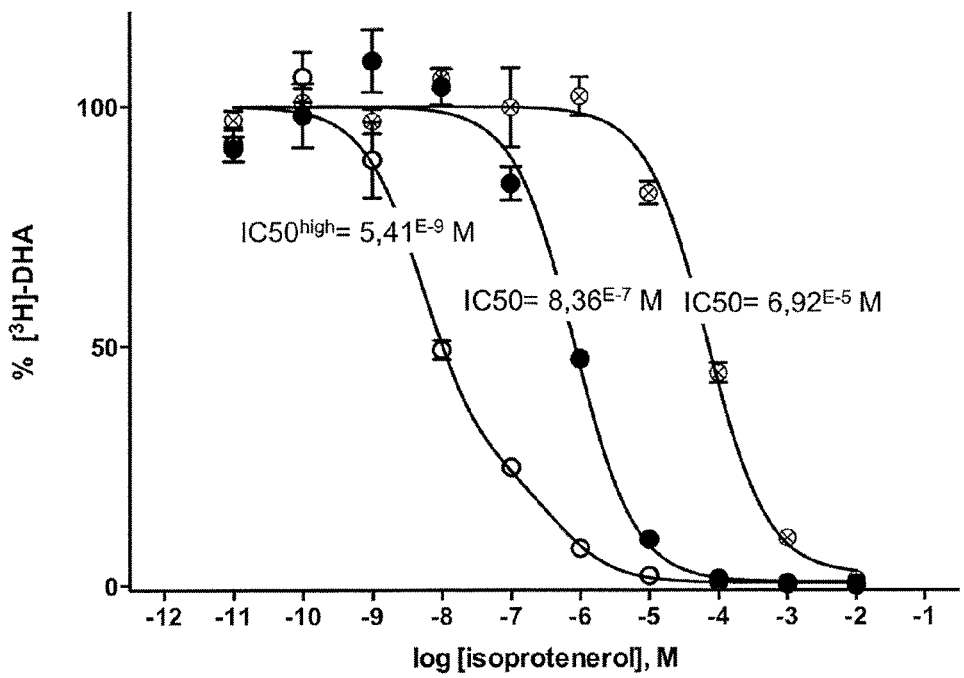
Figure 13C:
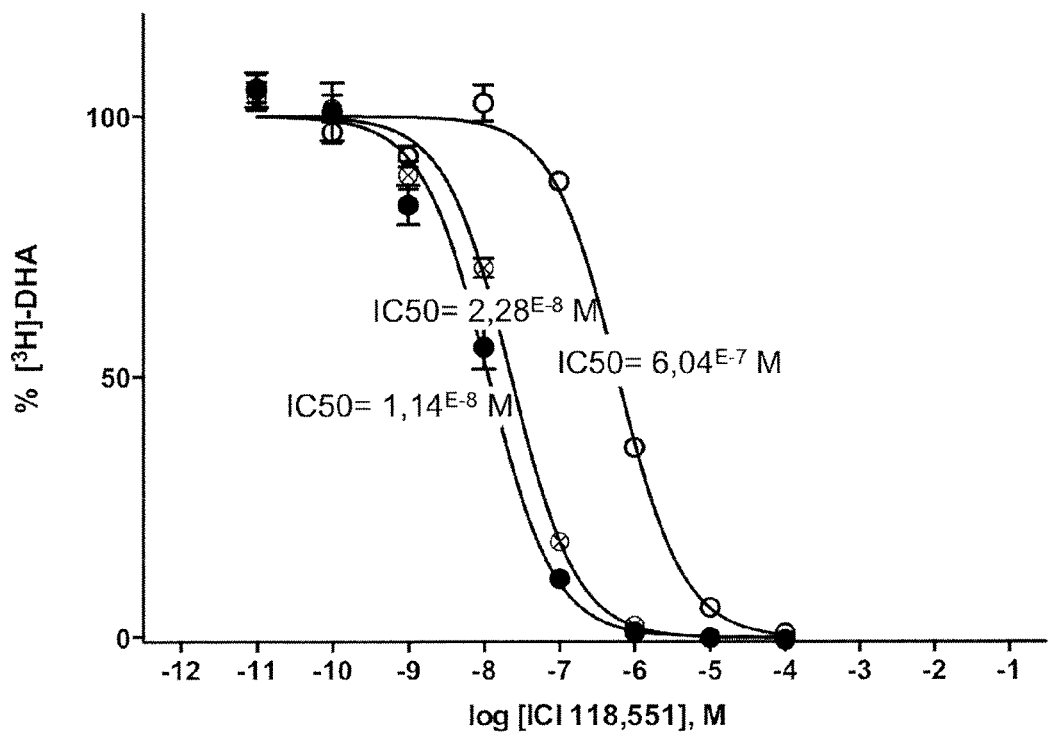

FIGS. 13A-13C: Ligand binding properties of β2AR365N-Nb60 fusion compared to β2AR365N-Nb69 mock fusion. Radioligand displacement assays of different ligands competing with [$^3$H]-dihydroalprenolol ([$^3$H]-DHA) for binding to β2AR365N-Nb80 (open circles), β2AR365N-Nb60 (crossed open circles), using the β2AR365N-Nb69 chimer (closed circles) as an internal reference for the non-constrained β2 adrenergic receptor, as described in Example 19. Competition assays were performed on the β2-receptors fusions using the natural agonist epinephrine (FIG. 13A), the agonist (−)-isoproterenol (FIG. 13B) and the inverse agonist ICI-118,551 (FIG. 13C) as the competing ligand, respectively. Curves have been fitted by non-linear regression to a model for competitive binding using the standard settings of Graphpad Prism 6.0. IC50 labeled values have been fitted to a one binding site competitive model. IC50$^{high}$ labeled values have been fitted to a two binding site competitive binding model and correspond to the IC50 of the highest affinity site.

FIG. 14. AA sequence alignment of full length wild-type human Mor1 (Uniprot code P35372; SEQ ID NO:46) and mouse Mor1 (Uniprot code P42866; SEQ ID NO:45). For the purification of mouse Mor1, expressing in sf9 cells, an N-terminal TEV (N-terminus; insect cell expression of mouse Mor1) protease cleavage site has been introduced between the two underlined Glycines. A C-terminal 3C protease cleavage site has also been introduced between the underlined isoleucine and the underlined glutamic acid in mouse and human Mor1 expressed in Sf9. The theoretical intracellular loops (ICL) and the intracellular C-terminus according to the Uniprot database are depicted in grey shade. AA residues that have been deleted in the Mor-Single-domain antibody fusion constructs are striked-through.

FIGS. 15A-15E: The Mor1-Single-domain antibody fusions, described in Example 20 contain two different proteins connected with a peptide linker: the GPCR Mor1, the 34 GS linker (underlined and highlighted in bold) and a Single-domain antibody. Underlined is the HA signal peptide and the His$_6$ peptide tag. The FLAG-tag is represented in bold. The 3C cleavage site is indicated in grey shade. FIG. 15A. Cartoon representation of the Mor1-Single-domain antibody fusion constructs. FIG. 15B-FIG. 15E. The amino acid sequence of the four Mor-Nb open reading frames (SEQ ID NO:9, SEQ ID NO:10, SEQ ID NO:11, and SEQ ID NO:12, respectively).

Figure 16A:
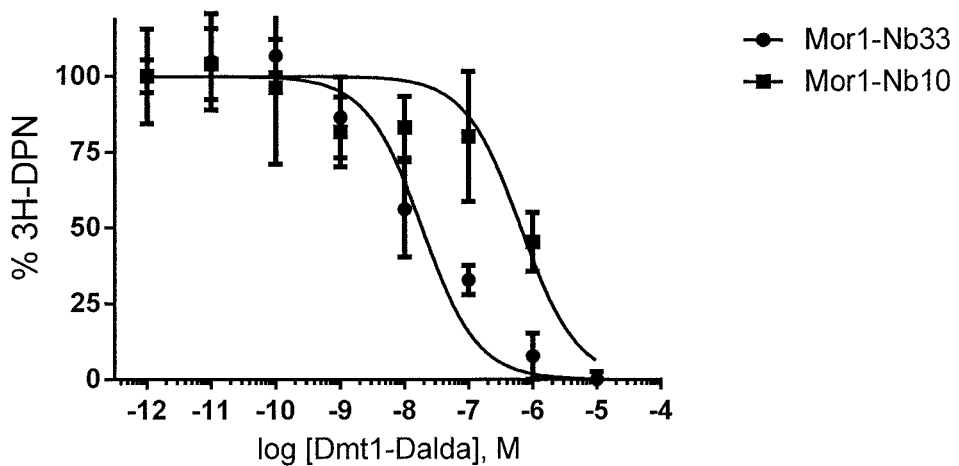
Figure 16B:
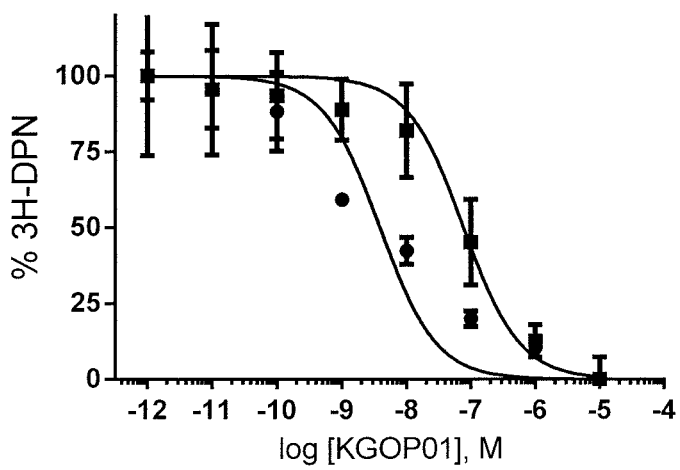
Figure 16C:
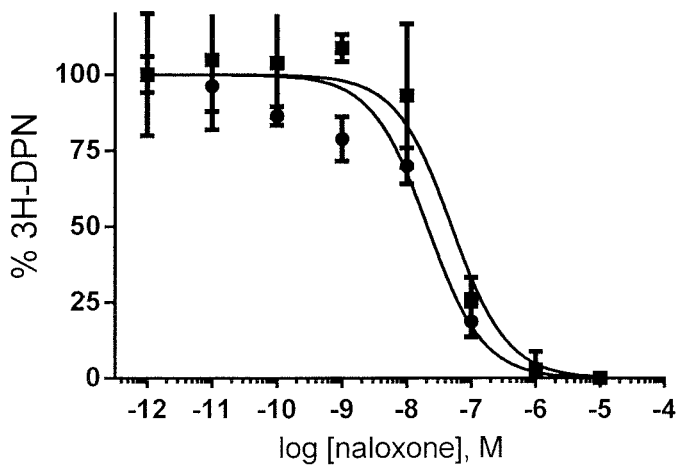

FIGS. 16A-FIG. 16C: Ligand binding properties of hMor1-Nb33 fusion compared to hMor1-Nb10 mock fusion. Radioligand displacement assays of different ligands competing with radioligand for binding to hMor1-Nb33 (circles) using the hMor1-Nb10 chimer (squares) as an internal reference for the non-constrained receptor. Competition assays were performed on both receptors using agonists Dmt1-Dalda (FIG. 16A), KGOP01 (FIG. 16B), and antagonist naloxone (FIG. 16C) as the competing ligand.

Figure 17:
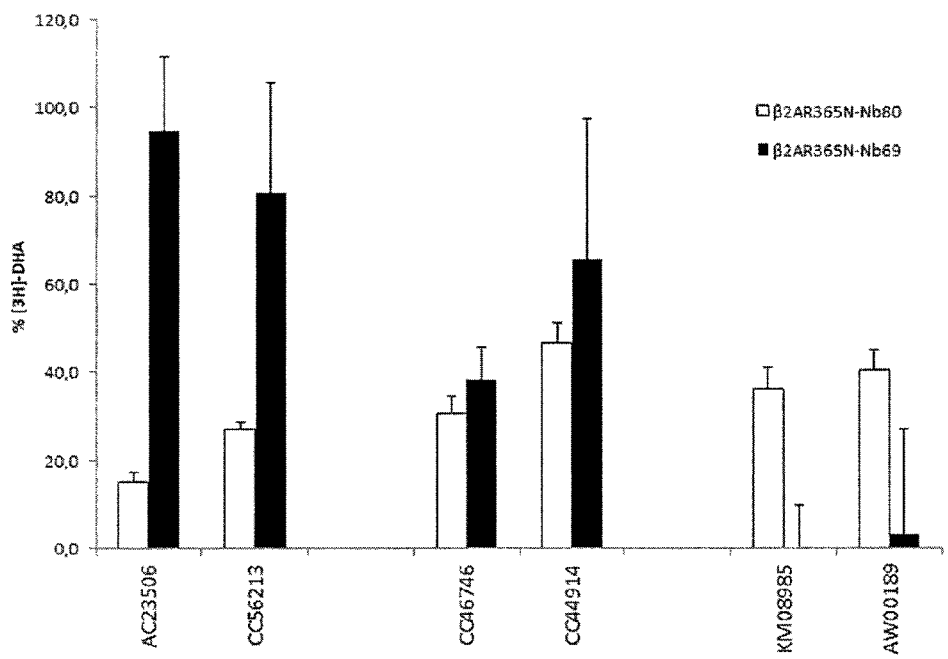

FIG. 17. Comparative fragment binding with different activity profiles to β2AR-fusions.

Representative example of binding of 6 fragments to the active-state stabilized β2AR365N-Nb80 fusion (open bars) versus the prominent, non-constrained conformation β2AR365N-Nb69 fusion (black bars), measured by radioligand displacement assays using [$^3$H]-dihydroalprenolol ([$^3$H]-DHA) as the radioligand. 2 fragments (AC23506, CC56213) show an agonist profile, 2 fragments (CC46746, CC44914) have an antagonistic profile and 2 fragments KM08985) show an inverse agonist profile.

Figure 18A:
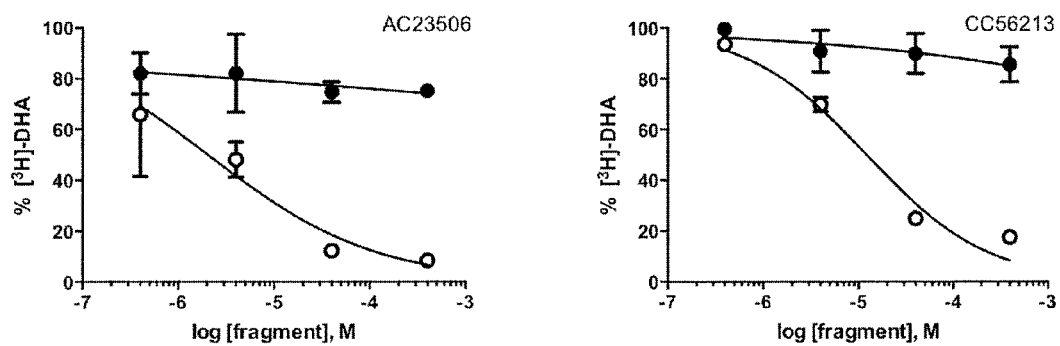
Figure 18B:
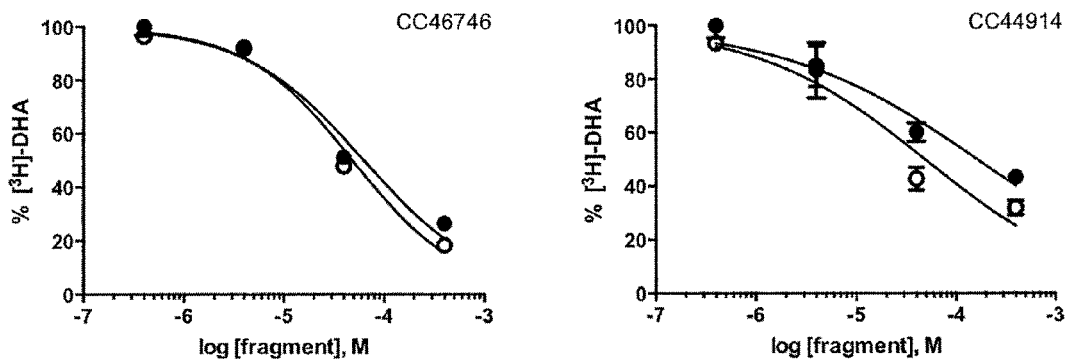
Figure 18C:
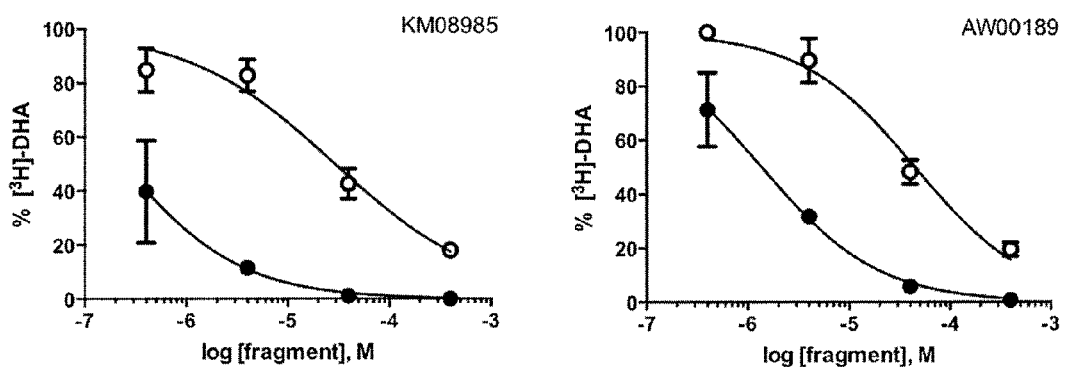

FIGS. 18A-18C. Dose response curves of 6 fragments to β2AR-Nb80 fusion compared to β2AR-Nb69 fusion.

Radioligand displacement assays of 6 different fragments competing with [$^3$H]-dihydroalprenolol ([$^3$H]-DHA) for binding to β2AR365N-Nb80 (open circles) and using the β2AR365N-Nb69 chimer (closed circles) as an internal reference for the non-constrained β2 adrenergic receptor, as described in Example 24. Competition assays were performed on the β2-receptors fusions using 2 fragments with agonist profile (A), 2 fragments with antagonist profile (B) and 2 fragments with the inverse agonist profile (C) as the competing ligand, respectively. Curves have been fitted by non-linear regression with the log(agonist) versus response-variable slope (four parameters) equation using Prism using Graphpad Prism 6.0. (GraphPad Software, San Diego, Calif.).

Figure 19:
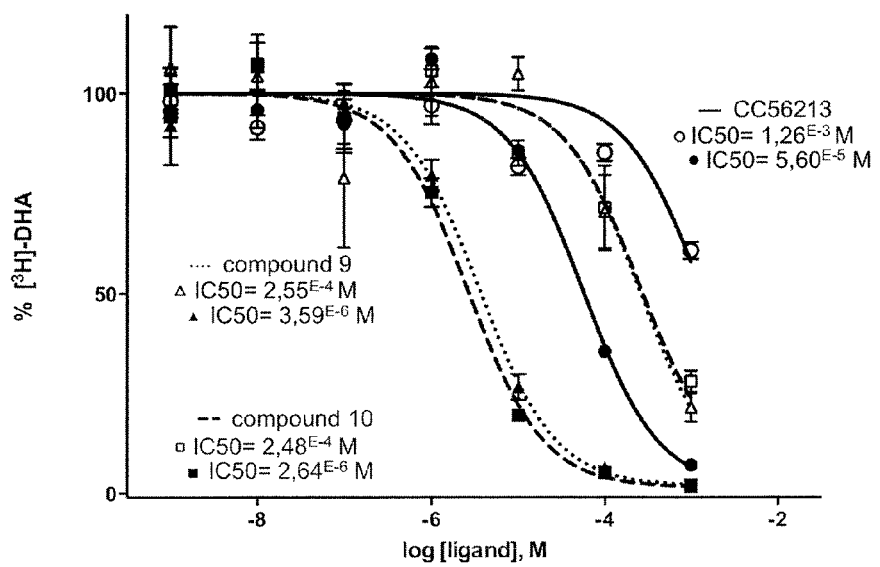

FIG. 19: Binding properties of elaborated fragments to the β2AR-Nb80 fusion compared to the β2AR-Nb69 mock fusion. Radioligand displacement assays of different elaborated and original parent fragments competing with [$^3$H]-dihydroalprenolol ([$^3$H]-DHA) for binding to β2AR365N-Nb80 (closed symbols), using the β2AR365N-Nb69 chimer (open symbols) as an internal reference for the non-constrained β2 adrenergic receptor. Competition assays were performed on the β2-receptors fusions using (A) the CC40246 (full line), the elaborated fragments: compound 2 (dashed line) and compound 3 (dotted line) as the competing ligand, respectively, and (B) the CC56213 (full line), the elaborated fragments: compound 9 (dashed line) and compound 10 (dotted line) as the competing ligand, respectively. Curves have been fitted by non-linear regression to a model for competitive binding using the standard settings of Graphpad Prism 6.0. IC50 labeled values have been fitted to a one binding site competitive model.

DETAILED DESCRIPTION

Definitions

The disclosure will be described with respect to particular embodiments and with reference to certain drawings but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a" or "an," "the," this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

Unless otherwise defined herein, scientific and technical terms and phrases used in connection with the disclosure shall have the meanings that are commonly understood by those of ordinary skill in the art. Generally, nomenclatures used in connection with, and techniques of molecular and cellular biology, structural biology, biophysics, pharmacology, genetics and protein and nucleic acid chemistry described herein are those well-known and commonly used in the art. The methods and techniques of the disclosure are generally performed according to conventional methods well known in the art and as described in various general and more specific references that are cited and discussed throughout the present specification unless otherwise indicated. See, for example, Sambrook et al. Molecular Cloning: A Laboratory Manual, 3th ed., Cold Spring Harbor Laboratory Press, Cold Spring Harbor, N.Y. (2001); Ausubel et al., Current Protocols in Molecular Biology, Greene Publishing Associates (1992, and Supplements to 2002); Rup, Biomolecular crystallography: principles, Practice and Applications to Structural Biology, $1^{st}$ edition, Garland Science, Taylor & Francis Group, LLC, an informa Business, N.Y. (2009); Limbird, Cell Surface Receptors, 3d ed., Springer (2004).

The terms "chimeric polypeptide," "chimeric protein," "fusion polypeptide," "fusion protein" are used interchangeably herein and refer to a protein that comprises at least two separate and distinct polypeptide components that may or may not originate from the same protein. The polypeptide components, while typically unjoined in their native state, are joined by their respective amino and carboxyl termini through a peptide linkage to form a single continuous polypeptide. For example, a protein of interest fused to an antibody is an example of a chimeric protein. A convenient means for linking or fusing two polypeptides is by expressing them as a fusion protein from a recombinant nucleic acid molecule, which comprises a first polynucleotide encoding a first polypeptide operably linked to a second polynucleotide encoding the second polypeptide. Otherwise, the polypeptides comprised in a fusion protein can be linked through peptide bonds that result from intein-mediated protein splicing (Muralidharan and Muir 2006) or sortagging (Popp et al., 2007) or may be chemically linked by any other means. Typically, a chimeric polypeptide will not exist as a contiguous polypeptide in a protein encoded by a gene in a non-recombinant genome. The term "chimeric polypeptide" and grammatical equivalents refer to a non-naturally occurring molecule which means that it is man-made. The term "fused to," and other grammatical equivalents, when referring to a chimeric polypeptide, as defined herein, refers to any chemical or recombinant mechanism for linking two or more polypeptide components. The fusion of the two or more polypeptide components may be a direct fusion of the sequences or it may be an indirect fusion, e.g., with intervening amino acid sequences or linker sequences. Examples will be provided further herein.

The term "membrane protein," as used herein, refers to a protein that is attached to or associated with a membrane of a cell or an organelle. They are often subdivided into several categories including integral membrane proteins, peripheral membrane proteins and lipid-anchored proteins. Preferably, the membrane protein is an integral membrane protein that is permanently bound to the lipid bilayer and which requires a detergent or another apolar solvent to be removed. Integral membrane proteins include transmembrane proteins that are permanently attached to the lipid membrane and span across the membrane one or several times. Examples of suitable membrane proteins include receptors such as GPCRs, amongst others.

As used herein, the terms "polypeptide," "protein," "peptide" are used interchangeably herein, and refer to a polymeric form of amino acids of any length, which can include coded and non-coded amino acids, chemically or biochemically modified or derivatized amino acids, and polypeptides having modified peptide backbones. Throughout the application, the standard one letter notation of amino acids will be used. Typically, the term "amino acid" will refer to "proteinogenic amino acid," i.e., those amino acids that are naturally present in proteins. Most particularly, the amino acids are in the L isomeric form, but D amino acids are also envisaged.

As used herein, the terms "nucleic acid molecule," "polynucleotide," "polynucleic acid," "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

Any of the peptides, polypeptides, nucleic acids, etc., disclosed herein may be "isolated" or "purified." "Isolated" is used herein to indicate that the material referred to is (i) separated from one or more substances with which it exists in nature (e.g., is separated from at least some cellular material, separated from other polypeptides, separated from its natural sequence context), and/or (ii) is produced by a process that involves the hand of man such as recombinant DNA technology, chemical synthesis, etc.; and/or (iii) has a sequence, structure, or chemical composition not found in nature. "Purified," as used herein, denote that the indicated nucleic acid or polypeptide is present in the substantial absence of other biological macromolecules, e.g., polynucleotides, proteins, and the like. In one embodiment, the polynucleotide or polypeptide is purified such that it constitutes at least 90% by weight, e.g., at least 95% by weight, e.g., at least 99% by weight, of the polynucleotide(s) or polypeptide(s) present (but water, buffers, ions, and other small molecules, especially molecules having a molecular weight of less than 1000 Dalton, can be present).

The term "sequence identity," as used herein, refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Determining the percentage of sequence identity can be done manually, or by making use of computer programs that are available in the art. Examples of useful algorithms are PILEUP (Higgins & Sharp, CABIOS 5:151 (1989), BLAST and BLAST 2.0 (Altschul et al. J. Mol. Biol. 215: 403 (1990). Software for performing BLAST analyses is publicly available through the National Center for Biotechnology Information (on the World Wide Web at ncbi.nlm.nih.gov/).

"Similarity" refers to the percentage number of amino acids that are identical or constitute conservative substitutions. Similarity may be determined using sequence comparison programs such as GAP (Deveraux et al., 1984). In this way, sequences of a similar or substantially different length to those cited herein might be compared by insertion of gaps into the alignment, such gaps being determined, for example, by the comparison algorithm used by GAP. As used herein, "conservative substitution" is the substitution of amino acids with other amino acids whose side chains have similar biochemical properties (e.g., are aliphatic, are aromatic, are positively charged, . . . ) and is well known to the skilled person. Non-conservative substitution is then the substitution of amino acids with other amino acids whose side chains do not have similar biochemical properties (e.g., replacement of a hydrophobic with a polar residue). Conservative substitutions will typically yield sequences which are not identical anymore, but still highly similar. By conservative substitutions is intended combinations such as gly, ala; val, ile, leu, met; asp, glu; asn, gin; ser, thr; lys, arg; cys, met; and phe, tyr, trp.

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein, a deletion can involve deletion of about 2, about 5, about 10, up to about 20, up to about 30 or up to about 50 or more amino acids. A protein or a fragment thereof may contain more than one deletion. Within the context of a GPCR, a deletion may also be a loop deletion, or an N- and/or C-terminal deletion, or a combination thereof. As will be clear to the skilled person, an N- and/or C-terminal deletion of a GPCR is also referred to as a truncation of the amino acid sequence of the GPCR or a truncated GPCR.

An "insertion" or "addition" is that change in an amino acid or nucleotide sequences which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about 1, about 3, about 5, about 10, up to about 20, up to about 30 or up to about 50 or more amino acids. A protein or fragment thereof may contain more than one insertion.

A "substitution," as used herein, results from the replacement of one or more amino acids or nucleotides by different amino acids or nucleotides, respectively, as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express nucleic acids or polypeptides that are not found within the native (non-recombinant) form of the cell or express native genes that are otherwise abnormally expressed, under expressed, over expressed or not expressed at all.

As used herein, the term "expression" refers to the process by which a polypeptide is produced based on the nucleic acid sequence of a gene. The process includes both transcription and translation.

The term "operably linked," as used herein, refers to a linkage in which the regulatory sequence is contiguous with the gene of interest to control the gene of interest, as well as regulatory sequences that act in trans or at a distance to control the gene of interest. For example, a DNA sequence is operably linked to a promoter when it is ligated to the promoter downstream with respect to the transcription initiation site of the promoter and allows transcription elongation to proceed through the DNA sequence. A DNA for a signal sequence is operably linked to DNA coding for a polypeptide if it is expressed as a pre-protein that participates in the transport of the polypeptide. Linkage of DNA sequences to regulatory sequences is typically accomplished by ligation at suitable restriction sites or adapters or linkers inserted in lieu thereof using restriction endonucleases known to one of skill in the art.

The term "regulatory sequence," as used herein, and also referred to as "control sequence," refers to polynucleotide sequences which are necessary to affect the expression of coding sequences to which they are operably linked. Regulatory sequences are sequences which control the transcription, post-transcriptional events and translation of nucleic acid sequences. Regulatory sequences include appropriate transcription initiation, termination, promoter and enhancer sequences; efficient RNA processing signals such as splicing and polyadenylation signals; sequences that stabilize cytoplasmic mRMA; sequences that enhance translation efficiency (e.g., ribosome binding sites); sequences that enhance protein stability; and when desired, sequences that enhance protein secretion. The nature of such control sequences differs depending upon the host organism. The term "regulatory sequence" is intended to include, at a minimum, all components whose presence is essential for expression, and can also include additional components whose presence is advantageous, for example, leader sequences and fusion partner sequences.

The term "vector," as used herein, is intended to refer to a nucleic acid molecule capable of transporting another nucleic acid molecule to which it has been linked. The vector may be of any suitable type including, but not limited to, a phage, virus, plasmid, phagemid, cosmid, bacmid or even an artificial chromosome. Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of certain genes of interest. Such vectors are referred to herein as "recombinant expression vectors" (or simply, "expression vectors"). Suitable vectors have regulatory sequences, such as promoters, enhancers, terminator sequences, and the like as desired and according to a particular host organism (e.g., bacterial cell, yeast cell). Typically, a recombinant vector, according to the disclosure, comprises at least one "chimeric gene" or "expression cassette." Expression cassettes are generally DNA constructs preferably including (5' to 3' in the direction of transcription): a promoter region, a polynucleotide sequence, homologue, variant or fragment thereof of the disclosure operably linked with the transcription initiation region, and a termination sequence including a stop signal for RNA polymerase and a polyadenylation signal. It is understood that all of these regions should be capable of operating in biological cells, such as prokaryotic or eukaryotic cells, to be transformed. The promoter region comprising the transcription initiation region, which preferably includes the RNA polymerase binding site, and the polyadenylation signal may be native to the biological cell to be transformed or may be derived from an alternative source, where the region is functional in the biological cell.

The term "host cell," as used herein, is intended to refer to a cell into which a recombinant vector has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell," as used herein. A host cell may be an isolated cell or cell line grown in culture or may be a cell which resides in a living tissue or organism. In particular, host cells are of bacterial or fungal origin, but may also be of plant or mammalian origin. The wordings "host cell," "recombinant host cell," "expression host cell," "expression host system," "expression system," are intended to have the same meaning and are used interchangeably herein.

An "epitope," as used herein, refers to an antigenic determinant of a polypeptide. An epitope could comprise 3 amino acids in a spatial conformation, which is unique to the epitope. Generally, an epitope consists of at least 4, 5, 6, 7 such amino acids, and more usually, consists of at least 8, 9, 10 such amino acids. Methods of determining the spatial conformation of amino acids are known in the art, and include, for example, x-ray crystallography and multi-dimensional nuclear magnetic resonance.

A "conformational epitope," as used herein, refers to an epitope comprising amino acids in a spacial conformation that is unique to a folded three-dimensional conformation of a polypeptide. Generally, a conformational epitope consists of amino acids that are discontinuous in the linear sequence but that come together in the folded structure of the protein. However, a conformational epitope may also consist of a linear sequence of amino acids that adopts a conformation that is unique to a folded three-dimensional conformation of the polypeptide (and not present in a denatured state). In protein complexes, conformational epitopes consist of amino acids that are discontinuous in the linear sequences of one or more polypeptides that come together upon folding of the different folded polypeptides and their association in a unique quaternary structure. Similarly, conformational epitopes may here also consist of a linear sequence of amino acids of one or more polypeptides that come together and adopt a conformation that is unique to the quaternary structure.

The term "conformation" or "conformational state" of a protein refers generally to the range of structures that a protein may adopt at any instant in time. One of skill in the art will recognize that determinants of conformation or conformational state include a protein's primary structure as reflected in a protein's amino acid sequence (including modified amino acids) and the environment surrounding the protein. The conformation or conformational state of a protein also relates to structural features such as protein secondary structures (e.g., α-helix, β-sheet, among others), tertiary structure (e.g., the three-dimensional folding of a polypeptide chain), and quaternary structure (e.g., interactions of a polypeptide chain with other protein subunits). Post-translational and other modifications to a polypeptide chain such as ligand binding, phosphorylation, sulfation, glycosylation, or attachments of hydrophobic groups, among others, can influence the conformation of a protein. Furthermore, environmental factors, such as pH, salt concentration, ionic strength, and osmolality of the surrounding solution, and interaction with other proteins and co-factors, among others, can affect protein conformation. The conformational state of a protein may be determined by either functional assay for activity or binding to another molecule or by means of physical methods such as X-ray crystallography, NMR, or spin labeling, among other methods. For a general discussion of protein conformation and conformational states, one is referred to Cantor and Schimmel, Biophysical Chemistry, Part I: The Conformation of Biological Macromolecules, W.H. Freeman and Company, 1980, and Creighton, Proteins: Structures and Molecular Properties, W.H. Freeman and Company, 1993.

A "functional conformation" or a "functional conformational state" refers to the fact that proteins, in particular GPCRs, possess different conformational states having a dynamic range of activity, in particular ranging from no activity to maximal activity. It should be clear that "a functional conformational state," as used herein, is meant to cover any conformational state of a protein, in particular a GPCR, having any activity, including no activity, and is not meant to cover the denatured states of proteins. Non-limiting examples of functional conformations of GPCRs include active conformations, inactive conformations or basal conformations. A particular class of functional conformations is defined as "druggable conformation" and generally refers to a unique therapeutically relevant conformational state of a target protein. As an illustration, the agonist-bound active conformation of the β2 adrenergic receptor corresponds to the druggable conformation of this receptor relating to smooth muscle relaxation, dilation of bronchial passages (asthma), vasodilation in muscle and liver, relaxation of uterine muscle, and release of insulin. It will thus be understood that druggability is confined to particular conformations depending on the therapeutic indication. More details are provided further herein.

The term "stabilizing" or "stabilized," with respect to a functional conformational state of a GPCR, as used herein, refers to the retaining or holding of a GPCR in a subset of the possible conformations that it could otherwise assume, due to the effects of the intramolecular interaction of the GPCR moiety with the binding domain moiety of the chimeric polypeptide of the disclosure. Within this context, a binding domain that specifically or selectively binds to a particular conformation of a GPCR refers to a binding domain that binds with a higher affinity to the GPCR in a subset of conformations than to other conformations that the GPCR may assume. One of skill in the art will recognize that binding domains that specifically or selectively bind to a particular conformation of a GPCR will stabilize this particular conformation, and its related activity. More details are provided further herein.

The term "affinity," as used herein, generally refers to the degree to which a ligand (as defined further herein) binds to a target protein so as to shift the equilibrium of target protein and ligand toward the presence of a complex formed by their binding. Thus, for example, where a chimeric polypeptide and a ligand are combined in relatively equal concentration, a ligand of high affinity will bind to the chimeric polypeptide so as to shift the equilibrium toward high concentration of the resulting complex. The dissociation constant Kd is commonly used to describe the affinity between a ligand and a target protein. Typically, the dissociation constant has a value that is lower than $10^{-5}$ M. Preferably, the dissociation constant is lower than $10^{-6}$ M, more preferably, lower than $10^{-7}$ M. Most preferably, the dissociation constant is lower than $10^{-8}$ M. Other ways of describing the affinity between a ligand and its target protein are the association constant (Ka), the inhibition constant (Ki), or indirectly by evaluating the potency of ligands by measuring the half maximal inhibitory concentration (IC50) or half maximal effective concentration (EC50). It will be appreciated that within the scope of the disclosure, the term "affinity" is used in the context of a binding domain that binds a conformational epitope of a target GPCR as well as in the context of a test compound (as defined further herein) that binds to the chimeric polypeptide of the disclosure, more particularly to an orthosteric or allosteric site of a target GPCR comprised in the chimeric polypeptide.

It should be noted that, in intramolecular interactions, such as the specific interaction of the binding domain moiety to the GPCR moiety of the chimeric polypeptide of the disclosure, the two interacting groups are contained within a single molecule. The dissociation constant between the binding domain and the target, might be known when they are individual molecules, but for an intramolecular interaction, their concentration within the solution is irrelevant. Instead, it is the "effective concentration" of the two groups within the macromolecule that is important for the intramolecular interaction. The term "effective intramolecular concentration" or "effective molarity" ($M_{eff}$), as used herein, refers to the effective concentration and can be calculated as $K_d^{inter}/K_d^{intra}$, wherein the dissociation constant $K_d^{intra}$, which is dimensionless, is the dissociation constant that is used to describe an intramolecular reaction, which is a fusion of a target GPCR and a binding domain, and wherein $K_d^{inter}$, which has units of concentration (e.g., molarity), is the dissociation constant for an analogous intermolecular interaction, which is a non-covalent complex of a binding domain and a target GPCR. The effective molarity will depend upon the structure of the macromolecule, in particular the extent to which it brings the two reactants together or keeps them apart, plus the environment in which the two groups are kept. The effective molarity for the intramolecular reaction will be essentially zero if the macromolecular structure keeps the two groups apart, which is the case when a binding domain is not directed against and/or is not capable of specifically binding (as defined further herein) to a target GPCR. At the other extreme, when the macromolecular structure keeps the two groups in the correct proximity and orientation for reaction, their effective molarity can be extremely high, up to $10^{10}$ M, concentrations that are not feasible with two independent molecules. According to the disclosure, this is the case when a binding domain is capable of specifically binding (as defined further herein) to a target GPCR. Such values are predicted by theoretical considerations and are also observed experimentally, from the ratio of the rate or equilibrium constants for the same reaction when the groups are on the same molecule and on separate molecules.

The term "specificity," as used herein, refers to the ability of a binding domain, in particular an immunoglobulin or an immunoglobulin fragment, such as a VHH or Single-domain antibody, to bind preferentially to one antigen, versus a different antigen, and does not necessarily imply high affinity.

The terms "specifically bind" and "specific binding," as used herein, generally refers to the ability of a binding domain, in particular an immunoglobulin, such as an antibody, or an immunoglobulin fragment, such as a VHH or Single-domain antibody, to preferentially bind to a particular antigen that is present in a homogeneous mixture of different antigens. In certain embodiments, a specific binding interaction will discriminate between desirable and undesirable antigens in a sample, in some embodiments more than about 10 to 100-fold or more (e.g., more than about 1000- or 10,000-fold). Within the context of the spectrum of conformational states of GPCRs, the terms particularly refer to the ability of a binding domain (as defined herein) to preferentially recognize and/or bind to a particular conformational state of a GPCR as compared to another conformational state. Accordingly, as used herein, the term "conformation-selective binding domain" in the context of the disclosure refers to a binding domain that binds to a target GPCR in a conformation-selective manner. A binding domain that selectively binds to a particular conformation of a GPCR refers to a binding domain that binds with a higher affinity to a GPCR in a subset of conformations than to other conformations that the GPCR may assume. One of skill in the art will recognize that binding domains that selectively bind to a particular conformation of a GPCR will stabilize or retain the GPCR it this particular conformation. For example, an active state conformation-selective binding domain will preferentially bind to a GPCR in an active conformational state and will not or to a lesser degree bind to a GPCR in an inactive conformational state, and will thus have a higher affinity for the active conformational state, or vice versa. The terms "specifically bind," "selectively bind,"

"preferentially bind," and grammatical equivalents thereof, are used interchangeably herein. The terms "conformational specific" or "conformational selective" are also used interchangeably herein.

The term "compound" or "test compound" or "candidate compound" or "drug candidate compound," as used herein, are intended to have the same meaning and describe any molecule, either naturally occurring or synthetic that is tested in an assay, such as a screening assay for drug discovery purposes. As such, these compounds comprise organic or inorganic compounds. The compounds include small molecules, polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies, antibody fragments or antibody conjugates. Test compounds can also be protein scaffolds or synthetic scaffolds. For high-throughput purposes, test compound libraries may be used, such as combinatorial or randomized libraries that provide a sufficient range of diversity. Examples include, but are not limited to, natural compound libraries, allosteric compound libraries, peptide libraries, antibody fragment libraries, synthetic compound libraries, fragment-based libraries, phage-display libraries, and the like. A more detailed description can be found further in the specification.

As used herein, the term "ligand" means a molecule that binds to a polypeptide, in particular a GPCR. A ligand may be, without the purpose of being limitative, a protein, a (poly)peptide, a lipid, a small molecule, a protein scaffold, a nucleic acid, an ion, a carbohydrate, an antibody or an antibody fragment. A ligand may be synthetic or naturally occurring. A ligand also includes a "native ligand," which is a ligand that is an endogenous, natural ligand for a native protein. Within the context of the disclosure, a ligand means a molecule that binds to a GPCR, either at the intracellular site or extracellular site and/or at the transmembrane domains. Usually, but not necessarily, a GPCR will adopt a particular conformation upon binding of a ligand. Thus, a ligand may also be a "conformation-selective ligand" or "conformation-specific ligand." The team includes agonists, full agonists, partial agonists, and inverse agonists, binding at either the orthosteric site or at an allosteric site. For the sake of clarity, the term "conformation-selective ligand" or "conformation-specific ligand" does not include a neutral antagonist, since a neutral antagonist does not selectively bind a particular conformation of a GPCR.

An "orthosteric ligand," as used herein, refers to a ligand (both natural and synthetic), that binds to the active site of a receptor, such as a GPCR, and are further classified according to their efficacy or in other words to the effect they have on signaling through a specific pathway. As used herein, an "agonist" refers to a ligand that, by binding a receptor protein, increases the receptor's signaling activity. Full agonists are capable of maximal protein stimulation; partial agonists are unable to elicit full activity even at saturating concentrations. Partial agonists can also function as "blockers" by preventing the binding of more robust agonists. An "antagonist," also referred to as a "neutral antagonist," refers to a ligand that binds a receptor without stimulating any activity. An "antagonist" is also known as a "blocker" because of its ability to prevent binding of other ligands and, therefore, block agonist-induced activity. Further, an "inverse agonist" refers to an antagonist that, in addition to blocking agonist effects, reduces a receptor's basal or constitutive activity below that of the unliganded protein.

Ligands, as used herein, may also be "biased ligands" with the ability to selectively stimulate a subset of a receptor's signaling activities, for example, in the case of GPCRs the selective activation of G-protein or β-arrestin function. Such ligands are known as "biased ligands," "biased agonists" or "functionally selective agonists." More particularly, ligand bias can be an imperfect bias characterized by a ligand stimulation of multiple receptor activities with different relative efficacies for different signals or can be a perfect bias characterized by a ligand stimulation of one receptor protein activity without any stimulation of another known receptor protein activity.

Another kind of ligands is known as allosteric regulators. "Allosteric regulators" or otherwise "allosteric modulators," "allosteric ligands" or "effector molecules," as used herein, refer to ligands that bind at an allosteric site (that is, a regulatory site physically distinct from the protein's active site) of a receptor protein such as a GPCR. In contrast to orthosteric ligands, allosteric modulators are non-competitive because they bind receptor proteins at a different site and modify their function even if the endogenous ligand also is binding. Allosteric regulators that enhance the protein's activity are referred to herein as "allosteric activators" or "positive allosteric modulators" (PAMs), whereas those that decrease the protein's activity are referred to herein as "allosteric inhibitors" or otherwise "negative allosteric modulators" (NAMs).

As used herein, the terms "determining," "measuring," "assessing," "monitoring" and "assaying" are used interchangeably and include both quantitative and qualitative determinations.

As used herein, the terms "complementarity determining region" or "CDR" within the context of antibodies refer to variable regions of either H (heavy) or L (light) chains (also abbreviated as VH and VL, respectively) and contains the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains. Immunoglobulin single variable domains, in particular VHHs or Nanobodies, generally comprise a single amino acid chain that can be considered to comprise 4 "framework sequences or regions" or FRs and 3 "complementarity determining regions" or CDRs. The Nanobodies have 3 CDR regions, each non-contiguous with the others (termed CDR1, CDR2, CDR3). The delineation of the FR and CDR sequences can, for example, be based on the IMGT unique numbering system for V-domains and V-like domains (Lefranc et al., 2003).

Chimeric Polypeptides

A first aspect of the disclosure relates to a chimeric polypeptide comprising a G protein-coupled receptor (GPCR) fused to a binding domain, wherein the binding domain is directed against and/or specifically binds to the GPCR. The disclosure, thus, provides a chimeric polypeptide, which is a fusion protein of at least two moieties, in particular at least a GPCR moiety and a binding domain moiety, wherein the binding domain is directed against and/or specifically binds to the GPCR.

In general, the choice of the GPCR moiety forming part of the chimeric polypeptide is not critical to the disclosure, and will typically be selected according to the intended use and application. A prerequisite of the binding domain moiety is its capability to specifically bind (as defined herein) to the GPCR of choice. Thus, the binding domain moiety may generally be directed against any desired GPCR, and may in particular be directed against any conformational epitope (as defined herein) of any GPCR. A binding domain that specifically binds to a "conformational epitope" specifically binds to a tertiary (i.e., three-dimensional) structure of a folded protein, and binds at much reduced (i.e., by a factor of at least 2, 5, 10, 50 or 100) affinity to the linear (i.e., unfolded, denatured) form of the protein. In particular, the conformational epitope can be part of an intracellular or extracellular region, or an intramembraneous region, or a domain or loop structure of any desired GPCR. Thus, according to particular embodiments, the binding domain moiety may be directed against an extracellular region, domain, loop or other extracellular conformational epitope of any desired GPCR, but is preferably directed against the extracellular parts of the transmembrane domains or more preferably against the extracellular loops that link the transmembrane domains. Alternatively, the binding domain moiety may be directed against an intracellular region, domain, loop or other intracellular conformational epitope of any desired GPCR, but is preferably directed against one of the intracellular parts of the transmembrane domains or more preferably against the intracellular loops that link the transmembrane domains. In other specific embodiments, the binding domain moiety may be directed against a conformational epitope that forms part of the binding site of a natural ligand including, but not limited to, an endogenous orthosteric agonist. In still other embodiments, the binding domain moiety may be directed against a conformational epitope, in particular an intracellular epitope, that is comprised in a binding site for a downstream signaling protein including, but not limited to, a G protein binding site, a β-arrestin binding site.

According to a preferred embodiment, the chimeric polypeptide of the disclosure comprises a GPCR fused to a binding domain wherein, upon binding of the binding domain to the GPCR in an intramolecular reaction, the GPCR is stabilized in a particular conformation without the need for an additional ligand. Preferably, the chimeric polypeptide of the disclosure comprises a GPCR that is stabilized by the binding domain in a functional conformation, as defined herein. With the term "stabilized," as defined hereinbefore, is meant an increased stability of a GPCR with respect to the structure (e.g., conformational state) and/or particular biological activity (e.g., intracellular signaling activity, ligand binding affinity, . . . ). In relation to increased stability with respect to structure and/or biological activity, this may be readily determined either by means of physical methods such as X-ray crystallography, NMR, or spin labeling, among other methods or by a functional assay for activity (e.g., $Ca^{2+}$ release, cAMP generation or transcriptional activity, β-arrestin recruitment, . . . ) or ligand binding, among other methods. The term "stabilize" also includes increased thermostability of the GPCR under non-physiological conditions induced by denaturants or denaturing conditions. The term "thermostabilize," "thermostabilizing," "increasing the thermostability of," as used herein, refers to the functional rather than to the thermodynamic properties of a GPCR and to the protein's resistance to irreversible denaturation induced by thermal and/or chemical approaches including, but not limited to, heating, cooling, freezing, chemical denaturants, pH, detergents, salts, additives, proteases or temperature. Irreversible denaturation leads to the irreversible unfolding of the functional conformations of the protein, loss of biological activity and aggregation of the denatured protein. In relation to an increased stability to heat, this can be readily determined by measuring ligand binding or by using spectroscopic methods such as fluorescence, CD or light scattering that are sensitive to unfolding at increasing temperatures. It is preferred that the binding domain moiety is capable of increasing the stability as measured by an increase in the thermal stability of a GPCR in a functional conformational state with at least 2° C., at least 5° C., at least 8° C., and more preferably at least 10° C. or 15° C. or 20° C. In relation to an increased stability to a detergent or to a chaotrope, typically the GPCR is incubated for a defined time in the presence of a test detergent or a test chaotropic agent and the stability is determined using, for example, ligand binding or a spectroscoptic method, optionally at increasing temperatures as discussed above. Otherwise, the binding domain moiety is capable of increasing the stability to extreme pH of a functional conformational state of a GPCR. In relation to an extreme of pH, a typical test pH would be chosen, for example, in the range 6 to 8, the range 5.5 to 8.5, the range 5 to 9, the range 4.5 to 9.5, more specifically in the range 4.5 to 5.5 (low pH) or in the range 8.5 to 9.5 (high pH). The term "(thermo)stabilize," "(thermo)stabilizing," "increasing the (thermo)stability of," as used herein, applies to GPCRs embedded in lipid particles or lipid layers (for example, lipid monolayers, lipid bilayers, and the like) and to GPCRs that have been solubilized in detergent.

It is, thus, particularly envisaged that the chimeric polypeptides of the disclosure comprises a GPCR moiety that is stabilized in a functional conformation upon binding of the binding domain moiety. According to a preferred embodiment of the disclosure, the GPCR moiety is stabilized in an active conformation upon binding of a binding domain that is selective for an active conformation. The term "active conformation," as used herein, refers to a spectrum of receptor conformations that upon binding of a ligand allows signal transduction towards an intracellular effector system, including G protein dependent signaling and G protein-independent signaling (e.g., β-arrestin signaling). An "active conformation," thus, encompasses a range of ligand-specific conformations, including an agonist-bound active conformation, a partial agonist-bound active conformation or a biased agonist conformation that induces the cooperative binding of an intracellular effector protein. In another preferred embodiment, the GPCR moiety is stabilized in an inactive conformation upon binding of a binding domain that is conformation-selective for an inactive conformation. The term "inactive conformation," as used herein, refers to a spectrum of receptor conformations that does not allow or blocks signal transduction towards an intracellular effector system. An "inactive conformation," thus, encompasses a range of ligand-specific conformations, including an inverse agonist-bound inactive conformation that prevents the cooperative binding of an intracellular effector protein. It will be understood that the site of binding of the ligand is not critical for obtaining an active or inactive conformation. Hence, orthosteric ligands as well as allosteric modulators may equally be capable of stabilizing a GPCR in an active or inactive conformation. Thus, according to a particular embodiment of the disclosure, the binding domain moiety that is capable of stabilizing the GPCR moiety may bind at the orthosteric site or at an allosteric site. In other specific embodiments, the binding domain moiety that is capable of stabilizing the GPCR moiety may be a binding domain that is selective for an agonist-bound active conformation, or that is selective for a partial agonist-bound active conformation or that is selective for a biased agonist-bound functional conformation binding domain, or that is selective for an inverse agonist-bound inactive conformation.

It will, thus, be understood that the chimeric polypeptides of the disclosure are conformationally constrained proteins since the GPCR moiety of the fusion is stabilized in a particular functional conformation, due to the high local concentration of the tethered binding domain. To illustrate this further, without the purpose of being limitative, a chimeric polypeptide of the disclosure comprising a GPCR that is stabilized in an active conformation will have an increased or enhanced affinity for an agonist, more particularly for a full agonist, a partial agonist or a biased agonist, as compared to the to the corresponding non-fused GPCR or as compared to a chimeric polypeptide of the corresponding GPCR fused to a mock binding moiety (also referred to as control binding moiety or irrelevant binding moiety, and that is not directed to and/or does not specifically bind to the GPCR). Also, a chimeric polypeptide of the disclosure comprising a GPCR that is stabilized in an active conformation will have a decreased affinity for an inverse agonist, as compared to the corresponding non-fused GPCR or to a chimeric polypeptide of the corresponding GPCR fused to a mock binding moiety. In contrast, a chimeric polypeptide of the disclosure comprising a GPCR that is stabilized in an inactive conformation will have an enhanced affinity for an inverse agonist and/or will have a decreased affinity for an agonist as compared to the corresponding non-fused GPCR or to a chimeric polypeptide of the corresponding GPCR fused to a mock binding moiety. An increase or decrease in affinity for a ligand may be directly measured by and/or calculated from a decrease or increase, respectively in $EC_{50}$, $IC_{50}$, $K_d$, $K_i$ or any other measure of affinity or potency known to one of skill in the art. Preferably, the affinity of a chimeric polypeptide of the disclosure for a ligand is increased or decreased at least 2 fold, at least 5 fold, at least 10 fold, at least 50 fold, and more preferably at least 100 fold, at least 200 fold, at least 300 fold, at least 400 fold, at least 500 fold, even more preferably at least 1000 fold or 2000 fold or more, upon binding to the constrained GPCR. It will be appreciated that affinity measurements for conformation-selective ligands that trigger/inhibit particular signaling pathways may be carried with any type of ligand, including natural ligands, small molecules, as well as biologicals; with orthosteric ligands as well as allosteric modulators; with single compounds as well as compound libraries; with lead compounds or fragments; etc.

Further, the way the different moieties that form part of the chimeric polypeptides as described are fused to each other will typically depend on both the type of GPCR and the characteristics of the binding domain (e.g., conformational epitope to which it binds). As is known by the person skilled in the art, GPCRs are characterized by an extracellular N-terminus, followed by seven transmembrane α-helices connected by three intracellular and three extracellular loops, and finally an intracellular C-terminus (see also further herein). Depending on the site of binding (extracellular or intracellular or transmembrane), the binding domain moiety will preferably be fused to the N-terminal end of the GPCR or to the C-terminal end. Preferably, a binding domain that binds the GPCR at an intracellular site will be fused to the C-terminus of the GPCR. Likewise, a binding domain that binds the GPCR at an extracellular site will be fused to the N-terminus of the GPCR. The binding domain moiety will be fused with its C-terminal end to N-terminal end of the GPCR or the binding domain can be fused with its N-terminal end to the C-terminal end of the GPCR. Further, the fusion may be a direct fusion of the sequences or it may be an indirect fusion, e.g., with intervening amino acid sequences or linker sequences, as described further herein. A person skilled in the art will know how to design a fusion construct. If available, one will make use of the atomic structure of the GPCR separately and/or the atomic structure of the binding domain separately and/or the atomic structure of the GPCR in complex with the binding domain. Alternatively, the GPCR could be linked to the binding domain using intein-mediated protein splicing (Muralidharan and Muir 2006) or sortagging (Popp et al., 2007) or other chemoenzymatic methods for site-specific labeling or engineering of proteins with small molecules or other proteins, for example, as described in Chen and Ting (2005) and Rabuka (2010) and incorporated herein by reference.

Particular embodiments of the different moieties that form part of the chimeric polypeptides of the disclosure will be further detailed here below.

GPCR Moiety

The chimeric polypeptide of the disclosure comprises at least two polypeptide components, one of which is a GPCR. As a GPCR, any GPCR of interest can be used. The skilled person can choose a suitable GPCR depending on the intended application, as described further herein. In the same line, and depending on the intended use, a GPCR from any organism may be selected, such as fungus (including yeast), nematode, virus, insect, plant, bird (e.g., chicken, turkey), reptile, or mammal (e.g., a mouse, rat, rabbit, hamster, gerbil, dog, cat, goat, pig, cow, horse, whale, monkey, camelid, or human).

"G-protein coupled receptors," or "GPCRs," as used herein, are well-known by the skilled person and refer to polypeptides that share a common structural motif, having seven regions of between 22 to 24 hydrophobic amino acids that form seven alpha helices, each of which spans the membrane. Each span is identified by number, i.e., transmembrane-1 (TM1), transmembrane-2 (TM2), etc. The transmembrane helices are joined by regions of amino acids between transmembrane-2 and transmembrane-3, transmembrane-4 and transmembrane-5, and transmembrane-6 and transmembrane-7 on the exterior, or "extracellular" side, of the cell membrane, referred to as "extracellular" regions 1, 2 and 3 (EC1, EC2 and EC3), respectively. The transmembrane helices are also joined by regions of amino acids between transmembrane-1 and transmembrane-2, transmembrane-3 and transmembrane-4, and transmembrane-5 and transmembrane-6 on the interior, or "intracellular" side, of the cell membrane, referred to as "intracellular" regions 1, 2 and 3 (IC1, IC2 and IC3), respectively. The "carboxy" ("C") terminus of the receptor lies in the intracellular space within the cell, and the "amino" ("N") terminus of the receptor lies in the extracellular space outside of the cell. Any of these regions are readily identifiable by analysis of the primary amino acid sequence of a GPCR.

GPCR structure and classification is generally well known in the art and further discussion of GPCRs may be found in Probst et al., 1992; Marchese et al., 1994; Lagerströom & Schiöth, 2008; Rosenbaum et al., 2009; and the following books: Jurgen Wess (Ed) Structure-Function Analysis of G Protein-Coupled Receptors published by Wiley-Liss (1$^{st}$ edition; Oct. 15, 1999); Kevin R. Lynch (Ed) Identification and Expression of G Protein-Coupled Receptors published by John Wiley & Sons (March 1998) and Tatsuya Haga (Ed), G Protein-Coupled Receptors, published by CRC Press (Sep. 24, 1999); and Steve Watson (Ed) G-Protein Linked Receptor Factsbook, published by Academic Press (1st edition; 1994). GPCRs can be grouped on the basis of sequence homology and functional similarity into several families, each of which can be used in the creation and use of the chimeric polypeptides of the disclosure. Most of the human GPCRs can be found in five main families, termed Glutamate, Rhodopsin, Adhesion, Frizzled/Taste2 and Secretin (Fredriksson et al., 2003). Members of the Rhodopsin family corresponding to class A (Kolakowski, 1994) or Class 1 (Foord et al., 2005) in older classification systems only have small extracellular loops and the interaction of the ligands occurs with residues within the transmembrane cleft. This is by far the largest group (>90% of the GPCRs) and contains receptors for odorants, small molecules such as catecholamines and amines, (neuro)peptides and glycoprotein hormones. Rhodopsin, a representative of this family, is the first GPCR for which the structure has been solved (Palczewski et al., 2000). β2AR, the first receptor interacting with a diffusible ligand for which the structure has been solved (Rosenbaum et al., 2007) also belongs to this family. Based on phylogenetic analysis, class B GPCRs or Class 2 (Foord et al., 2005) receptors have recently been subdivided into two families: adhesion and secretin (Fredriksson et al., 2003). Adhesion and secretin receptors are characterized by a relatively long amino terminal extracellular domain involved in ligand-binding. Little is known about the orientation of the transmembrane domains, but it is probably quite different from that of rhodopsin. Ligands for these GPCRs are hormones, such as glucagon, secretin, gonadotropin-releasing hormone and parathyroid hormone. The Glutamate family receptors (Class C or Class 3 receptors) also have a large extracellular domain, which functions like a "Venus fly trap" since it can open and close with the agonist bound inside. Family members are the metabotropic glutamate, the $Ca^{2+}$-sensing and the γ-aminobutyric acid (GABA)-B receptors.

Thus, according to particular embodiments of the disclosure, the chimeric polypeptide of the disclosure comprises a GPCR that is chosen from the group comprising a GPCR of the Glutamate family of GPCRs, a GPCR of the Rhodopsin family of GPCRs, a GPCR of the Adhesion family of GPCRs, a GPCR of the Frizzled/Taste2 family of GPCRs, and a GPCR of the Secretin family of GPCRs. Preferably, the GPCR comprised in the chimeric polypeptide is a mammalian protein, or a plant protein, or a microbial protein, or a viral protein, or an insect protein. Even more preferably, the GPCR is a human protein.

More specifically, GPCRs include, without limitation, 5-hydroxytryptamine receptors, acetylcholine receptors (muscarinic), adenosine receptors, adrenoceptors, anaphylatoxin receptors, angiotensin receptors, apelin receptors, bile acid receptors, bombesin receptors, bradykinin receptors, cannabinoid receptors, chemokine receptors, cholecystokinin receptors, dopamine receptors, endothelin receptors, estrogen (G protein coupled) receptors, formylpeptide receptors, free fatty acid receptors, galanin receptors, ghrelin receptors, glycoprotein hormone receptors, gonadotrophin-releasing hormone receptors, histamine receptors, KiSS1-derived peptide receptor, leukotriene receptors, lysophospholipid receptors, melanin-concentrating hormone receptors, melanocortin receptors, melatonin receptors, motilin receptors, neuromedin U receptors, neuropeptide FF/neuropeptide AF receptors, neuropeptide S receptors, neuropeptide W/neuropeptide B receptors, neuropeptide Y receptors, neurotensin receptors, nicotinic acid receptor family, opioid receptors, orexin receptors, P2Y receptors, peptide P518 receptor, platelet-activating factor receptor, prokineticin receptors, prolactin-releasing peptide receptor, prostanoid receptors, protease-activating receptors, relaxin family peptide receptors, somatostatin receptors, tachykinin receptors, thyrotropin-releasing hormone receptor, trace amine receptor, urotensin receptor, vasopressin and oxytocin receptors, class A orphans, non-signaling 7TM chemokine-binding proteins, calcitonin receptors, corticotropin-releasing factor receptors, glucagon receptor family, parathyroid hormone receptors, VIP and PACAP receptors, class B orphans, calcium-sensing receptors, GABA B receptors, GPRC5 receptors, metabotropic glutamate receptors, class C orphans, Frizzled receptors, the rhodopsins and other G-protein coupled seven transmembrane segment receptors. GPCRs also include these GPCR receptors associated with each other as homomeric or heteromeric dimers or as higher-order oligomers. The amino acid sequences (and the nucleotide sequences of the cDNAs which encode them) of GPCRs are readily available, for example, by reference to GenBank (on the World Wide Web at ncbi.nlm.nih.gov/entrez). HGNC standardized nomenclature to human genes; accession numbers of different isoforms from different organisms are available from Uniprot (on the World Wide Web at uniprot.org). Moreover, a comprehensive overview of receptor nomenclature, pharmacological, functional and pathophysiological information on GPCRs can be retrieved from the IUPHAR database (on the World Wide Web at iuphar-db.org/).

According to a preferred embodiment, the GPCR that forms part of the chimeric polypeptide of the disclosure, is chosen from the group comprising the adrenergic receptors, preferably the α adrenergic receptors, such as the α1 adrenergic receptors and the α2 adrenergic receptors, and the β3 adrenergic receptors, such as the β1 adrenergic receptors, the β2 adrenergic receptors and the β3 adrenergic receptors; or from the group comprising the muscarinic receptors, preferably the M1 muscarinic receptors, the M2 muscarinic receptors, the M3 muscarinic receptors, the M4 muscarinic receptors and the M5 muscarinic receptors; or from the group comprising the opioid receptor family, preferably the μ opioid receptors (mu or MOP or Mor1), the δ opioid receptors (delta or DOP), the κ opioid receptors (kappa or KOP), the NOP opioid receptors, all of which are well known in the art.

It will be understood that, depending on the purpose and application, the GPCR comprised in the fusion protein may be a naturally occurring or non-naturally occurring (i.e., altered by man) receptor. The term "naturally-occurring" in reference to a GPCR means a GPCR that is naturally produced. In particular, wild-type polymorphic variants and isoforms of GPCRs, as well as orthologs across different species are examples of naturally occurring proteins, and are found, for example, and without limitation, in a mammal, more specifically in a human, or in a virus, or in a plant, or in an insect, amongst others). Such GPCRs are found in nature. In addition, the term is intended to encompass wild-type polymorphic variants and certain other variants of the $β_2$ adrenergic receptor from a particular species, including mutants. For example, a "human $β_2$ adrenergic receptor" has an amino acid sequence that is at least 95% identical to (e.g., at least 95% or at least 98% identical to) the naturally occurring "human $β_2$ adrenoreceptor" of GenBank accession number NP_000015. Or also, a "human muscarinic acetylcholine receptor M2" has an amino acid sequence that is at least 95% identical to (e.g., at least 95% or at least 98% identical to) the naturally occurring "human muscarinic acetylcholine receptor M2" of GenBank accession number AAA51570.1. Or also, a "human mu opioid receptor" has an amino acid sequence that is at least 95% identical to (e.g., at least 95% or at least 98% identical to) the naturally occurring "human mu opioid receptor" of GenBank accession number NP_000905. The term "non-naturally occurring" in reference to a GPCR means a GPCR that is not naturally-occurring. Wild-type GPCRs that have been mutated and variants of naturally-occurring GPCRs are examples of non-naturally occurring GPCRs. Non-naturally occurring GPCR may have an amino acid sequence that is at least 80% identical to, at least 90% identical to, at least 95% identical to or at least 99% identical to, a naturally-occurring GPCR. In certain circumstances, it may be advantageous that the GPCR comprised in the chimeric polypeptide is a non-naturally occurring protein. For example, and for illustration purposes only, to increase the probability of obtaining crystals of the chimeric polypeptide comprising the GPCR stabilized in a particular conformation, it might be desired to perform some protein engineering without or only minimally affecting the conformation (e.g., active conformation with increased affinity for agonists). Or, alternatively or additionally, to increase cellular expression levels of a GPCR, or to increase the stability, one might also consider introducing certain mutations in the GPCR of interest. Non-limiting examples of non-naturally occurring GPCRs include, without limitation, GPCRs that have been made constitutively active through mutation, GPCRs with a loop deletion, GPCRs with an N- and/or C-terminal deletion, GPCRs with a substitution, an insertion or addition, or any combination thereof, in relation to their amino acid or nucleotide sequence, or other variants of naturally-occurring GPCRs. Also comprised within the scope of the disclosure are target GPCRs comprising a chimeric or hybrid GPCR, for example, a chimeric GPCR with an N- and/or C-terminus from one GPCR and loops of a second GPCR, or comprising a GPCR fused to a moiety, such as T4 lysozyme, Flavodoxin, Xylanase, Rubredoxin or cytochrome b as an utility in GPCR crystallization (Chun et al., 2012 and also described in patent applications WO2012/158555, WO2012/030735, WO2012/148586).

According to specific embodiments within the scope of the disclosure, a non-naturally occurring GPCR, as comprised in the chimeric polypeptide, may have an amino acid sequence that is at least 80% identical to, at least 90% identical to, at least 95% identical to, at least 97% identical to, or at least 99% identical to, a naturally-occurring GPCR. Further, it will be appreciated that the disclosure also envisages GPCRs with a loop deletion, or an N- and/or C-terminal deletion, or a substitution, or an insertion or addition in relation to its amino acid or nucleotide sequence, or any combination thereof (as defined hereinbefore, and see also Example section).

Binding Domain Moiety

The chimeric polypeptide of the disclosure comprises at least two polypeptide moieties, one of which is a GPCR, as described hereinbefore, and another one which is a binding domain that is directed against and/or specifically binds to the GPCR.

The term "binding domain," as used herein, means the whole or part of a proteinaceous (protein, protein-like or protein containing) molecule that is capable of binding using specific intermolecular interactions to a GPCR. According to a particular embodiment, the term "binding domain" does not include a naturally-occurring binding partner of a GPCR, e.g., a G protein, an arrestin, an endogenous ligand; or variants or derivatives (including fragments) thereof. More specifically, the term "binding domain" refers to a polypeptide, more particularly a protein domain. A protein binding domain is an element of overall protein structure that is self-stabilizing and often folds independently of the rest of the protein chain. Binding domains vary in length from between about 25 amino acids up to 500 amino acids and more. Many binding domains can be classified into folds and are recognizable, identifiable, 3-D structures. Some folds are so common in many different proteins that they are given special names. Non-limiting examples are binding domains selected from a 3- or 4-helix bundle, an armadillo repeat domain, a leucine-rich repeat domain, a PDZ domain, a SUMO or SUMO-like domain, a cadherin domain, an immunoglobulin-like domain, phosphotyrosine-binding domain, pleckstrin homology domain, src homology 2 domain, amongst others. A binding domain can thus be derived from a naturally occurring molecule, e.g., from components of the innate or adaptive immune system, or it can be entirely artificially designed.

In general, a binding domain can be immunoglobulin-based or it can be based on domains present in proteins including, but not limited to, microbial proteins, protease inhibitors, toxins, fibronectin, lipocalins, single chain antiparallel coiled coil proteins or repeat motif proteins. Particular examples of binding domains which are known in the art include, but are not limited to: antibodies, heavy chain antibodies (hcAb), single domain antibodies (sdAb), minibodies, the variable domain derived from camelid heavy chain antibodies (VHH or Nanobodies), the variable domain of the new antigen receptors derived from shark antibodies (VNAR), alphabodies, protein A, protein G, designed ankyrin-repeat domains (DARPins), fibronectin type III repeats, anticalins, knottins, engineered CH2 domains (nanoantibodies), engineered SH3 domains, affibodies, peptides and proteins, lipopeptides (e.g., pepducins) (see, e.g., Gebauer & Skerra, 2009; Skerra, 2000; Starovasnik et al., 1997; Binz et al., 2004; Koide et al., 1998; Dimitrov, 2009; Nygren et al., 2008; WO2010066740). Frequently, when generating a particular type of binding domain using selection methods, combinatorial libraries comprising a consensus or framework sequence containing randomized potential interaction residues are used to screen for binding to a molecule of interest, such as a protein.

According to a preferred embodiment, it is particularly envisaged that the binding domain that forms part of the chimeric polypeptide of the disclosure is derived from an innate or adaptive immune system. Preferably, the binding domain is derived from an immunoglobulin. Preferably, the binding domain, according to the disclosure, is derived from an antibody or an antibody fragment. The term "antibody" (Ab) refers generally to a polypeptide encoded by an immunoglobulin gene, or a functional fragment thereof, that specifically binds and recognizes an antigen, and is known to the person skilled in the art. An antibody is meant to include a conventional four-chain immunoglobulin, comprising two identical pairs of polypeptide chains, each pair having one "light" (about 25 kDa) and one "heavy" chain (about 50 kDa). Typically, in conventional immunoglobulins, a heavy chain variable domain (VH) and a light chain variable domain (VL) interact to form an antigen binding site. The term "antibody" is meant to include whole antibodies, including single-chain whole antibodies, and antigen-binding fragments. In some embodiments, antigen-binding fragments may be antigen-binding antibody fragments that include, but are not limited to, Fab, Fab' and F(ab')2, Fd, single-chain Fvs (scFv), single-chain antibodies, disulfide-linked Fvs (dsFv) and fragments comprising or consisting of either a VL or VH domain, and any combination of those or any other functional portion of an immunoglobulin peptide capable of binding to the target antigen. The term "antibodies" is also meant to include heavy chain only antibodies, or fragments thereof, including immunoglobulin single variable domains, as defined further herein.

The term "immunoglobulin single variable domain" defines molecules wherein the antigen binding site is present on, and formed by, a single immunoglobulin domain (which is different from conventional immunoglobulins or their fragments, wherein typically two immunoglobulin variable domains interact to form an antigen binding site). It should, however, be clear that the term "immunoglobulin single variable domain" does comprise fragments of conventional immunoglobulins wherein the antigen binding site is formed by a single variable domain. Preferably, the binding domain moiety within the scope of the disclosure is an immunoglobulin single variable domain.

Generally, an immunoglobulin single variable domain will be an amino acid sequence comprising 4 framework regions (FR1 to FR4) and 3 complementary determining regions (CDR1 to CDR3), preferably according to the following formula (1): FR1-CDR1-FR2-CDR2-FR3-CDR3-FR4 (1), or any suitable fragment thereof (which will then usually contain at least some of the amino acid residues that form at least one of the complementarity determining regions). Immunoglobulin single variable domains comprising 4 FRs and 3 CDRs are known to the person skilled in the art and have been described, as a non-limiting example, in Wesolowski et al., 2009. Typical, but non-limiting, examples of immunoglobulin single variable domains include light chain variable domain sequences (e.g., a VL domain sequence) or a suitable fragment thereof, or heavy chain variable domain sequences (e.g., a VH domain sequence or VHH domain sequence) or a suitable fragment thereof, as long as it is capable of forming a single antigen binding unit. Thus, according to a preferred embodiment, the binding domain moiety is an immunoglobulin single variable domain that is a light chain variable domain sequence (e.g., a VL domain sequence) or a heavy chain variable domain sequence (e.g., a VH domain sequence); more specifically, the immunoglobulin single variable domain is a heavy chain variable domain sequence that is derived from a conventional four-chain antibody or a heavy chain variable domain sequence that is derived from a heavy chain antibody. The immunoglobulin single variable domain may be a domain antibody, or a single domain antibody, or a "dAB" or dAb, or a Single-domain antibody (as defined herein), or another immunoglobulin single variable domain, or any suitable fragment of any one thereof. For a general description of single domain antibodies, reference is made to the following book: "Single domain antibodies," Methods in Molecular Biology, Eds. Saerens and Muyldermans, 2012, Vol. 911. The immunoglobulin single variable domains generally comprise a single amino acid chain that can be considered to comprise 4 "framework sequences" or FR's and 3 "complementary determining regions" or CDR's, as defined hereinbefore. It should be clear that framework regions of immunoglobulin single variable domains may also contribute to the binding of their antigens (Desmyter et al., 2002; Korotkov et al., 2009). The delineation of the CDR sequences (and thus also the FR sequences) can be based on the IMGT unique numbering system for V-domains and V-like domains (Lefranc et al., 2003). Alternatively, the delineation of the FR and CDR sequences can be done by using the Kabat numbering system as applied to VHH domains from Camelids in the article of Riechmann and Muyldermans (2000).

It should be noted that the immunoglobulin single variable domains as binding domain moiety in their broadest sense are not limited to a specific biological source or to a specific method of preparation. The term "immunoglobulin single variable domain" encompasses variable domains of different origin, comprising mouse, rat, rabbit, donkey, human, shark, camelid variable domains. According to specific embodiments, the immunoglobulin single variable domains are derived from shark antibodies (the so-called immunoglobulin new antigen receptors or IgNARs), more specific from naturally occurring heavy chain shark antibodies, devoid of light chains, and are known as VNAR domain sequences. Preferably, the immunoglobulin single variable domains are derived from camelid antibodies. More preferably, the immunoglobulin single variable domains are derived from naturally occurring camelid heavy chain only antibodies, devoid of light chains, and are known as VHH domain sequences or Nanobodies.

According to a particularly preferred embodiment, the binding domain moiety as comprised in the chimeric polypeptide of the disclosure is an immunoglobulin single variable domain that is a NANOBODY®, as defined further herein, and including, but not limited to, a VHH. The term "NANOBODY® or single domain antibody" (Nb), as used herein, is a single domain antigen binding fragment. It particularly refers to a single variable domain derived from naturally occurring heavy chain only antibodies and is known to the person skilled in the art. NBs are usually derived from heavy chain only antibodies (devoid of light chains) seen in camelids (Hamers-Casterman et al., 1993; Desmyter et al., 1996) and consequently are often referred to as VHH antibody or VHH sequence. Camelids comprise old world camelids (*Camelus bactrianus* and *Camelus dromedarius*) and new world camelids (for example, *Lama paccos, Lama glama, Lama guanicoe* and *Lama vicugna*). NANOBODY® and NANOBODIES® are registered trademarks of Ablynx NV (Belgium). For a further description of VHHs or Nanobodies, reference is made to the book "Single domain antibodies," Methods in Molecular Biology, Eds. Saerens and Muyldermans, 2012, Vol 911, in particular to the Chapter by Vincke and Muyldermans (2012), as well as to a non-limiting list of patent applications, which are mentioned as general background art, and include: WO 94/04678, WO 95/04079, WO 96/34103 of the Vrije Universiteit Brussel; WO 94/25591, WO 99/37681, WO 00/40968, WO 00/43507, WO 00/65057, WO 01/40310, WO 01/44301, EP 1 134 231 and WO 02/48193 of Unilever; WO 97/49805, WO 01/21817, WO 03/035694, WO 03/054016 and WO 03/055527 of the Vlaams Instituut voor Biotechnologie (VIB); WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N. V. and the further published patent applications by Ablynx N. V. As will be known by the person skilled in the art, the Nanobodies are particularly characterized by the presence of one or more Camelidae "hallmark residues" in one or more of the framework sequences, according to Kabat numbering, as described, for example, in WO 08/020079, on page 75, Table A-3, incorporated herein by reference. It should be noted that the Nanobodies, of the disclosure in their broadest sense are not limited to a specific biological source or to a specific method of preparation. For example, Nanobodies, can generally be obtained: (1) by isolating the VHH domain of a naturally occurring heavy chain only antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a mammalian species, such as from a human being, or by expression of a nucleic acid encoding such a camelized VH domain; (5) by "camelization" of a "domain antibody" or "Dab," as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a Single-domain antibody using techniques for nucleic acid synthesis known per se, followed by expression of the nucleic acid thus obtained; and/or (8) by any combination of one or more of the foregoing. A further description of NANOBODIES®, including humanization and/or camelization of NANOBODIES®, can be found, e.g., in WO08/101985 and WO08/142164, as well as further herein. A particular class of Nanobodies that interacts with conformational epitopes of native targets and that stabilizes the target in a unique non-prominent conformation (different than the basal conformation) are called Xaperones and are particularly envisaged here. Xaperones are unique tools in structural biology. X$_\text{APERONE}$™ is a trademark of VIB and VUB (Belgium). By rigidifying flexible regions and obscuring aggregative surfaces, X$_\text{APERONE}$™ complexes warrant conformationally uniform samples that are key to protein structure determination by X-ray crystallography. Major advantages for the use of camelid antibody fragments as crystallization aid are that Xaperones (1) bind cryptic epitopes and lock proteins in unique native conformations, (2) increase the stability of soluble proteins and solubilized membrane proteins, (3) reduce the conformational complexity of soluble proteins and solubilized membrane proteins, (4) increase the polar surface enabling the growth of diffracting crystals, (5) sequester aggregative or polymerizing surfaces, (6) allow to affinity-trap active protein.

Within the scope of the disclosure, the term "immunoglobulin single variable domain" also encompasses variable domains that are "humanized" or "camelized," in particular Nanobodies that are "humanized" or "camelized." For example, both "humanization" and "camelization" can be performed by providing a nucleotide sequence that encodes a naturally occurring V$_H$H domain or VH domain, respectively, and then changing, in a manner known per se, one or more codons in the nucleotide sequence in such a way that the new nucleotide sequence encodes a "humanized" or "camelized" immunoglobulin single variable domains of the disclosure, respectively. This nucleic acid can then be expressed in a manner known per se, so as to provide the desired immunoglobulin single variable domains of the disclosure. Alternatively, based on the amino acid sequence of a naturally occurring V$_H$H domain or VH domain, respectively, the amino acid sequence of the desired humanized or camelized immunoglobulin single variable domains of the disclosure, respectively, can be designed and then synthesized de novo using techniques for peptide synthesis known per se. Also, based on the amino acid sequence or nucleotide sequence of a naturally occurring VHH domain or VH domain, respectively, a nucleotide sequence encoding the desired humanized or camelized immunoglobulin single variable domains of the disclosure, respectively, can be designed and then synthesized de novo using techniques for nucleic acid synthesis known per se, after which the nucleic acid thus obtained can be expressed in a manner known per se, so as to provide the desired immunoglobulin single variable domains of the disclosure. Other suitable methods and techniques for obtaining the immunoglobulin single variable domains of the disclosure and/or nucleic acids encoding the same, starting from naturally occurring VH sequences or preferably VHH sequences, will be clear from the skilled person, and may, for example, comprise combining one or more parts of one or more naturally occurring VH sequences (such as one or more FR sequences and/or CDR sequences), one or more parts of one or more naturally occurring VHH sequences (such as one or more FR sequences or CDR sequences), and/or one or more synthetic or semi-synthetic sequences, in a suitable manner, so as to provide a Single-domain antibody of the disclosure or a nucleotide sequence or nucleic acid encoding the same.

Also within the scope of the disclosure are natural or synthetic analogs, mutants, variants, alleles, parts or fragments (herein collectively referred to as "variants") of the immunoglobulin single variable domains, in particular the Nanobodies, as defined herein, and in particular variants of the immunoglobulin single variable domains of SEQ ID NOs:13-20 (see Tables 1-2). Thus, according to one embodiment of the disclosure, the term "immunoglobulin single variable domain of the disclosure" or "Nanobody of the disclosure" in its broadest sense also covers such variants. Generally, in such variants, one or more amino acid residues may have been replaced, deleted and/or added compared to the immunoglobulin single variable domains of the disclosure, as defined herein. Such substitutions, insertions or deletions may be made in one or more of the FRs and/or in one or more of the CDRs, and in particular variants of the FRs and CDRs of the immunoglobulin single variable domains of SEQ ID NOs:13-20 (see Tables 1-2). Variants, as used herein, are sequences wherein each or any framework region and each or any complementarity determining region shows at least 80% identity, preferably at least 85% identity, more preferably 90% identity, even more preferably 95% identity or, still even more preferably 99% identity with the corresponding region in the reference sequence (i.e., FR1_variant versus FR1_reference, CDR1_variant versus CDR1_reference, FR2_variant versus FR2_reference, CDR2_variant versus CDR2_reference, FR3_variant versus FR3_reference, CDR3_variant versus CDR3_reference, FR4_variant versus FR4_reference), as can be measured electronically by making use of algorithms such as PILEUP and BLAST. Software for performing BLAST analyses is publicly available through the National Center for Biotechnology Information (on the World Wide Web at ncbi.nlm.nih.gov/). It will be understood that for determining the degree of amino acid identity of the amino acid sequences of the CDRs of one or more sequences of the immunoglobulin single variable domains, the amino acid residues that form the framework regions are disregarded. Similarly, for determining the degree of amino acid identity of the amino acid sequences of the FRs of one or more sequences of the immunoglobulin single variable domains of the disclosure, the amino acid residues that form the complementarity regions are disregarded. Such variants of immunoglobulin single variable domains may be of particular advantage since they may have improved potency/affinity.

By means of non-limiting examples, a substitution may, for example, be a conservative substitution, as described herein, and/or an amino acid residue may be replaced by another amino acid residue that naturally occurs at the same position in another VHH domain. Thus, any one or more substitutions, deletions or insertions, or any combination thereof, that either improve the properties of the immunoglobulin single variable domains or that do not detract from the desired properties or from the balance or combination of desired properties of the immunoglobulin single variable domain (i.e., to the extent that the immunoglobulin single variable domains is no longer suited for its intended use) are included within the scope of the disclosure. A skilled person will generally be able to determine and select suitable substitutions, deletions or insertions, or suitable combinations of thereof, based on the disclosure herein and optionally after a limited degree of routine experimentation, which may, for example, involve introducing a limited number of possible substitutions and determining their influence on the properties of the immunoglobulin single variable domains thus obtained.

Also encompassed within the scope of the disclosure are immunoglobulin single variable domains that are in a "multivalent" form and are formed by bonding, chemically or by recombinant DNA techniques, together two or more monovalent immunoglobulin single variable domains. Non-limiting examples of multivalent constructs include "bivalent" constructs, "trivalent" constructs, "tetravalent" constructs, and so on. The immunoglobulin single variable domains comprised within a multivalent construct may be identical or different. In another particular embodiment, the immunoglobulin single variable domains of the disclosure are in a "multispecific" form and are formed by bonding together two or more immunoglobulin single variable domains, of which at least one with a different specificity. Non-limiting examples of multi-specific constructs include "bi-specific" constructs, "tri-specific" constructs, "tetra-specific" constructs, and so on. To illustrate this further, any multivalent or multispecific, as defined herein, immunoglobulin single variable domain of the disclosure may be suitably directed against two or more different epitopes on the same antigen, for example, against two or more different epitopes of the GPCR; or may be directed against two or more different antigens, for example, against an epitope of the GPCR and an epitope of a natural binding partner of the GPCR (e.g., G protein, β-arrestin). In particular, a monovalent immunoglobulin single variable domain of the disclosure is such that it will bind to the target GPCR with an affinity less than 500 nM, preferably less than 200 nM, more preferably less than 10 nM, such as less than 500 pM. Multivalent or multispecific immunoglobulin single variable domains of the disclosure may also have (or be engineered and/or selected for) increased avidity and/or improved selectivity for the desired GPCR, and/or for any other desired property or combination of desired properties that may be obtained by the use of such multivalent or multispecific immunoglobulin single variable domains. In a particular embodiment, such multivalent or multispecific binding domains of the disclosure may also have (or be engineered and/or selected for) improved efficacy in modulating signaling activity of a GPCR (see also further herein).

Further, and depending on the host organism used to express the chimeric polypeptide of the disclosure, deletions and/or substitutions within the binding domain moiety may be designed in such a way that, e.g., one or more sites for post-translational modification (such as one or more glycosylation sites) are removed, as will be within the ability of the person skilled in the art. Alternatively, substitutions or insertions may be designed so as to introduce one or more sites for attachment of functional groups, as described further herein.

Screening and Selection of Binding Domain Moieties Suitable for the Disclosure

A preferred class of binding domains, in particular immunoglobulin single variable domains that form part of the chimeric polypeptide of the disclosure, is directed against and/or specifically binds to a functional conformational state of a GPCR, as described hereinbefore. Conformationally-selective binding domains, in particular immunoglobulin single variable domains, can be identified in several ways, and will be illustrated hereafter in a non-limiting way for VHHs. Preferably, conformation-selective binding domains can be selected after the step of immunization of a Camelidae with a GPCR in a functional conformational state, optionally bound to a receptor ligand, to expose the immune system of the animal with the conformational epitopes that are unique to the GPCR (for example, agonist-bound GPCR so as to raise antibodies directed against a GPCR in its active conformational state). Optionally, a particular ligand can be coupled to the GPCR of interest by chemical cross-linking. Thus, as further described herein, such VHH sequences can preferably be generated or obtained by suitably immunizing a species of Camelid with a GPCR, preferably a GPCR in a functional conformational state (i.e., so as to raise an immune response and/or heavy chain only antibodies directed against the GPCR), by obtaining a suitable biological sample from the Camelid (such as a blood sample, or any sample of B-cells), and by generating VHH sequences directed against the GPCR, starting from the sample. Such techniques will be clear to the skilled person. Yet another technique for obtaining the desired VHH sequences involves suitably immunizing a transgenic mammal that is capable of expressing heavy chain only antibodies (i.e., so as to raise an immune response and/or heavy chain only antibodies directed against a GPCR in a functional conformational state), obtaining a suitable biological sample from the transgenic mammal (such as a blood sample, or any sample of B-cells), and then generating VHH sequences directed against the GPCR starting from the sample, using any suitable technique known per se. For example, for this purpose, the heavy chain antibody-expressing mice and the further methods and techniques described in WO02085945 and in WO04049794 can be used.

For the immunization of an animal with a GPCR, the GPCR may be produced and purified using conventional methods that may employ expressing a recombinant form of the GPCR in a host cell, and purifying the GPCR using affinity chromatography and/or antibody-based methods. In particular embodiments, the baculovirus/Sf-9 system may be employed for expression, although other expression systems (e.g., bacterial, yeast or mammalian cell systems) may also be used. Exemplary methods for expressing and purifying GCPRs are described in, for example, Kobilka (1995), Eroglu et al., 2002, Chelikani et al., 2006, and the book "Identification and Expression of G Protein-Coupled Receptors" (Kevin R. Lynch (Ed.), 1998), among many other references. A GPCR may also be reconstituted in phospholipid vesicles. Likewise, methods for reconstituting an active GPCR in phospholipid vesicles are known, and are described in: Luca et al., 2003, Mansoor et al., 2006, Niu et al., 2005, Shimada et al., 2002, and Eroglu et al., 2003, among others. In certain cases, the GPCR and phospholipids may be reconstituted at high phospholipid density (e.g., 1 mg receptor per mg of phospholipid). In particular embodiments, the phospholipids vesicles may be tested to confirm that the GPCR is active. In many cases, a GPCR may be present in the phospholipid vesicle in both orientations (in the normal orientation, and in the "inside-out" orientation in which the intracellular loops are on the outside of the vesicle). Other immunization methods with a GPCR include, without limitation, the use of complete cells expressing a GPCR or fractions thereof, vaccination with a nucleic acid sequence encoding a GPCR (e.g., DNA vaccination), immunization with viruses or virus like particles expressing a GPCR, amongst others (e.g., as described in WO2010070145, WO2011083141).

Any suitable animal, in particular a mammal such as a rabbit, mouse, rat, camel, sheep, cow, shark, pig, amongst others, or a bird such as a chicken or turkey, may be immunized using any of the techniques well known in the art suitable for generating an immune response.

The selection for NANOBODIES®, as a non-limiting example, specifically binding to a conformational epitope of a functional conformational state of the GPCR may, for example, be performed by screening a set, collection or library of cells that express heavy chain only antibodies on their surface (e.g., B-cells obtained from a suitably immunized Camelid), or bacteriophages that display a fusion of genIII and Single-domain antibody at their surface, or yeast cells that display a fusion of the mating factor protein Aga2p, by screening of a (naïve or immune) library of VHH sequences or Single-domain antibody sequences, or by screening of a (naïve or immune) library of nucleic acid sequences that encode VHH sequences or Single-domain antibody sequences, which may all be performed in a manner known per se, and which method may optionally further comprise one or more other suitable steps, such as, for example, and without limitation, a step of affinity maturation, a step of expressing the desired amino acid sequence, a step of screening for binding and/or for activity against the desired antigen (in this case, the GPCR), a step of determining the desired amino acid sequence or nucleotide sequence, a step of introducing one or more humanizing substitutions, a step of formatting in a suitable multivalent and/or multispecific format, a step of screening for the desired biological and/or physiological properties (i.e., using a suitable assay known in the art), and/or any combination of one or more of such steps, in any suitable order.

Various methods may be used to determine specific binding, as defined hereinbefore, between the binding domain and a target GPCR, including, for example, enzyme linked immunosorbent assays (ELISA), flow cytometry, radioligand binding assays, surface plasmon resonance assays, phage display, and the like, which are common practice in the art, for example, in discussed in Sambrook et al., 2001, Molecular Cloning, A Laboratory Manual. Third Edition. Cold Spring Harbor Laboratory Press, Cold Spring Harbor, N.Y., and are further illustrated in the Example section. It will be appreciated that for this purpose often a unique label or tag will be used, such as a peptide label, a nucleic acid label, a chemical label, a fluorescent label, or a radio isotope label, as described further herein.

A particularly preferred way of selecting for conformation-selective binding agents is as described in, e.g. WO 2012/007593. In an alternative preferred embodiment, selection for conformation-selective binding agents can also be performed by using cell sorting to select, from a population of cells comprising a library of cell-surface tethered extracellular binding agents, cells that are specifically bound to either the GPCR in its active conformation or the GPCR in its inactive conformation, but not both, for example, as described in Kruse et al., 2013. Without the purpose of being limitative, selection for conformation-selective binding agents is also further illustrated in the Example section.

It is also expected that the binding domain will generally be capable of binding to all naturally occurring or synthetic analogs, variants, mutants, alleles, parts, fragments, and isoforms of a particular GPCR as comprised in the chimeric polypeptide of the disclosure; or at least to those analogs, variants, mutants, alleles, parts, fragments, and isoforms of a particular GPCR that contain one or more antigenic determinants or epitopes that are essentially the same as the antigenic determinant(s) or epitope(s) to which the binding domains of the disclosure bind to a particular GPCR.

Linker Moiety

Within the context of the disclosure, the binding domain moiety and the GPCR moiety (or eventually to still other moieties, as described further herein) may be fused to each other directly or indirectly, whereby indirect coupling usually occurs through the use of intervening amino acid sequences or linker moieties. Preferred "linker molecules" or "linkers" are peptides of 1 to 200 amino acids length, and are typically, but not necessarily, chosen or designed to be unstructured and flexible. For instance, one can choose amino acids that form no particular secondary structure. Or, amino acids can be chosen so that they do not form a stable tertiary structure. Or, the amino acid linkers may form a random coil. Such linkers include, but are not limited to, synthetic peptides rich in Gly, Ser, Thr, Gln, Glu or further amino acids that are frequently associated with unstructured regions in natural proteins (Dosztányi, Z., Csizmok, V., Tompa, P., & Simon, I. (2005). IUPred: web server for the prediction of intrinsically unstructured regions of proteins based on estimated energy content. Bioinformatics (Oxford, England), 21(16), 3433-4). Non-limiting examples include $(GS)_5$ or $(GS)_{10}$. Other non-limiting examples of suitable linker sequences are also described in the Example section.

In many cases, though not necessarily, the effective intramolecular concentration, as defined herein, will depend on the linker length in a GPCR-binding domain fusion. Accordingly, an optimal linker length will be chosen so that the effective intramolecular concentration reaches a maximum value. Preferably, the amino acid linker sequence has a low susceptibility to proteolytic cleavage and does not interfere with the biological activity of chimeric polypeptide.

Thus, according to specific embodiments, the amino acid (AA) linker sequence is a peptide of between 0 and 200 AA, between 0 and 150 AA, between 0 and 100 AA, between 0 and 90 AA, between 0 and 80 AA, between 0 and 70 AA, between 0 and 60 AA, between 0 and 50 AA, between 0 and 40 AA, between 0 and 30 amino acids, between 0 and 20 AA, between 0 and 10 amino acids, between 0 and 5 amino acids. Examples of sequences of short linkers include, but are not limited to, PPP, PP or GS.

For certain applications, it may be advantageous that the linker molecule comprises or consists of one or more particular sequence motifs. For example, a proteolytic cleavage site can be introduced into the linker molecule such that GPCR moiety and binding domain moiety can be released. Useful cleavage sites are known in the art, and include a protease cleavage site such as Factor Xa cleavage site having the sequence IEGR (SEQ ID NO:47), the thrombin cleavage site having the sequence LVPR (SEQ ID NO:48), the enterokinase cleaving site having the sequence DDDDK (SEQ ID NO:49), or the PreScission (or 3C) cleavage site LEVLFQGP (SEQ ID NO:50).

In case the binding domain moiety and the GPCR moiety are linked using chemoenzymatic methods for protein modification, the linker moiety may exist of different chemical entities, depending on the enzymes or the synthetic chemistry that is used to produce the covalent chimer in vivo or in vitro (Rabuka 2010).

Other Moieties and Modifications

The chimeric polypeptide of the disclosure may be further modified and/or may comprise (or can be further fused to) other moieties, as described further herein. Examples of modifications, as well as examples of amino acid residues within the chimeric polypeptide of the disclosure that can be modified (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the chimeric polypeptide, in particular into or onto the binding domain moiety or into or onto the GPCR moiety, and/or optionally into or onto the linker moiety. Examples of such functional groups and of techniques for introducing them will be clear to the skilled person, and can generally comprise all functional groups and techniques mentioned in the art as well as the functional groups and techniques known per se for the modification of pharmaceutical proteins, and in particular for the modification of antibodies or antibody fragments (including ScFv's and single domain antibodies), for which reference is, for example, made to Remington's Pharmaceutical Sciences, 16th ed., Mack Publishing Co., Easton, Pa. (1980). Such functional groups may, for example, be linked directly (for example, covalently) to the chimeric polypeptide, or optionally via a suitable linker or spacer, as will again be clear to the skilled person. A usually less preferred modification comprises N-linked or O-linked glycosylation, usually as part of co-translational and/or post-translational modification, depending on the host cell used for expressing the chimeric polypeptide of the disclosure. Yet another modification may comprise the introduction of one or more detectable labels or other signal-generating groups or moieties, depending on the intended use of the labeled chimeric polypeptide. Suitable labels and techniques for attaching, using and detecting them will be clear to the skilled person, and, for example, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ detection and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person, and, for example, include moieties that can be detected using NMR or ESR spectroscopy. Such labeled chimeric polypeptides of the disclosure may, for example, be used for in vitro, in vivo or in situ assays (including immunoassays known per se such as ELISA, RIA, EIA and other "sandwich assays," etc.) as well as in vivo targeting and imaging purposes, depending on the choice of the specific label. As will be clear to the skilled person, another modification may involve the introduction of a chelating group, for example, to chelate one of the metals or metallic cations referred to above. Suitable chelating groups, for example, include, without limitation, diethyl-enetriamine-pentaacetic acid (DTPA) or ethylenediaminetetraacetic acid (EDTA). Yet another modification may comprise the introduction of a functional group that is one part of a specific binding pair, such as the biotin-(strept)avidin binding pair. Such a functional group may be used to link the chimeric polypeptide of the disclosure to another protein, polypeptide or chemical compound that is bound to the other half of the binding pair, i.e., through formation of the binding pair. For example, a chimeric polypeptide of the disclosure may be conjugated to biotin, and linked to another protein, polypeptide, compound or carrier conjugated to avidin or streptavidin. For example, such a conjugated chimeric polypeptide may be used as a reporter, for example, in a detection system where a detectable signal-producing agent is conjugated to avidin or streptavidin. Such binding pairs may, for example, also be used to bind the chimeric polypeptide of the disclosure to a carrier, including carriers suitable for pharmaceutical purposes. One non-limiting example are the liposomal formulations described by Cao and Suresh, Journal of Drug Targeting, 8, 4, 257 (2000). Such binding pairs may also be used to link a therapeutically active agent to the chimeric polypeptide of the disclosure.

Compositions Comprising a Chimeric Polypeptide

The chimeric polypeptide of the disclosure may also comprise (or can be further fused to) other molecules, in particular ligands, including a receptor ligand (such as a full agonist, partial agonist, antagonist, inverse agonist, biased agonist, natural binding partner, and the like). Thus, according to one aspect, the disclosure also envisages a complex comprising a chimeric polypeptide, as described hereinbefore, and a receptor ligand. As a non-limiting example, a stable complex may be purified by size exclusion chromatography. In a preferred embodiment, the complex, according to the disclosure, is in a solubilized form, such as in a detergent. In an alternative preferred embodiment, the complex, according to the disclosure, is immobilized to a solid support. Non-limiting examples of solid supports as well as methods and techniques for immobilization are described further in the detailed description. In still another embodiment, the complex, according to the disclosure, is in a cellular composition, including an organism, a tissue, a cell, a cell line, or in a membrane composition or liposomal composition derived from the organism, tissue, cell or cell line. Examples of membrane or liposomal compositions include, but are not limited to, organelles, membrane preparations, viruses, virus like lipoparticles (VLPs), and the like. It will be appreciated that a cellular composition, or a membrane or liposomal composition may comprise natural or synthetic lipids. In yet another preferred embodiment, the complex is crystalline. So, a crystal of the complex is also provided, as well as methods of making the crystal, which are described in greater detail below. Preferably, a crystalline form of a complex comprising a chimeric polypeptide, according to the disclosure, and a receptor ligand is envisaged.

Accordingly, the disclosure also relates to a membrane or liposomal composition comprising a chimeric polypeptide or a complex, as described above. Membrane compositions may be derived from a tissue, cell or cell line and include organelles, membrane extracts or fractions thereof, VLPs, viruses, and the like, as long as sufficient functionality of the chimeric polypeptides is retained.

Expression Systems

In another aspect, the disclosure relates to a nucleic acid molecule comprising a nucleic acid sequence encoding the chimeric polypeptide of the disclosure and as described hereinbefore. According to a particular embodiment, the disclosure relates to a nucleic acid molecule comprising a nucleic acid sequence encoding the chimeric polypeptide of the disclosure, wherein the nucleic acid encodes from 5' to 3':

a signal peptide,
an epitope tag,
a protease cleavage site,
a GPCR of interest,
a conformation-selective binding domain targeting the GPCR of interest.

Alternatively, according to another particular embodiment, the disclosure relates to a nucleic acid molecule comprising a nucleic acid sequence encoding the chimeric polypeptide of the disclosure, wherein the nucleic acid encodes from 5' to 3':

a signal peptide,
an epitope tag,
a protease cleavage site,
a conformation-selective binding domain targeting a GPCR of interest,
the GPCR of interest.

Such nucleic acid molecules are exemplified further in the Example section.

Further, the disclosure also envisages expression vectors comprising nucleic acid sequences encoding any of chimeric polypeptides of the disclosure, as well as host cells expressing such expression vectors. Suitable expression systems include constitutive and inducible expression systems in bacteria or yeasts, virus expression systems, such as baculovirus, semliki forest virus and lentiviruses, or transient transfection in insect or mammalian cells. The cloning and/or expression of the chimeric polypeptides of the disclosure can be done according to techniques known by the skilled person in the art.

The "host cell," according to the disclosure, can be of any prokaryotic or eukaryotic organism. According to a preferred embodiment, the host cell is a eukaryotic cell and can be of any eukaryotic organism, but in particular embodiments yeast, plant, mammalian and insect cells are envisaged. The nature of the cells used will typically depend on the ease and cost of producing the chimeric polypeptide, the desired glycosylation properties, the origin of the chimeric polypeptide, the intended application, or any combination thereof. Mammalian cells may, for instance, be used for achieving complex glycosylation, but it may not be cost-effective to produce proteins in mammalian cell systems. Plant and insect cells, as well as yeast typically achieve high production levels and are more cost-effective, but additional modifications may be needed to mimic the complex glycosylation patterns of mammalian proteins. Yeast cells are often used for expression of proteins because they can be economically cultured, give high yields of (medium-secreted) protein, and when appropriately modified are capable of producing proteins having suitable glycosylation patterns. Further, yeast offers established genetics allowing for rapid transformations, tested protein localization strategies, and facile gene knock-out techniques. Insect cells are also an attractive system to express GPCRs because insect cells offer an expression system without interfering with mammalian GPCR signaling. Eukaryotic cell or cell lines for protein production are well known in the art, including cell lines with modified glycosylation pathways, and non-limiting examples Will be provided hereafter.

Animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986; Kolkekar et al., 1997), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/–DHFR, Urlaub and Chasin, 1980), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293T cells, or 293 cells subcloned for growth in suspension culture, Graham et al., 1977, J. Gen. Virol., 36:59, or GnTI KO HEK293S cells, Reeves et al., 2002); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, Biol. Reprod., 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982); MCR 5 cells; FS4 cells. According to a particular embodiment, the cells are mammalian cells selected from Hek293 cells or COS cells.

Exemplary non-mammalian cell lines include, but are not limited to, insect cells, such as Sf9 cells/baculovirus expression systems (e.g., review Jarvis, Virology Volume 310, Issue 1, 25 May 2003, Pages 1-7), plant cells such as tobacco cells, tomato cells, maize cells, algae cells, or yeasts such as *Saccharomyces* species, *Schizosaccharomyces* species, *Hansenula* species, *Yarrowia* species or *Pichia* species. According to particular embodiments, the eukaryotic cells are yeast cells from a *Saccharomyces* species (e.g., *Saccharomyces cerevisiae*), *Schizosaccharomyces* sp. (for example, *Schizosaccharomyces pombe*), a *Hansenula* species (e.g., *Hansenula polymorpha*), a *Yarrowia* species (e.g., *Yarrowia lipolytica*), a *Kluyveromyces* species (e.g., *Kluyveromyces lactic*), a *Pichia* species (e.g., *Pichia pastoris*), or a *Komagataella* species (e.g., *Komagataella pastoris*). According to a specific embodiment, the eukaryotic cells are *Pichia* cells, and in a most particular embodiment *Pichia pastoris* cells.

Transfection of target cells (e.g., mammalian cells) can be carried out following principles outlined by Sambrook and Russel (Molecular Cloning, A Laboratory Manual, 3$^{rd}$ Edition, Volume 3, Chapter 16, Section 16.1-16.54). In addition, viral transduction can also be performed using reagents such as adenoviral vectors. Selection of the appropriate viral vector system, regulatory regions and host cell is common knowledge within the level of ordinary skill in the art. The resulting transfected cells are maintained in culture or frozen for later use according to standard practices.

Accordingly, another aspect of the disclosure relates to a method for producing a chimeric polypeptide, according to the disclosure, the method comprising at least the steps of:

a) Expressing in a suitable cellular expression system (as defined hereinabove) a nucleic acid encoding a chimeric polypeptide, according to the disclosure, and optionally.

b) Isolating and/or purifying the chimeric polypeptide.

The above-described conformationally constrained chimeric polypeptides can, thus, be considered as novel single-protein tools that are particularly useful for screening and drug discovery (in its broadest sense), all of which is now detailed further herein.

Applications

The herein described chimeric polypeptides and nucleic acids encoding the same, complexes, cells, and cellular compositions derived thereof, can be used in a variety of contexts and applications, for example, and without limitation, (1) for direct separation and/or purification of a chimeric polypeptide as a single protein, wherein the GPCR of interest is stabilized in a constitutive manner in a conformation of interest; (2) for crystallization studies and high-resolution structural analysis of GPCRs by making use of a chimeric polypeptide of the disclosure; (3) for ligand screening and (structure-based) drug discovery, (4) for stably and constitutively expressing a GPCR as a single fusion protein in a conformation of interest at a cellular surface or in another cellular membrane fraction, all of which will be described into further detail below.

Separation and Purification Methods

One key advantage of the disclosure is that a GPCR can be separated and purified in a conformation of interest in a defined 1:1 stoichiometry of GPCR to binding domain. A particular advantage of the disclosure is that the binding domain in the chimeric polypeptide can stabilize a particular receptor conformation at a very high effective intramolecular concentration, even in the absence of any ligand. In addition, persons of ordinary skill in the art will recognize that binding domains that selectively bind a folded state of a GPCR will protect this GPCR against chemical or thermal denaturation, thus increasing the conformational stability and/or thermostability. Therefore, the chimeric polypeptide can be separated from a mixture, and optionally purified as a single protein wherein the receptor adopts the conformation that is stabilized by the binding domain. This separated or purified chimeric polypeptide is a very useful and direct tool for subsequent crystallization, ligand characterization and compound screening, immunizations, amongst others.

Accordingly, the disclosure envisages a method of separating and/or purifying a chimeric polypeptide comprising a GPCR fused to a binding domain that specifically binds to the GPCR, the method comprising the step of separating and/or purifying the chimeric polypeptide by any suitable means.

Alternatively, it may be desired to first generate a complex of a chimeric polypeptide, as described hereinbefore, and a receptor ligand (e.g., an orthosteric ligand, an allosteric ligand, a natural binding protein such as a G protein, and the like), which can then subsequently be separated and eventually purified.

Thus, the disclosure also envisages a method of separating and/or purifying a complex of a chimeric polypeptide and a receptor ligand, the method comprising the step of separating and/or purifying the complex by any suitable means.

In essence, the same methods that are commonly used to produce and purify GPCRs (see above) can be equally used for the production and purification of the chimeric polypeptides of the disclosure. Methods for isolating/purifying chimeric polypeptides, as described above, include, without limitation, affinity-based methods such as affinity chromatography, affinity purification, immunoprecipitation, protein detection, immunochemistry, surface-display, size exclusion chromatography, ion exchange chromatography, amongst others, and are all well-known in the art. For example, the chimeric polypeptide can be expressed in recombinant form in a host cell, and subsequently purified using affinity chromatography and/or antibody-based methods. In particular embodiments, the baculovirus/Sf-9 system may be employed for expression, although other expression systems (e.g., bacterial, yeast or mammalian cell systems) may also be used as described further herein.

Crystallography and Applications in Structure-Based Drug Design

One aspect of the disclosure relates to the usefulness of the chimeric polypeptides of the disclosure in X-ray crystallography of GPCRs and its applications in structure-based drug design.

Crystallization of membrane proteins including GPCRs remains a challenge. Although expression and purification methods are appearing that allow for the generation of milligram quantities, achieving stability with these molecules is perhaps the most difficult hurdle to overcome, especially in view of the multiple conformations these proteins can adopt. Increased receptor stability of detergent solubilized GPCRs protects them from proteolytic degradation and/or aggregation and facilitates the purification and concentration of homogenous samples of correctly folded proteins. Persons of ordinary skill in the art will recognize that such samples are the preferred starting point for the generation of diffracting crystals.

The crystallization process itself is another major bottleneck in the process of macromolecular structure determination by X-ray crystallography. Successful crystallization requires the formation of nuclei and their subsequent growth to crystals of suitable size. Crystal growth generally occurs spontaneously in a supersaturated solution as a result of homogenous nucleation. Proteins may be crystallized in a typical sparse matrix screening experiment, in which precipitants, additives and protein concentration are sampled extensively, and supersaturation conditions suitable for nucleation and crystal growth can be identified for a particular protein. Related to the sparse matrix screening approach is to generate structural variation in the protein itself, for example, by adding ligands that bind the protein, or by making different mutations, preferentially in surface residues of the target protein or by trying to crystallize different species orthologues of the target protein.

Because crystallization involves an unfavorable loss of conformational entropy in the molecule to be assembled in the crystal lattice, methods that reduce the conformational entropy of the target while still in solution should enhance the likelihood of crystallization by lowering the net entropic penalty of lattice formation. The "surface entropy reduction" approach has proved to be highly effective (Derewenda 2004). Likewise, binding partners such as ions, small molecule ligands, and peptides can reduce the conformational heterogeneity by binding to and stabilizing a subset of conformational states of a protein. Although such binding partners are effective, not all proteins have a known binding partner, and even when a binding partner is known, its affinity, solubility, and chemical stability may not be compatible with crystallization trials.

Crystallization of GPCRs for high-resolution structural studies is particularly difficult because of the amphipathic surface of these membrane proteins. Embedded in the membrane bilayer, the contact sites of the protein with the acyl chains of the phospholipids are hydrophobic, whereas the polar surfaces are exposed to the polar head groups of the lipids and to the aqueous phases. To obtain well-ordered three-dimensional crystals, a prerequisite to X-ray structural analysis at high resolution, GPCRs are solubilized with the help of detergents and purified as protein-detergent complexes. The detergent micelle covers the hydrophobic surface of the membrane protein in a belt-like manner (Hunte and Michel 2002; Ostermeier et al., 1995). GPCR-detergent complexes form three-dimensional crystals in which contacts between adjacent protein molecules are made by the polar surfaces of the protein protruding from the detergent micelle (Day et al., 2007). Obviously, the detergent micelle requires space in the crystal lattice. Although attractive interactions between the micelles might stabilize the crystal packing (Rasmussen et al., 2007), these interactions do not lead to rigid crystal contacts. Because many membrane proteins, including GPCRs contain relatively small or highly flexible hydrophilic domains, a strategy to increase the probability of getting well-ordered crystals is to enlarge the polar surface of the protein and/or to reduce their flexibility. The most physiologic approach is to use a native signaling partner such as a G protein or arrestin. Unfortunately, interactions of GPCRs with G proteins or arrestins are highly lipid dependent, and it has been difficult to form complexes of sufficient stability for crystallography.

It is, thus, a particular advantage of the chimeric polypeptide of the disclosure that the binding domain binds a conformational epitope on the GPCR at a very high effective intramolecular concentration, thus stabilizing the receptor, reducing its conformational flexibility and increasing its polar surface, facilitating the crystallization of a rigid 1 to 1 receptor-binding domain fusion. It is a particular advantage that the chimeric polypeptide of the disclosure can be crystallized in the absence of any ligand.

It was surprisingly found that the chimeric polypeptides of the disclosure can be used as tools to increase the probability of obtaining well-ordered crystals by minimizing the conformational heterogeneity in the GPCR of choice by fusion to a conformationally-selective binding domain in a defined 1:1 stoichiometry. Thus, according to one embodiment, it is envisaged to use the chimeric polypeptides of the disclosure for crystallization purposes. Advantageously, crystals can be formed of fusion proteins wherein the GPCR is trapped in a particular receptor conformation, more particularly a therapeutically relevant receptor conformation (e.g., an active conformation), as ensured by the choice of a conformationally-selective binding domain that forms part of the fusion protein. The binding domain will also reduce the flexibility of extracellular regions upon binding the GPCR to grow well-ordered crystals. Immunoglobulin single variable domains, including Nanobodies, are especially suited for this purpose because they bind conformational epitopes and are composed of one single rigid globular domain, devoid of flexible linker regions unlike conventional antibodies or fragments derived such as Fab's.

Thus, according to a preferred embodiment, the disclosure provides for chimeric polypeptides comprising a GPCR fused to a binding domain useful as direct tools for crystallizing a GPCR, and eventually to solve the structure. According to a specific embodiment, the disclosure also envisages to crystallize a complex of a chimeric polypeptide and a receptor ligand, as defined hereinbefore. In a particularly preferred embodiment of the above method, the GPCR comprised in the chimeric polypeptide or complex is in an active state conformation revealing new structural features that are suitable for targeting with small molecules or biologicals and may enable the identification of compounds that are selective for the active conformation. In particular, these new structural features may occur at the orthosteric site or at an allosteric site, allowing the development of new conformation-specific orthosteric or allosteric compounds or fragments thereof, respectively. In another embodiment the GPCR comprised in the chimeric polypeptide or complex is in an inactive state conformation (characterized by an increased affinity for inverse agonists and/or by a decreased affinity for agonists as compared to the non-constrained GPCR) or in a functional conformation that leads to β-arrestin dependent signaling (characterized by an increased affinity for β-arrestin biased agonists as compared to the non-constrained GPCR).

Thus, the chimeric polypeptide of the disclosure, optionally in complex with a receptor ligand, may be crystallized using any of a variety of specialized crystallization methods for membrane proteins, many of which are reviewed in Caffrey (2003 & 2009). In general terms, the methods are lipid-based methods that include adding lipid to the complex prior to crystallization. Such methods have previously been used to crystallize other membrane proteins. Many of these methods, including the lipidic cubic phase crystallization method and the bicelle crystallization method, exploit the spontaneous self-assembling properties of lipids and detergent as vesicles (vesicle-fusion method), discoidal micelles (bicelle method), and liquid crystals or mesophases (in meso or cubic-phase method). Lipidic cubic phases crystallization methods are described in, for example: Landau et al., 1996; Gouaux 1998; Rummel et al., 1998; Nollert et al., 2004, Rasmussen et al., 2011a,b, which publications are incorporated by reference for disclosure of those methods. Bicelle crystallization methods are described in, for example: Faham et al., 2005; Faham et al., 2002, which publications are incorporated by reference for disclosure of those methods.

According to another embodiment, the disclosure relates to the use of a chimeric polypeptide, as described herein, to solve a structure of a GPCR-binding domain fusion, and optionally further comprising a receptor ligand. "Solving the structure," as used herein, refers to determining the arrangement of atoms or the atomic coordinates of a protein, and is often done by a biophysical method, such as X-ray crystallography.

In many cases, obtaining a diffraction-quality crystal is the key barrier to solving its atomic-resolution structure. Thus, according to specific embodiments, the herein described chimeric polypeptides can be used to improve the diffraction quality of the crystals so that the crystal structure of the GPCR-binding domain fusion can be solved.

Further, obtaining structural information of GPCR targets, for example, to help guide GPCR drug discovery, is highly desired. Beyond the crystallization of more GPCRs, especially methods for acquiring structures of receptors bound to lead compounds that have pharmacological or biological activity and whose chemical structure is used as a starting point for chemical modifications in order to improve potency, selectivity, or pharmacokinetic parameters. Persons of ordinary skill in the art will recognize that the chimeric polypeptide of the disclosure is particularly suited for co-crystallization with lead compounds that are selective for a non-prominent functional conformation (different from the basal conformation) induced by the binding domain because this binding domain is able to substantially increase the affinity for conformation-selective compounds.

According to another embodiment, the disclosure allows to crystallize the chimeric polypeptide in the absence of any ligand starting from a defined 1:1 stoichiometry between receptor and binding domain whereby the high effective intramolecular concentration of the conformation-selective binding domain can stabilize the receptor in the desired conformation within the crystal lattice. Persons of ordinary skill in the art will recognize that such preformed crystals of a free receptor, stabilized in a particular functional conformation are an ideal starting point for soaking experiments, aiming at solving structures of the receptor in complex with fragments or compounds that bind to the receptor in the conformation induced by the binding domain.

According to another embodiment, the disclosure encompasses a method of determining the crystal structure of a chimeric polypeptide comprising a GPCR-binding domain fusion, the method comprising the steps of:

a) Providing a chimeric polypeptide, according to the disclosure, and b) Allowing the chimeric polypeptide to crystallize.

In particular embodiments of the above method of determining the crystal structure, the chimeric polypeptide comprising a GPCR-binding domain fusion further comprises a receptor ligand, more specifically an agonist, an inverse agonist, etc., bound to the GPCR.

The determining of the crystal structure may be done by a biophysical method such as X-ray crystallography. The method may further comprise a step for obtaining the atomic coordinates of the crystal, as defined hereinbefore.

Ligand Screening and Drug Discovery

Other applications are particularly envisaged by making use of the chimeric polypeptides of the disclosure, or advantageously, by making direct use of the host cells or cell cultures comprising chimeric polypeptides, according to the disclosure, or by using membrane preparations derived thereof, including compound screening and immunizations, which will be described further herein.

In the process of compound screening, lead optimization and drug discovery, including antibody discovery, there is a requirement for faster, more effective, less expensive and especially information-rich screening assays that provide simultaneous information on various compound characteristics and their effects on various cellular pathways (i.e., efficacy, specificity, toxicity and drug metabolism). Thus, there is a need to quickly and inexpensively screen large numbers of compounds in order to identify new specific ligands of a protein of interest, preferably conformation-selective ligands, which may be potential new drug candidates. The disclosure solves this problem by providing GPCR drug targets that are stabilized in a non-prominent druggable conformation, due to the high effective intramolecular concentration of the conformation-selective binding domain that is covalently bound in a 1 to 1 stoichiometry. This allows to quickly and reliably identify and differentiate between ligands of different functional profiles, including ligands with an agonist profile, an inverse agonist profile, an antagonist profile, a biased agonist profile, etc., in a single assay, so increasing the speed and likelihood of identifying a ligand with the desired pharmacological properties. In particular, the chimeric polypeptides and host cells comprising the same, as well as host cell cultures or membrane preparations derived thereof are provided, for which specific preferences have been described hereinbefore, are particularly suitable for this purpose. Thus, these chimeric polypeptides, host cells, as well as host cell cultures or membrane preparations derived thereof, can then be used as immunogens or selection reagents for screening in a variety of contexts.

Thus, according to a preferred embodiment, the disclosure encompasses the use of the chimeric polypeptides, host cells, host cell cultures, or membrane preparations derived thereof, according to the disclosure and as described hereinbefore, in screening and/or identification programs for conformation-selective compounds of a GPCR, which ultimately might lead to potential new drug candidates.

According to one embodiment, the disclosure envisages a method of identifying conformation-selective compounds, the method comprising the steps of:

(i) Providing a chimeric polypeptide, according to the disclosure, and (ii) Providing a test compound, and (iii) Evaluating the selective binding of the test compound to the GPCR comprised in the chimeric polypeptide, and (iv) Selecting a conformationally-selective compound.

Specific preferences for the chimeric polypeptides, host cells, host cell cultures and membrane preparations thereof are as defined above with respect to earlier aspects of the disclosure.

In a particular embodiment of the above method, the conformation-selective compound is a compound selective for an active conformation of the GPCR comprised in the chimeric polypeptide. In another particular embodiment of the above method, the conformation-selective compound is a compound selective for an inactive conformation of the GPCR comprised in the chimeric polypeptide. In still another embodiment of the above method, the conformation-selective compound is a compound selective for a functional conformation that leads to β-arrestin dependent signaling or any other functional conformation of interest.

In a preferred embodiment, the chimeric polypeptides as used in any of the screening methods described further herein, are provided as whole cells, or cell (organelle) extracts such as membrane extracts or fractions thereof, or may be incorporated in lipid layers or vesicles (comprising natural and/or synthetic lipids), high-density lipoparticles, or any nanoparticle, such as nanodisks, or are provided as virus or virus-like particles (VLPs), so that sufficient functionality of the respective proteins is retained. Methods for preparations of GPCR-containing chimeric polypeptides from membrane fragments or membrane-detergent extracts are reviewed in detail in Cooper (2004), incorporated herein by reference. Alternatively, the chimeric polypeptides may also be solubilized in detergents.

Screening assays for drug discovery can be solid phase (e.g., beads, columns, slides, chips or plates) or solution phase assays, e.g., a binding assay, such as radioligand binding assays. In high-throughput assays, it is possible to screen up to several thousand different compounds in a single day in 96-, 384- or 1536-well formats. For example, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. It is possible to assay many plates per day; assay screens for up to about 6,000, 20,000, 50,000 or more different compounds are possible today.

Various methods may be used to determine binding between the stabilized GPCR and a test compound, including, for example, flow cytometry, radioligand binding assays, enzyme linked immunosorbent assays (ELISA), surface plasmon resonance assays, chip-based assays, immunocytofluorescence, yeast two-hybrid technology and phage display, which are common practice in the art, for example, in Sambrook et al., 2001, Molecular Cloning, A Laboratory Manual. Third Edition. Cold Spring Harbor Laboratory Press, Cold Spring Harbor, N.Y. Other methods of detecting binding between a test compound and a membrane protein include ultrafiltration with ion spray mass spectroscopy/HPLC methods or other (bio)physical and analytical methods. Fluorescence Energy Resonance Transfer (FRET) methods, for example, well known to those skilled in the art, may also be used. It will be appreciated that a bound test compound can be detected using a unique label or tag associated with the compound, such as a peptide label, a nucleic acid label, a chemical label, a fluorescent label, or a radio isotope label, as described further herein.

In one embodiment, it is determined whether the compound alters the binding of the GPCR as comprised in the chimeric polypeptide to a receptor ligand, as defined herein. Binding of a GPCR to its ligand can be assayed using standard ligand binding methods known in the art, as described herein. For example, a ligand may be radiolabeled or fluorescently labeled. The assay may be carried out on whole cells or on membranes obtained from the cells or aqueous solubilized receptor with a detergent. The compound will be characterized by its ability to alter the binding of the labeled ligand (see also Example section). The compound may decrease the binding between the GPCR and its ligand, or may increase the binding between the GPCR and its ligand, for example, by a factor of at least 2 fold, 3 fold, 4 fold, 5 fold, 10 fold, 20 fold, 30 fold, 50 fold, 100 fold.

According to a particularly preferred embodiment, the above-described method of identifying conformation-selective compounds is performed by a ligand binding assay or competition assay, even more preferably a radioligand binding or competition assay. Most preferably, the above-described method of identifying conformation-selective compounds is performed in a comparative assay, more specifically, a comparative ligand competition assay, even more specifically a comparative radioligand competition assay, which is illustrated further in the Example section.

In case the above-described method is performed in a comparative assay, it will be understood that the method will comprise the step of comparing the binding of a test compound for a GPCR comprised in a chimeric polypeptide wherein the GPCR is stabilized by a conformation-selective binding domain moiety in a functional conformation of interest (e.g., an active conformation or an inactive conformation) with the binding of the test compound to a control. Within the scope of the disclosure, the control can be the corresponding non-fused GPCR or a chimeric polypeptide of the corresponding GPCR fused to a mock binding domain moiety (also referred to as control binding moiety or irrelevant binding moiety) which is a binding domain moiety that is not directed to and/or does not specifically bind to the corresponding GPCR.

In a particular preferred embodiment, the step of evaluating the selective binding of the test compound to the GPCR comprised in the chimeric polypeptide in any of the above-described methods, is done by measuring and/or calculating the affinity, as defined herein, of the test compound for the chimeric polypeptide, as is also further illustrated in the Example section.

Often high-throughput screening of GPCR targets for conformation-selective compounds will be preferred. This will be facilitated by immobilization of a chimeric polypeptide, according to the disclosure, onto a suitable solid surface or support that can be arrayed or otherwise multiplexed. Non-limiting examples of suitable solid supports include beads, columns, slides, chips or plates.

More particularly, the solid supports may be particulate (e.g., beads or granules, generally used in extraction columns) or in sheet form (e.g., membranes or filters, glass or plastic slides, microtitre assay plates, dipstick, capillary fill devices or such like) which can be flat, pleated, or hollow fibers or tubes. The following matrices are given as examples and are not exhaustive, such examples could include silica (porous amorphous silica), i.e., the FLASH series of cartridges containing 60A irregular silica (32-63 um or 35-70 um) supplied by Biotage (a division of Dyax Corp.), agarose or polyacrylamide supports, for example, the Sepharose range of products supplied by Amersham Pharmacia Biotech, or the Affi-Gel supports supplied by Bio-Rad. In addition there are macroporous polymers, such as the pressure-stable Affi-Prep supports as supplied by Bio-Rad. Other supports that could be utilized include; dextran, collagen, polystyrene, methacrylate, calcium alginate, controlled pore glass, aluminum, titanium and porous ceramics. Alternatively, the solid surface may comprise part of a mass dependent sensor, for example, a surface plasmon resonance detector. Further examples of commercially available supports are discussed in, for example, Protein Immobilization, R. F. Taylor ed., Marcel Dekker, Inc., New York, (1991).

Immobilization may be either non-covalent or covalent. In particular, non-covalent immobilization or adsorption on a solid surface of chimeric polypeptide, according to the disclosure, may occur via a surface coating with any of an antibody, or streptavidin or avidin, or a metal ion, recognizing a molecular tag attached to the chimeric polypeptide, according to standard techniques known by the skilled person (e.g., Strep tag, Histidine tag, etc.).

In particular, the chimeric polypeptide may be attached to a solid surface by covalent cross-linking using conventional coupling chemistries. A solid surface may naturally comprise cross-linkable residues suitable for covalent attachment or it may be coated or derivatized to introduce suitable cross-linkable groups, according to methods well known in the art. In one particular embodiment, sufficient functionality of the immobilized protein is retained following direct covalent coupling to the desired matrix via a reactive moiety that does not contain a chemical spacer arm. Further examples and more detailed information on immobilization methods of antibody (fragments) on solid supports are discussed in Jung et al., 2008; similarly, membrane receptor immobilization methods are reviewed in Cooper, 2004; both herein incorporated by reference.

Advances in molecular biology, particularly through site-directed mutagenesis, enable the mutation of specific amino acid residues in a protein sequence. The mutation of a particular amino acid (in a protein with known or inferred structure) to a lysine or cysteine (or other desired amino acid) can provide a specific site for covalent coupling, for example. It is also possible to reengineer a specific protein to alter the distribution of surface available amino acids involved in the chemical coupling (Kallwass et al., 1993), in effect controlling the orientation of the coupled protein. A similar approach can be applied to the chimeric polypeptides, according to the disclosure, so providing a means of oriented immobilization without the addition of other peptide tails or domains containing either natural or unnatural amino acids. It will be understood that a mutation can be introduced in the GPCR moiety and/or the binding domain moiety of the chimeric polypeptide and needs to be carefully chosen so not to interfere with structural conformations and/or biological activity. For example, in case a mutation will be introduced in the binding domain moiety that is an antibody or an antibody fragment, such as a Single-domain antibody, introduction of mutations in the framework region is preferred, minimizing disruption to the antigen-binding activity of the antibody (fragment).

Conveniently, the immobilized proteins may be used in immunoadsorption processes such as immunoassays, for example, ELISA, or immunoaffinity purification processes by contacting the immobilized proteins, according to the disclosure, with a test sample, according to standard methods conventional in the art. Alternatively, and particularly for high-throughput purposes, the immobilized proteins can be arrayed or otherwise multiplexed. Preferably, the immobilized proteins, according to the disclosure are used for the screening and selection of compounds that selectively bind to a particular conformation of a GPCR.

It will be appreciated that either the binding domain moiety or the GPCR moiety that form part of the fusion may be immobilized, depending on the type of application or the type of screening that needs to be done. Also, the choice of the GPCR-stabilizing binding domain (targeting a particular conformational epitope of the GPCR), will determine the orientation of the GPCR and accordingly, the desired outcome of the compound identification, e.g., compounds specifically binding to extracellular parts, intramembranal parts or intracellular parts of the conformationally stabilized GPCR.

In an alternative embodiment, the test compound (or a library of test compounds) may be immobilized on a solid surface, such as a chip surface, whereas the chimeric polypeptide are provided, for example, in a detergent solution or in a membrane-like preparation.

Accordingly, in one specific embodiment, a solid support to which is immobilized a chimeric polypeptide, according to the disclosure, is provided for use in any of the above screening methods.

Most preferably, neither the chimeric polypeptide, nor the test compound is immobilized, for example, in phage-display selection protocols in solution, or radioligand binding assays.

The compounds to be tested can be any small chemical compound, or a macromolecule, such as a protein, a sugar, nucleic acid or lipid. Typically, test compounds will be small chemical compounds, peptides, antibodies or fragments thereof. It will be appreciated that in some instances the test compound may be a library of test compounds. In particular, high-throughput screening assays for therapeutic compounds such as agonists, antagonists or inverse agonists and/or modulators form part of the disclosure. For high-throughput purposes, compound libraries or combinatorial libraries may be used such as allosteric compound libraries, peptide libraries, antibody libraries, fragment-based libraries, synthetic compound libraries, natural compound libraries, phage-display libraries and the like. Methodologies for preparing and screening such libraries are known to those of skill in the art.

The test compound may optionally be covalently or non-covalently linked to a detectable label. Suitable detectable labels and techniques for attaching, using and detecting them will be clear to the skilled person, and include, but are not limited to, any composition detectable by spectroscopic, photochemical, biochemical, immunochemical, electrical, optical or chemical means. Useful labels include magnetic beads (e.g., dynabeads), fluorescent dyes (e.g., all Alexa Fluor dyes, fluorescein isothiocyanate, Texas red, rhodamine, green fluorescent protein and the like), radiolabels (e.g., $^{3}H$, $^{125}I$, $^{35}S$, $^{14}C$, or $^{32}P$), enzymes (e.g., horse radish peroxidase, alkaline phosphatase), and colorimetric labels such as colloidal gold or colored glass or plastic (e.g., polystyrene, polypropylene, latex, etc.) beads. Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label. Other suitable detectable labels were described earlier within the context of the first aspect of the disclosure relating to the chimeric polypeptide of the disclosure.

Thus, according to specific embodiments, the test compound as used in any of the above screening methods is selected from the group comprising a polypeptide, a peptide, a small molecule, a natural product, a peptidomimetic, a nucleic acid, a lipid, lipopeptide, a carbohydrate, an antibody or any fragment derived thereof, such as Fab, Fab' and F(ab')2, Fd, single-chain Fvs (scFv), single-chain antibodies, disulfide-linked Fvs (dsFv) and fragments comprising either a VL or VH domain, a heavy chain antibody (hcAb), a single domain antibody (sdAb), a minibody, the variable domain derived from camelid heavy chain antibodies (VHH or Single-domain antibody), the variable domain of the new antigen receptors derived from shark antibodies (VNAR), a protein scaffold including an alphabody, protein A, protein G, designed ankyrin-repeat domains (DARPins), fibronectin type III repeats, anticalins, knottins, engineered CH2 domains (nanoantibodies), as defined hereinbefore.

In one preferred embodiment, high throughput screening methods involve providing a combinatorial chemical or peptide library containing a large number of potential therapeutic ligands. Such "combinatorial libraries" or "compound libraries" are then screened in one or more assays, as described herein, to identify those library members (particular chemical species or subclasses) that display a desired characteristic activity. A "compound library" is a collection of stored chemicals usually used ultimately in high-throughput screening. A "combinatorial library" is a collection of diverse chemical compounds generated by either chemical synthesis or biological synthesis, by combining a number of chemical "building blocks." Preparation and screening of combinatorial libraries are well known to those of skill in the art. The compounds thus identified can serve as conventional "lead compounds" or can themselves be used as potential or actual therapeutics. Thus, in one further embodiment, the screening methods, as described hereinabove, further comprises modifying a test compound, which has been shown to selectively bind to a chimeric polypeptide comprising a chimeric polypeptide comprising a GPCR in a particular conformation, and determining whether the modified test compound binds to the GPCR when residing in the particular conformation.

Thus, according to more specific embodiments, a complex comprising a chimeric polypeptide of the disclosure and a receptor ligand may be used in any of the above screening methods. Preferably, the receptor ligand is chosen from the group comprising a small molecule, a polypeptide, an antibody or any fragment derived thereof, a natural product, and the like. More preferably, the receptor ligand is a full agonist, or a partial agonist, a biased agonist, an antagonist, or an inverse agonist, as described hereinbefore.

It may be desirable to identify and characterize natural or endogenous ligands of target GPCRs. In particular, there is a need to "de-orphanize" GPCRs for which a natural activating ligand has not been identified. Such ligands may be recovered from biological samples such as blood or tissue extract or from libraries of ligands. Thus, according to a particular embodiment, the test compound as used in any of the above screening methods is provided as a biological sample. In particular, the sample can be any suitable sample taken from an individual. For example, the sample may be a body fluid sample such as blood, serum, plasma, spinal fluid.

Although the screening methods, as described above, are sufficient to determine the functional profile of compounds, the functional effect of a compound on downstream signaling of the target GPCR may be additionally evaluated in secondary assays. Therefore, the efficacy of the compounds and/or compositions comprising the same, can be tested using any suitable in vitro assay, cell-based assay, in vivo assay and/or animal model known per se, or any combination thereof, depending on the specific disease or disorder involved.

It will be appreciated that the chimeric polypeptides, host cells and derivatives thereof, according to the disclosure, may be further engineered and are, thus, particularly useful tools for the development or improvement of cell-based assays. Cell-based assays are critical for assessing the mechanism of action of new biological targets and biological activity of chemical compounds. For example, without the purpose of being limitative, current cell-based assays for GPCRs include measures of pathway activation ($Ca^{2+}$ release, cAMP generation or transcriptional activity); measurements of protein trafficking by tagging GPCRs and downstream elements with GFP; and direct measures of interactions between proteins using Fluorescence resonance energy transfer (FRET), bioluminescence resonance energy transfer (BRET) or yeast two-hybrid approaches.

Further, it may be particularly advantageous to immunize an animal with a chimeric polypeptide of the disclosure, or a host cell or derivative thereof comprising the same, in order to raise antibodies, preferably conformationally-selective antibodies against the target GPCR. Thus, such immunization methods are also envisaged here. Methods for raising antibodies in vivo are known in the art, and are also described hereinbefore. Any suitable animal, e.g., a mammal such as a rabbit, mouse, rat, camel, sheep, cow, pig, or a bird such as a chicken or turkey, or a fish, such as a shark, may be immunized using any of the techniques well known in the art suitable for generating an immune response. Following immunization, expression libraries encoding immunoglobulin genes, or portions thereof, expressed in bacteria, yeast, filamentous phages, ribosomes or ribosomal subunits or other display systems, can be made according to well-known techniques in the art. Further to that, the antibody libraries that are generated comprise a collection of suitable test compounds for use in any of the screening methods, as described hereinbefore. The antibodies that have been raised, as described hereinabove, may also be useful diagnostic tools to specifically detect GPCRs in a particular conformational state, and thus also form part of the disclosure.

In one embodiment, the immobilized chimeric polypeptides, as described hereinbefore, may be used for the selection of binding domains including antibodies or antibody fragments or peptides that bind the conformationally stabilized receptor. Persons of ordinary skill in the art will recognize that such binding domains, as a non-limiting example, can be selected by screening a set, collection or library of cells that express binding domains on their surface, or bacteriophages that display a fusion of genIII and Single-domain antibody at their surface, or yeast cells that display a fusion of the mating factor protein Aga2p, or by ribosome display amongst others.

One particular embodiment relates to the use of such immobilized chimeric polypeptides for the isolation of binding domains that are selective for the conformation of the receptor that is induced by the high effective intramolecular concentration of the conformation-selective binding domain that is covalently bound to the receptor in a 1 to 1 stoichiometry Still another aspect of the disclosure relates to a kit comprising a chimeric polypeptide of the disclosure, or a host cell or a host cell culture or a membrane preparation, according to the disclosure. The kit may further comprise a combination of reagents such as buffers, molecular tags, vector constructs, reference sample material, as well as a suitable solid supports, and the like. Such a kit may be useful for any of the applications of the disclosure, as described herein. For example, the kit may comprise (a library of) test compounds useful for compound screening applications.

The following examples are intended to promote a further understanding of the disclosure. While the disclosure is described herein with reference to illustrated embodiments, it should be understood that the disclosure is not limited hereto. Those having ordinary skill in the art and access to the teachings herein will recognize additional modifications and embodiments within the scope thereof. Therefore, the disclosure is limited only by the claims attached herein.

EXAMPLES

Example 1

Generation of β2AR-Single-Domain Antibody Fusion Protein Constructs

The GPCR-Single-domain antibody fusions described in this example are chimeric polypeptides that contain two different proteins connected with a peptide linker: the GPCR β2AR, the linker GGGGSGGGS (SEQ ID NO:51) and a Single-domain antibody, all of which were fused in this order from the amino to the carboxy terminus. Genes encoding these proteins were fused, as described below (FIG. 2) and cloned in the pFastBac1 vector (Invitrogen, cat. Nr 10359-016).

The GPCR part was amplified from DNA encoding the cleavable hemagglutinin (HA) protein signal peptide (SP) derived from influenza virus (MKTIIALSYIFCLVFA; SEQ ID NO:52) followed by the Flag epitope (DYKDDDDA; SEQ ID NO:53) followed by a TEV cleavage site (ENLYFQGF; SEQ ID NO:54) followed by the coding sequence of human β2 adrenergic receptor encompassing Gly2 to Gly365 (SEQ ID NO:55). A point mutation of N187E was also introduced to the construct to disrupt this unwanted glycosylation site (β2AR365N; Rasmussen et al., 2011b). The β2 adrenergic receptor engineering to β2AR365N was performed to increase the receptor's cellular expression levels in Sf9 cells.

Single-domain antibody gene segments were amplified from phagemids encoding the respective Nanobodies. Nb80 (SEQ ID NO:13) is a β2AR specific Single-domain antibody that stabilizes the active state of the β2AR bound to full agonists such as BI-167107 (Rasmussen et al., 2011b). Nb71 (SEQ ID NO:14) is another β2AR specific Xaperone that stabilizes an active state (WO2012007593). Nb69 (SEQ ID NO:15) is specific for the Muscarinic3 receptor and has no detectable affinity for β2AR.

The GPCR and the Single-domain antibody were genetically fused in frame by an overlap extension PCR. Therefore, 20 ng of plasmid containing the GPCR cDNA was used as the template in a 50 μl PCR reaction (Pfu polymerase, Fermentas, cat. Nr EP0501) containing 4% of DMSO to amplify the β2AR encoding DNA using primer EP211

(5'-GCGGAATTCGAGCTCGCC-3'; SEQ ID NO:56) and primer EP207 (5'-CCTCCGCCGGATCCGCCACCTC-CTCCACTCTGCTCCCCTGTG-3'; SEQ ID NO:57). Primer EP211 harbors an EcoRI restriction site at the 5' end of the coding sequence. Primer EP207 incorporates part of the GGGGSGGGS (SEQ ID NO:51) linker at the C-terminus of the receptor. The amplification conditions for this reaction were 2 min 95° C., 35 cycles of 30 sec 94° C., 30 sec 50° C., 1 min30 sec 72° C. followed by 10 min at 72° C. to amplify the GPCR encoding part of the open reading frame of the fusion.

Nb69, Nb71 and Nb80 all have identical N-terminal and C-terminal sequences. Single-domain antibody DNA's were amplified with a Pfu polymerase in a PCR in 50 µl using 5 ng of each construct with primer EP206 (GGCGGATCCG-GCGGAGGTTCGCAGGTGCAGCTGCAG-GAGTCTGGGGGAGG; SEQ ID NO:58) to incorporate an overlapping part of the GGGGSGGGS linker at the N-terminus of the Single-domain antibody and EP202 (TGGAAT-TCTAGATTAGTGATGGTGATGGTGGTGTGAGGA-GACGGTGACCTGGGT; SEQ ID NO:59) to add the sequence of a His6-tag at the C-terminal end of the fusion protein incorporating an XbaI cloning site at the 3' end of the gene. The following amplification conditions were used 2 min 95° C., 30 cycles of 30 sec 94° C., 30 sec 50° C., 1 min 72° C. followed by 10 min at 72° C. to amplify the Single-domain antibody encoding part of the hybrids.

PCR fragments encoding the GPCR or a Single-domain antibody were purified using the PCR purification kit (Promega) and used as templates in a new 50 µl PCR reaction: 20 ng of the EP211-β2AR-EP207 (EP211 and EP207 refers to the primers that have been used for PCR amplification) amplified PCR fragment was mixed with approximately 20 ng of amplified EP206-Single-domain antibody-EP202 fragment and fused with KapaTaq polymerase (Sopaghem, cat. Nr BK1002) by overlap extension as follows. After melting for 2 min at 95° C. and 5 cycles of 30 sec 95° C., 30 sec 55° C., 1 min 45 sec, the fused β2AR-Single-domain antibody open reading frames were amplified using primers EP202 and EP211 in 28 cycles (30 sec 95° C., 30 sec 55° C., 1 min 45 sec 72° C.) followed by 10 min at 72° C. PCR fragments containing the different β2AR-Single-domain antibody open reading frames were purified separately, cloned as an EcoRI-XbaI fragment in pFastBac1 and transformed in *E. coli* Top10. Plasmid DNA was prepared from single colonies and the sequence of the open reading frames was confirmed by sequencing. Constructs were designated pFastBac β2AR365N-Nb80 (Lab reference CA6836), pFastBac β2AR365N-Nb69 (Lab reference CA6833), and pFastBac β2AR365N-Nb71 (Lab reference CA6835). The amino acid sequences encoded by the different β2AR365N-Nb fusion constructs are given in FIG. 2 (SEQ ID NOs:1-4).

Example 2

Expression of β2AR-Single-Domain Antibody Fusions in Baculovirus-Infected Sf9 Cells To produce bacmids encoding PAR-Single-domain antibody fusions, one ng of each pFastBac β2AR365N-Single-domain antibody fusion was transformed into the DH10BAC™ cells using the BAC-TO-BAC® Baculovirus Expression system, according to the manufacturer's instructions (Invitrogen, cat. Nr 10359-016) and plated overnight on a fresh LB agar plate with 50 µg/ml kanamycin, 7 µg/ml gentamicin, 10 µg/ml tetracycline, 100 µg/ml X-gal and 40 µg/ml IPTG. White colonies were picked, bacmids were purified and the sequences of the β2AR-Single-domain antibody open reading frames confirmed. A plasmid encoding the β2AR open reading frame, devoid of the linker and a Single-domain antibody (pFastBac β2AR365N) was also transformed into the DH10BAC™ cells to produce a bacmid encoding non-fused receptor as a control. Recombinant baculovirus was produced by transfecting the β2AR-Single-domain antibody bacmids and the βAR365N bacmid in Sf9 cells.

For each bacmid a transfection mix was prepared by mixing 1 ml Grace's unsupplemented insect cell culture medium (Sigma, cat. Nr G8142), 15 µL of Cellfectin II (Invitrogen, cat. Nr 10362-100) and 5 µL of bacmid DNA (approximately 3 µg). This transfection mix was preincubated for 20 minutes at RT. Next, $1\times10^7$ pelleted Sf9 cells were resuspended in the transfection mix and shaken at 27° C. After 4 hours 4 ml of protein free ESF 921 Sf9 medium (Expression systems LLC, cat. Nr 96-001) was added and cells were grown for 48 hrs at 27° C. and 130 rpm. An extra 5 ml of ESF 921 Sf9 medium was added and cells were incubated for another 24 h to 40 h before harvesting the P1 recombinant baculovirus stock (P1) by centrifugation. A P2 recombinant baculovirus stock was made by diluting P1 100 times in a fresh Sf9 culture at a density of $3\times10^6$ cells/ml and culturing at 27° C. and 130 rpm. P2 virus stocks were harvested by centrifugation 72 h after infection. Recombinant expression of the different β2AR365N-Nb fusions was accomplished through the infection of freshly grown Sf9 cells at a density of 4 million/ml (1:100 to 1:250) with the P2 baculovirus stocks. Infected cells were cultured for 48 h to 55 h at 27° C. (130 rpm) before harvesting. The expression of GPCR-Single-domain antibody hybrids was confirmed by fluorescence microscopy on live cells (Example 3). Cells expressing the recombinant protein were washed twice with ice cold PBS (Life technologies, cat. Nr 10010-023) supplemented with 1.5 mM EDTA, pelleted and stored at −80° C.

Example 3

Confirming Expression of β2AR-Single-Domain Antibody Fusion Proteins by Fluorescence Microscopy To monitor the expression of the different β2AR365N-Nb fusions, non-infected Sf9 cells and Sf9 cells infected with a P1 recombinant baculovirus stock (harvested after 72 hrs of infection) were analyzed for receptor expression using fluorescence microscopy. For this purpose 15 µl of each cell culture was diluted in 8-well µ-slides (Ibidi, cat. Nr 80821) into 200 W of PBS containing 1 µg of a mouse anti Flag (M2) monoclonal antibody (Sigma, cat. Nr F3165) and 1 µg of a rat anti mouse-IgG conjugated to FITC (ebioscience, cat. Nr 11-4011) and incubated for 15 min in the dark. Once cells were surface attached, excess of staining solution was carefully removed. Images of infected cells and non-infected cells were taken with the Eclipse TE2000 (Nikon) inverted microscope. Images were taken using transmission microscopy, and using epifluorescence transmission microscopy using the FITC filter. All fluorescence measurements were performed using the same exposure settings.

Comparing the fluorescence images of non-infected Sf9 cells with cells expressing β2AR365N-Nb80, β2AR365N-Nb71, β2AR365N-Nb69 or non-fused β2AR365N demonstrate that the chimeric polypeptides are mainly expressed on the cell surface of the insect cells, similar to the non-fused receptor (data not shown).

Example 4

Preparation of Membranes from Insect Cells Expressing the β2AR-Single-Domain Antibody Fusions Cell pellets obtained by centrifugation of fresh 50 ml cultures of Sf9 cells expressing recombinant β2AR-Nb fusions were resuspended in 8 ml lysis buffer containing protease inhibitors (10 mM Tris/HCl pH7.4, 1 mM EDTA, 10 µg/ml leupeptin, 0.2 mM PMSF). Cells were lysed by thoroughly crushing the resuspended pellets using a small glass grinder and a teflon pestle. Membranes were recovered by centrifugation at 26000 g. Membrane pellets were resuspended in 1.5 ml of storage buffer (10 mM Tris/HCl pH7.4, 1 mM EDTA, 10% saccharose) and stored in aliquots at 80° C. Total protein concentrations were measured with the BCA protein assay kit (Thermo Scientific Pierce, cat. Nr 23225), according to the manufacturer's instructions. The expression of GPCR-Single-domain antibody hybrids in baculovirus-infected Sf9 cells was further confirmed by analyzing the protein content of these Sf9 membranes by western blot analysis (Example 5). The pharmacological properties of these GPCR-Single-domain antibody hybrids have been analyzed by radioligand competition assays (Example 6).

Example 5

Expression of PAR-Single-Domain Antibody Fusion Proteins Confirmed by Western Blot Membrane preparations (25 µg total protein) of the different baculovirus infected Sf9 cells were loaded on a 12.5% SDS-PAGE gel. After electrophoresis, proteins were transferred to a nitrocellulose sheet and the membrane was blocked with 4% skimmed milk. Expression of the recombinant proteins was detected using the anti-flag M2 (Sigma, cat. Nr F3165) as the primary antibody and an anti-mouse alkaline phosphatase conjugate (Sigma, cat. Nr A3562) in combination with NBT and BCIP to develop the blot (FIG. 3). The detection of bands with the appropriate molecular weight (approximately 57 and 43 kDa for the Single-domain antibody-fused and non-fused β2AR, respectively) confirms expression of the fusion protein for all constructs generated.

Example 6

Analysis of the Pharmacological Properties of the β2AR-Single-Domain Antibody Fusions by Comparative Radioligand Competition Assays To analyze the pharmacological properties of the different β2AR365N-Single-domain antibody fusions we performed comparative radioligand competition experiments using the natural agonist epinephrine (Sigma cat. Nr E4250), (−)-isoproterenol hydrochloride (full agonist, Sigma cat. Nr I6504), salbutamol (partial agonist, Sigma cat. Nr S8260), ICI-118,551 hydrochloride (inverse agonist, Sigma cat. Nr I127) or alprenolol hydrochloride (neutral antagonist, Sigma cat. Nr A8676) and carvedilol (antagonist, Sigma cat. Nr C3993) as the competitor and the neutral antagonist [$^3$H]-dihydroalprenolol as the radioligand. The pharmacological effect of the different ligands is according to Kahsai et al., 2011.

Radioligand competition binding experiments were performed on Sf9 insect cell membranes expressing either β2AR365N (no Single-domain antibody fused), β2AR365N-Nb80, β2AR365N-Nb71 or β2AR365N-Nb69. Membranes of sf9 cells expressing the different recombinant proteins (Examples 2 & 4, 5 µg total protein) were mixed with either (−)-isoproterenol, epinephrine, salbutamol, ICI118,551 or alprenolol at concentrations ranging from $10^{-11}$M to $10^{-4}$M in binding buffer (75 mM Tris pH7.5, 12.5 mM MgCl2, 1 mM EDTA, 0.05% BSA). Next, the radioligand [$^3$H]-dihydroalprenolol was added (2 nM final concentration) to each dilution and samples were incubated for 2 hours at room temperature on a shaking platform (total reaction volume per assay point was 250 µl). Receptor-bound radioligand was separated from free radioligand by filtration over Whatman GF/C unifilters (Perkin Elmer, cat. Nr 6005174) using a 96 well FilterMate harvester (Perkin Elmer). After filtration, membranes retained on the filter plates were washed with ice-cold wash buffer (20 mM Tris-HCl pH 7.4), and filters were dried for 1 hour at 50° C. After adding 40 µl of scintillation fluid (MICROSCINT™-O, Perkin Elmer, cat. Nr 6013611), radioactivity (cpm) retained on the filters was measured in a Wallac MICROBETA® TriLux scintillation counter. Data represent the mean±SEM (standard error of the mean) of each experiment performed in triplicate. The IC50 values were determined by nonlinear regression analysis using Prism (GraphPad Software, San Diego, Calif.).

In a first series of experiments, we compared the pharmacological properties of the β2AR365N-Nb80 fusion with the properties of the β2AR365N-Nb69 chimer (FIG. 4). Nb80 is a Xaperone that selectively binds to agonist bound β2AR and exhibits G protein-like behavior, thus stabilizing the active-state conformation of the receptor in the agonist·β2AR-Nb 80 complex (Rasmussen et al., 2011b). Nb69 is a mock Single-domain antibody that specifically binds to the rat muscarinic receptor M3 with no detectable affinity for β2AR. We found that the pharmacological properties of the β2AR365N-Nb80 chimer are profoundly different from the properties of the control Nb69-fused receptor. Compared to the Nb69 chimer, β2AR fused to the Single-domain antibody with G protein-like behavior (Nb80) exhibits increased affinities for agonists (epinephrine, isoproterenol, salbutamol) and decreased affinities for inverse agonists (ICI-118,551), exemplified by the modulated IC50s of the tested ligands on the Nb80 and mock fusion (Table 3). This proves that the β2AR365N-Nb80 chimer—but not the control mock β2AR365N-Nb69 chimer-adopts an active-state conformation characterized by increased affinities for agonists and decreased affinities for inverse agonists.

The increased affinity of the β2AR365N-Nb80 chimer, compared to control β2AR365N-Nb69 for the natural agonist epinephrine can be calculated from the ratio of the IC50 values from the competitive binding experiments depicted in FIG. 4A by dividing the IC50 of β2AR365N-Nb69 by the IC50$^{high}$ of β2AR365N-Nb80, resulting in an apparent potency shift of ≈2080. The increased affinity of the β2AR365N-Nb80 chimer for the synthetic agonist isoproterenol can be calculated from the ratio of the IC50 values from the competitive binding experiments by dividing the IC50 of β2AR365N-Nb69 by the IC50$^{high}$ of β2AR365N-Nb80 (FIG. 4B), resulting in an apparent potency shift of ≅670. The increased affinity of the β2AR365N-Nb80 chimer for the synthetic partial agonist salbutamol can be calculated from the ratio of the IC50 values from the competitive binding experiments depicted in FIG. 4D by dividing the IC50 of β2AR365N-Nb69 by the IC50$^{high}$ of β2AR365N-Nb80, resulting in an apparent potency shift of ≅370.

Figure 4E:
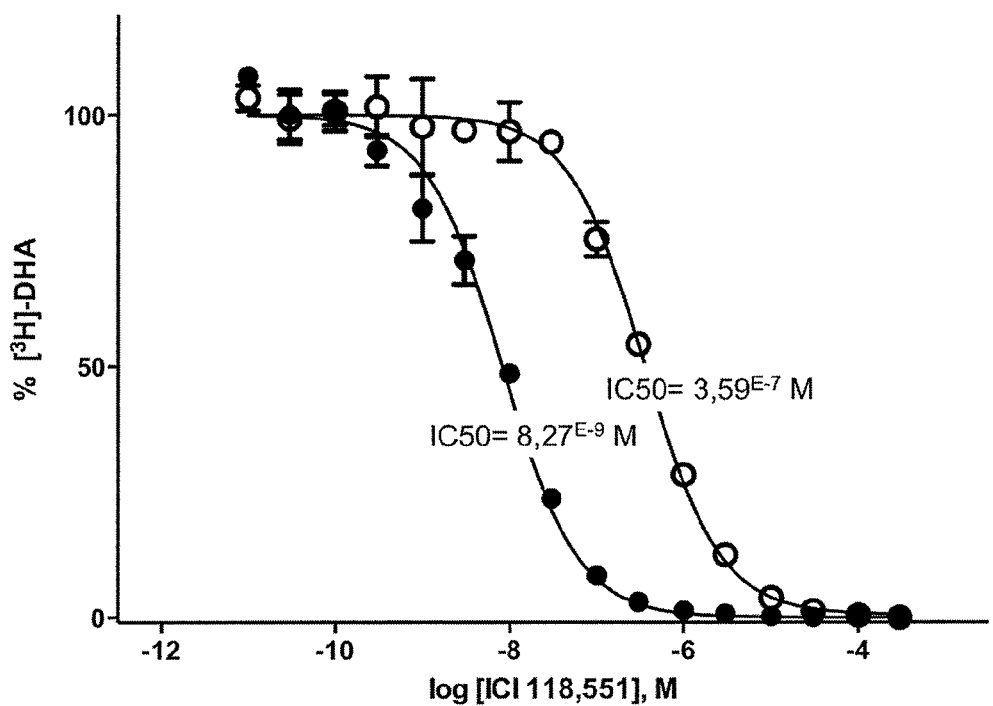
Figure 4F:
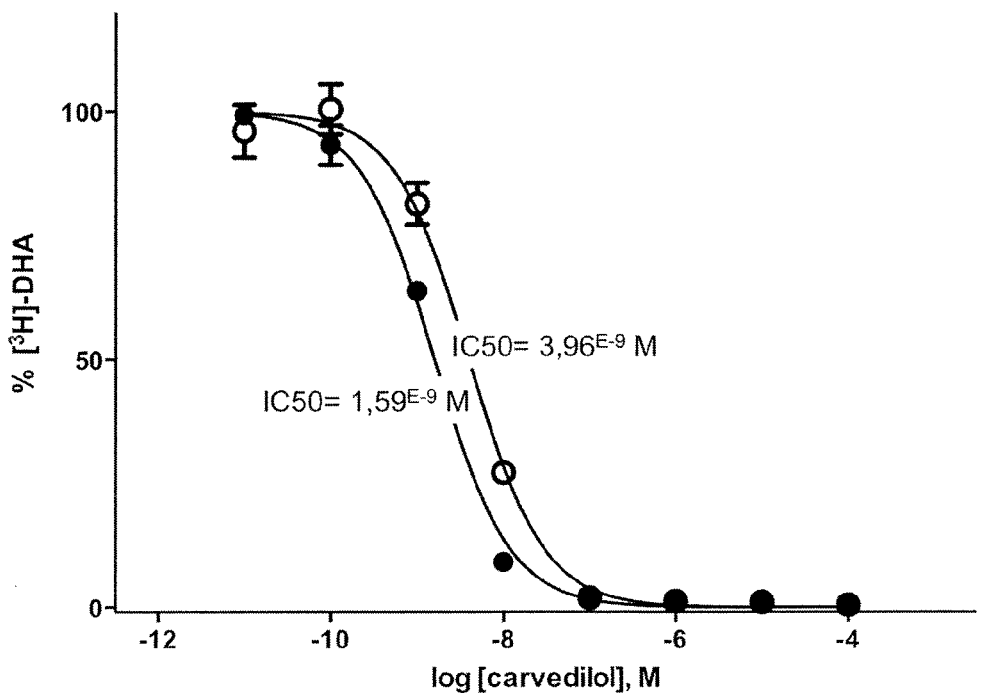

Similarly, the decreased affinity of the β2AR365N-Nb80 chimer, compared to control β2AR365N-Nb69 for the inverse agonist ICI-118,551 can be calculated from the ratio of the IC50 values from the competitive binding experiments depicted in FIG. 4E by dividing the IC50 of β32AR365N-Nb69 by the IC50 of β2AR365N-Nb80, resulting in an apparent potency shift of ≅0.023.

Notably, the β2AR-Nb80 fusion has little effect on the affinity for the neutral antagonist alprenolol as compared to the control β2AR365N-Nb69 chimer. The IC50's β2AR365N-Nb80 and β2AR365N-Nb69 for alprenolol (FIG. 4C) are indeed very similar, consistent with the fact that neutral antagonists are non-selective ligands that bind different functional conformations.

Remarkably, the β2AR-Nb80 fusion has little effect on the affinity for the antagonist carvedilol as compared to the control β2AR365N-Nb69 chimer. The IC50's of carvedilol detected on β2AR365N-Nb80 and β2AR365N-Nb69 (FIG. 4F) are indeed very similar (difference less than a factor 2).

In a second series of experiments, we compared the pharmacological properties of the β2AR365N-Nb80 fusion with the properties of the non-fused β2AR365N receptor (FIG. 5). (32AR fused to the Single-domain antibody with G protein-like behavior (Nb80) exhibits 3 orders of magnitude higher affinities for the natural agonist epinephrine, indicating that the β2AR365N-Nb80 chimer—but not the non-fused control receptor—adopts an active-state conformation characterized by increased affinities for agonists. The increased affinity of the β2AR365N-Nb80 chimer, compared to control non-fused β2AR365N for the natural agonist epinephrine can be calculated from the ratio of the IC50 values from the competitive binding experiments depicted in FIG. 5A by dividing the IC50 of non-fused β2AR365N by the IC50$^{high}$ of β2AR365N-Nb80, resulting in an apparent potency shift of ≅1370 (Table 3).

Remarkably, the β2AR365N-Nb80 fusion has little effect on the affinity for the antagonist carvedilol as compared to the control non-fused β2AR365N. The IC50's of β2AR365N-Nb80 and non-fused β2AR365N-Nb69 for carvedilol (FIG. 5B and Table 3) are indeed very similar.

In a third experiment, we compared the pharmacological properties of the β2AR365N-Nb71 fusion with the properties of the β2AR365N-Nb69 chimer (FIG. 6 and Table 3). Nb71 is another Single-domain antibody that selectively binds the active conformation of β2AR (WO2012007594). We found that the pharmacological properties of the β2AR365N-Nb71 chimer also exhibits increased affinities for agonists (isoproterenol, salbutamol) and decreased affinities for the inverse agonist ICI-118,551, showing that the β2AR365N-Nb71 chimer—but not the control β2AR365N-Nb69 chimer—adopts an active-state conformation characterized by increased affinities for agonists and decreased affinities for inverse agonists. The increased affinity of the β2AR365N-Nb71 chimer, compared to control β2AR365N-Nb69 for the natural agonist epinephrine can be calculated from the ratio of the IC50 values from the competitive binding experiments depicted in FIG. 6A by dividing the IC50 of β2AR365N-Nb69 by the IC50$^{high}$ of β2AR365N-Nb71, resulting in an apparent potency shift of ≅2030. The increased affinity of the β2AR365N-Nb71 chimer for the synthetic agonist isoproterenol can be calculated from the ratio of the IC50 values from the competitive binding experiments depicted in FIG. 6B by dividing the IC50 of β2AR365N-Nb69 by the IC50$^{high}$ of β2AR365N-Nb71, resulting in an apparent potency shift of ≅80. The increased affinity of the β2AR365N-Nb71 chimer for the synthetic partial agonist salbutamol can be calculated from the ratio of the IC50 values from the competitive binding experiments depicted in FIG. 6D by dividing the IC50 of β2AR365N-Nb69 by the IC50$^{high}$ of β2AR365N-Nb71, resulting in an apparent potency shift of ≅450.

Figure 6A:
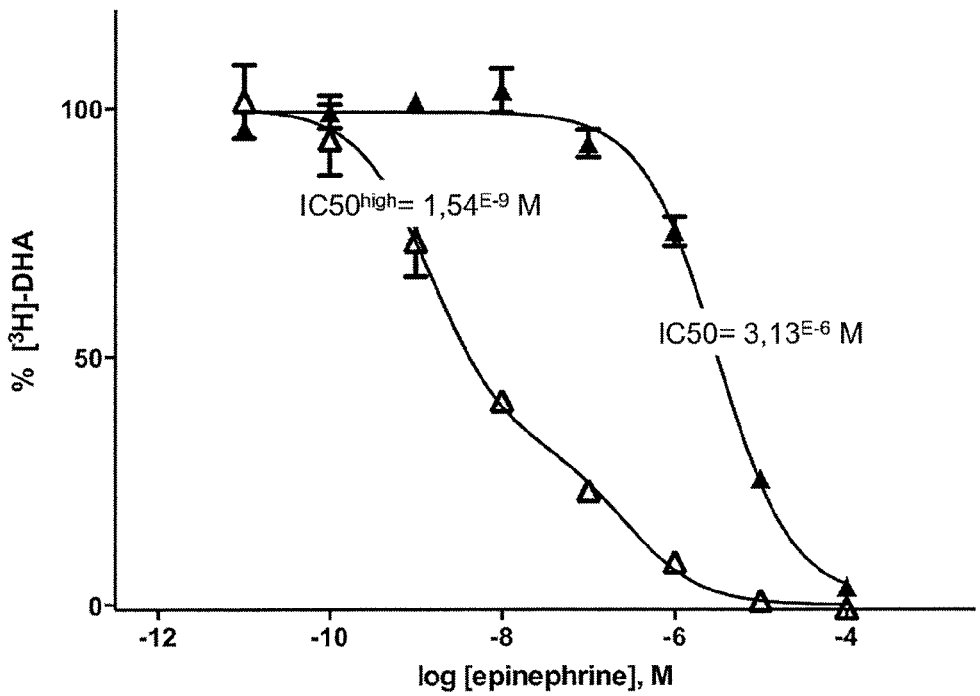
Figure 6B:
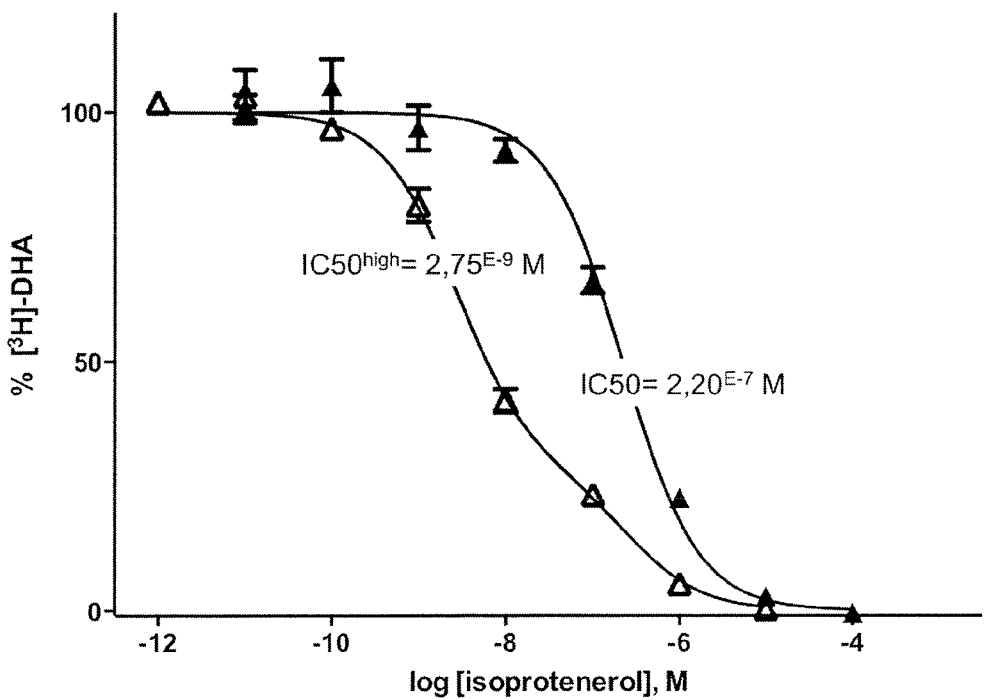
Figure 6C:
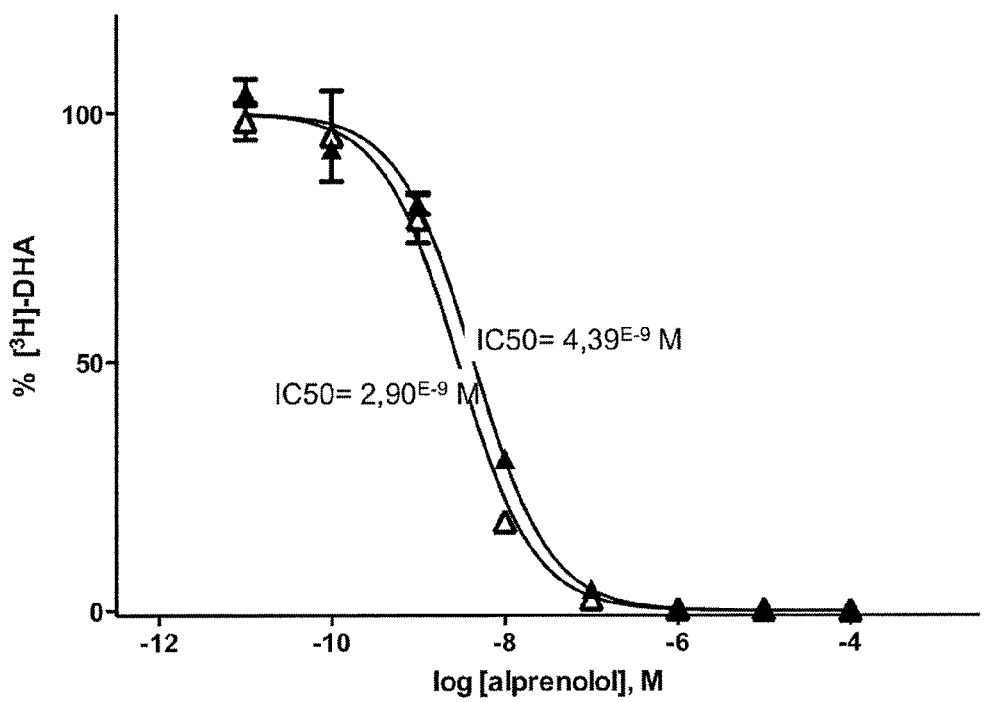
Figure 6D:
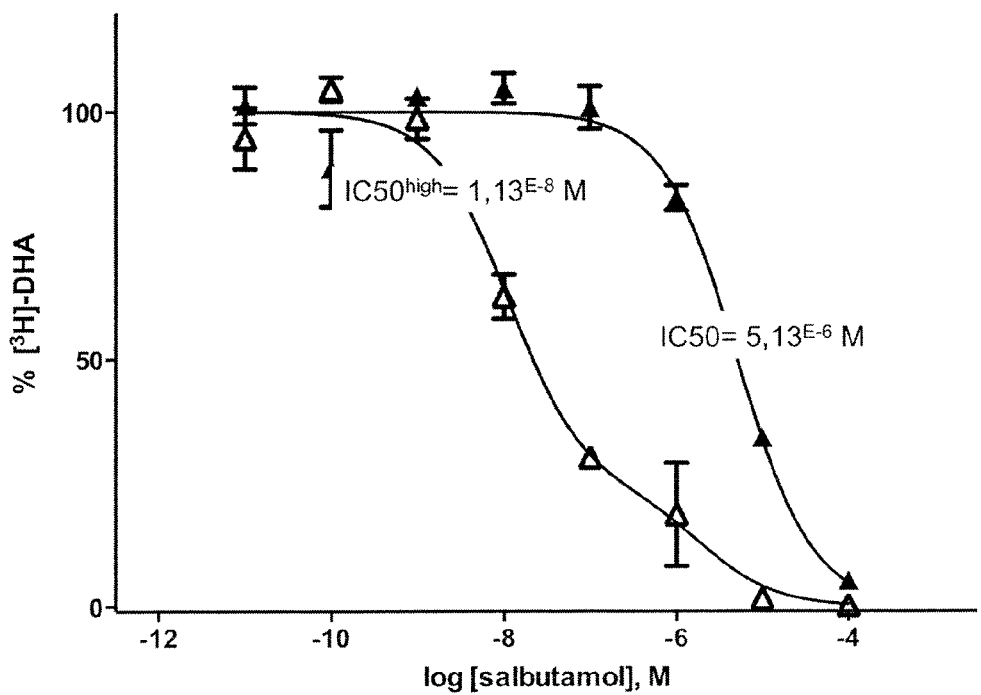
Figure 6E:
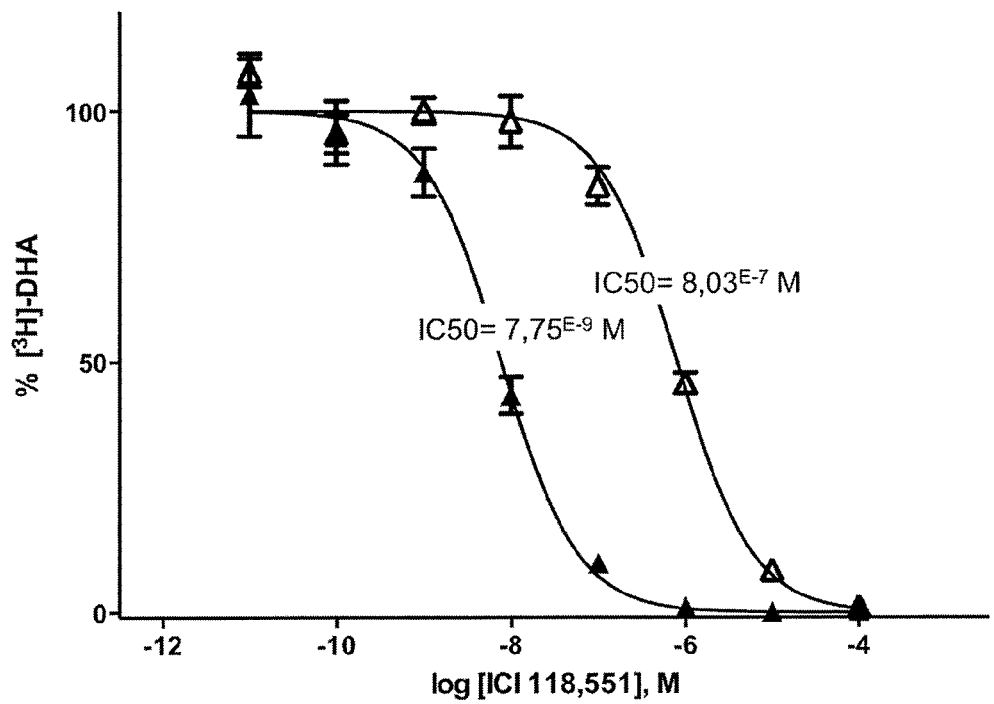
Figure 6F:
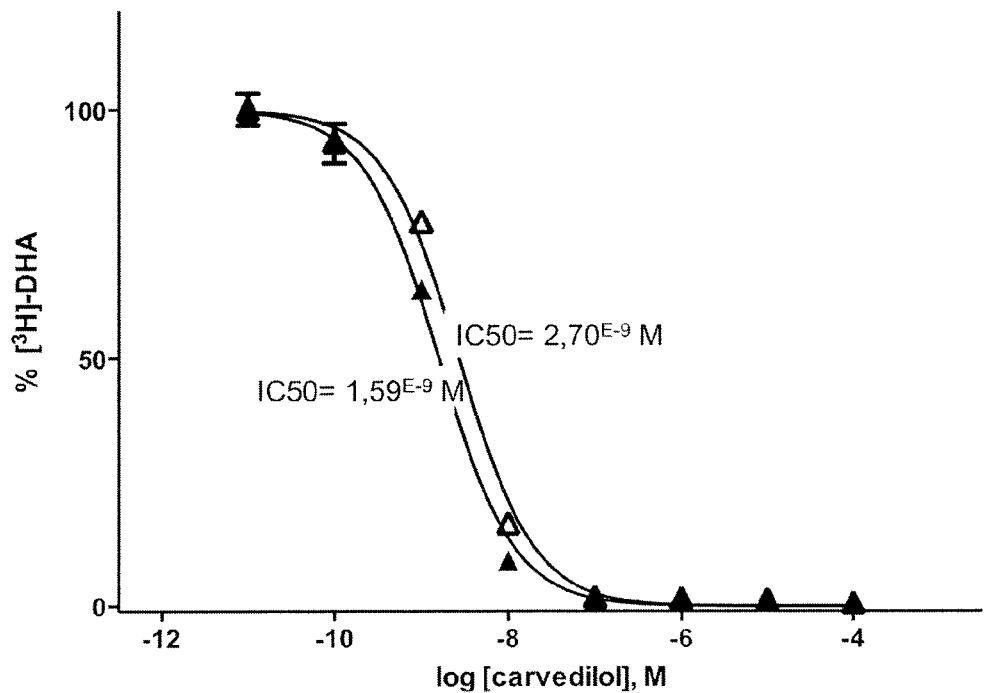

Similarly, the decreased affinity of the β2AR365N-Nb71 chimer, compared to control β2AR365N-Nb69 for the inverse agonist ICI-118,551 can be calculated from the ratio of the IC50 values from the competitive binding experiments depicted in FIG. 6E by dividing the IC50 of β2AR365N-Nb69 by the IC50 of β2AR365N-Nb71, resulting in an apparent potency shift of ≅0.01.

Notably, the β2AR-Nb71 fusion has little effect on the affinity for the neutral antagonist alprenolol as compared to the control β2AR365N-Nb69 chimer. The IC50's β2AR365N-Nb71 and β2AR365N-Nb69 for alprenolol (FIG. 6C) are indeed very similar, consistent with the fact that neutral antagonists are non-selective ligands that bind different functional conformations.

Remarkably, the β2AR-Nb71 fusion has little effect on the affinity for the antagonist carvedilol as compared to the control β2AR365N-Nb69 chimer. The IC50's β2AR365N-Nb71 and β2AR365N-Nb69 for carvedilol (FIG. 6F) are indeed very similar.

Example 7

Conformational Thermostability of the PAR-Single-Domain Antibody Fusion

One of the strategies for the stabilization of GPCRs, namely the thermostabilization of GPCRs is based on the systematic mutagenesis coupled with thermostability assays in the presence of (radio)ligands to screen for mutants with improved thermostability (Tate 2012). Unfortunately, receptors that are thermostabilized in the presence of an agonist show no significant increase in the affinities for their respective agonists (Serrano-Vegaet et al., 2008, Shibata et al., 2009, Lebon et al., 2011), indicating that these thermostabilized receptors do not adopt the fully active conformation of the receptor.

To test if the β2AR365N-Nb80 fusion, a fusion protein with all properties of the active-state ββ2AR receptor has an increased thermostability, we performed thermostability assays on β2AR365N-Nb80 and β2AR365N-Nb69 to measure if a Single-domain antibody with G protein-like behavior (Nb80) that stabilizes the active conformation of the receptor also increases its thermostability, leading to a genuine conformational thermostabilized receptor.

To solubilize the receptors, we incubated membranes (approximately 1 mg of total membrane protein) from Sf9 cells expressing either β2AR365N-Nb80 or β2AR365N-Nb69 for one hour on ice in 1% DDM (20 mM Tris HCl, pH7.4, 500 mM NaCl, 1% n-Dodecyl β-D-maltoside, 10 µg/ml leupeptine, 0.2 mM PMSF). Next insoluble material was removed by centrifugation for 5 min at 17000 g. Next, solubilized receptors were diluted with buffer (20 mM Tris HCl, pH7.4, 500 mM NaCl) to a DDM concentration of 0.08% DDM and insoluble material was removed again by centrifugation (20000 g for 20 min at 4° C.). 20 µl aliquots of the solubilized receptor were diluted to 90 µl with assay buffer (20 mM Tris HCl, pH7.4, 500 mM NaCl, 1% n-Dodecyl β-D-maltoside) and left on ice for 30 min.

Thermostability was assessed by incubating diluted aliquots in the absence of any ligand at a specified temperature for 30 min. After 30 minutes, excess radioligand (5 nM final concentration) was added to each sample and samples were left on ice for 45 min.

To quantify the remaining fraction of functional receptor, receptor-bound radioligand was separated from free radioligand by gel filtration on a 2 ml SEPHADEX® G50 column equilibrated with ice cold assay buffer. The receptor bound radioligand was collected in a volume of 1 ml and diluted in 6 ml of scintillation fluid (Optiphase Hisafe2, PerkinElmer, cat. Nr 1200-436) to count the radioactivity (cpm) in a liquid scintillation analyzer Tri-carb2810TR (Perkin Elmer). The nonspecific binding was estimated by measuring the radioactivity remaining in the protein fraction in the presence of 1 µM of cold alprenolol.

Data represent the mean±SEM (experiments performed in triplicate) of the radioligand that specifically binds to the receptor at a given temperature, relative to the receptor bound ligand at 0° C. These experiments indicate that the solubilized β2AR365N-Nb80 chimer (Tm=33° C.) has a higher thermostability than β2AR365N-Nb69 (Tm=29° C.) in 0.08% DDM (FIG. 7). Because Nb80 stabilizes the active conformation of β2AR we conclude that the β2AR365N-Nb80 chimer represents a conformational thermostabilized receptor.

Example 8

Comparison of the Pharmacological Properties of the β2AR-Single-Domain Antibody Fusion to the Non-Fused PAR in Complex with Exogenously Added Single-Domain Antibody To compare the efficiency of fused versus non-fused Nb80 to stabilize the active state of β2AR, the pharmacological properties of the β2AR365N-Nb80 fusion was compared to the non-fused β2AR365N in complex with exogenously added Nb80. We performed similar comparative radioligand competition experiments as described in Example 6. The natural agonist epinephrine (Sigma cat. Nr E4250) was used as the competitor and [$^3$H]-dihydroalprenolol as the radioligand. The β2AR365N-Nb69 fusion and β2AR365N in complex with exogenously added Nb69 were assayed in parallel as controls.

Radioligand competition binding experiments were performed on Sf9 insect cell membranes (5 µg total protein) expressing either β2AR365N (no Single-domain antibody fused), β2AR365N-Nb80 or β2AR365N-Nb69. Membranes of Sf9 cells expressing the β2AR365N-Nb80 fusion or the β2AR365N-Nb69 fusion were mixed with different concentrations of epinephrine ranging from $10^{-10}$ M to $10^{-4}$M in binding buffer (75 mM Tris pH7.5, 12.5 mM MgCl2, 1 mM EDTA, 0.05% BSA). In parallel, different concentrations of purified Nb80 or Nb69, ranging from 50 pM to 500 nM, were added to membranes of Sf9 cells expressing the non-fused β32AR365N before mixing them with the different concentrations of epinephrine ranging from $10^{-10}$ M to $10^{-4}$ M in binding buffer. Next, the radioligand [$^3$H]-dihydroalprenolol was added (2 nM final concentration) to each condition and samples were incubated for 2 hours at room temperature on a shaking platform (total reaction volume per assay point was 250 µl). Ligand bound membranes were harvested and radioactivity was measured as described in Example 6. Data represent the mean±SEM of each data point performed in triplicate.

Data represent the mean±SEM, of each experiment performed in triplicate. The IC50 values were determined by nonlinear regression analysis using Prism (GraphPad Software, San Diego, Calif.).

As can be observed in FIG. 8, the affinity of non-fused β2AR365N for the natural agonist epinephrine is depending on the concentration of Nb80, with increasing apparent affinity concomitant with increasing concentrations of exogenously added Nb80. The epinephrine potency shift of β2AR365N in presence of 500 nM Nb80 is only 87-fold, while 534-fold for the β2AR365N-Nb80 fusion (calculated by dividing the IC50 of the mock fusion by the respective IC50s of the non-fused β2AR365N in presence of exogenously added Nb80 and β2AR365N-Nb80). Only in the presence of 5 µM exogenous Nb80, the IC50 obtained with the non-fused β2AR365N is identical to the one obtained with the β2AR365N-Nb80 fusion. 5 µM of free Nb80 has to be added to the non-fused receptor to measure a comparable affinity of non-fused β2AR365N and the β2AR365N-Nb80 fusion for the natural agonist epinephrine. The effective intramolecular concentration of Nb80 in the β2AR365N-Nb80 fusion thus appears to be higher than 500 nM.

The amount of B2AR in the Sf9 membranes was determined to be approximately 20 pmol/mg total membrane protein for the β2AR365N-Nb80 fusion. Five µg of the β2AR365N-Nb80 Sf9 membranes thus contain approximately 0.1 pmol of β2AR. Five µM of exogenously added Nb80 (in 250 µl of reaction volume) corresponds to approximately 1.25 nmol of Nb80. A 12500 fold molar excess of exogenously added Nb80 over β2AR is required to constrain the receptor in its epinephrine bound active state with the same efficiency as compared to the β2AR-Nb80 fusion under the conditions tested and assuming equal expression of β2AR whether or not fused to Nb80.

The results obtained via the comparative radioligand competition assay on the active state constrained versus the non-constrained β2AR (Examples 6 and 8) allow to discriminate (partial) agonists (IC50 ratios >10) from antagonists and inverse agonists (IC50 ratios <1) (Table 3). The ability to discriminate and predict the mode of action of tested compounds at nM-µM concentrations (agonist, partial agonist, antagonist, inverse agonist) without the need for a cellular receptor signaling assay is an asset for compound screening.

Example 9

Generation of M2R-Single-Domain Antibody Fusion Protein Constructs

The GPCR-Single-domain antibody fusion described in this example is a chimeric polypeptide that contains two different proteins connected with a peptide linker: the GPCR M2 muscarinic acetylcholine receptor (M2R), the linker GGGSGGGGSGGGGSGGGGSGGGS (SEQ ID NO:49) and a Single-domain antibody, all of which were fused in this order from the amino to the carboxy terminus. Genes encoding these proteins were fused as described below (FIG. 9) and cloned in the pFastBac1 vector.

The GPCR part, synthetically synthesized, encodes the cleavable hemagglutinin (HA) protein signal peptide (SP) derived from influenza virus (MKTIIALSYIFCLVFA; SEQ ID NO:52) followed by the Flag epitope (DYKDDDD; SEQ ID NO:50) followed by a TEV cleavage site (ENLYFQG;

SEQ ID NO:51) followed by the coding sequence of human M2 muscarinic acetylcholine receptor encompassing Met1 to Arg466 with a deletion of the intracellular loop 3: replacing the amino acids Pro233 till Lys374 with Thr and Arg. Point mutations (N2D, N3D, N6D, N9D) were introduced to the construct to disrupt glycosylation sites (M2Δi3R; SEQ ID NO:5). This muscarinic receptor engineering was performed to increase the receptor's cellular expression levels in Sf9 cells.

Nb9-1 (SEQ ID NO:16) is a single domain antibody that selectively binds to agonist bound M2Δi3R and exhibits G protein-like behavior (also referred to as a G protein mimetic), thus stabilizing the active-state conformation of the receptor in the agonist·M2Δi3R·Nb9-1 complex. The M2Δi3R-Nb9-1 fusion was optimized for insect cell expression and synthesized by Geneart (pMK-RQM2Δi3-Nb9-1; Lab reference CA7908; Life technologies). The receptor-Single-domain antibody fusion was cloned as a BglII-XbaI fragment in the BamHI-XbaI opened pFastBac1 vector resulting in pFastBac1-M2Δi3R-Nb9-1 (Lab reference CA7911). A control construct encoding only the M2Δi3R open reading frame without linker and a Single-domain antibody (pFastBac1-M2Δi3R; Lab reference CA7914) was constructed by cloning the BglII-XbaI fragment from pMK-RQM2Δi3R (synthesized by Geneart, Lab reference 7909) in the pFastBac1 vector. All constructs were transformed in E. coli Top10 cells. The amino acid sequences encoded by the M2Δi3R control construct and the M2Δi3R-Nb fusion construct are shown in FIGS. 9B and C (SEQ ID NOs:5 and 6). The M2Δi3R-Nb9-8 fusion construct has been made in a similar way. Nb9-8 (SEQ ID NO:17) is another example of a M2R specific Single-domain antibody with G protein-like behavior (Kruse, 2013).

Example 10

Expression of M2Δi3R-Single-Domain Antibody Fusion and of M2Δi3R in Baculovirus-Infected Sf9 Cells To produce bacmids encoding the M2Δi3R-Single-domain antibody fusion, one ng of pFastBac1-M2Δi3R-Nb9-1 was transformed into DH10BAC™ cells using the BAC-TO-BAC® Baculovirus Expression system according to the manufacturer's instructions and plated overnight as described in Example 2. White colonies were picked, bacmids were purified and the sequences of the open reading frames reconfirmed. Recombinant baculovirus was produced in Sf9 cells by transfecting the M2Δi3R-Single-domain antibody 9-1 bacmid and the M2Δi3R bacmid.

P1 and P2 baculovirus stocks were prepared as described in Example 2. Recombinant expression of M2Δi3R or the M2Δi3R-Nb9-1 fusion was accomplished through the infection of freshly grown Sf9 cells at a density of $4 \times 10^6$/ml with 100 fold diluted P2 baculovirus stocks. Infected cells were cultured for 48 h to 60 h at 27° C. (130 rpm) before harvesting. The expression of GPCR-Single-domain antibody hybrids was confirmed by fluorescence microscopy on live cells. Cells expressing the recombinant protein were washed twice with ice cold PBS (pH 7.4, 1.5 mM EDTA), pelleted and stored at −80° C.

Example 11

Preparation of Membranes from Insect Cells Expressing the M2Δi3R or M2Δi3R-Nb Fusion Cell pellets obtained by centrifugation of fresh 50 ml cultures of Sf9 cells expressing recombinant M2Δi3R or M2Δi3R-Nb fusion were processed into membrane extracts and stored exactly as described in Example 4. Total protein concentrations were measured with the BCA protein assay kit according to the manufacturer's instructions. The pharmacological properties of these GPCR-Single-domain antibody hybrids were analyzed by radioligand competition assays (Example 12).

Example 12

Analysis of the Pharmacological Properties of the M2Δi3R-Single-Domain Antibody Fusion by Comparative Radioligand Competition Assays To analyze the pharmacological properties of the M2Δi3R-Single-domain antibody fusion we performed comparative radioligand competition experiments using carbachol (full agonist, Sigma cat. Nr C4382) and oxotremorine M (agonist, Sigma cat. Nr 0100) as the competitor and [$^3$H]-N methyl scopolamine (Perkin Elmer cat. No. NET636001MC) as the radioligand.

Radioligand competition binding experiments were performed on Sf9 insect cell membranes expressing either M2Δi3R (no Single-domain antibody fused) or M2Δi3R-Nb9-1. Membranes of Sf9 cells expressing the different recombinant proteins (examples 10 & 11, 10 μg total protein) were mixed with either carbachol or oxotremorine M at concentrations ranging from $10^{-9}$M to $10^{-2}$M in binding buffer (75 mM Tris pH7.5, 12.5 mM MgCl2, 1 mM EDTA, 0.05% BSA). Next, the radioligand [$^3$H]-N methyl scopolamine was added (0.5 nM final concentration) to each dilution and samples were incubated for 2 hours at room temperature on a shaking platform (total reaction volume per assay point was 250 μl). Receptor-bound radioligand was separated from free radioligand by filtration over Whatman GFC unifilters (Perkin Elmer, cat nr 6005174) using a 96 well FilterMate harvester (Perkin Elmer). After filtration, membranes retained on the filter plates were washed with ice-cold wash buffer (20 mM Tris-HCl pH7.4), and filters were dried for 1 hour at 50° C. After adding 35 μl of scintillation fluid (MICROSCINT™-O, Perkin Elmer, cat. Nr 6013611), radioactivity (cpm) retained on the filters was measured in a Wallac MICROBETA® TriLux scintillation counter.

We compared the pharmacological properties of the M2Δi3R-Nb9-1 fusion with the properties of M2Δi3R (FIG. 10). We found that the pharmacological properties of the M2Δi3R-Nb9-1 chimer is different from the properties of the control M2Δi3R, exemplified by the IC50s and IC50 ratio of the tested ligands on the M2Δi3R-Nb9-1 fusion and M2Δi3R (Table 4). The increased affinity of the M2Δi3R-Nb9-1 chimer, compared to control non-fused M2Δi3R for the synthetic agonist carbachol is calculated as the ratio $IC50_{M2\Delta i3R}/IC50^{high}_{M2\Delta i3R-Nb9-1}$ (FIG. 10A), resulting in an apparent potency shift of ≈67. The ratio obtained for the synthetic agonist oxotremorine M is 316, showing that the M2Δi3R-Nb9-1 chimer adopts an active-state conformation (FIG. 10B). Similarly, the M2Δi3R-Nb9-8 fusion has a higher affinity for the synthetic agonist carbachol as compared to non-fused M2Δi3R (data not shown).

Example 13

Generation of β1AR-Single-Domain Antibody Fusion Protein Constructs

The GPCR-Single-domain antibody fusion described in this example is a chimeric polypeptide that contains two different proteins connected with a peptide linker: the β1 adrenergic receptor (β1AR), the linker GGGGSGGGGSGGGGSGGGGSGGGS (SEQ IDNO:60) and a Single-domain antibody, all of which were fused in this order from the amino to the carboxy terminus. Genes encoding these proteins (FIG. FHA) were fused, as described below.

A synthetic β1AR gene was synthesized by Geneart (pMK-RQ hbeta1 AR; Lab reference CA CA7910). It encodes the cleavable hemagglutinin (HA) protein signal peptide (SP) derived from influenza virus (MKTIIALSYIF-CLVFA; SEQ ID NO:52) followed by the Flag epitope (DYKDDDDA; SEQ ID NO:53) followed by a TEV cleavage site (ENLYFQG; SEQ ID NO:51) followed by the coding sequence of human β1 adrenergic receptor encompassing Pro50 to Arg401 (hβ1AR, Uniprot P08588). The β1AR coding sequence contains a deletion of the intracellular loop 3 (Ser260 till Gly304) and two point mutations C392S, C393S to improve the receptor's cellular expression levels in Sf9 cells. Alignments of the amino acid sequences of β1 AR and β2AR indicate that the amino acid side-chains that constitute the Nb80 epitope in the β2AR·Gs complex (Rasmussen et al., 2011a) are identical amongst β1AR and β2AR except R318 (β1AR numbering; Uniprot P08588) that is replaced by lysine in β2AR. Based on this observation, one extra point mutation R318K was introduced to create the full Nb80 epitope in the β1AR.

Single-domain antibody gene segments encoding the respective Nanobodies were cloned from the plasmids described in Example 1. Nb80 (SEQ ID NO:13) is a β2AR Single-domain antibody that stabilizes the active state of the β2AR bound to full agonists such as BI-167107 (Rasmussen et al., 2011b). Nb69 (SEQ ID NO:15) is specific for the Muscarinic3 receptor and has no detectable affinity for β2AR.

The β1AR receptor was cloned as a BglII-BamHI fragment from pMK-RQ hbeta1AR (Lab reference CA7910) in the BamHI opened pFastBac β2AR365N-Nb80 (CA6836) vector to replace the β2AR receptor resulting in pFastBac-hβ1AR-Nb80 (Lab reference CA7923). A control construct pFastBac-hβ1AR-Nb69 (Lab reference CA7924) encoding the β1AR open reading frame linked to Nb69 was constructed by cloning the same BglII-BamHI fragment from pMK-RQ hbeta1AR in the pFastBac β2AR365N-Nb69 (CA6833) to replace the β2AR receptor. All constructs were transformed in E. coli Top 10 cells. The amino acid sequences encoded the hbeta1AR-Nb fusion constructs are shown in FIGS. 11B and 11C (SEQ ID NOs:7 and 8).

Example 14

Expression of β1AR-Single-Domain Antibody Fusions in Baculovirus-Infected Sf9 Cells To produce bacmids encoding one of the β1AR-Single-domain antibody fusions, one ng of pFastBac-hβ1AR-Nb80 or pFastBac-β1AR-Nb69 was transformed into DH10Bac™ cells using the Bac-to-Bac® Baculovirus Expression system, according to the manufacturer's instructions, and plated overnight as described in Example 2. White colonies were picked, bacmids were purified and the sequences of the open reading frames reconfirmed. Recombinant baculovirus was produced in Sf9 cells by transfecting the β1 AR-Nb80 bacmid and the β1AR-Nb69 bacmid.

P1 and P2 baculovirus stocks were prepared as described in Example 2. Recombinant expression of the β1AR-Nb80 or the β1AR-Nb69 fusion was accomplished through the infection of freshly grown Sf9 cells at a density of $4 \times 10^6$/ml with 100 fold diluted P2 baculovirus stocks. Infected cells were cultured for 48 h to 60 h at 27° C. (130 rpm) before harvesting. Cells expressing the recombinant protein were washed twice with ice cold PBS (pH7.4, 1.5 mM EDTA), pelleted and stored at −80° C.

Example 15

Preparation of Membranes from Insect Cells Expressing the hβ1AR-Nb80 or hβ1AR-Nb69 Fusion Cell pellets obtained by centrifugation of fresh 50 ml cultures of Sf9 cells expressing recombinant hβ1AR-Nb80 or hβ1AR-Nb69 fusion were processed into membrane extracts and stored exactly as described in Example 4. Total protein concentrations were measured with the BCA protein assay kit, according to the manufacturer's instructions. The pharmacological properties of these GPCR-Single-domain antibody hybrids were analyzed by radioligand competition assays (Example 16).

Example 16

Analysis of the Pharmacological Properties of the hβ1AR-Single-Domain Antibody Fusion by Comparative Radioligand Competition Assays To analyze the pharmacological properties of the different hβ31AR-Single-domain antibody fusions, we performed comparative radioligand competition experiments using the natural agonist epinephrine, then inverse agonist ICI-118, 551 hydrochloride or the neutral antagonist alprenolol hydrochloride as the competitor and the neutral antagonist [$^3$H]-dihydroalprenolol as the radioligand. The pharmacological effect of the different ligands is according to Kahsai et al., 2011.

Membranes of Sf9 cells expressing the different recombinant proteins (Examples 14 & 15, 5 μg total protein) were mixed with either epinephrine, ICI118,551 or alprenolol at concentrations ranging from $10^{-11}$M to $10^{-4}$M in binding buffer (75 mM Tris pH7.5, 12.5 mM MgCl2, 1 mM EDTA, 0.05% BSA). Next, the radioligand [$^3$H]-dihydroalprenolol was added (2 nM final concentration) to each dilution and samples were incubated for 2 hours at room temperature on a shaking platform (total reaction volume per assay point was 250 μl). Receptor-bound radioligand was separated from free radioligand as described in Example 6. Data represent the mean±SEM (standard error of the mean) of each experiment performed in triplicate. The IC50 values were determined by nonlinear regression analysis using Prism (GraphPad Software, San Diego, Calif.).

In this series of experiments, we compared the pharmacological properties of the hβ1AR-Nb80 fusion with the properties of the hβ1AR-Nb69 fusion (FIG. 12A). We found that the pharmacological properties of the hβ1AR-Nb80 chimer are profoundly different from the properties of the control Nb69-fused receptor. Compared to the Nb69 chimer, hβ1AR fused to the Single-domain antibody with G protein-like behavior (Nb80) exhibits increased affinity for the agonist epinephrine and a decreased affinity for the inverse agonist (ICI-118,551), exemplified by the modulated IC50s of the tested ligands on the hβ1AR-Nb80 fusion and hβ1AR-Nb69 fusion (Table 5). This proves that the hβ1AR-Nb80 chimer, but not the control mock β2AR365N-Nb69 chimer, adopts an active-state conformation characterized by increased affinities for agonists and decreased affinities for inverse agonists.

The increased affinity of the hβ1AR-Nb80 chimer, compared to control hβ1AR-Nb69 for the natural agonist epinephrine can be calculated from the ratio of the IC50 values from the competitive binding experiments depicted in FIG. 12A by dividing the IC50 of hβ1AR-Nb69 by the IC50$^{high}$ of hβ1AR-Nb80, resulting in an apparent potency shift of ≈68. The decreased affinity of the hβ1AR-Nb80 chimer, compared to control hβ1AR-Nb69 for the inverse agonist ICI-118,551 can be calculated from the ratio of the IC50 values from the competitive binding experiments depicted in FIG. 12B by dividing the IC50 of hβ1AR-Nb69 by the IC50$^{high}$ of hβ1AR-Nb80, resulting in an apparent potency shift of ≈0.077.

Notably, the hβ1AR-Nb80 fusion has little effect on the affinity for the neutral antagonist alprenolol as compared to the control hβ1AR-Nb69 chimer. The IC50's β2AR365N-Nb80 and β2AR365N-Nb69 for alprenolol (FIG. 12C) are indeed very similar, consistent with the fact that neutral antagonists are non-selective ligands that bind different functional conformations.

Example 17

Generation of β2AR-Nb60 Fusion Construct

The GPCR-Single-domain antibody fusions described in this Example is a chimeric polypeptides that contain two different proteins connected with a peptide linker: the GPCR β2AR, the linker GGGGSGGGS (SEQ ID NO:51) and Nb60, all of which were fused in this order from the amino to the carboxy terminus. The genes encoding this protein were fused as described in Example 1 with minor adjustments.

The GPCR part was amplified from DNA encoding the cleavable hemagglutinin (HA) protein signal peptide (SP) derived from influenza virus (MKTIIALSYIFCLVFA; SEQ ID NO:52) followed by the Flag epitope (DYKDDDDA; SEQ ID NO:53) followed by a TEV cleavage site (ENLYFQGF; SEQ ID NO:54) followed by the coding sequence of human β2 adrenergic receptor encompassing Gly2 to Gly365 (SEQ ID NO:55). A point mutation of N187E was also introduced to the construct to disrupt this unwanted glycosylation site (β2AR365N; Rasmussen et al., 2011b). The β2 adrenergic receptor engineering to β2AR365N was performed to increase the receptor's cellular expression levels in SD cells.

The Single-domain antibody gene segment was amplified from a phagemids encoding the Nb60. Nb60 (SEQ ID NO:18) is a β2AR-specific Single-domain antibody that is described to stabilize an inactive β2AR conformation and significantly inhibit G-protein activation and β-arrestin recruitment (Staus et al., 2013).

The GPCR and the Single-domain antibody were genetically fused in frame by an overlap extension PCR. Therefore, 2 ng of plasmid containing the GPCR cDNA was used as the template in a 50 µl PCR reaction (Phusion polymerase, (Biolabs, cat. Nr M0530S) to amplify the β2AR encoding DNA (CA6817) using primer EP232 (5'-GCAGATCTCGGTCCGAAG-3'; SEQ ID NO:61) and primer EP207 (5'-CCTCCGCCGGATCCGCCACCTCCTCCACTCTGCTCCCCTGTG-3'; SEQ ID NO:57). Primer EP232 anneals 5' of the EcoRI restriction site at the 5' end of the coding sequence. Primer EP207 incorporates part of the GGGGSGGGS (SEQ ID NO:51) linker at the C-terminus of the receptor. The amplification conditions for this reaction were 30 sec 98° C., 25 cycles of 10 sec 98° C., 30 sec 64.5° C., 30 sec 72° C. followed by 5 min at 72° C. to amplify the GPCR encoding part of the open reading frame of the fusion.

Nb60 has an identical N-terminal and C-terminal sequence as the Nanobodies in Example 1. This Single-domain antibody DNA was amplified as described in Example 1 using 2 ng of template (CA2760) and Phusion polymerase in a 50 µl reaction. The following amplification conditions were used 30 min 98° C., 25 cycles of 10 sec 98° C. and 10 sec 72° C. followed by 5 min at 72° C. to amplify the Single-domain antibody encoding part of the hybrids.

PCR fragments encoding the GPCR or a Single-domain antibody were purified using the PCR purification kit (Promega) and used as templates in a new 50 µl PCR reaction: 6 ng of the EP232-β2AR-EP207 (EP232 and EP207 refers to the primers that have been used for PCR amplification) amplified PCR fragment was mixed with approximately 2 ng of amplified EP206-Single-domain antibody-EP202 fragment and fused with Phusion polymerase by overlap extension as follows. After melting for 30 sec at 98° C. and 5 cycles of 10 sec at 98° C., 30 sec at 72° C., the fused β2AR-Single-domain antibody open reading frames were amplified using primers EP232 and EP202 in 25 cycles (10 sec 98° C., 30 sec 67° C., 40 sec 72° C.) followed by 5 min at 72° C. The PCR fragment containing the β2AR-Nb60 open reading frame was purified, cloned as an EcoRI-XbaI fragment in pFastBac1 and transformed in E. coli Top10. Plasmid DNA was prepared from a single colony and the sequence of the open reading frame was confirmed by sequencing. Constructs were designated pFastBac β2AR365N-Nb60 (Lab reference CA8235). The amino acid sequences encoded by the different β2AR365N-Nb fusion constructs are given in FIG. 2E (SEQ ID NO:4).

Example 18

Expression of β2AR-Nb60 in Baculovirus-Infected Sf9 Cells and Preparation of Membranes from Insect Cells Expressing the β2AR-Nb60 Fusion To express the β2AR365N-Nb60 fusion in Sf9 cells, a bacmid encoding β2AR-Nb60 fusion was made and Sf9 cells were infected as described in Example 2. Membranes from insect cells expressing the β2AR-Nb60 fusion were prepared as described in Example 4. The pharmacological properties of these GPCR-Single-domain antibody hybrids have been analyzed by radioligand competition assays (Example 19).

Example 19

Analysis of the Pharmacological Properties of the β2AR-Nb60 Fusion by Comparative Radioligand Competition Assays To analyze the pharmacological properties of the β2AR365N-Nb60 fusion we performed comparative radioligand competition experiments using the natural agonist epinephrine, (−)-isoproterenol hydrochloride (full agonist), and ICI-118,551 hydrochloride (inverse agonist) as the competitor and the neutral antagonist [$^3$H]-dihydroalprenolol as the radioligand. The pharmacological effect of the different ligands is according to Kahsai et al., 2011.

Radioligand competition binding experiments were performed on Sf9 insect cell membranes expressing either β2AR365N-Nb80, β2AR365N-Nb60 or β2AR365N-Nb69. Membranes of Sf9 cells expressing the different recombinant proteins (Examples 2 & 4, 5 µg total protein) were mixed with either, epinephrine, (−)-isoproterenol or ICH 18.551 concentrations ranging from $10^{-11}$M to $10^{-2}$M in binding buffer (75 mM Tris pH7.5, 12.5 mM MgCl2, 1 mM EDTA, 0.05% BSA). Next, the radioligand [$^3$H]-dihydroalprenolol was added (2 nM final concentration) to each dilution and samples were incubated for 2 hours at room temperature on a shaking platform (total reaction volume per assay point was 2500. Receptor-bound radioligand was separated from free radioligand as described in Example 6. Data represent the mean±SEM (standard error of the mean) of each experiment performed in triplicate. The IC50 values were determined by nonlinear regression analysis using Prism (GraphPad Software, San Diego, Calif.).

In these experiments, we compared the pharmacological properties of the β2AR365N-Nb60 fusion with the properties of the β2AR365N-Nb80 and the β2AR365N-Nb69 chimer (FIG. 13A). Nb60 is a Single-domain antibody that is claimed to stabilize an inactive β2AR conformation (Staus et al., 2013), Nb80 is a Single-domain antibody that selectively binds to agonist bound β2AR and exhibits G protein-like behavior, thus stabilizing the active-state conformation of the receptor in the agonist·β2AR·Nb 80 complex (Rasmussen et al., 2011b). Nb69 is a mock Single-domain antibody that specifically binds to the rat muscarinic receptor M3 with no detectable affinity for β2AR. We found that the pharmacological properties of the β2AR365N-Nb60 chimer are profoundly different from the properties of the control Nb69-fused receptor. Compared to the Nb69 chimer, β2AR fused to Nb60 exhibits decreased affinities for agonists (epinephrine, isoproterenol) and has little effect on the affinity for the inverse agonist ICI-118,551, exemplified by the modulated IC50s of the tested ligands on the Nb60 and Nb69 fusion (Table 6). This proves that the β2AR365N-Nb60 chimer, but not the control mock β2AR365N-Nb69 chimer, adopts a conformation that differs from the agonist-bound active state conformation and differs from the basal conformation of the receptor. This conformation is characterized by decreased affinities for agonists. Our results clearly show that different Nanobodies are able to stabilize different conformational states of a receptor.

The decreased affinity of the β2AR365N-Nb60 chimer (versus the increased affinity of the β2AR365N-Nb80 chimer), compared to control β2AR365N-Nb69 for the natural agonist epinephrine can be calculated from the ratio of the IC50 values from the competitive binding experiments depicted in FIG. 13A by dividing the IC50 of β2AR365N-Nb69 by the IC50 of β2AR365N-Nb60, resulting in an apparent potency shift of ≈0.0046 (versus≈855 for Nb80 fusion compared to Nb69 fusion). The decreased affinity of the β2AR365N-Nb60 chimer for the synthetic agonist isoprotenerol can be calculated from the ratio of the IC50 values from the competitive binding experiments by dividing the IC50 of β2AR365N-Nb69 by the IC50 of β2AR365N-Nb60 (FIG. 13B), resulting in an apparent potency shift of ≈0.012 (versus ≈155 for Nb80 fusion compared to Nb69 fusion).

Example 20

Generation of Mu-Opioid Receptor-Single-Domain Antibody Fusion Constructs

The Mor1 AA sequence is highly conserved between different mammalian species. More specifically, the cross species sequence homology for the predicted intracellular topological domains (ICLs+C-terminus) between mouse, bovine, pig and human Mor1 is >90%. Knowing that Nb33 interacts with intracellular epitopes of mouse Mor1, we anticipated that Nb33 also stabilizes the active conformation of hMor1, as there is only one conserved substitution in ICL2 (indicated by ':' in FIG. 14) and one semi-conserved substitution in the C-terminus (indicated by '.' in FIG. 14).

The GPCR-Single-domain antibody fusions described in this example encode chimeric polypeptides similar to those described in Example 1. Here we describe the human mu-opioid receptor (hMor1, NCBI reference sequence NM_000914.1) genetically fused to Single-domain antibody Nb33 (Lab reference XA8633) and separated by a 34 AA Gly-Ser linker (GGGGSGGGGSGGGGSGGGGSGGGGSGGGGSGGGS; SEQ ID NO:62). An open reading frame encoding hMor1 was optimized for insect cell expression and was custom synthesized as an EcoRI-HindIII fragment at GeneArt (Life Technologies). A cartoon of the synthetic hybrid gene is represented in FIG. 15. Compared to the β2AR fusions depicted in FIG. 2A, for the opioid receptor fusions i) the TEV cleavage site is omitted and ii) β2AR365N is replaced by the human Mor1 nt sequence encoding for AA residues 1-360 with an extra deletion of AA residues 2-5 (DSSA) and immediately followed by a 3C cleavage site insertion (LEVLFQGP) before the 34GS linker. Nb33 (Lab reference XA8633; SEQ ID NO:19) exhibits$G_{i/o}$ protein-like behavior (also referred to as $G_{i/o}$ protein mimetic), and selectively stabilizes the active state conformation of Mor1 in the agonist·Mor1·Nb33 complex. Similar to $G_i$, adding excess amounts of Nb33 increases the affinity of mouseMor1 for agonist Dmt1-Dalda at least 10-fold. In the fusion construct, the coding sequence of Nb33 was engineered to introduce a unique PstI restriction site in FR1. The synthetic gene encoding hMOR1-34GS-Nb33 was cloned as an EcoRI-HindIII fragment in pFastBac1 and transformed to E. coli TG1, resulting in pFastBac1::hMOR1-34GS-Nb33 (Lab reference XA8901). The encoding AA sequence of the fusion is depicted in FIG. 15A. In parallel, another fusion of hMOR1 with an irrelevant Single-domain antibody was generated as the control construct expressing the prominent conformation of Mor1. Therefore, the Nb33 encoding sequence in pFastBac1::hMOR1-34GS-Nb33 was exchanged by a gene segment coding for Single-domain antibody Nb10 (Lab reference CA4910). Nb10 (SEQ ID NO:20) is a well characterized Single-domain antibody specific for extracellular epitopes of a chemokine GPCR and has no detectable affinity for Mor1. To prepare the Nb10 coding gene segment for the fusion, Nb10 was reamplified by PCR using primers A6E (5'-GATGTGCAGCTGCAG-GAGTCTGGRGGAGG-3'; SEQ ID NO:63) introducing a PstI site in FR1 (changing V into Q) of the Single-domain antibody and GIII (5'-CCACAGACAGCCCTCATAG-3'; SEQ ID NO:64), the latter oligo hybridizing to gene III. As template, 5 ng of a DNA prep of the phagemid pXAP100 expressing the Nb10 gene III fusion was used. The amplification conditions for this reaction were 3 min 94° C. and 25 cycles of 30 sec 94° C., 30 sec 55° C., 45 sec 72° C. followed by 10 min at 72° C. After purification, the amplicon was double digested with PstI (introduced via oligo A6E) and BstEII (a naturally occurring unique site in FR4), purified and ligated into the 6.2 kbp gel purified PstI-BstEII fragment derived of pFastBac1::hMOR1-34GS-Nb33, resulting in pFastBac1::hMOR1-34GS-Nb10. The encoding AA sequence of the fusion hMOR1-34GS-Nb10 (SEQ ID NO:20) is depicted in FIG. 15C. Following cloning, plasmid DNA of both fusion constructs was prepared from single colonies and the sequence of the hybrid gene was confirmed by sequencing.

Example 21

Expression of Mu Opioid Receptor-Single-Domain Antibody Fusions in Baculovirus-Infected Sf9 Cells To produce bacmids encoding Mor1-Single-domain antibody fusions, five ng of pFastBac1::hMOR1-34GS-Nb33 or pFastBac1::hMOR1-34GS-Nb10 was transformed into the DH10BAC™ cells. Recombinant baculovirus was produced by transfecting the Mor1-Single-domain antibody bacmids in Sf9 cells. Each bacmid was used for Cellfectin II mediated SD transfection as described in Example 2, except that the P1 recombinant baculovirus was harvested 72 h after the transfection for the Nb10 fusion and 48 h for the Nb33 fusion. P1 virus stocks were stored at −80° C. as aliquots of snap frozen culture supernatant adding 5% (final concentration) fetal calf serum (FCS). A P2 recombinant baculovirus stock was made by diluting P1 50 to 1000 fold in a fresh Sf9 culture at a density of $1\times10^6$ cells/ml and culturing at 27° C. and 130 rpm. P2 virus stocks were harvested by centrifugation 48 h and 72 h after infection and stored as described above at −80° C. until further use. The cell pellets were washed twice with ice cold PBS (Life Technologies, cat nr 10010-023), supplemented with 1.5 mM EDTA), stored at −80° C. to prepare membranes. Recombinant expression of the different MOR1-Nb fusions was accomplished through the infection of freshly grown Sf9 cells at a density of 2e6 cells/ml with 50, 200 and 1000 fold diluted P2 baculovirus stocks. As a negative control expression, Sf9 cells were infected in parallel with P2 of Flag tagged non-related M2R. Infected cells were cultured for 48 h at 27° C. (130 rpm) before harvesting. The cell pellets were washed twice with ice cold PBS (pH 7.4, 1.5 mM EDTA) and stored at −80° C. until membranes were prepared. Overexpression of GPCR-Single-domain antibody chimers was confirmed via flow cytometry (data not shown).

Example 22

Analysis of the Pharmacological Properties of the hMOR1-Nb Fusion by Comparative Radioligand Competition Assays Overexpression of hMOR1-34GS-Nb33 or hMOR1-34GS-Nb10 in Sf9 cells was assessed via a radioligand assay on membranes (P2) to verify native Mor1 folding and stabilization of the active conformer by Nb33. To prepare membranes, aliquots of 1E7 hMor1 Sf9 cells were resuspended in 1 ml of ice cold lysis buffer containing protease inhibitors (Example 4). The cell suspension was homogenized on ice applying 6 10-sec pulses with a small volume Ultraturrax cell mixer (IKA). The cell homogenate was centrifuged for 35 min at 15000×g in a pre-cooled centrifuge. The supernatant was discarded and the membrane pellet was resuspended in 75 mM Tris HCl pH7.4, 1 mM EDTA, 5 mM MgCl2, 10% sucrose and stored at −80° C. until further use. The total protein content of the membrane prep was determined using the BCA protein assay kit, according to the manufacturer's instructions.

The overexpression of recombinant Mor1 as a Single-domain antibody fusion (hMOR1-34GS-Nb33 and hMOR1-34GS-Nb10 membranes; P2, 72 h incubation) was confirmed in a radioligand assay by measuring total (TB) and non-specific (NS) binding of [3H]-Diprenorphine antagonist radioligand (Perkin Elmer, cat nr NET1121).

The pharmacological properties of recombinant Mor1 is assessed in a radioligand competition assay (Manglik et al., 2012) on hMOR1-34GS-Nb33 or hMOR1-34GS-Nb10 membranes (P2, 72 h expression). Fifteen μg of hMor1-34GS-Nb33 or hMor1-34GS-Nb10 Sf9 membranes in TBB (75 mM Tris-HCl pH7.4, 1 mM EDTA, 5 mM MgCl2, 100 mM NaCl) containing 1% BSA as binding buffer are transferred to a 96 well plate. Subsequently, a serial dilution of cold agonist competitor (Dmt1-Dalda or KGOP01) or antagonist (naloxone) is added. After adding one nM [3H]-diprenorphine (final concentration), the reaction mix (total volume of 125 μl) is incubated for 1 hr at room temperature. Membrane bound [3H]-diprenorphine is separated from unbound radioligand on 96 well FilterMate harvester by passing over a Whatman GF/C filter presoaked in TBB with 1% BSA and washed in ice cold TBB. Filters were dried for 1 hour at 50° C. After adding 35 ml of scintillation fluid (MICROSCINT™-O), radioactivity (cpm) retained on the filters was measured in a Wallac MICROBETA® TriLux scintillation counter. The percentage of residual radioligand binding is calculated and the curves of a representative experiment are represented in FIG. 16. Each value in the graph represents the average of 3 data points. The IC50 values were determined by nonlinear regression analysis, with the one site: fit log IC50 equation using Prism (GraphPad Software, San Diego, Calif.). The IC50s obtained for all ligands tested are indicated in Table x. The IC50 of agonist Dmt-DALDA on hMor1-34GS-Nb33 and hMor1-34GS-Nb10 Sf9 membranes are 655 and 18, respectively. For each agonist ligand tested (Dmt1-Dalda or KGOP01), the highest affinities (lowest IC50s) are demonstrated on the hMor1-34GS-Nb33 membranes compared to those obtained on hMor1-34GS-Nb10 membranes. For each agonist, an IC50 ratio ≥20 (Table 7) indicate their preference for the active state constrained Mor1 receptor. For the antagonist naloxone, the IC50s do not significantly differ whether determined on hMor1-34GS-Nb33 or on hMor1-34GS-Nb10 membranes. This data supports that the Nb33 fusion expresses Mor1 as the active conformer and has a higher affinity for agonists than for the antagonist naloxone.

Example 23

Fragment Library Screening Using a Comparative Radioligand Displacement Assay on the β2AR-Nb Fusions Example 6 illustrates that the pharmacological properties of the β2AR365N-Nb80 fusion is fundamentally different compared to the β2AR365N-Nb69 fusion: the Nb80 fusion preferentially binds natural and synthetic agonists, whereas it shows lower affinity for inverse agonists. Examples 12, 16, 19 further illustrate the modified pharmacological properties of particular GPCR-Nb fusions. Building on this knowledge, we tested if these pharmacological differences can be exploited for drug discovery. As an example, we screened a fragment library to identify fragments that bind with different affinities to β2AR365N-Nb80 versus β2AR365N-Nb69.

To identify fragments that bind with different affinities to β2AR365N-Nb80 versus β2AR365N-Nb69, we screened 1000 fragments of the Maybridge RO3 fragment library containing fragments with a molecular weight in the range of 80 to 300 Da, for conformation selective fragments. All fragments were dissolved in 100% DMSO at a concentration of 200 mM. The 1000 different Maybridge fragments were first diluted to 20 mM in 100% DMSO, next they were diluted 40 times in binding buffer (75 mM Tris pH7.5, 12.5 mM MgCl2, 1 mM EDTA, 0.05% BSA). In a comparative radioligand competition binding experiment, membranes of Sf9 cells (5 µg total protein in 100 µl binding buffer) expressing the β2AR365N-Nb80 fusion were mixed with 100 µl of each of the 1000 diluted fragments in 12 96-well plates. In parallel, membranes of Sf9 cells (5 µg total protein in 100 µl binding buffer) expressing the β2AR365N-Nb69 fusion were mixed with 100 µl of each of the same 1000 diluted fragments in separate series of 96-well plates. Next, radioligand [$^3$H]-dihydroalprenolol was added (50 µl, 2 nM final concentration) to each sample (2000 samples in total) and all were incubated for 2 hours at room temperature on a shaking platform (total reaction volume per assay point was 250 µl). The final screening concentration of each fragment was 200 µM. Each 96-well plate also included membranes incubated with epinephrine (1E-7M) and alprenolol (1E-6M, 1E-8M) as controls. Membranes were harvested and remaining [$^3$H]-dihydroalprenolol radioactivity was measured as described in Example 6. Reasoning that most fragments would not displace the radioligand, we calculated for each 96-well plate the average number of counts per well (excluding the controls) and used this average value to normalize all data points on that plate (expressed in %). These normalized data were used to compare the binding of each fragment for β2AR365N-Nb80 versus β2AR365N-Nb69 by dividing the normalized value obtained on β2AR365N-Nb69 by the normalized value obtained on β2AR365N-Nb80. Ratios higher than 1 indicate that a fragment is selective (has a higher affinity) for β2AR365N-Nb80. Ratios lower than 1 indicate that a fragment is selective for β2AR365N-Nb69.

To measure the reproducibility of this assay, the 44 fragments most selective for β2AR365N-Nb80, the 44 fragments most selective for β2AR365N-Nb69 and the 44 fragments that displace the radioligand on β2AR365N-Nb80 and β2AR365N-Nb69 to a similar extend were reassayed in duplicate and ranked once more using the data of the three independent assays. This comparative assay enables to triage 132AR fragment hits into three separate functional profiles:

Fragments that are more selective for β2AR365N-Nb80 compared to β2AR365N-Nb69, similar to the natural and synthetic β2AR agonist epinephrine and isoproterenol, respectively (agonist profile).

Fragments that displace radioligand on β2AR365N-Nb80 and β2AR365N-Nb69 to a similar extend, similar to alprenolol (antagonist profile)

Fragments that are more selective for β2AR365N-Nb69 compared to β2AR365N-Nb80, similar to ICI118551 (inverse agonist profile).

As a representative example, the % [$^3$H]-dihydroalprenolol binding of 6 fragments is presented in FIG. 17 showing that we can profile the different fragments according to their efficacy: 2 fragments, represented by AC23506, CC56213, from the 12 highest ranked fragments having an agonist profile, preferentially bind the active conformation of β2AR, 2 fragments (KM08985, AW00189) from the best ranked fragments having an inverse agonist profile preferentially bind the prominent conformation (inverse agonist profile) and 2 fragments (CC46746, CC44914) bind both conformations with the same affinity (antagonists profile). Remarkably, only one fragment of the top 12 hits with agonist profile has a catecholamine structure, characteristic for the endogenous and several synthetic 132AR agonists.

Example 24

Analysis of the Activity Profiles of the Selected Fragments by Comparative Radioligand Competition Assays The profiles of the selected 18 fragment hits, 12 with the agonist activity profile, 3 with the antagonistic activity profile and the 3 with the inverse agonist activity profile were subsequently confirmed by comparing the dose response curves on the β2AR365N-Nb80 fusion versus the β2AR365N-Nb69 fusion as described in Example 6. Briefly, membranes of Sf9 cells expressing the different recombinant fusion proteins were mixed with each of the 18 fragment hits, concentrations ranging from $4\times10^{-7}$M to $4\times10^{-4}$M in binding buffer, the radioligand [$^3$H]-dihydroalprenolol was added to each mixture and samples were incubated for 2 hours at room temperature on a shaking platform. Receptor-bound radioligand was separated from free radioligand as described in Example 6. Data represent the mean±SD (standard deviation) of each experiment performed in triplicate. Graphs were generated by nonlinear regression analysis using Prism (GraphPad Software, San Diego, Calif.). The dose response curves on the active state stabilized β2AR365N-Nb80 fusion versus the β2AR365N-Nb69 fusion (the prominent conformation of the receptor) confirms the activity profiles of the 18 fragments chosen in Example 23. Surprisingly, 11 out of the 12 identified fragments belonging to the agonist profile have never been associated with β2AR ligands with agonist activity. (A representative example of a dose response curve of 2 fragments for each activity profile (agonist, antagonist, inverse agonist) is shown in FIG. 18). Fragments AC23506, CC56213 clearly bind with a higher affinity the active state stabilized β2AR365N-Nb80 fusion then the β2AR365N-Nb69 fusion (FIG. 18A). For fragments KM08985, AW00189 we see the opposite (FIG. 18C) while the fragments CC46746, CC44914 with an antagonistic profile bind both conformations with the same affinity (FIG. 18B).

Example 25

Analysis of Pharmacological Properties of Elaborated Fragments by Comparative Radioligand Assays To demonstrate that the comparative radioligand assay can guide elaboration of fragments with an agonistic profile, a fragment CC56213 was chosen on the basis of their dose response curves to elaborate. Multiple chemical variants were subsequently tested in the comparative radioligand assay as (FIG. 19) as described in Example 6. Briefly, membranes of Sf9 cells expressing the β2AR365N-Nb80 fusion or the β2AR365N-Nb69 fusion proteins were mixed with each of the elaborated fragments (called compound 8, 9, 10) as well as with the original fragment CC56213, concentrations ranging from $10^{-9}$M to $10^{-3}$M in binding buffer, the radioligand [$^3$H]-dihydroalprenolol was added to each mixture and samples were incubated for 2 hours at room temperature on a shaking platform. Receptor-bound radioligand was separated from free radioligand as described in Example 6. Data represent the mean±SEM (standard error of Mean) of each experiment performed in triplicate. Graphs were generated by nonlinear regression analysis using Prism (GraphPad Software, San Diego, Calif.).

Compound 8 had a decreased affinity compared to the parent fragment (data not shown) while compound 9 and 10 had increased potency compared to the parent fragment CC56213. The improved affinity of the elaborated fragments (compounds 9, 10) versus the parent compounds were demonstrated by calculating the IC50 values for each P2AR conformer. The increase affinity of the β2AR365N-Nb80 chimer for the elaborated compounds 9, 10 and the parent fragment CC56213 compared to the control β2AR365N-Nb69 can be calculated from the ratio of the IC50 values from the competitive binding experiments depicted in FIG. 19 by dividing the IC50 of β2AR365N-Nb69 by the IC50 of β2AR365N-Nb80, resulting in an apparent potency shift of ≈71, 94, 22 for compound 9, 10, CC56213, respectively. Notably, compound 10 is not only more potent than its parent fragment CC56213 and but is a fivefold more selective for the active state stabilized β32AR.

Example 26

Profiling for Agonism with the ADRB2 cAMP Biosensor Assays (HitHunter-DiscoveRx)

To test if the fragments with an "agonist profile" (12 fragments described in Examples 23 and 24) are able to induce β2AR signaling, the 18 fragments from Example 23 were tested at the DiscoveRx facility at 2 concentrations (2 mM and 100 µM) in a cellular assay, measuring G protein mediated β2AR activation. The % of DMSO in the Hit-Hunter assay was ≤1%, a concentration that was demonstrated not to be toxic for the β2AR cells used. As controls epinephrine (1 µM & 50 nM) and alprenolol (0.1 µM & 5 nM) were included in the assay. The HITHUNTER® cAMP assay (DiscoveRx) monitors the activation of a GPCR via secondary messenger cAMP accumulation. The maximal synthesis of cAMP caused by the control agonist isoproterenol was set as 100% and the agonistic behavior of the tested compounds was expressed relative to isoproterenol agonism (data not shown). Remarkably, at the concentrations tested, the HITHUNTER® bio-assay only identifies three fragments, including CC56213, that cause a detectable and dose depending β2AR signaling activity. It is a well-known feature of fragment libraries that many fragments are toxic for cells at mM concentrations and will not be identified in cellular assays. It thus appears that we can identify multiple fragments with a particular biological activity profile that cannot be identified in cellular assays, currently used for fragment screening and HTS.

TABLE 1

List of Nanobodies

| Single-domain antibody reference number | Single-domain antibody short notation | SEQ ID NO | Sequence |
|---|---|---|---|
| CA2780 | Nb80 | 13 | QVQLQESGGGLVQAGGSLRLSCAA SGSIFSINTMGWYRQAPGKQRELV AAIHSGGSTNYANSVKGRFTISRD NAANTVYLQMNSLKPEDTAVYYCN VKDYGAVLYEYDYWGQGTQVTVSS |
| CA2771 | Nb71 | 14 | QVQLQESGGGLVQPGGSLRLSCAA SGFAFSSYELRWYRQAPGKQHELV AGITTGGNTYYADSVKGRFTISRD NAKNTVYLQMSNLRPEDTAVYACN ANWDLLSDYWGQGTQVTVSS |
| CA5669 | Nb69 | 15 | QVQLQESGGGLVQAGGSLRLSCTA SGLTLSNYAMGWFRQAPGKEREFV AADTWNGNTYHQDSVKGRFTISRD NAKNTVYLQMNYLKPEDTAVYYCA ARGSRRSAYYSSSDYTYRGQGTQV TVSS |
|  | Nb9-1 | 16 | QVQLQESGGGLVQAGGSLRLSCAA SGHTFSSARMYWVRQAPGKEREFV AAISRSGFTYSADSVKGRFTISRD IANNTVYLQMNSLQPEDTAIYTCY AAYLDEFYNDYTHYWGLGTQVTVS S |
|  | Nb9-8 | 17 | QVQLQESGGGLVQAGDSLRLSCAA SGFDFDNFDDYAIGWFRQAPGQER EGVSCIDPSDGSTIYADSAKGRFT ISSDNAENTVYLQMNSLKPEDTAV YVCSAWTLFHSDEYWGQGTQVTVS S |
| CA2760 | Nb60 | 18 | QVQLQESGGGLVQAGGSLRLSCAA SGSIFSLNDMGWYRQAPGKLRELV AAITSGGSTKYADSVKGRFTISRD NAKNTVYLQMNSLKAEDTAVYYCN AKVAGTFSIYDYWGQGTQVTVSS |
| XA8633 | Nb33 | 19 | QVQLQESGGGLVRPGGSRRLSCVD SERTSYPMGWFRRAPGKEREFVAS ITWSGIDPTYADSVADRFTISRDV ANNTLYLQMNSLKHEDTAVYYCAA RAPVGQSSSPYDYDYWGQGTQVTV SS |
| CA4910 | Nb10 | 20 | QVQLQESGGGLVQPGGSLRLSCAA SGSFRSIVSMAWYRQAPGKQRELV ASSNSGGSTNYADSVKGRFTISRD NAKNTVYLQMNSLKPEDTAVYWCN VQNRLPGFDAFSGRSIAETYWGQG TQVTVSS |

TABLE 2

CDRs of listed Nanobodies

| Single-domain antibody reference number | Single-domain antibody short notation | CDR1 | CDR2 | CDR3 |
|---|---|---|---|---|
| CA2780 | Nb80 | GSIFSINT (SEQ ID NO: 21) | IHSGGST (SEQ ID NO: 29) | NVKDYGAVLYEYDY (SEQ ID NO: 37) |
| CA2771 | Nb71 | GFAFSSYE (SEQ ID NO: 22) | ITTGGNT (SEQ ID NO: 30) | NANWDLLSDY (SEQ ID NO: 38) |
| CA5669 | Nb69 | GLTLSNYA (SEQ ID NO: 23) | DTWNGNT (SEQ ID NO: 31) | AARGSRRSAYYSSSDYTY (SEQ ID NO: 39) |
|  | Nb9-1 | GHTFSSAR (SEQ ID NO: 24) | ISRSGFT (SEQ ID NO: 32) | YAAYLDEFYNDYTHY (SEQ ID NO: 40) |
|  | Nb9-8 | GFDFDNFDDYA (SEQ ID NO: 25) | IDPSDGST (SEQ ID NO: 33) | SAWTLFHSDEY (SEQ ID NO: 41) |
|  | Nb60 | GSIFSLND (SEQ ID NO: 26) | ITSGGST (SEQ ID NO: 34) | NAKVAGTFSIYDY (SEQ ID NO: 42) |
| XA8633 | Nb33 | ERTSYP (SEQ ID NO: 27) | ITWSGIDP (SEQ ID NO: 35) | AARAPVGQSSSPYDYDY (SEQ ID NO: 43) |
| CA4910 | Nb10 | GSFRSIVS (SEQ ID NO: 28) | SNSGGST (SEQ ID NO: 36) | NVQNRLPGFDAFSGRSIAETY (SEQ ID NO: 44) |

TABLE 3

Ligand dependent potency shifts on active state constrained β2AR. Values represent the ratio of the IC50 of the indicated non-constrained β2AR (as a fusion to mock Nb69 or as non-fused receptor) to the IC50 of the receptor constrained in the active state (Nb80 or Nb71 fusion).

| Ligand | Biological activity | IC50 ratios β2AR365N-Nb80 (vs β2AR365N-Nb69 mock fusion) | β2AR365N-Nb80 (vs β2AR365N) | β2AR365N-Nb71 (vs β2AR365N-Nb69 mock fusion) |
|---|---|---|---|---|
| epinephrine | Full agonist (endogenous ligand) | 2072 | 1375 | 2032 |
| isoproterenol | Full agonist | 670 | ND | 80 |
| alprenolol | Neutral antagonist | 4 | ND | 1.5 |
| salbutamol | Partial agonist | 373 | ND | 454 |
| ICI-118,551 | Inverse agonist | 0.023 | ND | 0.01 |
| carvedilol | Antagonist | 0.4 | 0.22 | 0.6 |

ND: not determined

TABLE 4

IC50s of ligands for M2Δi3R-Nb9-1 compared to M2Δi3R

| Ligand | Biological activity | IC50 (μM) M2Δi3R-Nb9-1 | M2Δi3R | IC50 ratio IC50$_{m2\Delta i3R}$/IC50$^{high}_{M2\Delta i3R\text{-}Nb9\text{-}1}$ |
|---|---|---|---|---|
| carbachol | Full agonist | 7.17 | 482 | 67.22 |
| oxotremorine M | Full agonist | 0.31 | 98.4 | 316 |

TABLE 5

IC50s of ligands for hβ1AR-Nb80 compared to β2AR-Nb69

| Ligand | Biological activity | IC50 (μM) hβ1AR-Nb80 | hβ1AR-Nb69 | IC50 ratio IC50$_{h\beta1AR\text{-}Nb69}$/IC50$^{high}_{h\beta1ARNb80}$ |
|---|---|---|---|---|
| epinephrine | Full agonist (endogenous ligand) | 5.48 | 376 | 68.67 |
| alprenolol | Neutral antagonist | 14.61 | 14.44 | 0.988 |
| ICI-118,551 | Inverse agonist | 10450 | 805 | 0.077 |

TABLE 6

IC50s of ligands for hβ2AR-Nb60 compared to β2AR-Nb69

| Ligand | Biological activity | IC50 (μM) β2AR-Nb60 | β2AR-Nb69 | IC50 ratio IC50$_{\beta2AR\text{-}Nb69}$/IC50$_{\beta2AR\text{-}b60}$ |
|---|---|---|---|---|
| epinephrine | Full agonist (endogenous ligand) | 284000 | 1310 | 0.0046 |
| isoproterenol | Full agonist | 69200 | 836 | 0.012 |
| ICI-118,551 | Inverse agonist | 22.8 | 11.4 | 0.5 |

TABLE 7

IC50s and fold preference of ligands for prominent (hMor1-34GS-Nb10) and active state stabilized (hMor1-34GS-Nb33) Mor1 conformers.

| Ligand | IC50 (nM) | | $IC50_{Nb33}/IC50_{Nb10}$ |
|---|---|---|---|
| | hMor1-34GS-Nb33 | hMor1-34GS-Nb10 | |
| Dmt1-Dalda (agonist) | 18 | 655 | 36 |
| KGOP01 (agonist) | 3.8 | 76.7 | 20 |
| Naloxone (antagonist) | 21 | 49 | 2 |

REFERENCES

Binz et al., Nature Biotech., 22: 575-582 (2004)

Bokoch, M. P., Y. Zou, S. G. Rasmussen, C. W. Liu, R. Nygaard, D. M. Rosenbaum, J. J. Fung, H. J. Choi, F. S. Thian, T. S. Kobilka, J. D. Puglisi, W. I. Weis, L. Pardo, R. S. Prosser, L. Mueller and B. K. Kobilka (2010). "Ligand-specific regulation of the extracellular surface of a G-protein-coupled receptor." Nature 463 (7277): 108-112.

Caffrey (2003). Membrane protein crystallization. J Struct. Biol. 2003 142:108-32.

Caffrey, M. & Cherezov, V. Crystallizing membrane proteins using lipidic mesophases. Nat Protoc 4, 706-731, (2009).

Chasin et al., 1986, Som. Cell Molec. Genet., 12:555-556.

Chelikani et al., Protein Sci. 2006 15:1433-40

Chen, I. and A. Y. Ting (2005). "Site-specific labeling of proteins with small molecules in live cells." Curr Opin Biotechnol 16(1): 35-40.

Cherezov, V. et al., High-resolution crystal structure of an engineered human beta2-adrenergic G protein-coupled receptor. Science 318, 1258-1265, doi:1150577 [pii] 10.1126/science.1150577 (2007).

Christopoulos, A. (2002). "Allosteric binding sites on cell-surface receptors: novel targets for drug discovery." Nat Rev Drug Discov 1(3): 198-210.

Chun, E., A. A. Thompson, W. Liu, C. B. Roth, M. T. Griffith, V. Katritch, J. Kunken, F. Xu, V. Cherezov, M. A. Hanson and R. C. Stevens (2012). "Fusion partner toolchest for the stabilization and crystallization of G protein-coupled receptors." Structure 20(6): 967-976.

Danley, D. E. (2006). "Crystallization to obtain protein-ligand complexes for structure-aided drug design." Acta Crystallogr D Biol Crystallogr 62(Pt 6): 569-575.

Day P. W., Rasmussen S. G., Parnot C., Fung J. J., Masood A., Kobilka T. S., Yao X. J., Choi H. J., Weis W. I. and Rohrer D. K. et al., A monoclonal antibody for G protein-coupled receptor crystallography, Nat Methods 4 (2007), pp. 927-929.

Derewenda Z. S. Rational protein crystallization by mutational surface engineering, Structure (Camb) 12 (2004), pp. 529-535.

Desmyter A, Spinelli S, Payan F, Lauwereys M, Wyns L, Muyldermans S, Cambillau C. Three camelid VHH domains in complex with porcine pancreatic alpha-amylase. Inhibition and versatility of binding topology. J Biol Chem. 2002 Jun. 28; 277(26):23645-50.

Deveraux et al., 1984, Nucleic Acids Research 12, 387-395

Dimitrov D S. Engineered CH2 domains (nanoantibodies). MAbs. 2009 January-February; 1(1):26-8.

Eroglu et al., EMBO 2002 3: 491^96

Eroglu et al., Proc. Natl. Acad. Sci. 2003 100: 10219-10224

Faham et al., Crystallization of bacteriorhodopsin from bicelle formulations at room temperature. Protein Sci. 2005 14:836-40. 2005

Faham et al., Bicelle crystallization: a new method for crystallizing membrane proteins yields a monomeric bacteriorhodopsin structure. J MoI Biol. 2002 Feb. 8; 316(1): 1-6.

Foord, S. M., T. I. Bonner, et al., 2005. "International Union of Pharmacology. XLVI. G protein-coupled receptor list." Pharmacological reviews 57(2): 279-288.

Fredriksson, R., M. C. Lagerstrom, et al., 2003. "The G-protein-coupled receptors in the human genome form five main families. Phylogenetic analysis, paralogon groups, and fingerprints." Molecular Pharmacology 63(6): 1256-1272.

Früh V, Zhou Y, Chen D, Loch C, Ab E, Grinkova Y N, Verheij H, Sligar S G, Bushweller J H, Siegal G. Application of fragment-based drug discovery to membrane proteins: identification of ligands of the integral membrane enzyme DsbB. Chem Biol. 2010 Aug. 27; 17(8):881-91.

Galandrin S, Oligny-Longpre G, Bouvier M. The evasive nature of drug efficacy: implications for drug discovery. Trends Pharmacol Sci. 2007 August; 28(8):423-30.

Gebauer M, Skerra A. Engineered protein scaffolds as next-generation antibody therapeutics. Curr Opin Chem Biol. 2009 June; 13(3):245-55.

George et al., 2002, Nat Rev Drug Discov 1:808.

Gouaux, It's not just a phase: crystallization and X-ray structure determination of bacteriorhodopsin in lipidic cubic phases. Structure. 1998 6:5-10;

Granier S, Manglik A, Kruse A C, Kobilka T S, Thian F S, Weis W I, Kobilka B K. Structure of the δ-opioid receptor bound to naltrindole. Nature. 2012 May 16; 485(7398):400-4.

Haga K, Kruse A C, Asada H, Yurugi-Kobayashi T, Shiroishi M, Zhang C, Weis W I, Okada T, Kobilka B K, Haga T, Kobayashi T. Structure of the human M2 muscarinic acetylcholine receptor bound to an antagonist. Nature. 2012 Jan. 25; 482(7386):547-51.

Hamers-Casterman, C., T. Atarhouch, S. Muyldermans et al., Naturally occurring antibodies devoid of light chains. Nature 363, 446-448, doi:10.1038/363446a0 (1993).

Hanson M A, Roth C B, Jo E, Griffith M T, Scott F L, Reinhart G, Desale H, Clemons B, Cahalan S M, Schuerer S C, Sanna M G, Han G W, Kuhn P, Rosen H, Stevens R C. Crystal structure of a lipid G protein-coupled receptor. Science. 2012 Feb. 17; 335(6070): 851-5.

Heilker et al., 2009. Drug Discovery Today 14:231-240.

Hunte C. and Michel H., Crystallisation of membrane proteins mediated by antibody fragments, Curr Opin Struct Biol 12 (2002), pp. 503-508.

Kahsai, A. W., K. Xiao, S. Rajagopal, S. Aim, A. K. Shukla, J. Sun, T. G. Oas and R. J. Lefkowitz (2011). "Multiple ligand-specific conformations of the beta2-adrenergic receptor." Nat Chem Biol 7(10): 692-700.

Kallwass et al., Biotechnol. Lett., 15 (1), 29-34, 1993

Kenakin 2002, Trends Pharmacol Sci 25:186.

Kenakin TP (2009) Cellular assays as portals to seven-transmembrane receptor-based drug discovery. *Nature reviews Drug discovery* 8: 617-626

Kobilka, B. K. Amino and carboxyl terminal modifications to facilitate the production and purification of a G protein-coupled receptor. Anal Biochem 231, 269-271 (1995).

Koide et al., J. Mol Biol, 284: 1141-1151 (1998)

Kolakowski, L. F. (1994). "GCRDB—A G-PROTEIN-COUPLED RECEPTOR DATABASE." Receptors & Channels 2(1): 1-7.

Kolkekar et al., 1997, Biochemistry, 36:10901-10909.

Korotkov K V, Pardon E, Steyaert J, Hol W G. Crystal structure of the N-terminal domain of the secretin GspD from ETEC determined with the assistance of a nanobody. Structure. 2009 Feb. 13; 17(2):255-65.

Kruse A C, Hu J, Pan A C, Arlow D H, Rosenbaum D M, Rosemond E, Green H F, Liu T, Chae P S, Dror R O, Shaw D E, Weis W I, Wess J, Kobilka B K. Structure and dynamics of the M3 muscarinic acetylcholine receptor. Nature. 2012 Feb. 22; 482(7386):552-6.

Kruse A C, Ring A M, Manglik A, Hu J, Hu K, Eitel K, Hubner H, Pardon E, Valant C, Sexton P M, Christopoulos A, Felder C C, Gmeiner P, Steyaert J, Weis W I, Garcia K C, Wess J, Kobilka B K. Activation and allosteric modulation of a muscarinic acetylcholine receptor. Nature. 2013 Dec. 5; 504(7478).

Lagerström, M. C. and H. B. Schioth (2008). "Structural diversity of G protein-coupled receptors and significance for drug discovery." Nature reviews. Drug discovery 7: 339-357.

Landau et al., Lipidic cubic phases: a novel concept for the crystallization of membrane proteins. Proc. Natl. Acad. Sci. 1996 93:14532-5

Lawson, A. D. (2012). "Antibody-enabled small-molecule drug discovery." Nat Rev Drug Discov 11(7): 519-525.

Lebon, G., K. Bennett, A. Jazayeri and C. G. Tate (2011). "Thermostabilisation of an agonist-bound conformation of the human adenosine A(2A) receptor." J Mol Biol 409(3): 298-310.

Lebon, G., T. Warne and C. G. Tate (2012). "Agonist-bound structures of G protein-coupled receptors." Curr Opin Struct Biol 22(4): 482-490.

Lee G M, Craik C S (2009). Trapping moving targets with small molecules. Science. April 10; 324(5924):213-5.

Lefranc, M. P., C. Pommie, et al., 2003. "IMGT unique numbering for immunoglobulin and T cell receptor variable domains and Ig superfamily V-like domains." Developmental and Comparative Immunology 27(1): 55-77.

Liu J J, Horst R, Katritch V, Stevens R C, Wtithrich K. Biased signaling pathways in β2-adrenergic receptor characterized by 19F-NMR. Science. 2012 Mar. 2; 335(6072):1106-10.

Luca et al., Proc. Natl. Acad. Sci. 2003 100:10706-11

Manglik A, Kruse A C, Kobilka T S, Thian F S, Mathiesen J M, Sunahara R K, Pardo L, Weis W I, Kobilka B K, Granier S. Crystal structure of the μ-opioid receptor bound to a morphinan antagonist. Nature. 2012 Mar. 21; 485(7398):321-6.

Mansoor et al., Proc. Natl. Acad. Sci. 2006 103: 3060-3065

Marchese et al., Genomics 23: 609-618, 1994

Mary, S., M. Damian, M. Louet, N. Floquet, J. A. Fehrentz, J. Marie, J. Martinez and J. L. Baneres (2012). "Ligands and signaling proteins govern the conformational landscape explored by a G protein-coupled receptor." Proc Natl Acad Sci USA 109(21): 8304-8309.

Mather, 1982, Annals NY Acad. Sci., 383:44-68

Muralidharan, V. and T. W. Muir (2006). "Protein ligation: an enabling technology for the biophysical analysis of proteins." Nat Methods 3(6): 429-438.

Niu et al., Biophys J. 2005 89: 1833-1840

Nollert et al., Lipidic cubic phases as matrices for membrane protein crystallization Methods. 2004 34:348-53

Nygren, P-A. (2008) Alternative binding proteins: affibody binding proteins developed from a small three-helix bundle scaffold. FEBS J. 275, 2668-2676.

Ostermeier C., Iwata S., Ludwig B. and Michel H., Fv fragment-mediated crystallization of the membrane protein bacterial cytochrome c oxidase, Nat Struct Biol 2 (1995), pp. 842-846.

Palczewski, K. et al., Crystal structure of rhodopsin: A G protein-coupled receptor. Science 289, 739-745 (2000).

Popp, M. W., J. M. Antos, G. M. Grotenbreg, E. Spooner and H. L. Ploegh (2007). "Sortagging: a versatile method for protein labeling." Nature chemical biology 3: 707-708.

Probst et al., 1992, DNA Cell Biol. 1992 1 1 : 1-20

Rabuka, D. (2010). "Chemoenzymatic methods for site-specific protein modification." Curr Opin Chem Biol 14(6): 790-796.

Rajagopal, S., K. Rajagopal and R. J. Lefkowitz (2010). "Teaching old receptors new tricks: biasing seven-transmembrane receptors." Nature reviews. Drug discovery 9: 373-386.

Rasmussen S G, DeVree B T, Zou Y, Kruse A C, Chung K Y, Kobilka T S, Thian F S, Chae P S, Pardon E, Calinski D, Mathiesen J M, Shah S T, Lyons J A, Caffrey M, Gellman S H, Steyaert J, Skiniotis G, Weis W I, Sunahara R K, Kobilka B K. Crystal structure of the β2 adrenergic receptor-Gs protein complex. Nature. 2011a Jul. 19; 477(7366):549-55.

Rasmussen, S. G., H. J. Choi, J. J. Fung, E. Pardon, P. Casarosa, P. S. Chae, B. T. Devree, D. M. Rosenbaum, F. S. Thian, T. S. Kobilka, A. Schnapp, I. Konetzki, R. K. Sunahara, S. H. Gellman, A. Pautsch, J. Steyaert, W. I. Weis and B. K. Kobilka (2011b). "Structure of a nanobody-stabilized active state of the beta(2) adrenoceptor." Nature 469(7329): 175-180.

Rasmussen, S. G. F., H.-J. Choi, D. M. Rosenbaum, T. S. Kobilka, F. S. Thian, P. C. Edwards, M. Burghammer, V. R. P. Ratnala, R. Sanishvili, R. F. Fischetti, G. F. X. Schertler, W. I. Weis and B. K. Kobilka (2007). "Crystal structure of the human beta2 adrenergic G-protein-coupled receptor." Nature 450: 383-387.

Reeves et al., 2002, PNAS, 99: 13419

Rich R L, Errey J, Marshall F, Myszka D G. Biacore analysis with stabilized G-protein-coupled receptors. Anal Biochem. 2011 Feb. 15; 409(2):267-72.

Riechmann and Muyldermans J. Immunol. Methods 2000; 240: 185-195.

Rios et al., 2001, Pharmacol Ther 92:71

Rosenbaum, D. M., V. Cherezov, M. A. Hanson, S. G. Rasmussen, F. S. Thian, T. S. Kobilka, H. J. Choi, X. J. Yao, W. I. Weis, R. C. Stevens and B. K. Kobilka (2007). "GPCR engineering yields high-resolution structural insights into beta2-adrenergic receptor function." Science 318(5854): 1266-1273.

Rosenbaum, D. M. et al. Structure and function of an irreversible agonist-beta(2) adrenoceptor complex. Nature 469, 236-240 (2011).

Rosenbaum D. M., S. G. Rasmussen, and B. K. Kobilka, Nature 459 (7245), 356 (2009).

Rummel et al., Lipidic Cubic Phases: New Matrices for the Three-Dimensional Crystallization of Membrane Proteins. J. Struct. Biol. 1998 121:82-91;

Serrano-Vega, M. J., F. Magnani, Y. Shibata and C. G. Tate (2008). "Conformational thermostabilization of the beta1-adrenergic receptor in a detergent-resistant foim." Proceedings of the National Academy of Sciences of the United States of America 105(3): 877-882.

Shibata, Y., J. F. White, M. J. Serrano-Vega, F. Magnani, A. L. Aloia, R. Grisshammer and C. G. Tate (2009). "Thermostabilization of the neurotensin receptor NTS1." Journal of Molecular Biology 390(2): 262-277.

Shimada et al., J. Biol. Chem. 2002 277:31774-80

Shimamura T, Shiroishi M, Weyand S, Tsujimoto H, Winter G, Katritch V, Abagyan R, Cherezov V, Liu W, Han G W, Kobayashi T, Stevens R C, Iwata S. Structure of the human histamine H1 receptor complex with doxepin. Nature. 2011 Jun. 22; 475(7354):65-70.

Shoichet, B. K. and B. K. Kobilka (2012). "Structure-based drug screening for G-protein-coupled receptors." Trends Pharmacol Sci 33(5): 268-272.

Skerra, J. Molecular Recognition, 13:167-187 (2000).

Starovasnik M A, Braisted A C, Wells J A. Structural mimicry of a native protein by a minimized binding domain. Proc Natl Acad Sci USA. 1997 Sep. 16; 94(19):10080-5.

Staus D P, Wingler L M, Strachan R T, Rasmussen S G F, Pardon E, Ahn S, et al. Regulation of Beta-2-Adrenergic Receptor Function by Conformationally Selective Single-domain Intrabodies. Mol Pharmacol. 2013 Dec. 6.

Steyaert J, Kobilka B K (2011). Nanobody stabilization of G protein-coupled receptor conformational states. Curr Opin Struct Biol. August; 21(4):567-72.

Tate, C. G. (2012). "A crystal clear solution for determining G-protein-coupled receptor structures." Trends Biochem Sci.

Urlaub and Chasin, 1980, Proc. Natl. Acad. Sci. USA, 77:4216

Warne, T., R. Moukhametzianov, J. G. Baker, R. Nehme, P. C. Edwards, A. G. W. Leslie, G. F. X. Schertler and C. G. Tate (2011). "The structural basis for agonist and partial agonist action on a β1-adrenergic receptor." Nature 469: 241-244.

Wesolowski et al., 2009, Med. Microbiol. Immunol. 198: 157

White, J. F., N. Noinaj, Y. Shibata, J. Love, B. Kloss, F. Xu, J. Gvozdenovic-Jeremic, P. Shah, J. Shiloach, C. G. Tate and R. Grisshammer (2012). "Structure of the agonist-bound neurotensin receptor." Nature 490 (7421): 508-513.

Wu H, Wacker D, Mileni M, Katritch V, Han G W, Vardy E, Liu W, Thompson A A, Huang X P, Carroll F I, Mascarella S W, Westkaemper R B, Mosier P D, Roth B L, Cherezov V, Stevens R C. Structure of the human κ-opioid receptor in complex with JDTic. Nature. 2012 Mar. 21; 485(7398):327-32.

Xu, F., et al., 2011. "Structure of an agonist-bound human A2A adenosine receptor." Science 332(6027): 322-327.

Yao, X., C. Parnot, X. Deupi, V. R. P. Ratnala, G. Swaminath, D. Farrens and B. Kobilka (2006). "Coupling ligand structure to specific conformational switches in the beta2-adrenoceptor." Nature chemical biology 2: 417-422.

Zhang C, Srinivasan Y, Arlow D H, Fung J J, Palmer D, Zheng Y, Green H F, Pandey A, Dror R O, Shaw D E, Weis W I, Coughlin S R, Kobilka B K. High-resolution crystal structure of human protease-activated receptor 1. Nature. 2012 Dec. 20; 492(7429):387-92.

The invention claimed is:

1. A chimeric polypeptide comprising:
   a G protein-coupled receptor (GPCR) fused to a conformation-selective binding domain,
   wherein the binding domain is a VHH antibody directed against and/or able to specifically bind to the GPCR;
   wherein the GPCR is stabilized in an active or inactive conformation upon binding of the binding domain to the GPCR; and
   wherein the stabilized GPCR has increased affinity for a conformation-selective ligand as compared to GPCR when not fused to the binding domain.

2. The chimeric polypeptide of claim 1, wherein the binding domain is fused to the GPCR either directly or through a linker.

3. The chimeric polypeptide of claim 1, wherein the GPCR is stabilized in an active conformation upon binding of the binding domain.

4. The chimeric polypeptide of claim 3, wherein the active conformation is an agonist conformation, a partial agonist conformation, or a biased agonist conformation.

5. The chimeric polypeptide of claim 1, wherein the GPCR is stabilized in an inactive conformation upon binding of the binding domain.

6. The chimeric polypeptide of claim 5, wherein the inactive conformation is an inverse agonist conformation.

7. The chimeric polypeptide of claim 1, wherein the binding domain binds to an intracellular epitope of the GPCR.

8. The chimeric polypeptide of claim 7, wherein said intracellular epitope is comprised in a binding site for a downstream signaling protein.

9. The chimeric polypeptide of claim 7, wherein said intracellular epitope is comprised in the G protein binding site.

10. The chimeric polypeptide of claim 1, wherein the GPCR is a naturally occurring GPCR.

11. The chimeric polypeptide of claim 1, wherein the GPCR is a variant of a naturally occurring GPCR or a truncated form of a naturally occurring GPCR.

12. The chimeric polypeptide of claim 1, wherein the GPCR is selected from the group consisting of a GPCR of the Glutamate family of GPCRs, a GPCR of the Rhodopsin family of GPCRs, a GPCR of the Adhesion family of GPCRs, a GPCR of the Frizzled/Taste2 family of GPCRs, and a GPCR of the Secretin family of GPCRs.

13. A complex comprising:
   the chimeric polypeptide of claim 1, and
   a receptor ligand.

14. The chimeric polypeptide of claim 1, which is crystalline.

15. A nucleic acid molecule comprising:
   a polynucleotide encoding the chimeric polypeptide of claim 1.

16. A host cell comprising the nucleic acid molecule of claim 15.

17. The host cell according to claim 16, which is a bacterial cell, a yeast cell, a mammalian cell, or an insect cell.

18. A method to produce a chimeric polypeptide comprising a G protein-coupled receptor (GPCR) fused to a binding domain, the method comprising:
   culturing the host cell of claim 16 under suitable conditions.

19. A method to display a G protein-coupled receptor (GPCR) in an active or inactive conformation at the cellular surface or in a particular cellular membrane fraction of a host cell, the method comprising:
   culturing the host cell of claim 16 under suitable conditions to express the chimeric polypeptide.

20. A membrane composition comprising the chimeric polypeptide of claim 1.

21. The method according to claim 18, further comprising:
   isolating the chimeric polypeptide.

22. A kit comprising the chimeric polypeptide of claim 1.

* * * * *

SEQUENCE LISTING

```
<160> NUMBER OF SEQ ID NOS: 64

<210> SEQ ID NO 1
<211> LENGTH: 531
<212> TYPE: PRT
<213> ORGANISM: Artificial Sequence
<220> FEATURE:
<223> OTHER INFORMATION: GPCR-Nanobody fusion

<400> SEQUENCE: 1

Met Lys Thr Ile Ile Ala Leu Ser Tyr Ile Phe Cys Leu Val Phe Ala
1               5                   10                  15

Asp Tyr Lys Asp Asp Asp Ala Glu Asn Leu Tyr Phe Gln Gly Phe
            20                  25                  30

Gly Gln Pro Gly Asn Gly Ser Ala Phe Leu Leu Ala Pro Asn Arg Ser
        35                  40                  45

His Ala Pro Asp His Asp Val Thr Gln Gln Arg Asp Glu Val Trp Val
    50                  55                  60

Val Gly Met Gly Ile Val Met Ser Leu Ile Val Leu Ala Ile Val Phe
65                  70                  75                  80

Gly Asn Val Leu Val Ile Thr Ala Ile Ala Lys Phe Glu Arg Leu Gln
                85                  90                  95

Thr Val Thr Asn Tyr Phe Ile Thr Ser Leu Ala Cys Ala Asp Leu Val
                100                 105                 110

Met Gly Leu Ala Val Val Pro Phe Gly Ala Ala His Ile Leu Met Lys
            115                 120                 125
```

```
Met Trp Thr Phe Gly Asn Phe Trp Cys Glu Phe Trp Thr Ser Ile Asp
    130                 135                 140
Val Leu Cys Val Thr Ala Ser Ile Glu Thr Leu Cys Val Ile Ala Val
145                 150                 155                 160
Asp Arg Tyr Phe Ala Ile Thr Ser Pro Phe Lys Tyr Gln Ser Leu Leu
                165                 170                 175
Thr Lys Asn Lys Ala Arg Val Ile Ile Leu Met Val Trp Ile Val Ser
            180                 185                 190
Gly Leu Thr Ser Phe Leu Pro Ile Gln Met His Trp Tyr Arg Ala Thr
        195                 200                 205
His Gln Glu Ala Ile Asn Cys Tyr Ala Glu Thr Cys Cys Asp Phe
    210                 215                 220
Phe Thr Asn Gln Ala Tyr Ala Ile Ala Ser Ser Ile Val Ser Phe Tyr
225                 230                 235                 240
Val Pro Leu Val Ile Met Val Phe Val Tyr Ser Arg Val Phe Gln Glu
                245                 250                 255
Ala Lys Arg Gln Leu Gln Lys Ile Asp Lys Ser Glu Gly Arg Phe His
            260                 265                 270
Val Gln Asn Leu Ser Gln Val Glu Gln Asp Gly Arg Thr Gly His Gly
        275                 280                 285
Leu Arg Arg Ser Ser Lys Phe Cys Leu Lys Glu His Lys Ala Leu Lys
    290                 295                 300
Thr Leu Gly Ile Ile Met Gly Thr Phe Thr Leu Cys Trp Leu Pro Phe
305                 310                 315                 320
Phe Ile Val Asn Ile Val His Val Ile Gln Asp Asn Leu Ile Arg Lys
                325                 330                 335
Glu Val Tyr Ile Leu Leu Asn Trp Ile Gly Tyr Val Asn Ser Gly Phe
            340                 345                 350
Asn Pro Leu Ile Tyr Cys Arg Ser Pro Asp Phe Arg Ile Ala Phe Gln
        355                 360                 365
Glu Leu Leu Cys Leu Arg Arg Ser Leu Lys Ala Tyr Gly Asn Gly
    370                 375                 380
Tyr Ser Ser Asn Gly Asn Thr Gly Glu Gln Ser Gly Gly Gly Gly
385                 390                 395                 400
Ser Gly Gly Gly Ser Gln Val Gln Leu Gln Glu Ser Gly Gly Gly Leu
                405                 410                 415
Val Gln Ala Gly Gly Ser Leu Arg Leu Ser Cys Ala Ala Ser Gly Ser
            420                 425                 430
Ile Phe Ser Ile Asn Thr Met Gly Trp Tyr Arg Gln Ala Pro Gly Lys
        435                 440                 445
Gln Arg Glu Leu Val Ala Ala Ile His Ser Gly Gly Ser Thr Asn Tyr
    450                 455                 460
Ala Asn Ser Val Lys Gly Arg Phe Thr Ile Ser Arg Asp Asn Ala Ala
465                 470                 475                 480
Asn Thr Val Tyr Leu Gln Met Asn Ser Leu Lys Pro Glu Asp Thr Ala
                485                 490                 495
Val Tyr Tyr Cys Asn Val Lys Asp Tyr Gly Ala Val Leu Tyr Glu Tyr
            500                 505                 510
Asp Tyr Trp Gly Gln Gly Thr Gln Val Thr Val Ser Ser His His His
        515                 520                 525
His His His
    530
```

```
<210> SEQ ID NO 2
<211> LENGTH: 527
<212> TYPE: PRT
<213> ORGANISM: Artificial Sequence
<220> FEATURE:
<223> OTHER INFORMATION: GPCR-Nanobody fusion

<400> SEQUENCE: 2

Met Lys Thr Ile Ile Ala Leu Ser Tyr Ile Phe Cys Leu Val Phe Ala
1               5                   10                  15

Asp Tyr Lys Asp Asp Asp Ala Glu Asn Leu Tyr Phe Gln Gly Phe
            20              25                  30

Gly Gln Pro Gly Asn Gly Ser Ala Phe Leu Leu Ala Pro Asn Arg Ser
        35                  40                  45

His Ala Pro Asp His Asp Val Thr Gln Gln Arg Asp Glu Val Trp Val
    50                  55                  60

Val Gly Met Gly Ile Val Met Ser Leu Ile Val Leu Ala Ile Val Phe
65              70                  75                  80

Gly Asn Val Leu Val Ile Thr Ala Ile Ala Lys Phe Glu Arg Leu Gln
                85                  90                  95

Thr Val Thr Asn Tyr Phe Ile Thr Ser Leu Ala Cys Ala Asp Leu Val
                100                 105                 110

Met Gly Leu Ala Val Val Pro Phe Gly Ala Ala His Ile Leu Met Lys
            115                 120                 125

Met Trp Thr Phe Gly Asn Phe Trp Cys Glu Phe Trp Thr Ser Ile Asp
130             135                 140

Val Leu Cys Val Thr Ala Ser Ile Glu Thr Leu Cys Val Ile Ala Val
145                 150                 155                 160

Asp Arg Tyr Phe Ala Ile Thr Ser Pro Phe Lys Tyr Gln Ser Leu Leu
                165                 170                 175

Thr Lys Asn Lys Ala Arg Val Ile Ile Leu Met Val Trp Ile Val Ser
            180                 185                 190

Gly Leu Thr Ser Phe Leu Pro Ile Gln Met His Trp Tyr Arg Ala Thr
        195                 200                 205

His Gln Glu Ala Ile Asn Cys Tyr Ala Glu Thr Cys Cys Asp Phe
    210                 215                 220

Phe Thr Asn Gln Ala Tyr Ala Ile Ala Ser Ser Ile Val Ser Phe Tyr
225                 230                 235                 240

Val Pro Leu Val Ile Met Val Phe Val Tyr Ser Arg Val Phe Gln Glu
                245                 250                 255

Ala Lys Arg Gln Leu Gln Lys Ile Asp Lys Ser Glu Gly Arg Phe His
            260                 265                 270

Val Gln Asn Leu Ser Gln Val Glu Gln Asp Gly Arg Thr Gly His Gly
        275                 280                 285

Leu Arg Arg Ser Ser Lys Phe Cys Leu Lys Glu His Lys Ala Leu Lys
    290                 295                 300

Thr Leu Gly Ile Ile Met Gly Thr Phe Thr Leu Cys Trp Leu Pro Phe
305                 310                 315                 320

Phe Ile Val Asn Ile Val His Val Ile Gln Asp Asn Leu Ile Arg Lys
                325                 330                 335

Glu Val Tyr Ile Leu Leu Asn Trp Ile Gly Tyr Val Asn Ser Gly Phe
            340                 345                 350

Asn Pro Leu Ile Tyr Cys Arg Ser Pro Asp Phe Arg Ile Ala Phe Gln
        355                 360                 365
```

```
Glu Leu Leu Cys Leu Arg Arg Ser Ser Leu Lys Ala Tyr Gly Asn Gly
    370                 375                 380

Tyr Ser Ser Asn Gly Asn Thr Gly Glu Gln Ser Gly Gly Gly Gly
385                 390                 395                 400

Ser Gly Gly Gly Ser Gln Val Gln Leu Gln Glu Ser Gly Gly Gly Leu
                405                 410                 415

Val Gln Pro Gly Gly Ser Leu Arg Leu Ser Cys Ala Ala Ser Gly Phe
            420                 425                 430

Ala Phe Ser Ser Tyr Glu Leu Arg Trp Tyr Arg Gln Ala Pro Gly Lys
        435                 440                 445

Gln His Glu Leu Val Ala Gly Ile Thr Thr Gly Gly Asn Thr Tyr Tyr
    450                 455                 460

Ala Asp Ser Val Lys Gly Arg Phe Thr Ile Ser Arg Asp Asn Ala Lys
465                 470                 475                 480

Asn Thr Val Tyr Leu Gln Met Ser Asn Leu Arg Pro Glu Asp Thr Ala
                485                 490                 495

Val Tyr Ala Cys Asn Ala Asn Trp Asp Leu Leu Ser Asp Tyr Trp Gly
            500                 505                 510

Gln Gly Thr Gln Val Thr Val Ser Ser His His His His His His
        515                 520                 525
```

<210> SEQ ID NO 3
<211> LENGTH: 535
<212> TYPE: PRT
<213> ORGANISM: Artificial Sequence
<220> FEATURE:
<223> OTHER INFORMATION: GPCR-Nanobody fusion

<400> SEQUENCE: 3

```
Met Lys Thr Ile Ile Ala Leu Ser Tyr Ile Phe Cys Leu Val Phe Ala
1               5                   10                  15

Asp Tyr Lys Asp Asp Asp Ala Glu Asn Leu Tyr Phe Gln Gly Phe
                20                  25                  30

Gly Gln Pro Gly Asn Gly Ser Ala Phe Leu Leu Ala Pro Asn Arg Ser
            35                  40                  45

His Ala Pro Asp His Asp Val Thr Gln Gln Arg Asp Glu Val Trp Val
    50                  55                  60

Val Gly Met Gly Ile Val Met Ser Leu Ile Val Leu Ala Ile Val Phe
65                  70                  75                  80

Gly Asn Val Leu Val Ile Thr Ala Ile Ala Lys Phe Glu Arg Leu Gln
                85                  90                  95

Thr Val Thr Asn Tyr Phe Ile Thr Ser Leu Ala Cys Ala Asp Leu Val
                100                 105                 110

Met Gly Leu Ala Val Val Pro Phe Gly Ala Ala His Ile Leu Met Lys
            115                 120                 125

Met Trp Thr Phe Gly Asn Phe Trp Cys Glu Phe Trp Thr Ser Ile Asp
    130                 135                 140

Val Leu Cys Val Thr Ala Ser Ile Glu Thr Leu Cys Val Ile Ala Val
145                 150                 155                 160

Asp Arg Tyr Phe Ala Ile Thr Ser Pro Phe Lys Tyr Gln Ser Leu Leu
                165                 170                 175

Thr Lys Asn Lys Ala Arg Val Ile Ile Leu Met Val Trp Ile Val Ser
            180                 185                 190

Gly Leu Thr Ser Phe Leu Pro Ile Gln Met His Trp Tyr Arg Ala Thr
        195                 200                 205
```

His Gln Glu Ala Ile Asn Cys Tyr Ala Glu Glu Thr Cys Cys Asp Phe
    210                 215                 220

Phe Thr Asn Gln Ala Tyr Ala Ile Ala Ser Ser Ile Val Ser Phe Tyr
225                 230                 235                 240

Val Pro Leu Val Ile Met Val Phe Val Tyr Ser Arg Val Phe Gln Glu
                245                 250                 255

Ala Lys Arg Gln Leu Gln Lys Ile Asp Lys Ser Glu Gly Arg Phe His
            260                 265                 270

Val Gln Asn Leu Ser Gln Val Glu Gln Asp Gly Arg Thr Gly His Gly
        275                 280                 285

Leu Arg Arg Ser Ser Lys Phe Cys Leu Lys Glu His Lys Ala Leu Lys
    290                 295                 300

Thr Leu Gly Ile Ile Met Gly Thr Phe Thr Leu Cys Trp Leu Pro Phe
305                 310                 315                 320

Phe Ile Val Asn Ile Val His Val Ile Gln Asp Asn Leu Ile Arg Lys
                325                 330                 335

Glu Val Tyr Ile Leu Leu Asn Trp Ile Gly Tyr Val Asn Ser Gly Phe
            340                 345                 350

Asn Pro Leu Ile Tyr Cys Arg Ser Pro Asp Phe Arg Ile Ala Phe Gln
        355                 360                 365

Glu Leu Leu Cys Leu Arg Arg Ser Ser Leu Lys Ala Tyr Gly Asn Gly
    370                 375                 380

Tyr Ser Ser Asn Gly Asn Thr Gly Glu Gln Ser Gly Gly Gly Gly Gly
385                 390                 395                 400

Ser Gly Gly Gly Ser Gln Val Gln Leu Gln Glu Ser Gly Gly Gly Leu
                405                 410                 415

Val Gln Ala Gly Gly Ser Leu Arg Leu Ser Cys Thr Ala Ser Gly Leu
            420                 425                 430

Thr Leu Ser Asn Tyr Ala Met Gly Trp Phe Arg Gln Ala Pro Gly Lys
        435                 440                 445

Glu Arg Glu Phe Val Ala Ala Asp Thr Trp Asn Gly Asn Thr Tyr His
    450                 455                 460

Gln Asp Ser Val Lys Gly Arg Phe Thr Ile Ser Arg Asp Asn Ala Lys
465                 470                 475                 480

Asn Thr Val Tyr Leu Gln Met Asn Tyr Leu Lys Pro Glu Asp Thr Ala
                485                 490                 495

Val Tyr Tyr Cys Ala Ala Arg Gly Ser Arg Arg Ser Ala Tyr Tyr Ser
            500                 505                 510

Ser Ser Asp Tyr Thr Tyr Arg Gly Gln Gly Thr Gln Val Thr Val Ser
        515                 520                 525

Ser His His His His His His
    530                 535

<210> SEQ ID NO 4
<211> LENGTH: 530
<212> TYPE: PRT
<213> ORGANISM: Artificial Sequence
<220> FEATURE:
<223> OTHER INFORMATION: GPCR-Nanobody fusion

<400> SEQUENCE: 4

Met Lys Thr Ile Ile Ala Leu Ser Tyr Ile Phe Cys Leu Val Phe Ala
1                   5                   10                  15

Asp Tyr Lys Asp Asp Asp Ala Glu Asn Leu Tyr Phe Gln Gly Phe
            20                  25                  30

-continued

Gly Gln Pro Gly Asn Gly Ser Ala Phe Leu Leu Ala Pro Asn Arg Ser
         35                  40                  45

His Ala Pro Asp His Asp Val Thr Gln Gln Arg Asp Glu Val Trp Val
 50                  55                  60

Val Gly Met Gly Ile Val Met Ser Leu Ile Val Leu Ala Ile Val Phe
 65                  70                  75                  80

Gly Asn Val Leu Val Ile Thr Ala Ile Ala Lys Phe Glu Arg Leu Gln
                 85                  90                  95

Thr Val Thr Asn Tyr Phe Ile Thr Ser Leu Ala Cys Ala Asp Leu Val
                100                 105                 110

Met Gly Leu Ala Val Val Pro Phe Gly Ala Ala His Ile Leu Met Lys
             115                 120                 125

Met Trp Thr Phe Gly Asn Phe Trp Cys Glu Phe Trp Thr Ser Ile Asp
         130                 135                 140

Val Leu Cys Val Thr Ala Ser Ile Glu Thr Leu Cys Val Ile Ala Val
145                 150                 155                 160

Asp Arg Tyr Phe Ala Ile Thr Ser Pro Phe Lys Tyr Gln Ser Leu Leu
                165                 170                 175

Thr Lys Asn Lys Ala Arg Val Ile Ile Leu Met Val Trp Ile Val Ser
             180                 185                 190

Gly Leu Thr Ser Phe Leu Pro Ile Gln Met His Trp Tyr Arg Ala Thr
         195                 200                 205

His Gln Glu Ala Ile Asn Cys Tyr Ala Glu Glu Thr Cys Cys Asp Phe
     210                 215                 220

Phe Thr Asn Gln Ala Tyr Ala Ile Ala Ser Ser Ile Val Ser Phe Tyr
225                 230                 235                 240

Val Pro Leu Val Ile Met Val Phe Val Tyr Ser Arg Val Phe Gln Glu
                245                 250                 255

Ala Lys Arg Gln Leu Gln Lys Ile Asp Lys Ser Glu Gly Arg Phe His
             260                 265                 270

Val Gln Asn Leu Ser Gln Val Glu Gln Asp Gly Arg Thr Gly His Gly
         275                 280                 285

Leu Arg Arg Ser Ser Lys Phe Cys Leu Lys Glu His Lys Ala Leu Lys
     290                 295                 300

Thr Leu Gly Ile Ile Met Gly Thr Phe Thr Leu Cys Trp Leu Pro Phe
305                 310                 315                 320

Phe Ile Val Asn Ile Val His Val Ile Gln Asp Asn Leu Ile Arg Lys
                325                 330                 335

Glu Val Tyr Ile Leu Leu Asn Trp Ile Gly Tyr Val Asn Ser Gly Phe
             340                 345                 350

Asn Pro Leu Ile Tyr Cys Arg Ser Pro Asp Phe Arg Ile Ala Phe Gln
         355                 360                 365

Glu Leu Leu Cys Leu Arg Arg Ser Leu Lys Ala Tyr Gly Asn Gly
     370                 375                 380

Tyr Ser Ser Asn Gly Asn Thr Gly Glu Gln Ser Gly Gly Gly Gly
385                 390                 395                 400

Ser Gly Gly Gly Ser Gln Val Gln Leu Gln Glu Ser Gly Gly Leu
                405                 410                 415

Val Gln Ala Gly Gly Ser Leu Arg Leu Ser Cys Ala Ala Ser Gly Ser
             420                 425                 430

Ile Phe Ser Leu Asn Asp Met Gly Trp Tyr Arg Gln Ala Pro Gly Lys
         435                 440                 445

Leu Arg Glu Leu Val Ala Ala Ile Thr Ser Gly Gly Ser Thr Lys Tyr

```
            450                 455                 460
Ala Asp Ser Val Lys Gly Arg Phe Thr Ile Ser Arg Asp Asn Ala Lys
465                 470                 475                 480

Asn Thr Val Tyr Leu Gln Met Asn Ser Leu Lys Ala Glu Asp Thr Ala
                485                 490                 495

Val Tyr Tyr Cys Asn Ala Lys Val Ala Gly Thr Phe Ser Ile Tyr Asp
                500                 505                 510

Tyr Trp Gly Gln Gly Thr Gln Val Thr Val Ser Ser His His His His
            515                 520                 525

His His
    530

<210> SEQ ID NO 5
<211> LENGTH: 356
<212> TYPE: PRT
<213> ORGANISM: Artificial Sequence
<220> FEATURE:
<223> OTHER INFORMATION: GPCR-Nanobody fusion

<400> SEQUENCE: 5

Met Lys Thr Ile Ile Ala Leu Ser Tyr Ile Phe Cys Leu Val Phe Ala
1               5                   10                  15

Asp Tyr Lys Asp Asp Asp Glu Asn Leu Tyr Phe Gln Gly Met Asp
                20                  25                  30

Asp Ser Thr Asp Ser Ser Asp Ser Leu Ala Leu Thr Ser Pro Tyr
        35                  40                  45

Lys Thr Phe Glu Val Val Phe Ile Val Leu Val Ala Gly Ser Leu Ser
    50                  55                  60

Leu Val Thr Ile Ile Gly Asn Ile Leu Val Met Val Ser Ile Lys Val
65                  70                  75                  80

Asn Arg His Leu Gln Thr Val Asn Asn Tyr Phe Leu Phe Ser Leu Ala
                85                  90                  95

Cys Ala Asp Leu Ile Ile Gly Val Phe Ser Met Asn Leu Tyr Thr Leu
                100                 105                 110

Tyr Thr Val Ile Gly Tyr Trp Pro Leu Gly Pro Val Val Cys Asp Leu
            115                 120                 125

Trp Leu Ala Leu Asp Tyr Val Val Ser Asn Ala Ser Val Met Asn Leu
    130                 135                 140

Leu Ile Ile Ser Phe Asp Arg Tyr Phe Cys Val Thr Lys Pro Leu Thr
145                 150                 155                 160

Tyr Pro Val Lys Arg Thr Thr Lys Met Ala Gly Met Met Ile Ala Ala
                165                 170                 175

Ala Trp Val Leu Ser Phe Ile Leu Trp Ala Pro Ala Ile Leu Phe Trp
            180                 185                 190

Gln Phe Ile Val Gly Val Arg Thr Val Glu Asp Gly Glu Cys Tyr Ile
        195                 200                 205

Gln Phe Phe Ser Asn Ala Ala Val Thr Phe Gly Thr Ala Ile Ala Ala
    210                 215                 220

Phe Tyr Leu Pro Val Ile Ile Met Thr Val Leu Tyr Trp His Ile Ser
225                 230                 235                 240

Arg Ala Ser Lys Ser Arg Ile Lys Lys Asp Lys Lys Glu Pro Val Ala
                245                 250                 255

Asn Gln Asp Pro Val Ser Thr Arg Lys Lys Pro Pro Pro Ser Arg Glu
            260                 265                 270

Lys Lys Val Thr Arg Thr Ile Leu Ala Ile Leu Leu Ala Phe Ile Ile
```

```
                    275                 280                 285
Thr Trp Ala Pro Tyr Asn Val Met Val Leu Ile Asn Thr Phe Cys Ala
            290                 295                 300
Pro Cys Ile Pro Asn Thr Val Trp Thr Ile Gly Tyr Trp Leu Cys Tyr
305                 310                 315                 320
Ile Asn Ser Thr Ile Asn Pro Ala Cys Tyr Ala Leu Cys Asn Ala Thr
                325                 330                 335
Phe Lys Lys Thr Phe Lys His Leu Leu Met Cys His Tyr Lys Asn Ile
            340                 345                 350
Gly Ala Thr Arg
        355

<210> SEQ ID NO 6
<211> LENGTH: 506
<212> TYPE: PRT
<213> ORGANISM: Artificial Sequence
<220> FEATURE:
<223> OTHER INFORMATION: GPCR-Nanobody fusion

<400> SEQUENCE: 6

Met Lys Thr Ile Ile Ala Leu Ser Tyr Ile Phe Cys Leu Val Phe Ala
1               5                   10                  15
Asp Tyr Lys Asp Asp Asp Glu Asn Leu Tyr Phe Gln Gly Met Asp Asp
            20                  25                  30
Asp Ser Thr Asp Ser Ser Asp Ser Leu Ala Leu Thr Ser Pro Tyr
            35                  40                  45
Lys Thr Phe Glu Val Val Phe Ile Val Leu Val Ala Gly Ser Leu Ser
    50                  55                  60
Leu Val Thr Ile Ile Gly Asn Ile Leu Val Met Val Ser Ile Lys Val
65                  70                  75                  80
Asn Arg His Leu Gln Thr Val Asn Asn Tyr Phe Leu Phe Ser Leu Ala
                85                  90                  95
Cys Ala Asp Leu Ile Ile Gly Val Phe Ser Met Asn Leu Tyr Thr Leu
            100                 105                 110
Tyr Thr Val Ile Gly Tyr Trp Pro Leu Gly Pro Val Val Cys Asp Leu
        115                 120                 125
Trp Leu Ala Leu Asp Tyr Val Val Ser Asn Ala Ser Val Met Asn Leu
    130                 135                 140
Leu Ile Ile Ser Phe Asp Arg Tyr Phe Cys Val Thr Lys Pro Leu Thr
145                 150                 155                 160
Tyr Pro Val Lys Arg Thr Thr Lys Met Ala Gly Met Met Ile Ala Ala
                165                 170                 175
Ala Trp Val Leu Ser Phe Ile Leu Trp Ala Pro Ala Ile Leu Phe Trp
            180                 185                 190
Gln Phe Ile Val Gly Val Arg Thr Val Glu Asp Gly Glu Cys Tyr Ile
        195                 200                 205
Gln Phe Phe Ser Asn Ala Ala Val Thr Phe Gly Thr Ala Ile Ala Ala
    210                 215                 220
Phe Tyr Leu Pro Val Ile Ile Met Thr Val Leu Tyr Trp His Ile Ser
225                 230                 235                 240
Arg Ala Ser Lys Ser Arg Ile Lys Lys Asp Lys Lys Glu Pro Val Ala
                245                 250                 255
Asn Gln Asp Pro Val Ser Thr Arg Lys Lys Pro Pro Pro Ser Arg Glu
            260                 265                 270
Lys Lys Val Thr Arg Thr Ile Leu Ala Ile Leu Leu Ala Phe Ile Ile
```

```
            275                 280                 285
Thr Trp Ala Pro Tyr Asn Val Met Val Leu Ile Asn Thr Phe Cys Ala
        290                 295                 300

Pro Cys Ile Pro Asn Thr Val Trp Thr Ile Gly Tyr Trp Leu Cys Tyr
305                 310                 315                 320

Ile Asn Ser Thr Ile Asn Pro Ala Cys Tyr Ala Leu Cys Asn Ala Thr
            325                 330                 335

Phe Lys Lys Thr Phe Lys His Leu Leu Met Cys His Tyr Lys Asn Ile
        340                 345                 350

Gly Ala Thr Arg Gly Gly Ser Gly Gly Gly Ser Gly Gly Gly
            355                 360                 365

Gly Ser Gly Gly Gly Ser Gly Gly Ser Gln Val Gln Leu Gln
        370                 375                 380

Glu Ser Gly Gly Leu Val Gln Ala Gly Gly Ser Leu Arg Leu Ser
385                 390                 395                 400

Cys Ala Ala Ser Gly His Thr Phe Ser Ser Ala Arg Met Tyr Trp Val
            405                 410                 415

Arg Gln Ala Pro Gly Lys Glu Arg Glu Phe Val Ala Ala Ile Ser Arg
        420                 425                 430

Ser Gly Phe Thr Tyr Ser Ala Asp Ser Val Lys Gly Arg Phe Thr Ile
            435                 440                 445

Ser Arg Asp Ile Ala Asn Asn Thr Val Tyr Leu Gln Met Asn Ser Leu
        450                 455                 460

Gln Pro Glu Asp Thr Ala Ile Tyr Thr Cys Tyr Ala Ala Tyr Leu Asp
465                 470                 475                 480

Glu Phe Tyr Asn Asp Tyr Thr His Tyr Trp Gly Leu Gly Thr Gln Val
                485                 490                 495

Thr Val Ser Ser His His His His His His
            500                 505

<210> SEQ ID NO 7
<211> LENGTH: 488
<212> TYPE: PRT
<213> ORGANISM: Artificial Sequence
<220> FEATURE:
<223> OTHER INFORMATION: GPCR-Nanobody fusion

<400> SEQUENCE: 7

Met Lys Thr Ile Ile Ala Leu Ser Tyr Ile Phe Cys Leu Val Phe Ala
1               5                   10                  15

Asp Tyr Lys Asp Asp Asp Ala Glu Asn Leu Tyr Phe Gln Gly Pro
            20                  25                  30

Glu Pro Leu Ser Gln Gln Trp Thr Ala Gly Met Gly Leu Leu Met Ala
        35                  40                  45

Leu Ile Val Leu Leu Ile Val Ala Gly Asn Val Leu Val Ile Val Ala
    50                  55                  60

Ile Ala Lys Thr Pro Arg Leu Gln Thr Leu Thr Asn Leu Phe Ile Met
65                  70                  75                  80

Ser Leu Ala Ser Ala Asp Leu Val Met Gly Leu Leu Val Val Pro Phe
                85                  90                  95

Gly Ala Thr Ile Val Val Trp Gly Arg Trp Glu Tyr Gly Ser Phe Phe
            100                 105                 110

Cys Glu Leu Trp Thr Ser Val Asp Val Leu Cys Val Thr Ala Ser Ile
        115                 120                 125

Glu Thr Leu Cys Val Ile Ala Leu Asp Arg Tyr Leu Ala Ile Thr Ser
```

```
                    130                 135                 140
Pro Phe Arg Tyr Gln Ser Leu Leu Thr Arg Ala Arg Ala Arg Gly Leu
145                 150                 155                 160

Val Cys Thr Val Trp Ala Ile Ser Ala Leu Val Ser Phe Leu Pro Ile
                165                 170                 175

Leu Met His Trp Trp Arg Ala Glu Ser Asp Glu Ala Arg Arg Cys Tyr
            180                 185                 190

Asn Asp Pro Lys Cys Cys Asp Phe Val Thr Asn Arg Ala Tyr Ala Ile
                195                 200                 205

Ala Ser Ser Val Val Ser Phe Tyr Val Pro Leu Cys Ile Met Ala Phe
            210                 215                 220

Val Tyr Leu Arg Val Phe Arg Glu Ala Gln Lys Gln Val Lys Lys Ile
225                 230                 235                 240

Asp Arg Ala Gly Lys Arg Pro Ser Arg Leu Val Ala Leu Lys Glu
                245                 250                 255

Gln Lys Ala Leu Lys Thr Leu Gly Ile Ile Met Gly Val Phe Thr Leu
            260                 265                 270

Cys Trp Leu Pro Phe Phe Leu Ala Asn Val Val Lys Ala Phe His Arg
            275                 280                 285

Glu Leu Val Pro Asp Arg Leu Phe Val Phe Phe Asn Trp Leu Gly Tyr
290                 295                 300

Ala Asn Ser Ala Phe Asn Pro Ile Ile Tyr Cys Arg Ser Pro Asp Phe
305                 310                 315                 320

Arg Lys Ala Phe Gln Arg Leu Leu Ser Ser Ala Arg Arg Ala Ala Arg
                325                 330                 335

Arg Arg Gly Gly Gly Gly Ser Gly Gly Gly Gly Ser Gly Gly Gly Gly
                340                 345                 350

Ser Gly Gly Gly Gly Ser Gly Gly Gly Ser Gln Val Gln Leu Gln Glu
            355                 360                 365

Ser Gly Gly Gly Leu Val Gln Ala Gly Gly Ser Leu Arg Leu Ser Cys
            370                 375                 380

Ala Ala Ser Gly Ser Ile Phe Ser Ile Asn Thr Met Gly Trp Tyr Arg
385                 390                 395                 400

Gln Ala Pro Gly Lys Gln Arg Glu Leu Val Ala Ala Ile His Ser Gly
                405                 410                 415

Gly Ser Thr Asn Tyr Ala Asn Ser Val Lys Gly Arg Phe Thr Ile Ser
            420                 425                 430

Arg Asp Asn Ala Ala Asn Thr Val Tyr Leu Gln Met Asn Ser Leu Lys
            435                 440                 445

Pro Glu Asp Thr Ala Val Tyr Tyr Cys Asn Val Lys Asp Tyr Gly Ala
450                 455                 460

Val Leu Tyr Glu Tyr Asp Tyr Trp Gly Gln Gly Thr Gln Val Thr Val
465                 470                 475                 480

Ser Ser His His His His His His
                485

<210> SEQ ID NO 8
<211> LENGTH: 492
<212> TYPE: PRT
<213> ORGANISM: Artificial Sequence
<220> FEATURE:
<223> OTHER INFORMATION: GPCR-Nanobody fusion

<400> SEQUENCE: 8

Met Lys Thr Ile Ile Ala Leu Ser Tyr Ile Phe Cys Leu Val Phe Ala
```

-continued

```
1               5                   10                  15
Asp Tyr Lys Asp Asp Asp Ala Glu Asn Leu Tyr Phe Gln Gly Pro
            20                  25                  30

Glu Pro Leu Ser Gln Gln Trp Thr Ala Gly Met Gly Leu Leu Met Ala
            35                  40                  45

Leu Ile Val Leu Leu Ile Val Ala Gly Asn Val Leu Val Ile Val Ala
50                  55                  60

Ile Ala Lys Thr Pro Arg Leu Gln Thr Leu Thr Asn Leu Phe Ile Met
65                  70                  75                  80

Ser Leu Ala Ser Ala Asp Leu Val Met Gly Leu Leu Val Val Pro Phe
                85                  90                  95

Gly Ala Thr Ile Val Val Trp Gly Arg Trp Glu Tyr Gly Ser Phe Phe
                100                 105                 110

Cys Glu Leu Trp Thr Ser Val Asp Val Leu Cys Val Thr Ala Ser Ile
                115                 120                 125

Glu Thr Leu Cys Val Ile Ala Leu Asp Arg Tyr Leu Ala Ile Thr Ser
            130                 135                 140

Pro Phe Arg Tyr Gln Ser Leu Leu Thr Arg Ala Arg Ala Arg Gly Leu
145                 150                 155                 160

Val Cys Thr Val Trp Ala Ile Ser Ala Leu Val Ser Phe Leu Pro Ile
                165                 170                 175

Leu Met His Trp Trp Arg Ala Glu Ser Asp Glu Ala Arg Arg Cys Tyr
                180                 185                 190

Asn Asp Pro Lys Cys Cys Asp Phe Val Thr Asn Arg Ala Tyr Ala Ile
            195                 200                 205

Ala Ser Ser Val Val Ser Phe Tyr Val Pro Leu Cys Ile Met Ala Phe
210                 215                 220

Val Tyr Leu Arg Val Phe Arg Glu Ala Gln Lys Gln Val Lys Lys Ile
225                 230                 235                 240

Asp Arg Ala Gly Lys Arg Pro Ser Arg Leu Val Ala Leu Lys Glu
            245                 250                 255

Gln Lys Ala Leu Lys Thr Leu Gly Ile Ile Met Gly Val Phe Thr Leu
            260                 265                 270

Cys Trp Leu Pro Phe Phe Leu Ala Asn Val Val Lys Ala Phe His Arg
            275                 280                 285

Glu Leu Val Pro Asp Arg Leu Phe Val Phe Asn Trp Leu Gly Tyr
            290                 295                 300

Ala Asn Ser Ala Phe Asn Pro Ile Ile Tyr Cys Arg Ser Pro Asp Phe
305                 310                 315                 320

Arg Lys Ala Phe Gln Arg Leu Leu Ser Ser Ala Arg Arg Ala Ala Arg
                325                 330                 335

Arg Arg Gly Gly Gly Gly Ser Gly Gly Gly Ser Gly Gly Gly Gly
            340                 345                 350

Ser Gly Gly Gly Ser Gly Gly Gly Ser Gln Val Gln Leu Gln Glu
            355                 360                 365

Ser Gly Gly Gly Leu Val Gln Ala Gly Gly Ser Leu Arg Leu Ser Cys
            370                 375                 380

Thr Ala Ser Gly Leu Thr Leu Ser Asn Tyr Ala Met Gly Trp Phe Arg
385                 390                 395                 400

Gln Ala Pro Gly Lys Glu Arg Glu Phe Val Ala Ala Asp Thr Trp Asn
            405                 410                 415

Gly Asn Thr Tyr His Gln Asp Ser Val Lys Gly Arg Phe Thr Ile Ser
            420                 425                 430
```

-continued

```
Arg Asp Asn Ala Lys Asn Thr Val Tyr Leu Gln Met Asn Tyr Leu Lys
        435                 440                 445

Pro Glu Asp Thr Ala Val Tyr Tyr Cys Ala Ala Arg Gly Ser Arg Arg
    450                 455                 460

Ser Ala Tyr Tyr Ser Ser Asp Tyr Thr Tyr Arg Gly Gln Gly Thr
465                 470                 475                 480

Gln Val Thr Val Ser Ser His His His His His His
                485                 490

<210> SEQ ID NO 9
<211> LENGTH: 550
<212> TYPE: PRT
<213> ORGANISM: Artificial Sequence
<220> FEATURE:
<223> OTHER INFORMATION: GPCR-Nanobody fusion

<400> SEQUENCE: 9

Met Lys Thr Ile Ile Ala Leu Ser Tyr Ile Phe Cys Leu Val Phe Ala
1               5                   10                  15

Asp Tyr Lys Asp Asp Asp Ala Met Ala Pro Thr Asn Ala Ser Asn
            20                  25                  30

Cys Thr Asp Ala Leu Ala Tyr Ser Ser Cys Ser Pro Ala Pro Ser Pro
        35                  40                  45

Gly Ser Trp Val Asn Leu Ser His Leu Asp Gly Asn Leu Ser Asp Pro
    50                  55                  60

Cys Gly Pro Asn Arg Thr Asp Leu Gly Gly Arg Asp Ser Leu Cys Pro
65                  70                  75                  80

Pro Thr Gly Ser Pro Ser Met Ile Thr Ala Ile Thr Ile Met Ala Leu
                85                  90                  95

Tyr Ser Ile Val Cys Val Val Gly Leu Phe Gly Asn Phe Leu Val Met
            100                 105                 110

Tyr Val Ile Val Arg Tyr Thr Lys Met Lys Thr Ala Thr Asn Ile Tyr
        115                 120                 125

Ile Phe Asn Leu Ala Leu Ala Asp Ala Leu Ala Thr Ser Thr Leu Pro
    130                 135                 140

Phe Gln Ser Val Asn Tyr Leu Met Gly Thr Trp Pro Phe Gly Thr Ile
145                 150                 155                 160

Leu Cys Lys Ile Val Ile Ser Ile Asp Tyr Tyr Asn Met Phe Thr Ser
                165                 170                 175

Ile Phe Thr Leu Cys Thr Met Ser Val Asp Arg Tyr Ile Ala Val Cys
            180                 185                 190

His Pro Val Lys Ala Leu Asp Phe Arg Thr Pro Arg Asn Ala Lys Ile
        195                 200                 205

Ile Asn Val Cys Asn Trp Ile Leu Ser Ser Ala Ile Gly Leu Pro Val
    210                 215                 220

Met Phe Met Ala Thr Thr Lys Tyr Arg Gln Gly Ser Ile Asp Cys Thr
225                 230                 235                 240

Leu Thr Phe Ser His Pro Thr Trp Tyr Trp Glu Asn Leu Leu Lys Ile
                245                 250                 255

Cys Val Phe Ile Phe Ala Phe Ile Met Pro Val Leu Ile Ile Thr Val
            260                 265                 270

Cys Tyr Gly Leu Met Ile Leu Arg Leu Lys Ser Val Arg Met Leu Ser
        275                 280                 285

Gly Ser Lys Glu Lys Asp Arg Asn Leu Arg Arg Ile Thr Arg Met Val
    290                 295                 300
```

-continued

Leu Val Val Ala Val Phe Ile Val Cys Trp Thr Pro Ile His Ile
305                 310                 315                 320

Tyr Val Ile Ile Lys Ala Leu Val Thr Ile Pro Glu Thr Thr Phe Gln
                325                 330                 335

Thr Val Ser Trp His Phe Cys Ile Ala Leu Gly Tyr Thr Asn Ser Cys
            340                 345                 350

Leu Asn Pro Val Leu Tyr Ala Phe Leu Asp Glu Asn Phe Lys Arg Cys
        355                 360                 365

Phe Arg Glu Phe Cys Ile Pro Thr Ser Ser Asn Ile Leu Glu Val Leu
370                 375                 380

Phe Gln Gly Pro Gly Gly Gly Ser Gly Gly Gly Ser Gly Gly
385                 390                 395                 400

Gly Gly Ser Gly Gly Gly Ser Gly Gly Gly Ser Gly Gly Gly
            405                 410                 415

Gly Ser Gly Gly Gly Ser Gln Val Gln Leu Gln Glu Ser Gly Gly Gly
        420                 425                 430

Leu Val Arg Pro Gly Gly Ser Arg Leu Ser Cys Val Asp Ser Glu
435                 440                 445

Arg Thr Ser Tyr Pro Met Gly Trp Phe Arg Arg Ala Pro Gly Lys Glu
            450                 455                 460

Arg Glu Phe Val Ala Ser Ile Thr Trp Ser Gly Ile Asp Pro Thr Tyr
465                 470                 475                 480

Ala Asp Ser Val Ala Asp Arg Phe Thr Ile Ser Arg Asp Val Ala Asn
                485                 490                 495

Asn Thr Leu Tyr Leu Gln Met Asn Ser Leu Lys His Glu Asp Thr Ala
            500                 505                 510

Val Tyr Tyr Cys Ala Ala Arg Ala Pro Val Gly Gln Ser Ser Ser Pro
        515                 520                 525

Tyr Asp Tyr Asp Tyr Trp Gly Gln Gly Thr Gln Val Thr Val Ser Ser
530                 535                 540

His His His His His His
545                 550

<210> SEQ ID NO 10
<211> LENGTH: 555
<212> TYPE: PRT
<213> ORGANISM: Artificial Sequence
<220> FEATURE:
<223> OTHER INFORMATION: GPCR-Nanobody fusion

<400> SEQUENCE: 10

Met Lys Thr Ile Ile Ala Leu Ser Tyr Ile Phe Cys Leu Val Phe Ala
1               5                   10                  15

Asp Tyr Lys Asp Asp Asp Ala Met Ala Pro Thr Asn Ala Ser Asn
                20                  25                  30

Cys Thr Asp Ala Leu Ala Tyr Ser Ser Cys Ser Pro Ala Pro Ser Pro
            35                  40                  45

Gly Ser Trp Val Asn Leu Ser His Leu Asp Gly Asn Leu Ser Asp Pro
        50                  55                  60

Cys Gly Pro Asn Arg Thr Asp Leu Gly Gly Arg Asp Ser Leu Cys Pro
65                  70                  75                  80

Pro Thr Gly Ser Pro Ser Met Ile Thr Ala Ile Thr Ile Met Ala Leu
                85                  90                  95

Tyr Ser Ile Val Cys Val Val Gly Leu Phe Gly Asn Phe Leu Val Met
            100                 105                 110

-continued

```
Tyr Val Ile Val Arg Tyr Thr Lys Met Lys Thr Ala Thr Asn Ile Tyr
            115                 120                 125
Ile Phe Asn Leu Ala Leu Ala Asp Ala Leu Ala Thr Ser Thr Leu Pro
        130                 135                 140
Phe Gln Ser Val Asn Tyr Leu Met Gly Thr Trp Pro Phe Gly Thr Ile
145                 150                 155                 160
Leu Cys Lys Ile Val Ile Ser Ile Asp Tyr Tyr Asn Met Phe Thr Ser
                165                 170                 175
Ile Phe Thr Leu Cys Thr Met Ser Val Asp Arg Tyr Ile Ala Val Cys
            180                 185                 190
His Pro Val Lys Ala Leu Asp Phe Arg Thr Pro Arg Asn Ala Lys Ile
        195                 200                 205
Ile Asn Val Cys Asn Trp Ile Leu Ser Ser Ala Ile Gly Leu Pro Val
    210                 215                 220
Met Phe Met Ala Thr Thr Lys Tyr Arg Gln Gly Ser Ile Asp Cys Thr
225                 230                 235                 240
Leu Thr Phe Ser His Pro Thr Trp Tyr Trp Glu Asn Leu Leu Lys Ile
                245                 250                 255
Cys Val Phe Ile Phe Ala Phe Ile Met Pro Val Leu Ile Ile Thr Val
            260                 265                 270
Cys Tyr Gly Leu Met Ile Leu Arg Leu Lys Ser Val Arg Met Leu Ser
        275                 280                 285
Gly Ser Lys Glu Lys Asp Arg Asn Leu Arg Arg Ile Thr Arg Met Val
    290                 295                 300
Leu Val Val Val Ala Val Phe Ile Val Cys Trp Thr Pro Ile His Ile
305                 310                 315                 320
Tyr Val Ile Ile Lys Ala Leu Val Thr Ile Pro Glu Thr Thr Phe Gln
                325                 330                 335
Thr Val Ser Trp His Phe Cys Ile Ala Leu Gly Tyr Thr Asn Ser Cys
            340                 345                 350
Leu Asn Pro Val Leu Tyr Ala Phe Leu Asp Glu Asn Phe Lys Arg Cys
        355                 360                 365
Phe Arg Glu Phe Cys Ile Pro Thr Ser Ser Asn Ile Leu Glu Val Leu
    370                 375                 380
Phe Gln Gly Pro Gly Gly Gly Ser Gly Gly Gly Ser Gly Gly
385                 390                 395                 400
Gly Gly Ser Gly Gly Gly Ser Gly Gly Gly Ser Gly Gly
                405                 410                 415
Gly Ser Gly Gly Gly Ser Gln Val Gln Leu Gln Glu Ser Gly Gly
            420                 425                 430
Leu Val Gln Pro Gly Gly Ser Leu Arg Leu Ser Cys Ala Ala Ser Gly
        435                 440                 445
Ser Phe Arg Ser Ile Val Ser Met Ala Trp Tyr Arg Gln Ala Pro Gly
    450                 455                 460
Lys Gln Arg Glu Leu Val Ala Ser Ser Asn Ser Gly Gly Ser Thr Asn
465                 470                 475                 480
Tyr Ala Asp Ser Val Lys Gly Arg Phe Thr Ile Ser Arg Asp Asn Ala
                485                 490                 495
Lys Asn Thr Val Tyr Leu Gln Met Asn Ser Leu Lys Pro Glu Asp Thr
            500                 505                 510
Ala Val Tyr Trp Cys Asn Val Gln Asn Arg Leu Pro Gly Phe Asp Ala
        515                 520                 525
```

```
Phe Ser Gly Arg Ser Ile Ala Glu Thr Tyr Trp Gly Gln Gly Thr Gln
        530                 535                 540

Val Thr Val Ser Ser His His His His His His
545                 550                 555

<210> SEQ ID NO 11
<211> LENGTH: 548
<212> TYPE: PRT
<213> ORGANISM: Artificial Sequence
<220> FEATURE:
<223> OTHER INFORMATION: GPCR-Nanobody fusion

<400> SEQUENCE: 11

Met Lys Thr Ile Ile Ala Leu Ser Tyr Ile Phe Cys Leu Val Phe Ala
1               5                   10                  15

Asp Tyr Lys Asp Asp Asp Asp Ala Met Gly Pro Gly Asn Ile Ser Asp
                20                  25                  30

Cys Ser Asp Pro Leu Ala Pro Ala Ser Cys Ser Pro Ala Pro Gly Ser
            35                  40                  45

Trp Leu Asn Leu Ser His Val Asp Gly Asn Gln Ser Asp Pro Cys Gly
        50                  55                  60

Pro Asn Arg Thr Gly Leu Gly Gly Ser His Ser Leu Cys Pro Gln Thr
65                  70                  75                  80

Gly Ser Pro Ser Met Val Thr Ala Ile Thr Ile Met Ala Leu Tyr Ser
                85                  90                  95

Ile Val Cys Val Val Gly Leu Phe Gly Asn Phe Leu Val Met Tyr Val
                100                 105                 110

Ile Val Arg Tyr Thr Lys Met Lys Thr Ala Thr Asn Ile Tyr Ile Phe
            115                 120                 125

Asn Leu Ala Leu Ala Asp Ala Leu Ala Thr Ser Thr Leu Pro Phe Gln
        130                 135                 140

Ser Val Asn Tyr Leu Met Gly Thr Trp Pro Phe Gly Asn Ile Leu Cys
145                 150                 155                 160

Lys Ile Val Ile Ser Ile Asp Tyr Tyr Asn Met Phe Thr Ser Ile Phe
                165                 170                 175

Thr Leu Cys Thr Met Ser Val Asp Arg Tyr Ile Ala Val Cys His Pro
                180                 185                 190

Val Lys Ala Leu Asp Phe Arg Thr Pro Arg Asn Ala Lys Ile Val Asn
            195                 200                 205

Val Cys Asn Trp Ile Leu Ser Ser Ala Ile Gly Leu Pro Val Met Phe
        210                 215                 220

Met Ala Thr Thr Lys Tyr Arg Gln Gly Ser Ile Asp Cys Thr Leu Thr
225                 230                 235                 240

Phe Ser His Pro Thr Trp Tyr Trp Glu Asn Leu Leu Lys Ile Cys Val
                245                 250                 255

Phe Ile Phe Ala Phe Ile Met Pro Val Leu Ile Ile Thr Val Cys Tyr
                260                 265                 270

Gly Leu Met Ile Leu Arg Leu Lys Ser Val Arg Met Leu Ser Gly Ser
            275                 280                 285

Lys Glu Lys Asp Arg Asn Leu Arg Arg Ile Thr Arg Met Val Leu Val
        290                 295                 300

Val Val Ala Val Phe Ile Val Cys Trp Thr Pro Ile His Ile Tyr Val
305                 310                 315                 320

Ile Ile Lys Ala Leu Ile Thr Ile Pro Glu Thr Thr Phe Gln Thr Val
                325                 330                 335
```

```
Ser Trp His Phe Cys Ile Ala Leu Gly Tyr Thr Asn Ser Cys Leu Asn
            340                 345                 350

Pro Val Leu Tyr Ala Phe Leu Asp Glu Asn Phe Lys Arg Cys Phe Arg
        355                 360                 365

Glu Phe Cys Ile Pro Thr Ser Ser Thr Ile Leu Glu Val Leu Phe Gln
    370                 375                 380

Gly Pro Gly Gly Gly Ser Gly Gly Gly Gly Ser Gly Gly Gly Gly
385             390                 395                 400

Ser Gly Gly Gly Gly Ser Gly Gly Gly Ser Gly Gly Gly Gly Ser
                405                 410                 415

Gly Gly Gly Ser Gln Val Gln Leu Gln Glu Ser Gly Gly Leu Val
            420                 425                 430

Arg Pro Gly Gly Ser Arg Arg Leu Ser Cys Val Asp Ser Glu Arg Thr
        435                 440                 445

Ser Tyr Pro Met Gly Trp Phe Arg Arg Ala Pro Gly Lys Glu Arg Glu
        450                 455                 460

Phe Val Ala Ser Ile Thr Trp Ser Gly Ile Asp Pro Thr Tyr Ala Asp
465                 470                 475                 480

Ser Val Ala Asp Arg Phe Thr Ile Ser Arg Asp Val Ala Asn Asn Thr
                485                 490                 495

Leu Tyr Leu Gln Met Asn Ser Leu Lys His Glu Asp Thr Ala Val Tyr
            500                 505                 510

Tyr Cys Ala Ala Arg Ala Pro Val Gly Gln Ser Ser Pro Tyr Asp
        515                 520                 525

Tyr Asp Tyr Trp Gly Gln Gly Thr Gln Val Thr Val Ser Ser His His
530                 535                 540

His His His His
545

<210> SEQ ID NO 12
<211> LENGTH: 553
<212> TYPE: PRT
<213> ORGANISM: Artificial Sequence
<220> FEATURE:
<223> OTHER INFORMATION: GPCR-Nanobody fusion

<400> SEQUENCE: 12

Met Lys Thr Ile Ile Ala Leu Ser Tyr Ile Phe Cys Leu Val Phe Ala
1               5                   10                  15

Asp Tyr Lys Asp Asp Asp Ala Met Gly Pro Gly Asn Ile Ser Asp
            20                  25                  30

Cys Ser Asp Pro Leu Ala Pro Ala Ser Cys Ser Pro Ala Pro Gly Ser
        35                  40                  45

Trp Leu Asn Leu Ser His Val Asp Gly Asn Gln Ser Asp Pro Cys Gly
    50                  55                  60

Pro Asn Arg Thr Gly Leu Gly Gly Ser His Ser Leu Cys Pro Gln Thr
65                  70                  75                  80

Gly Ser Pro Ser Met Val Thr Ala Ile Thr Ile Met Ala Leu Tyr Ser
                85                  90                  95

Ile Val Cys Val Val Gly Leu Phe Gly Asn Phe Leu Val Met Tyr Val
                100                 105                 110

Ile Val Arg Tyr Thr Lys Met Lys Thr Ala Thr Asn Ile Tyr Ile Phe
            115                 120                 125

Asn Leu Ala Leu Ala Asp Ala Leu Ala Thr Ser Thr Leu Pro Phe Gln
        130                 135                 140
```

```
Ser Val Asn Tyr Leu Met Gly Thr Trp Pro Phe Gly Asn Ile Leu Cys
145                 150                 155                 160

Lys Ile Val Ile Ser Ile Asp Tyr Tyr Asn Met Phe Thr Ser Ile Phe
                165                 170                 175

Thr Leu Cys Thr Met Ser Val Asp Arg Tyr Ile Ala Val Cys His Pro
            180                 185                 190

Val Lys Ala Leu Asp Phe Arg Thr Pro Arg Asn Ala Lys Ile Val Asn
        195                 200                 205

Val Cys Asn Trp Ile Leu Ser Ser Ala Ile Gly Leu Pro Val Met Phe
    210                 215                 220

Met Ala Thr Thr Lys Tyr Arg Gln Gly Ser Ile Asp Cys Thr Leu Thr
225                 230                 235                 240

Phe Ser His Pro Thr Trp Tyr Trp Glu Asn Leu Leu Lys Ile Cys Val
                245                 250                 255

Phe Ile Phe Ala Phe Ile Met Pro Val Leu Ile Ile Thr Val Cys Tyr
            260                 265                 270

Gly Leu Met Ile Leu Arg Leu Lys Ser Val Arg Met Leu Ser Gly Ser
        275                 280                 285

Lys Glu Lys Asp Arg Asn Leu Arg Arg Ile Thr Arg Met Val Leu Val
    290                 295                 300

Val Val Ala Val Phe Ile Val Cys Trp Thr Pro Ile His Ile Tyr Val
305                 310                 315                 320

Ile Ile Lys Ala Leu Ile Thr Ile Pro Glu Thr Thr Phe Gln Thr Val
                325                 330                 335

Ser Trp His Phe Cys Ile Ala Leu Gly Tyr Thr Asn Ser Cys Leu Asn
            340                 345                 350

Pro Val Leu Tyr Ala Phe Leu Asp Glu Asn Phe Lys Arg Cys Phe Arg
        355                 360                 365

Glu Phe Cys Ile Pro Thr Ser Ser Thr Ile Leu Glu Val Leu Phe Gln
    370                 375                 380

Gly Pro Gly Gly Gly Ser Gly Gly Gly Ser Gly Gly Gly Gly
385                 390                 395                 400

Ser Gly Gly Gly Ser Gly Gly Gly Ser Gly Gly Gly Gly Ser
                405                 410                 415

Gly Gly Gly Ser Gln Val Gln Leu Gln Glu Ser Gly Gly Gly Leu Val
            420                 425                 430

Gln Pro Gly Gly Ser Leu Arg Leu Ser Cys Ala Ala Ser Gly Ser Phe
        435                 440                 445

Arg Ser Ile Val Ser Met Ala Trp Tyr Arg Gln Ala Pro Gly Lys Gln
450                 455                 460

Arg Glu Leu Val Ala Ser Ser Asn Ser Gly Gly Ser Thr Asn Tyr Ala
465                 470                 475                 480

Asp Ser Val Lys Gly Arg Phe Thr Ile Ser Arg Asp Asn Ala Lys Asn
                485                 490                 495

Thr Val Tyr Leu Gln Met Asn Ser Leu Lys Pro Glu Asp Thr Ala Val
            500                 505                 510

Tyr Trp Cys Asn Val Gln Asn Arg Leu Pro Gly Phe Asp Ala Phe Ser
        515                 520                 525

Gly Arg Ser Ile Ala Glu Thr Tyr Trp Gly Gln Gly Thr Gln Val Thr
    530                 535                 540

Val Ser Ser His His His His His His
545                 550
```

-continued

<210> SEQ ID NO 13
<211> LENGTH: 120
<212> TYPE: PRT
<213> ORGANISM: Artificial Sequence
<220> FEATURE:
<223> OTHER INFORMATION: Nb80

<400> SEQUENCE: 13

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
        35                  40                  45

Ala Ala Ile His Ser Gly Gly Ser Thr Asn Tyr Ala Asn Ser Val Lys
    50                  55                  60

Gly Arg Phe Thr Ile Ser Arg Asp Asn Ala Ala Asn Thr Val Tyr Leu
65                  70                  75                  80

Gln Met Asn Ser Leu Lys Pro Glu Asp Thr Ala Val Tyr Tyr Cys Asn
                85                  90                  95

Val Lys Asp Tyr Gly Ala Val Leu Tyr Glu Tyr Asp Tyr Trp Gly Gln
            100                 105                 110

Gly Thr Gln Val Thr Val Ser Ser
        115                 120

<210> SEQ ID NO 14
<211> LENGTH: 116
<212> TYPE: PRT
<213> ORGANISM: Artificial Sequence
<220> FEATURE:
<223> OTHER INFORMATION: Nb71

<400> SEQUENCE: 14

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Glu Leu Arg Trp Tyr Arg Gln Ala Pro Gly Lys Gln His Glu Leu Val
        35                  40                  45

Ala Gly Ile Thr Thr Gly Gly Asn Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Ser Asn Leu Arg Pro Glu Asp Thr Ala Val Tyr Ala Cys Asn
                85                  90                  95

Ala Asn Trp Asp Leu Leu Ser Asp Tyr Trp Gly Gln Gly Thr Gln Val
            100                 105                 110

Thr Val Ser Ser
        115

<210> SEQ ID NO 15
<211> LENGTH: 124
<212> TYPE: PRT
<213> ORGANISM: Artificial Sequence
<220> FEATURE:
<223> OTHER INFORMATION: Nb69

<400> SEQUENCE: 15

Gln Val Gln Leu Gln Glu Ser Gly Gly Gly Leu Val Gln Ala Gly Gly
1               5                   10                  15

```
Ser Leu Arg Leu Ser Cys Thr Ala Ser Gly Leu Thr Leu Ser Asn Tyr
            20                  25                  30

Ala Met Gly Trp Phe Arg Gln Ala Pro Gly Lys Glu Arg Glu Phe Val
        35                  40                  45

Ala Ala Asp Thr Trp Asn Gly Asn Thr Tyr His Gln Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Tyr Leu Lys Pro Glu Asp Thr Ala Val Tyr Tyr Cys Ala
                85                  90                  95

Ala Arg Gly Ser Arg Arg Ser Ala Tyr Tyr Ser Ser Asp Tyr Thr
            100                 105                 110

Tyr Arg Gly Gln Gly Thr Gln Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: Nb9-1

<400> SEQUENCE: 16

Gln Val Gln Leu Gln Glu Ser Gly Gly Gly Leu Val Gln Ala Gly Gly
1               5                   10                  15

Ser Leu Arg Leu Ser Cys Ala Ala Ser Gly His Thr Phe Ser Ser Ala
            20                  25                  30

Arg Met Tyr Trp Val Arg Gln Ala Pro Gly Lys Glu Arg Glu Phe Val
        35                  40                  45

Ala Ala Ile Ser Arg Ser Gly Phe Thr Tyr Ser Ala Asp Ser Val Lys
    50                  55                  60

Gly Arg Phe Thr Ile Ser Arg Asp Ile Ala Asn Asn Thr Val Tyr Leu
65                  70                  75                  80

Gln Met Asn Ser Leu Gln Pro Glu Asp Thr Ala Ile Tyr Thr Cys Tyr
                85                  90                  95

Ala Ala Tyr Leu Asp Glu Phe Tyr Asn Asp Tyr Thr His Tyr Trp Gly
            100                 105                 110

Leu Gly Thr Gln Val Thr Val Ser Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: Nb9-8

<400> SEQUENCE: 17

Gln Val Gln Leu Gln Glu Ser Gly Gly Gly Leu Val Gln Ala Gly Asp
1               5                   10                  15

Ser Leu Arg Leu Ser Cys Ala Ala Ser Gly Phe Asp Phe Asp Asn Phe
            20                  25                  30

Asp Asp Tyr Ala Ile Gly Trp Phe Arg Gln Ala Pro Gly Gln Glu Arg
        35                  40                  45

Glu Gly Val Ser Cys Ile Asp Pro Ser Asp Gly Ser Thr Ile Tyr Ala
    50                  55                  60

Asp Ser Ala Lys Gly Arg Phe Thr Ile Ser Ser Asp Asn Ala Glu Asn
```

```
                65                  70                  75                  80
Thr Val Tyr Leu Gln Met Asn Ser Leu Lys Pro Glu Asp Thr Ala Val
                    85                  90                  95

Tyr Val Cys Ser Ala Trp Thr Leu Phe His Ser Asp Glu Tyr Trp Gly
                    100                 105                 110

Gln Gly Thr Gln Val Thr Val Ser Ser
            115                 120

<210> SEQ ID NO 18
<211> LENGTH: 119
<212> TYPE: PRT
<213> ORGANISM: Artificial Sequence
<220> FEATURE:
<223> OTHER INFORMATION: Nb60

<400> SEQUENCE: 18

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Phe Ser Leu Asn
                20                  25                  30

Asp Met Gly Trp Tyr Arg Gln Ala Pro Gly Lys Leu Arg Glu Leu Val
                35                  40                  45

Ala Ala Ile Thr Ser Gly Gly Ser Thr Lys Tyr Ala Asp Ser Val Lys
            50                  55                  60

Gly Arg Phe Thr Ile Ser Arg Asp Asn Ala Lys Asn Thr Val Tyr Leu
65                  70                  75                  80

Gln Met Asn Ser Leu Lys Ala Glu Asp Thr Ala Val Tyr Tyr Cys Asn
                    85                  90                  95

Ala Lys Val Ala Gly Thr Phe Ser Ile Tyr Asp Tyr Trp Gly Gln Gly
                100                 105                 110

Thr Gln Val Thr Val Ser Ser
            115

<210> SEQ ID NO 19
<211> LENGTH: 122
<212> TYPE: PRT
<213> ORGANISM: Artificial Sequence
<220> FEATURE:
<223> OTHER INFORMATION: Nb33

<400> SEQUENCE: 19

Gln Val Gln Leu Gln Glu Ser Gly Gly Gly Leu Val Arg Pro Gly Gly
1               5                   10                  15

Ser Arg Arg Leu Ser Cys Val Asp Ser Glu Arg Thr Ser Tyr Pro Met
                20                  25                  30

Gly Trp Phe Arg Arg Ala Pro Gly Lys Glu Arg Glu Phe Val Ala Ser
                35                  40                  45

Ile Thr Trp Ser Gly Ile Asp Pro Thr Tyr Ala Asp Ser Val Ala Asp
            50                  55                  60

Arg Phe Thr Ile Ser Arg Asp Val Ala Asn Asn Thr Leu Tyr Leu Gln
65                  70                  75                  80

Met Asn Ser Leu Lys His Glu Asp Thr Ala Val Tyr Tyr Cys Ala Ala
                    85                  90                  95

Arg Ala Pro Val Gly Gln Ser Ser Pro Tyr Asp Tyr Asp Tyr Trp
                100                 105                 110

Gly Gln Gly Thr Gln Val Thr Val Ser Ser
            115                 120
```

```
<210> SEQ ID NO 20
<211> LENGTH: 127
<212> TYPE: PRT
<213> ORGANISM: Artificial Sequence
<220> FEATURE:
<223> OTHER INFORMATION: Nb10

<400> SEQUENCE: 20

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Phe Arg Ser Ile Val
            20                  25                  30

Ser Met Ala Trp Tyr Arg Gln Ala Pro Gly Lys Gln Arg Glu Leu Val
        35                  40                  45

Ala Ser Ser Asn Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Trp Cys Asn
                85                  90                  95

Val Gln Asn Arg Leu Pro Gly Phe Asp Ala Phe Ser Gly Arg Ser Ile
            100                 105                 110

Ala Glu Thr Tyr Trp Gly Gln Gly Thr Gln Val Thr Val Ser Ser
        115                 120                 125

<210> SEQ ID NO 21
<211> LENGTH: 8
<212> TYPE: PRT
<213> ORGANISM: Artificial Sequence
<220> FEATURE:
<223> OTHER INFORMATION: CDR1 Nb80

<400> SEQUENCE: 21

Gly Ser Ile Phe Ser Ile Asn Thr
1               5

<210> SEQ ID NO 22
<211> LENGTH: 8
<212> TYPE: PRT
<213> ORGANISM: Artificial Sequence
<220> FEATURE:
<223> OTHER INFORMATION: CDR1 Nb71

<400> SEQUENCE: 22

Gly Phe Ala Phe Ser Ser Tyr Glu
1               5

<210> SEQ ID NO 23
<211> LENGTH: 8
<212> TYPE: PRT
<213> ORGANISM: Artificial Sequence
<220> FEATURE:
<223> OTHER INFORMATION: CDR1 Nb69

<400> SEQUENCE: 23

Gly Leu Thr Leu Ser Asn Tyr Ala
1               5

<210> SEQ ID NO 24
<211> LENGTH: 8
<212> TYPE: PRT
<213> ORGANISM: Artificial Sequence
<220> FEATURE:
```

```
<223> OTHER INFORMATION: CDR1 Nb9-1

<400> SEQUENCE: 24

Gly His Thr Phe Ser Ser Ala Arg
1               5

<210> SEQ ID NO 25
<211> LENGTH: 11
<212> TYPE: PRT
<213> ORGANISM: Artificial Sequence
<220> FEATURE:
<223> OTHER INFORMATION: CDR1 Nb9-8

<400> SEQUENCE: 25

Gly Phe Asp Phe Asp Asn Phe Asp Asp Tyr Ala
1               5                   10

<210> SEQ ID NO 26
<211> LENGTH: 8
<212> TYPE: PRT
<213> ORGANISM: Artificial Sequence
<220> FEATURE:
<223> OTHER INFORMATION: CDR1 Nb60

<400> SEQUENCE: 26

Gly Ser Ile Phe Ser Leu Asn Asp
1               5

<210> SEQ ID NO 27
<211> LENGTH: 6
<212> TYPE: PRT
<213> ORGANISM: Artificial Sequence
<220> FEATURE:
<223> OTHER INFORMATION: CDR1 Nb33

<400> SEQUENCE: 27

Glu Arg Thr Ser Tyr Pro
1               5

<210> SEQ ID NO 28
<211> LENGTH: 8
<212> TYPE: PRT
<213> ORGANISM: Artificial Sequence
<220> FEATURE:
<223> OTHER INFORMATION: CDR1 Nb10

<400> SEQUENCE: 28

Gly Ser Phe Arg Ser Ile Val Ser
1               5

<210> SEQ ID NO 29
<211> LENGTH: 7
<212> TYPE: PRT
<213> ORGANISM: Artificial Sequence
<220> FEATURE:
<223> OTHER INFORMATION: CDR2 Nb80

<400> SEQUENCE: 29

Ile His Ser Gly Gly Ser Thr
1               5

<210> SEQ ID NO 30
<211> LENGTH: 7
<212> TYPE: PRT
<213> ORGANISM: Artificial Sequence
<220> FEATURE:
<223> OTHER INFORMATION: CDR2 Nb71
```

<400> SEQUENCE: 30

Ile Thr Thr Gly Gly Asn Thr
1               5

<210> SEQ ID NO 31
<211> LENGTH: 7
<212> TYPE: PRT
<213> ORGANISM: Artificial Sequence
<220> FEATURE:
<223> OTHER INFORMATION: CDR2 Nb69

<400> SEQUENCE: 31

Asp Thr Trp Asn Gly Asn Thr
1               5

<210> SEQ ID NO 32
<211> LENGTH: 7
<212> TYPE: PRT
<213> ORGANISM: Artificial Sequence
<220> FEATURE:
<223> OTHER INFORMATION: CDR2 Nb9-1

<400> SEQUENCE: 32

Ile Ser Arg Ser Gly Phe Thr
1               5

<210> SEQ ID NO 33
<211> LENGTH: 8
<212> TYPE: PRT
<213> ORGANISM: Artificial Sequence
<220> FEATURE:
<223> OTHER INFORMATION: CDR2 Nb9-8

<400> SEQUENCE: 33

Ile Asp Pro Ser Asp Gly Ser Thr
1               5

<210> SEQ ID NO 34
<211> LENGTH: 7
<212> TYPE: PRT
<213> ORGANISM: Artificial Sequence
<220> FEATURE:
<223> OTHER INFORMATION: CDR2 Nb60

<400> SEQUENCE: 34

Ile Thr Ser Gly Gly Ser Thr
1               5

<210> SEQ ID NO 35
<211> LENGTH: 8
<212> TYPE: PRT
<213> ORGANISM: Artificial Sequence
<220> FEATURE:
<223> OTHER INFORMATION: CDR2 Nb33

<400> SEQUENCE: 35

Ile Thr Trp Ser Gly Ile Asp Pro
1               5

<210> SEQ ID NO 36
<211> LENGTH: 7
<212> TYPE: PRT
<213> ORGANISM: Artificial Sequence
<220> FEATURE:
<223> OTHER INFORMATION: CDR2 Nb10

```
<400> SEQUENCE: 36

Ser Asn Ser Gly Gly Ser Thr
1               5

<210> SEQ ID NO 37
<211> LENGTH: 14
<212> TYPE: PRT
<213> ORGANISM: Artificial Sequence
<220> FEATURE:
<223> OTHER INFORMATION: CDR3 Nb80

<400> SEQUENCE: 37

Asn Val Lys Asp Tyr Gly Ala Val Leu Tyr Glu Tyr Asp Tyr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: CDR3 Nb71

<400> SEQUENCE: 38

Asn Ala Asn Trp Asp Leu Leu Ser Asp Tyr
1               5                   10

<210> SEQ ID NO 39
<211> LENGTH: 18
<212> TYPE: PRT
<213> ORGANISM: Artificial Sequence
<220> FEATURE:
<223> OTHER INFORMATION: CDR3 Nb69

<400> SEQUENCE: 39

Ala Ala Arg Gly Ser Arg Arg Ser Ala Tyr Tyr Ser Ser Ser Asp Tyr
1               5                   10                  15

Thr Tyr

<210> SEQ ID NO 40
<211> LENGTH: 15
<212> TYPE: PRT
<213> ORGANISM: Artificial Sequence
<220> FEATURE:
<223> OTHER INFORMATION: CDR3 Nb9-1

<400> SEQUENCE: 40

Tyr Ala Ala Tyr Leu Asp Glu Phe Tyr Asn Asp Tyr Thr His Tyr
1               5                   10                  15

<210> SEQ ID NO 41
<211> LENGTH: 11
<212> TYPE: PRT
<213> ORGANISM: Artificial Sequence
<220> FEATURE:
<223> OTHER INFORMATION: CDR3 Nb9-8

<400> SEQUENCE: 41

Ser Ala Trp Thr Leu Phe His Ser Asp Glu Tyr
1               5                   10

<210> SEQ ID NO 42
<211> LENGTH: 13
<212> TYPE: PRT
<213> ORGANISM: Artificial Sequence
<220> FEATURE:
<223> OTHER INFORMATION: CDR3 Nb60
```

<400> SEQUENCE: 42

Asn Ala Lys Val Ala Gly Thr Phe Ser Ile Tyr Asp Tyr
1               5                   10

<210> SEQ ID NO 43
<211> LENGTH: 17
<212> TYPE: PRT
<213> ORGANISM: Artificial Sequence
<220> FEATURE:
<223> OTHER INFORMATION: CDR3 Nb33

<400> SEQUENCE: 43

Ala Ala Arg Ala Pro Val Gly Gln Ser Ser Pro Tyr Asp Tyr Asp
1               5                   10                  15

Tyr

<210> SEQ ID NO 44
<211> LENGTH: 21
<212> TYPE: PRT
<213> ORGANISM: Artificial Sequence
<220> FEATURE:
<223> OTHER INFORMATION: CDR3 Nb10

<400> SEQUENCE: 44

Asn Val Gln Asn Arg Leu Pro Gly Phe Asp Ala Phe Ser Gly Arg Ser
1               5                   10                  15

Ile Ala Glu Thr Tyr
            20

<210> SEQ ID NO 45
<211> LENGTH: 398
<212> TYPE: PRT
<213> ORGANISM: Mus musculus

<400> SEQUENCE: 45

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp

```
                     180                 185                 190
Ile Leu Ser Ser Ala Ile Gly Leu Pro Val Met Phe Met Ala Thr Thr
                195                 200                 205
Lys Tyr Arg Gln Gly Ser Ile Asp Cys Thr Leu Thr Phe Ser His Pro
            210                 215                 220
Thr Trp Tyr Trp Glu Asn Leu Leu Lys Ile Cys Val Phe Ile Phe Ala
225                 230                 235                 240
Phe Ile Met Pro Val Leu Ile Ile Thr Val Cys Tyr Gly Leu Met Ile
                245                 250                 255
Leu Arg Leu Lys Ser Val Arg Met Leu Ser Gly Ser Lys Glu Lys Asp
            260                 265                 270
Arg Asn Leu Arg Arg Ile Thr Arg Met Val Leu Val Val Val Ala Val
        275                 280                 285
Phe Ile Val Cys Trp Thr Pro Ile His Ile Tyr Val Ile Ile Lys Ala
        290                 295                 300
Leu Ile Thr Ile Pro Glu Thr Thr Phe Gln Thr Val Ser Trp His Phe
305                 310                 315                 320
Cys Ile Ala Leu Gly Tyr Thr Asn Ser Cys Leu Asn Pro Val Leu Tyr
                325                 330                 335
Ala Phe Leu Asp Glu Asn Phe Lys Arg Cys Phe Arg Glu Phe Cys Ile
            340                 345                 350
Pro Thr Ser Ser Thr Ile Glu Gln Gln Asn Ser Ala Arg Ile Arg Gln
        355                 360                 365
Asn Thr Arg Glu His Pro Ser Thr Ala Asn Thr Val Asp Arg Thr Asn
    370                 375                 380
His Gln Leu Glu Asn Leu Glu Ala Glu Thr Ala Pro Leu Pro
385                 390                 395

<210> SEQ ID NO 46
<211> LENGTH: 400
<212> TYPE: PRT
<213> ORGANISM: Homo sapiens

<400> SEQUENCE: 46

Met Asp Ser Ser Ala Ala Pro Thr Asn Ala Ser Asn Cys Thr Asp Ala
1               5                   10                  15
Leu Ala Tyr Ser Ser Cys Ser Pro Ala Pro Ser Pro Gly Ser Trp Val
                20                  25                  30
Asn Leu Ser His Leu Asp Gly Asn Leu Ser Asp Pro Cys Gly Pro Asn
            35                  40                  45
Arg Thr Asp Leu Gly Gly Arg Asp Ser Leu Cys Pro Pro Thr Gly Ser
        50                  55                  60
Pro Ser Met Ile Thr Ala Ile Thr Ile Met Ala Leu Tyr Ser Ile Val
65                  70                  75                  80
Cys Val Val Gly Leu Phe Gly Asn Phe Leu Val Met Tyr Val Ile Val
                85                  90                  95
Arg Tyr Thr Lys Met Lys Thr Ala Thr Asn Ile Tyr Ile Phe Asn Leu
            100                 105                 110
Ala Leu Ala Asp Ala Leu Ala Thr Ser Thr Leu Pro Phe Gln Ser Val
        115                 120                 125
Asn Tyr Leu Met Gly Thr Trp Pro Phe Gly Thr Ile Leu Cys Lys Ile
    130                 135                 140
Val Ile Ser Ile Asp Tyr Tyr Asn Met Phe Thr Ser Ile Phe Thr Leu
145                 150                 155                 160
```

```
Cys Thr Met Ser Val Asp Arg Tyr Ile Ala Val Cys His Pro Val Lys
            165                 170                 175

Ala Leu Asp Phe Arg Thr Pro Arg Asn Ala Lys Ile Ile Asn Val Cys
        180                 185                 190

Asn Trp Ile Leu Ser Ser Ala Ile Gly Leu Pro Val Met Phe Met Ala
    195                 200                 205

Thr Thr Lys Tyr Arg Gln Gly Ser Ile Asp Cys Thr Leu Thr Phe Ser
210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
            245                 250                 255

Met Ile Leu Arg Leu Lys Ser Val Arg Met Leu Ser Gly Ser Lys Glu
        260                 265                 270

Lys Asp Arg Asn Leu Arg Arg Ile Thr Arg Met Val Leu Val Val Val
    275                 280                 285

Ala Val Phe Ile Val Cys Trp Thr Pro Ile His Ile Tyr Val Ile Ile
290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
            325                 330                 335

Leu Tyr Ala Phe Leu Asp Glu Asn Phe Lys Arg Cys Phe Arg Glu Phe
        340                 345                 350

Cys Ile Pro Thr Ser Ser Asn Ile Glu Gln Gln Asn Ser Thr Arg Ile
    355                 360                 365

Arg Gln Asn Thr Arg Asp His Pro Ser Thr Ala Asn Thr Val Asp Arg
370                 375                 380

Thr Asn His Gln Leu Glu Asn Leu Glu Ala Glu Thr Ala Pro Leu Pro
385                 390                 395                 400

<210> SEQ ID NO 47
<211> LENGTH: 4
<212> TYPE: PRT
<213> ORGANISM: Artificial Sequence
<220> FEATURE:
<223> OTHER INFORMATION: Factor Xa cleavage site

<400> SEQUENCE: 47

Ile Glu Gly Arg
1

<210> SEQ ID NO 48
<211> LENGTH: 4
<212> TYPE: PRT
<213> ORGANISM: Artificial Sequence
<220> FEATURE:
<223> OTHER INFORMATION: thrombin cleavage site

<400> SEQUENCE: 48

Leu Val Pro Arg
1

<210> SEQ ID NO 49
<211> LENGTH: 5
<212> TYPE: PRT
<213> ORGANISM: Artificial Sequence
<220> FEATURE:
<223> OTHER INFORMATION: enterokinase cleaving site
```

```
<400> SEQUENCE: 49

Asp Asp Asp Asp Lys
1               5

<210> SEQ ID NO 50
<211> LENGTH: 8
<212> TYPE: PRT
<213> ORGANISM: Artificial Sequence
<220> FEATURE:
<223> OTHER INFORMATION: PreScission (or 3C) cleavage site

<400> SEQUENCE: 50

Leu Glu Val Leu Phe Gln Gly Pro
1               5

<210> SEQ ID NO 51
<211> LENGTH: 9
<212> TYPE: PRT
<213> ORGANISM: Artificial Sequence
<220> FEATURE:
<223> OTHER INFORMATION: Linker

<400> SEQUENCE: 51

Gly Gly Gly Gly Ser Gly Gly Gly Ser
1               5

<210> SEQ ID NO 52
<211> LENGTH: 16
<212> TYPE: PRT
<213> ORGANISM: Influenza A virus

<400> SEQUENCE: 52

Met Lys Thr Ile Ile Ala Leu Ser Tyr Ile Phe Cys Leu Val Phe Ala
1               5                   10                  15

<210> SEQ ID NO 53
<211> LENGTH: 8
<212> TYPE: PRT
<213> ORGANISM: Artificial Sequence
<220> FEATURE:
<223> OTHER INFORMATION: Flag epitope

<400> SEQUENCE: 53

Asp Tyr Lys Asp Asp Asp Asp Ala
1               5

<210> SEQ ID NO 54
<211> LENGTH: 8
<212> TYPE: PRT
<213> ORGANISM: Artificial Sequence
<220> FEATURE:
<223> OTHER INFORMATION: TEV cleavage site

<400> SEQUENCE: 54

Glu Asn Leu Tyr Phe Gln Gly Phe
1               5

<210> SEQ ID NO 55
<211> LENGTH: 413
<212> TYPE: PRT
<213> ORGANISM: Homo sapiens

<400> SEQUENCE: 55

Met Gly Gln Pro Gly Asn Gly Ser Ala Phe Leu Leu Ala Pro Asn Arg
1               5                   10                  15
```

-continued

Ser His Ala Pro Asp His Asp Val Thr Gln Gln Arg Asp Glu Val Trp
            20                  25                  30

Val Met Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
    370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 56
<211> LENGTH: 18
<212> TYPE: DNA

<213> ORGANISM: Artificial Sequence
<220> FEATURE:
<223> OTHER INFORMATION: Primer

<400> SEQUENCE: 56
gcggaattcg agctcgcc                                                     18

<210> SEQ ID NO 57
<211> LENGTH: 42
<212> TYPE: DNA
<213> ORGANISM: Artificial Sequence
<220> FEATURE:
<223> OTHER INFORMATION: Primer

<400> SEQUENCE: 57
cctccgccgg atccgccacc tcctccactc tgctcccctg tg                          42

<210> SEQ ID NO 58
<211> LENGTH: 50
<212> TYPE: DNA
<213> ORGANISM: Artificial Sequence
<220> FEATURE:
<223> OTHER INFORMATION: Primer

<400> SEQUENCE: 58
ggcggatccg gcggaggttc gcaggtgcag ctgcaggagt ctgggggagg                  50

<210> SEQ ID NO 59
<211> LENGTH: 54
<212> TYPE: DNA
<213> ORGANISM: Artificial Sequence
<220> FEATURE:
<223> OTHER INFORMATION: Primer

<400> SEQUENCE: 59
tggaattcta gattagtgat ggtgatggtg gtgtgaggag acggtgacct gggt             54

<210> SEQ ID NO 60
<211> LENGTH: 24
<212> TYPE: PRT
<213> ORGANISM: Artificial Sequence
<220> FEATURE:
<223> OTHER INFORMATION: Linker

<400> SEQUENCE: 60

Gly Gly Gly Gly Ser Gly Gly Gly Gly Ser Gly Gly Gly Gly Ser Gly
1               5                   10                  15

Gly Gly Gly Ser Gly Gly Gly Ser
            20

<210> SEQ ID NO 61
<211> LENGTH: 18
<212> TYPE: DNA
<213> ORGANISM: Artificial Sequence
<220> FEATURE:
<223> OTHER INFORMATION: Primer

<400> SEQUENCE: 61
gcagatctcg gtccgaag                                                     18

<210> SEQ ID NO 62
<211> LENGTH: 34
<212> TYPE: DNA
<213> ORGANISM: Artificial Sequence
<220> FEATURE:
<223> OTHER INFORMATION: Linker

```
<400> SEQUENCE: 62
ggggsggggs ggggsggggs ggggsggggs gggs                              34

<210> SEQ ID NO 63
<211> LENGTH: 29
<212> TYPE: DNA
<213> ORGANISM: Artificial Sequence
<220> FEATURE:
<223> OTHER INFORMATION: Primer

<400> SEQUENCE: 63
gatgtgcagc tgcaggagtc tggrggagg                                    29

<210> SEQ ID NO 64
<211> LENGTH: 19
<212> TYPE: DNA
<213> ORGANISM: Artificial Sequence
<220> FEATURE:
<223> OTHER INFORMATION: Primer

<400> SEQUENCE: 64
ccacagacag ccctcatag                                               19
```